(12) United States Patent
Liu et al.

(10) Patent No.: US 11,040,984 B2
(45) Date of Patent: Jun. 22, 2021

(54) QUINAZOLINE COMPOUND FOR EGFR INHIBITION

(71) Applicant: MEDSHINE DISCOVERY INC., Jiangsu (CN)

(72) Inventors: Xile Liu, Shanghai (CN); Charles Z. Ding, Shanghai (CN); Shuhui Chen, Shanghai (CN); Lingyun Wu, Shanghai (CN); Lihong Hu, Shanghai (CN); Haiwen Wan, Shanghai (CN)

(73) Assignee: MEDSHINE DISCOVERY INC., Jiangsu (CN)

( * ) Notice: Subject to any disclaimer, the term of this patent is extended or adjusted under 35 U.S.C. 154(b) by 0 days.

(21) Appl. No.: 16/474,999

(22) PCT Filed: Dec. 29, 2017

(86) PCT No.: PCT/CN2017/119993
§ 371 (c)(1),
(2) Date: Sep. 10, 2019

(87) PCT Pub. No.: WO2018/121758
PCT Pub. Date: Jul. 5, 2018

(65) Prior Publication Data
US 2020/0190107 A1  Jun. 18, 2020

(30) Foreign Application Priority Data
Dec. 30, 2016 (CN) .......................... 201611259071.9

(51) Int. Cl.
| | | |
|---|---|---|
| *C07D 498/04* | (2006.01) | |
| *A61P 35/00* | (2006.01) | |
| *C07D 403/14* | (2006.01) | |
| *C07D 413/10* | (2006.01) | |
| *C07D 498/10* | (2006.01) | |
| *A61K 45/06* | (2006.01) | |

(52) U.S. Cl.
CPC ............ *C07D 498/04* (2013.01); *A61P 35/00* (2018.01); *C07D 403/14* (2013.01); *C07D 413/10* (2013.01); *C07D 498/10* (2013.01); *A61K 45/06* (2013.01)

(58) Field of Classification Search
CPC .............................. C07D 498/04; A61P 35/00
See application file for complete search history.

(56) References Cited

U.S. PATENT DOCUMENTS

| | | | | |
|---|---|---|---|---|
| 5,457,105 A | | 10/1995 | Barker | |
| 5,475,001 A | * | 12/1995 | Barker | ..................... A61P 35/00 514/183 |
| 5,580,870 A | * | 12/1996 | Barker | ..................... A61P 35/00 514/234.5 |
| 5,616,582 A | * | 4/1997 | Barker | ................. C07D 403/04 514/234.5 |

FOREIGN PATENT DOCUMENTS

| | | |
|---|---|---|
| CN | 1094043 A | 10/1994 |
| CN | 106389435 A | 2/2017 |
| WO | 95/03283 A1 | 2/1995 |

OTHER PUBLICATIONS

Barker et al (1995): STN International CAPLUS database, (Columbus, Ohio), Accession No. 1995: 23238.*
Barker J (1994): STN International CAPLUS database, (Columbus, Ohio), Accession No. 1994: 217715.*

* cited by examiner

*Primary Examiner* — Golam M Shameem
(74) *Attorney, Agent, or Firm* — Novick, Kim & Lee, PLLC; Allen Xue

(57) ABSTRACT

Disclosed is a novel quinazoline compound. Specifically, disclosed are a compound represented by the formula (I) and a pharmacologically acceptable salt.

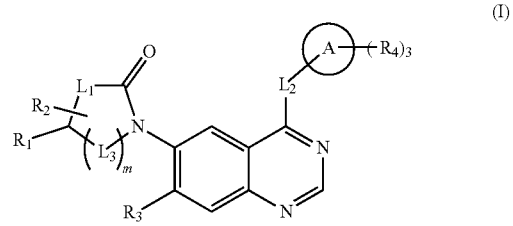

24 Claims, No Drawings

QUINAZOLINE COMPOUND FOR EGFR INHIBITION

CROSS-REFERENCES TO RELATED APPLICATIONS

This application is a national stage application of PCT/CN2017/119993, which claims priority to Chinese patent application CN201611259071.9 filed on Dec. 30, 2016, the content of which is hereby incorporated into this application.

TECHNICAL FIELD

The present invention relates to a class of quinazoline compounds as EGFR inhibitors, and their use in the treatment of brain metastatases. In particular, the present invention relates to a compound of formula (I) or (and) a pharmaceutically acceptable salt thereof as an EGFR mutation inhibitor for the treatment of brain metastases.

BACKGROUND ART

Lung cancer is one of the most common malignant tumors in the world, and has become the leading cause of malignant tumor-related deaths in urban areas in China. Non-small cell lung cancer (NSCLC) accounts for about 80% of all lung cancers, about 75% of patients are at an advanced stage at the time of diagnosis, and the 5-year survival rates are very low. Genetic aberrations in the tyrosine kinase domain of epidermal growth factor receptor (EGFR) have been identified as one of the key drivers of NSCLC progression.

EGFR (epidermal growth factor receptor, ErbB-1 or HER1 for short) is a member of the epidermal growth factor receptor (HER) family. The family includes HER1 (erbB 1, EGFR), HER2 (erbB2, NEU), HER3 (erbB3) and HER4 (erbB4). EGFR is a glycoprotein that is a receptor of epidermal growth factor (EGF) cell proliferation and signal transduction, belonging to a family of receptor tyrosine kinases, penetrating cell membranes and located on the surfaces of cell membranes. After ligand binding with epidermal growth factor receptor (EGFR), the receptor dimerization occurs, which includes the binding of two homomeric receptor molecules (homodimerization), and the binding of different human EGF-related receptor (HER) tyrosine kinase family members (heterodimerization). After EGFR dimerization, the kinase pathway in cells can be activated, including the active sites of Y992, Y1045, Y1068, Y1148, Y1173, etc. This autophosphorylation can lead to downstream phosphorylation, including the MAPK, Akt and JNK pathways, and induce cell proliferation.

EGFR is involved in tumor cell proliferation, angiogenesis, tumor invasion, metastasis and inhibition of tumor cell apoptosis. Studies have shown that there is high or abnormal expression of EGFR in many solid tumors. EGFR overexpression or activation mutation involves in the development and progress of many human malignant tumors. At present, many small molecule tyrosine kinase inhibitors (TKI) have been developed to target the ATP-binding domain of EGFR. Some of these inhibitors have been approved for clinical use. However, EGFR-TKI resistance may eventually develop after varying periods of treatment, and about one-third of patients develop CNS metastasis after acquisition of EGFR-TKI resistance.

Brain metastasis has become the leading cause of deaths in the course of lung cancer. It has been reported that the incidence of brain metastasis in patients with lung cancer is as high as 30%-50%. After brain metastasis from lung cancer, it is suggested that the lesion is advanced, and the average survival time of untreated patients with brain metastasis is only 1-2 months. The main treatments for brain metastasis from lung cancer are surgery, radiation therapy and drug therapy (including targeted drugs and chemotherapy). For patients with brain metastases, selective use of radiation therapy and surgery are the mainstay treatment but offer limited benefits. Surgery is mainly used for single tumors or rescue treatment in critical situations. Radiation therapy and drug therapy are the main methods. Whole-brain radiation therapy has become a standard treatment for brain metastases, especially for patients with multiple brain metastases and elderly patients in poor general condition. Radiation therapy can help patients to relieve symptoms, with an overall remission rate of 88%. Whole-brain radiation therapy can effectively improve the neurological symptoms and functions of patients and quality of life, and the median survival time ranges from 3 to 6 months. However, due to the existence of blood-brain barrier (BBB), many drugs can not reach effective therapeutic concentrations, so these drugs can not meet the market demand.

The blood-brain barrier (BBB) exists at the interface between the brain and the capillaries of brain tissues, which has very complex multicellular tissues, composed of brain endothelial cells that line blood vessels and form brain capillary endothelium, and peripheral cells including pericytes, astrocytes and neurons. BBB provides a completely autonomous environment for cells in CNS, allowing selective access to nutrients and hormones required, while removing waste and reducing exposure to potentially harmful exogenous substances. Most of CNS drugs are small molecules which pass through BBB via passive transcellular diffusion. In order to achieve efficacy in CNS and the surrounding environment, it is necessary to design EGFR inhibitors with the sufficient ability to cross BBB to achieve effective therapeutic concentrations in the brain.

DETAILED DESCRIPTION OF THE INVENTION

The present invention provides a compound of formula (I) or a pharmaceutically acceptable salt thereof,

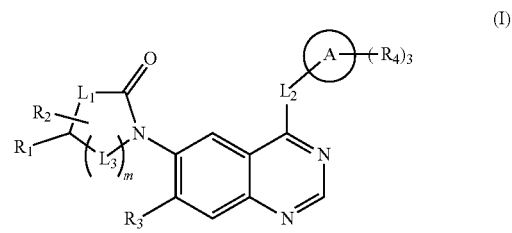

wherein,
$R_1$ and $R_2$ are independently selected from H, halogen, OH, CN, $NH_2$, respectively, or selected from $C_{1-5}$ alkyl and $C_{1-5}$ heteroalkyl, $C_{1-5}$ alkyl and $C_{1-5}$ heteroalkyl being optionally substituted with one, two or three R;
or, $R_1$ is connected with $R_2$ to form a 4-6-membered ring substituted with two $R_5$;
$L_1$ is selected from a single bond, —$(C(R)_2)_m$—, —$O(C(R)_2)_m$—, —$S(C(R)_2)_m$—;
m is independently selected from 0, 1, or 2, respectively;
$R_5$ is independently selected from H, halo, OH, CN, $NH_2$, respectively, or independently selected from $C_{1-5}$ alkyl, $C_{1-5}$ heteroalkyl, $C_{3-6}$ cycloalkyl and 3-6-membered heterocycloalkyl, $C_{1-5}$ alkyl, $C_{1-5}$ heteroalkyl, $C_{3-6}$ cycloalkyl and 3-6-membered heterocycloalkyl being optionally substituted with one, two or three R;

$R_3$ is H, or selected from $C_{1-3}$ alkyl and $C_{1-3}$ heteroalkyl, $C_{1-3}$ alkyl and $C_{1-3}$ heteroalkyl being optionally substituted with one, two or three R;

$L_2$ is selected from the group consisting of a single bond, —O—, —NH—;

$L_3$ is —C(R)$_2$—;

ring A is selected from the group consisting of phenyl, 5-10-membered heteroaryl; $R_4$ is independently selected from the group consisting of H, halo, $C_{1-3}$ alkyl, $C_{1-3}$ heteroalkyl, $C_{2-3}$ alkynyl, respectively;

R is independently selected from H, OH, CN, $NH_2$, halo, respectively, or selected from $C_{1-3}$ alkyl and $C_{1-3}$ heteroalkyl, $C_{1-3}$ alkyl and $C_{1-3}$ heteroalkyl being optionally substituted with one, two or three R';

the "hetero" of said $C_{1-5}$ heteroalkyl, said $C_{1-3}$ heteroalkyl, said 3-6-membered heterocycloalkyl, said 5-9-membered heteroaryl is selected from the group consisting of —O—, =O, N, —NH—, —S—, =S, —S(=O)—, —S(=O)$_2$—, —C(=O)O—, —C(=O)NH—, —S(=O)NH—;

R' is selected from the group consisting of F, Cl, Br, I, OH, CN, $NH_2$;

in any of the above cases, the number of heteroatoms or heteroatom-containing groups is independently selected from 1, 2 or 3, respectively.

In some aspects of the present invention, the R is selected from the group consisting of H, F, Cl, Br, OH, CN, $NH_2$, $CH_3$, $CH_3CH_2$, $CH_3O$, $CF_3$, $CHF_2$, $CH_2F$.

In some aspects of the present invention, the $R_1$ and $R_2$ are independently selected from H, halogen, OH, CN, $NH_2$, respectively, or selected from $CH_3$, $CH_3CH_2$, $CH_3O$, $CH_3NH$, $(CH_3)_2N$, $(CH_3)_2NCH_2$ and $CH_3OCH_2$, $CH_3$, $CH_3CH_2$, $CH_3O$, $CH_3NH$, $(CH_3)_2N$, $(CH_3)_2NCH_2$ and $CH_3OCH_2$ being optionally substituted with one, two or three R.

In some aspects of the present invention, the $R_1$ and $R_2$ are independently selected from the group consisting of H, F, Cl, Br, OH, CN, $NH_2$, $CH_3$, $CH_3CH_2$, $CH_3O$, $CH_3NH$, $(CH_3)_2N$, $(CH_3)_2NCH_2$, $CH_3OCH_2$, respectively.

In some aspects of the present invention, the $L_1$ is selected from a single bond, —O—, —S—, —C(R)$_2$—, —(C(R)$_2$)$_2$—, —OC(R)$_2$—, —O(C(R)$_2$)$_2$—.

In some aspects of the present invention, the $L_1$ is selected from a single bond, —O—, —S—, —$CH_2$—, —$(CH_2)_2$—, —$CH_2O$—, —$(CH_2)_2O$—.

In some aspects of the present invention, the structural unit

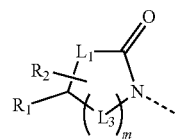

is selected from:

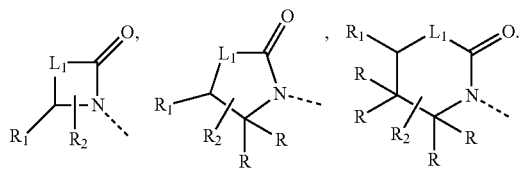

In some aspects of the present invention, the structural unit

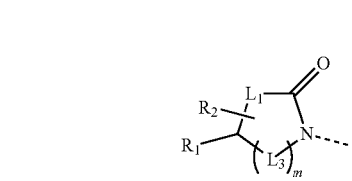

is selected from:

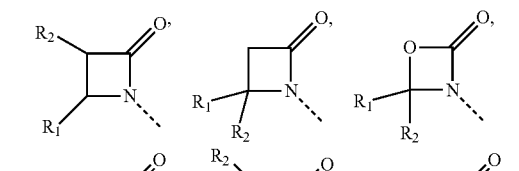
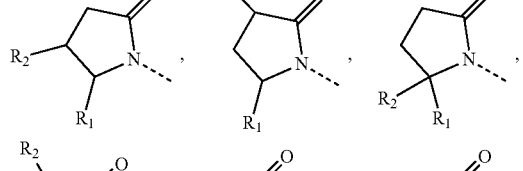
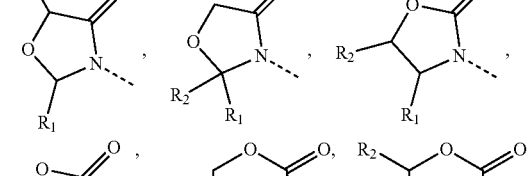
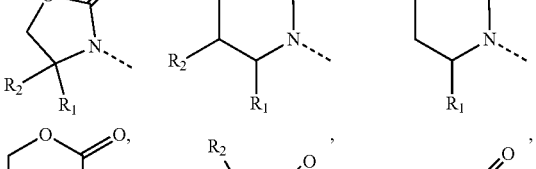
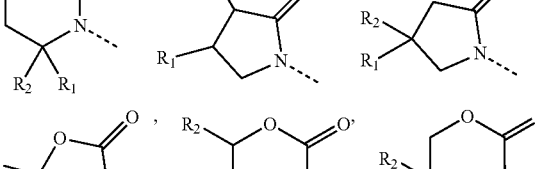
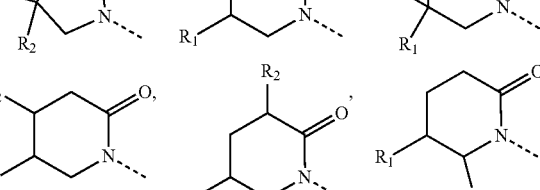

-continued

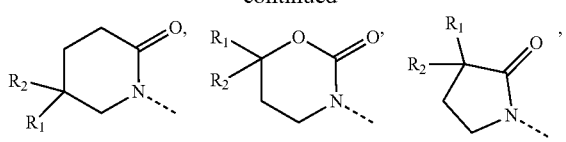

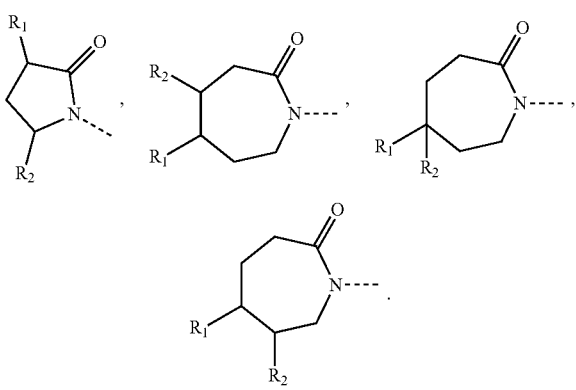

In some aspects of the present invention, the structural unit

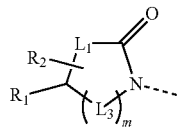

is selected from:

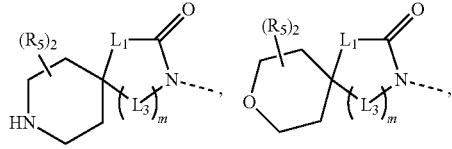

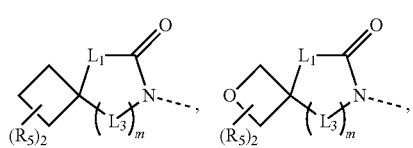

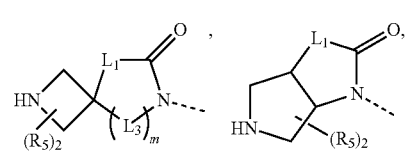

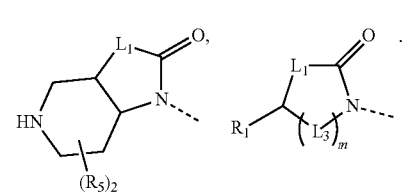

In some aspects of the present invention, the structural unit

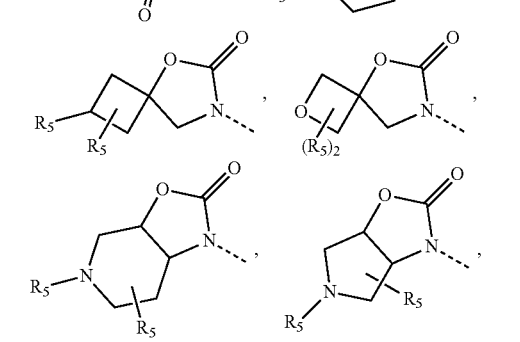

is selected from:

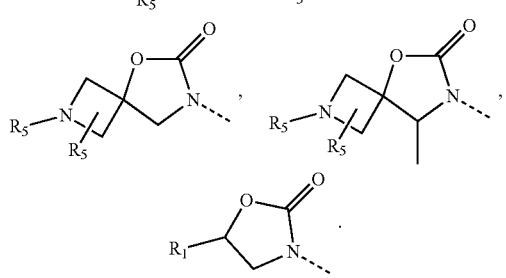

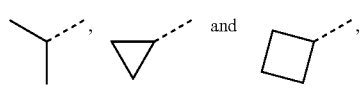

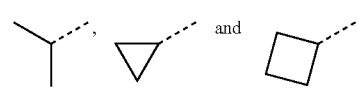

In some aspects of the present invention, the $R_5$ is independently selected from H, F, Cl, Br, OH, CN, $NH_2$, respectively, or selected from $CH_3$, $CH_3CH_2$, $CH_3CH_2CH_2$, $CH_3O$, $CH_3OCH_2$, $N(CH_3)_2$, $NH(CH_3)$, $CH_3$, $CH_3CH_2$, $CH_3CH_2CH_2$, $CH_3O$, $CH_3OCH_2$, $N(CH_3)_2$, $NH(CH_3)$, being optionally substituted with one, two or three R.

In some aspects of the present invention, the $R_5$ is independently selected from the group consisting of F, Cl, Br, OH, CN, $NH_2$, $CH_3$, $CH_3CH_2$, $CH_2CH_2F$, $CH_3CH_2CH_2$, $CH_3O$, $CH_3OCH_2$, $N(CH_3)_2$,

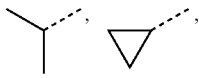

respectively.

In some aspects of the present invention, the structural unit

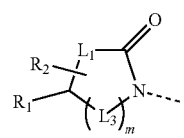

is selected from:

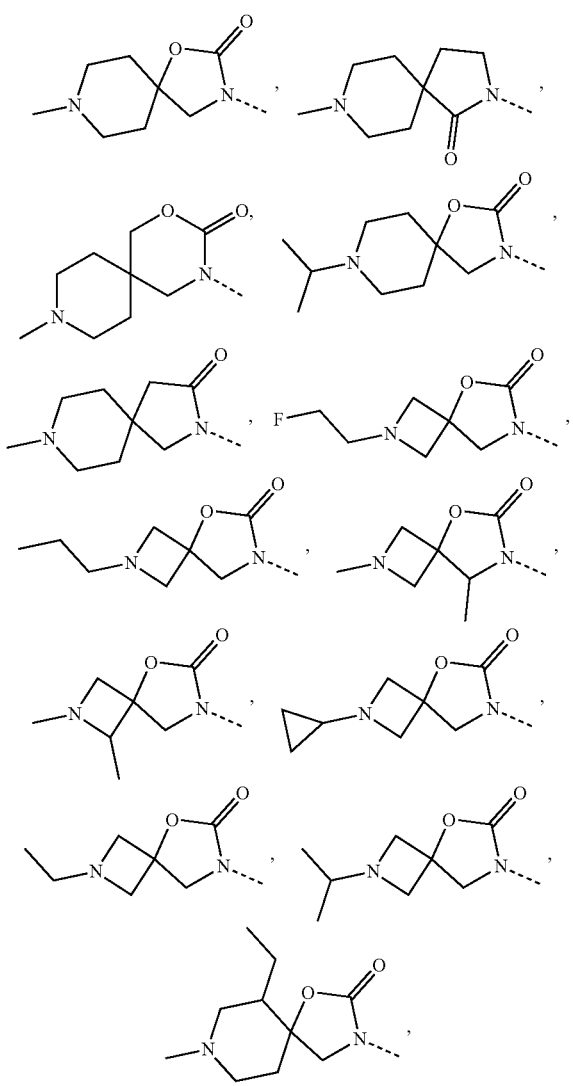

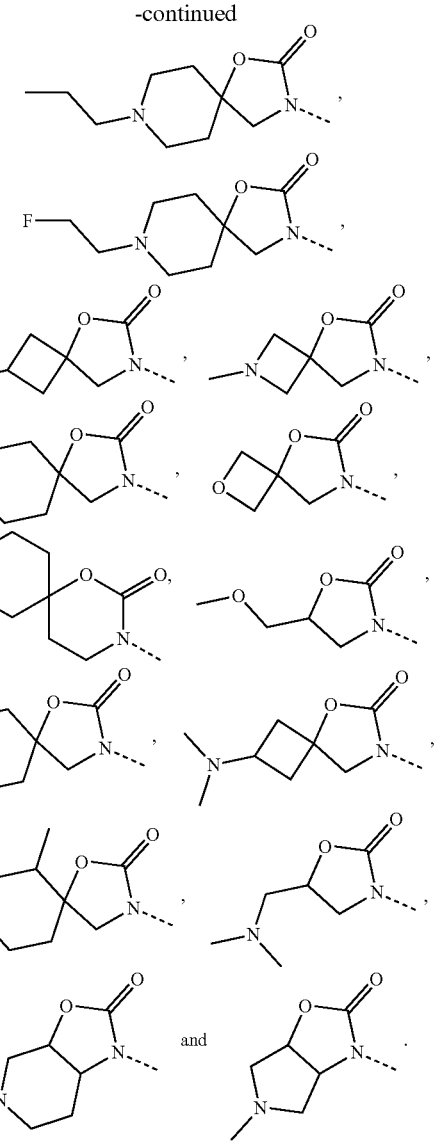

In some aspects of the present invention, the $R_3$ is selected from H, $CH_3$, $CH_3CH_2$, $CH_3CH_2CH_2$, $CH_3O$ and $CH_3OCH_2$, or selected from $CH_3$, $CH_3CH_2$, $CH_3CH_2CH_2$, $CH_3O$ and $CH_3OCH_2$, $CH_3$, $CH_3CH_2$, $CH_3CH_2CH_2$, $CH_3O$ and $CH_3OCH_2$ being optionally substituted with one, two or three R.

In some aspects of the present invention, the $R_3$ is selected from the group consisting of H, $CH_3$, $CH_3CH_2$, $CH_3CH_2CH_2$, $CH_3O$, $CHF_2O$, $CH_3OCH_2$.

In some aspects of the present invention, the $R_4$ is independently selected from the group consisting of H, F, Cl, Br, I, $CH_3$, $CH_3O$ and CH≡C—, respectively.

In some aspects of the present invention, the ring A is selected from the group consisting of phenyl, thienyl, pyrrolyl, furyl, pyridyl, indolyl and benzimidazolyl.

In some aspects of the present invention, the

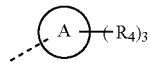

is selected from:

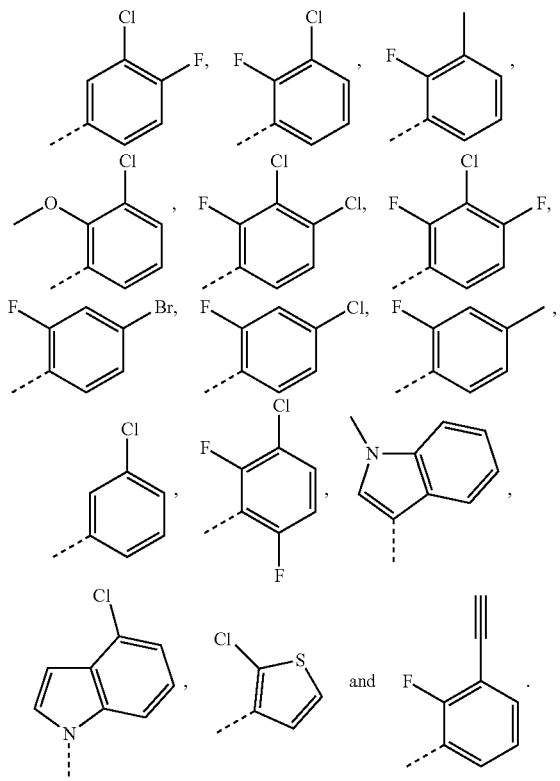

In some aspects of the present invention, the R is selected from the group consisting of H, F, Cl, Br, OH, CN, $NH_2$, $CH_3$, $CH_3CH_2$, $CH_3O$, $CF_3$, $CHF_2$, $CH_2F$, and other variables are as defined above.

In some aspects of the present invention, the $R_1$ and $R_2$ are independently selected from H, halogen, OH, CN, $NH_2$, respectively, or selected from $CH_3$, $CH_3CH_2$, $CH_3O$, $CH_3NH$, $(CH_3)_2N$, $(CH_3)_2NCH_2$ and $CH_3OCH_2$, $CH_3$, $CH_3CH_2$, $CH_3O$, $CH_3NH$, $(CH_3)_2N$, $(CH_3)_2NCH_2$ and $CH_3OCH_2$ being optionally substituted with one, two or three R, and other variables are as defined above.

In some aspects of the present invention, the $R_1$ and $R_2$ are independently selected from the group consisting of H, F, Cl, Br, OH, CN, $NH_2$, $CH_3$, $CH_3CH_2$, $CH_3O$, $CH_3NH$, $(CH_3)_2N$, $(CH_3)_2NCH_2$, $CH_3OCH_2$, respectively, and other variables are as defined above.

In some aspects of the present invention, the $L_1$ is selected from a single bond, —O—, —S—, —C(R)$_2$—, —(C(R)$_2$)$_2$—, —OC(R)$_2$— and —O(C(R)$_2$)$_2$—, and other variables are as defined above.

In some aspects of the present invention, the $L_1$ is selected from a single bond, —O—, —S—, —CH$_2$—, —(CH$_2$)$_2$—, —CH$_2$O— and —(CH$_2$)$_2$O—, and other variables are as defined above.

In some aspects of the present invention, the structural unit

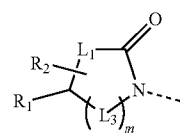

is selected from:

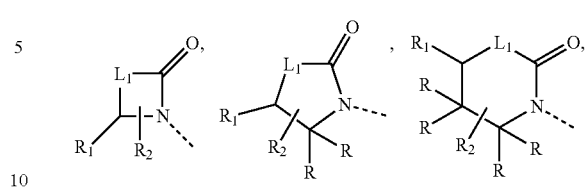

and other variables are as defined above.

In some aspects of the present invention, the structural unit

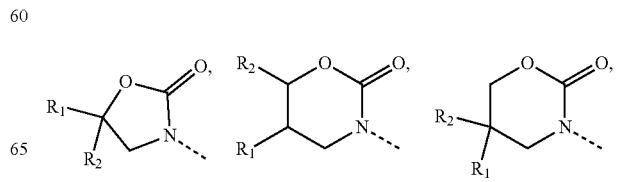

is selected from:

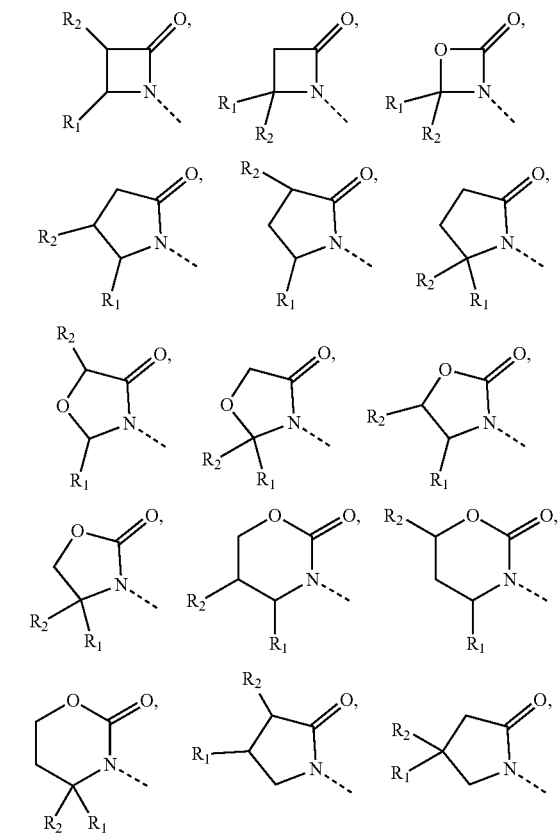

-continued

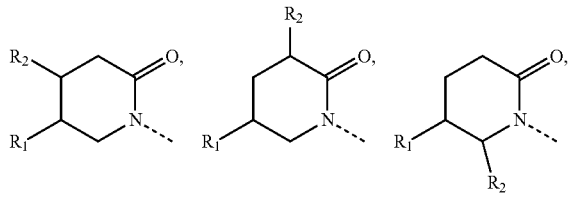

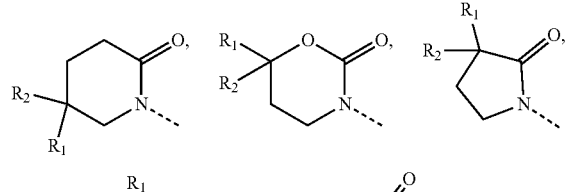

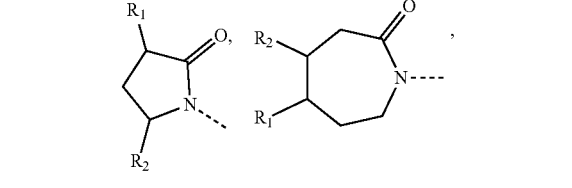

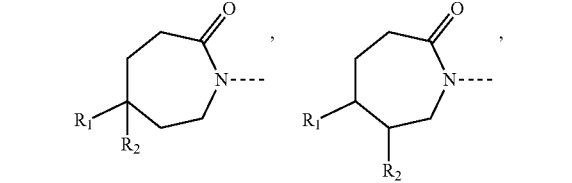

and other variables are as defined above.

In some aspects of the present invention, the structural unit

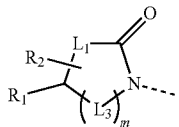

is selected from:

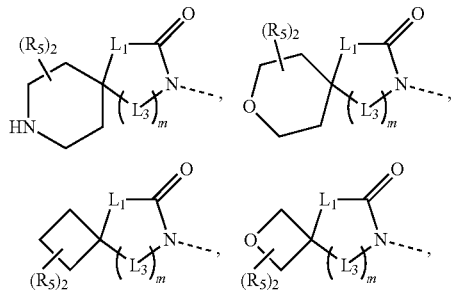

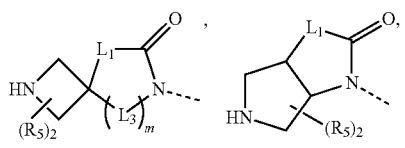

-continued

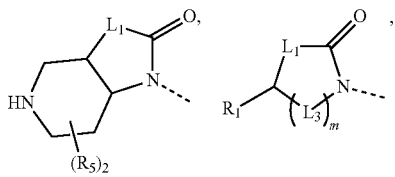

and other variables are as defined above.

In some aspects of the present invention, the structural unit

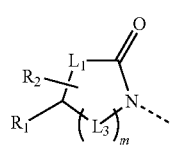

is selected from:

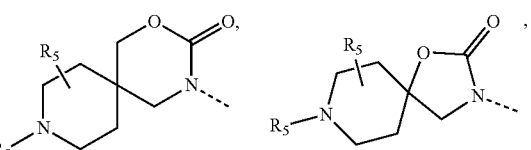

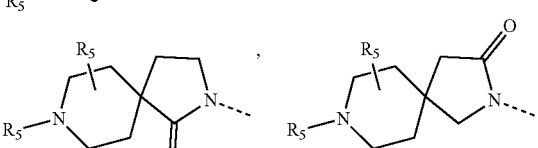

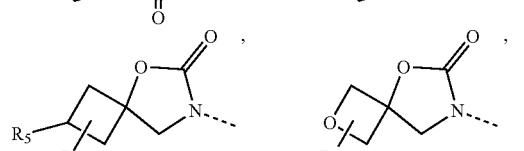

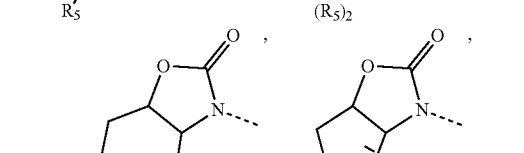

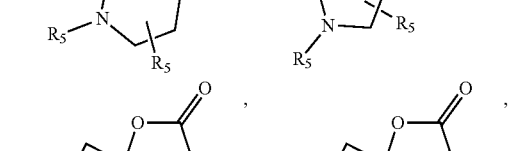

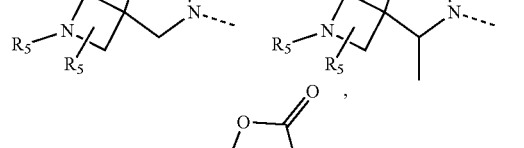

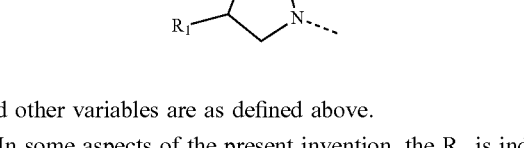

and other variables are as defined above.

In some aspects of the present invention, the $R_5$ is independently selected from H, F, Cl, Br, OH, CN, $NH_2$, respectively, or selected from $CH_3$, $CH_3CH_2$, $CH_3CH_2CH_2$, $CH_3O$, $CH_3OCH_2$, $N(CH_3)_2$, $NH(CH_3)$,

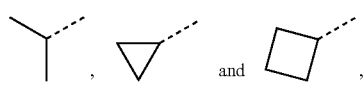

$CH_3$, $CH_3CH_2$, $CH_3CH_2CH_2$, $CH_3O$, $CH_3OCH_2$, $N(CH_3)_2$, $NH(CH_3)$,

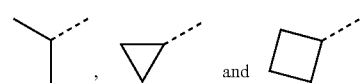

being optionally substituted with one, two or three R, and other variables are as defined above.

In some aspects of the present invention, the $R_5$ is independently selected from the group consisting of F, Cl, Br, OH, CN, $NH_2$, $CH_3$, $CH_3CH_2$, $CH_2CH_2F$, $CH_3CH_2CH_2$, $CH_3O$, $CH_3OCH_2$, $N(CH_3)_2$,

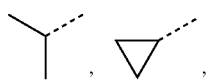

respectively, and other variables are as defined above.

In some aspects of the present invention, the structural unit

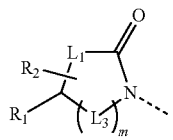

is selected from:

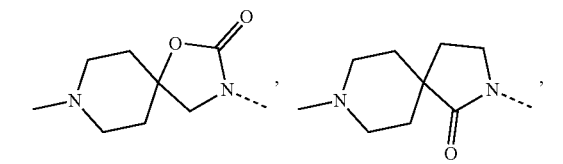

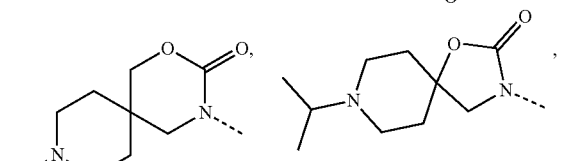

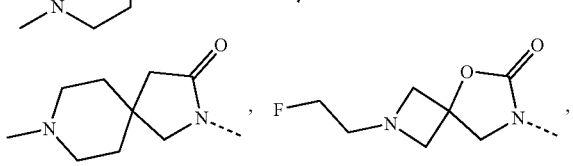

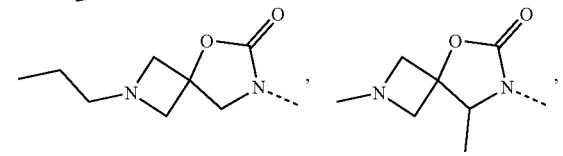

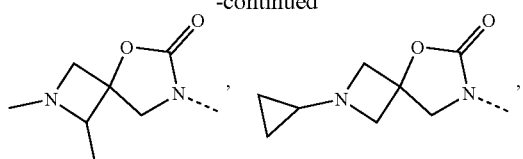

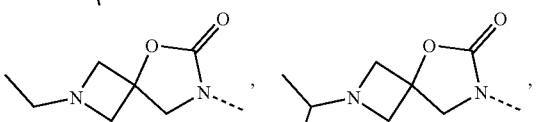

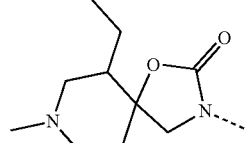

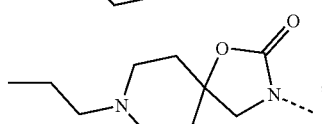

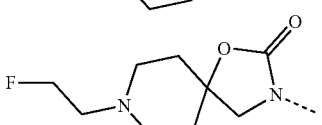

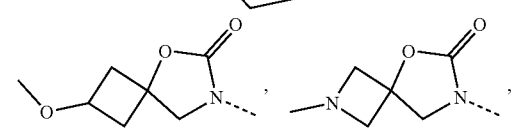

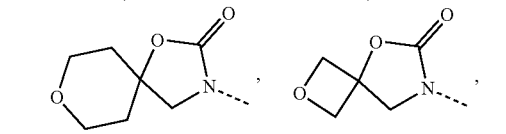

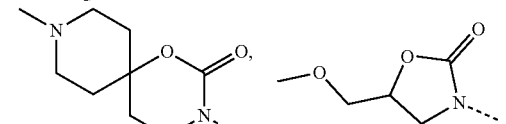

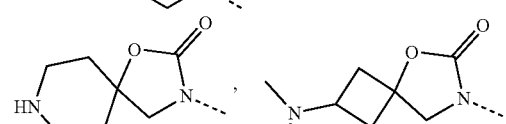

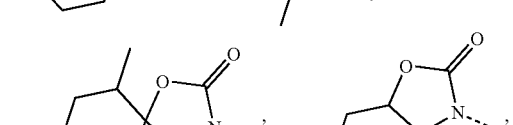

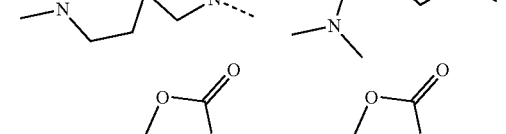

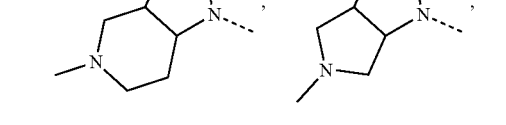

and other variables are as defined above.

In some aspects of the present invention, the $R_3$ is selected from H, $CH_3$, $CH_3CH_2$, $CH_3CH_2CH_2$, $CH_3O$ and $CH_3OCH_2$, or selected from $CH_3$, $CH_3CH_2$, $CH_3CH_2CH_2$, CH₃O and CH₃OCH₂, CH₃, CH₃CH₂, CH₃CH₂CH₂, CH₃O and CH₃OCH₂ being optionally substituted with one, two or three R, and other variables are as defined above.

In some aspects of the present invention, the R₃ is selected from the group consisting of H, CH₃, CH₃CH₂, CH₃CH₂CH₂, CH₃O, CHF₂O, CH₃OCH₂, and other variables are as defined above.

In some aspects of the present invention, the R₄ is independently selected from the group consisting of H, F, Cl, Br, I, CH₃, CH₃O and CH≡C—, respectively.

In some aspects of the present invention, the ring A is selected from the group consisting of phenyl, thienyl, pyrrolyl, furyl, pyridyl, indolyl and benzimidazolyl, and other variables are as defined above.

In some aspects of the present invention, the

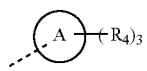

is selected from:

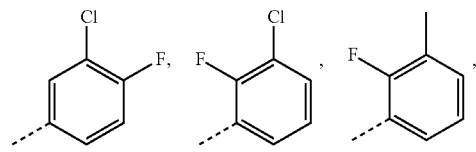

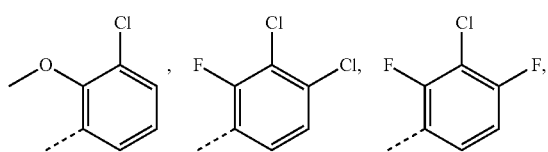

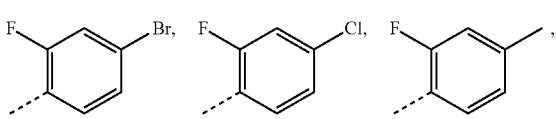

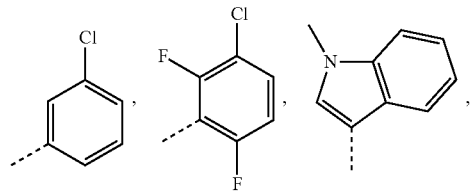

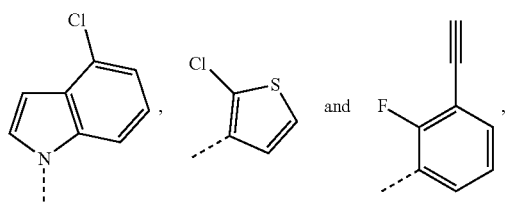

and other variables are as defined above.

In some aspects of the present invention, the compounds are selected from:

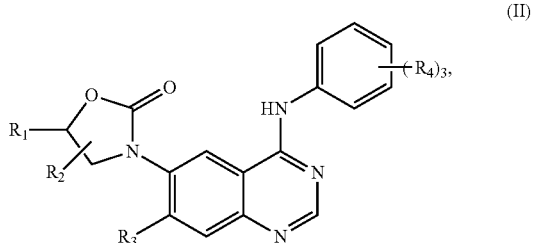
(II)

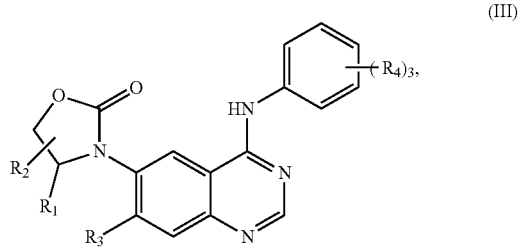
(III)

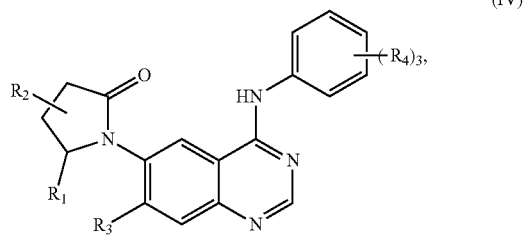
(IV)

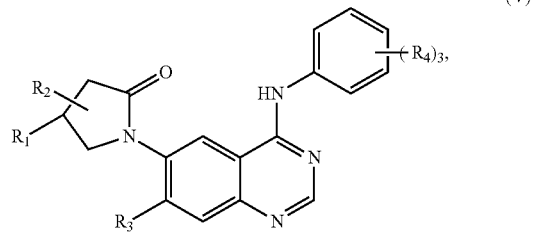
(V)

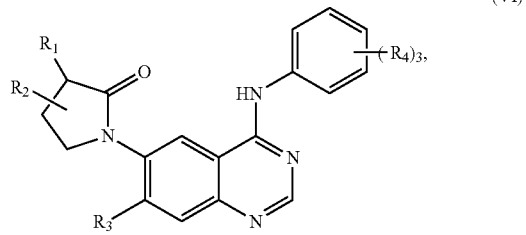
(VI)

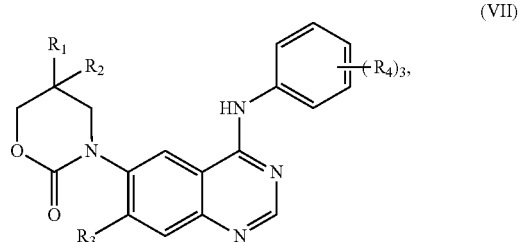
(VII)

-continued
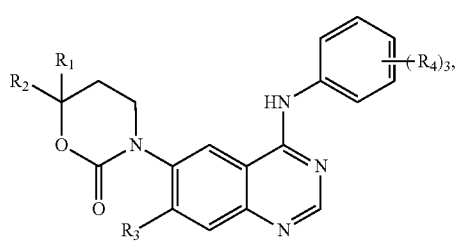
(VIII)
wherein, $R_1$, $R_2$, $R_3$, $R_4$ are as defined above.
In some aspects of the present invention, the compounds are selected from:
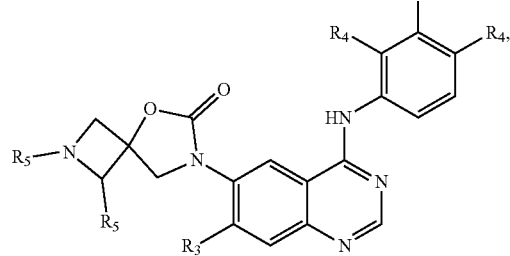
(IX)
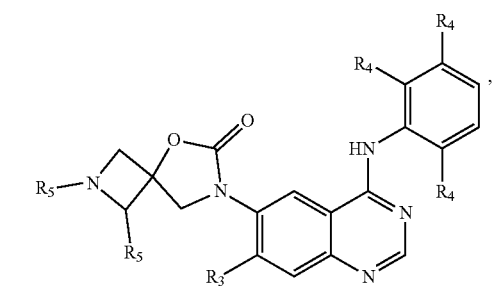
(X)
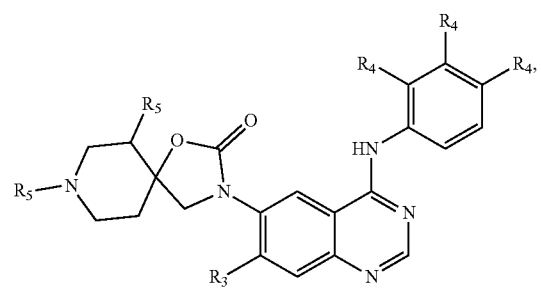
(XI)
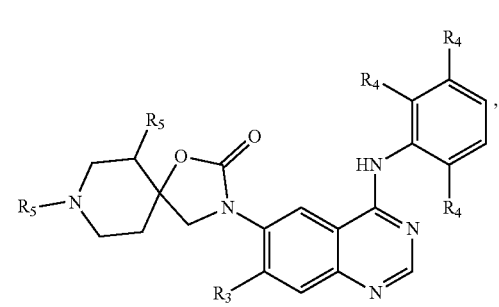
(XII)
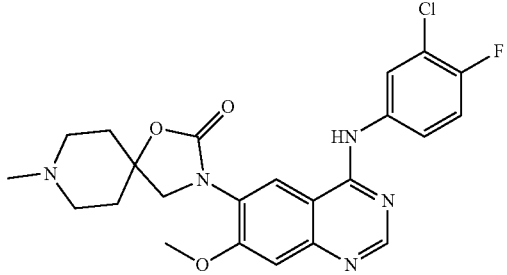
(XIII)
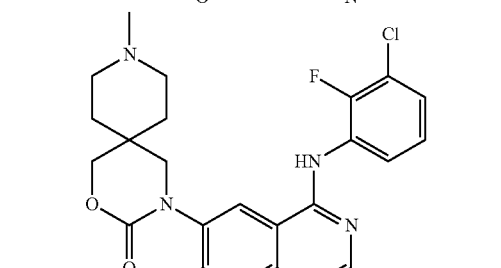
(XIV)
wherein, R, $R_3$, $R_4$, $R_5$ are as defined above.
The present invention also provides compounds selected from:
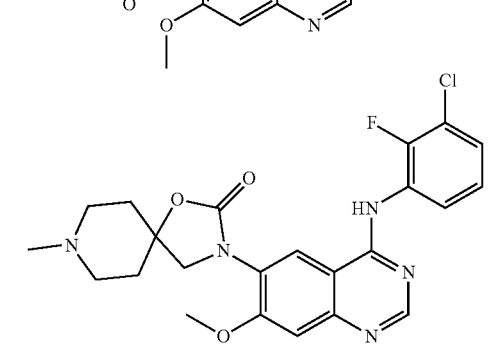

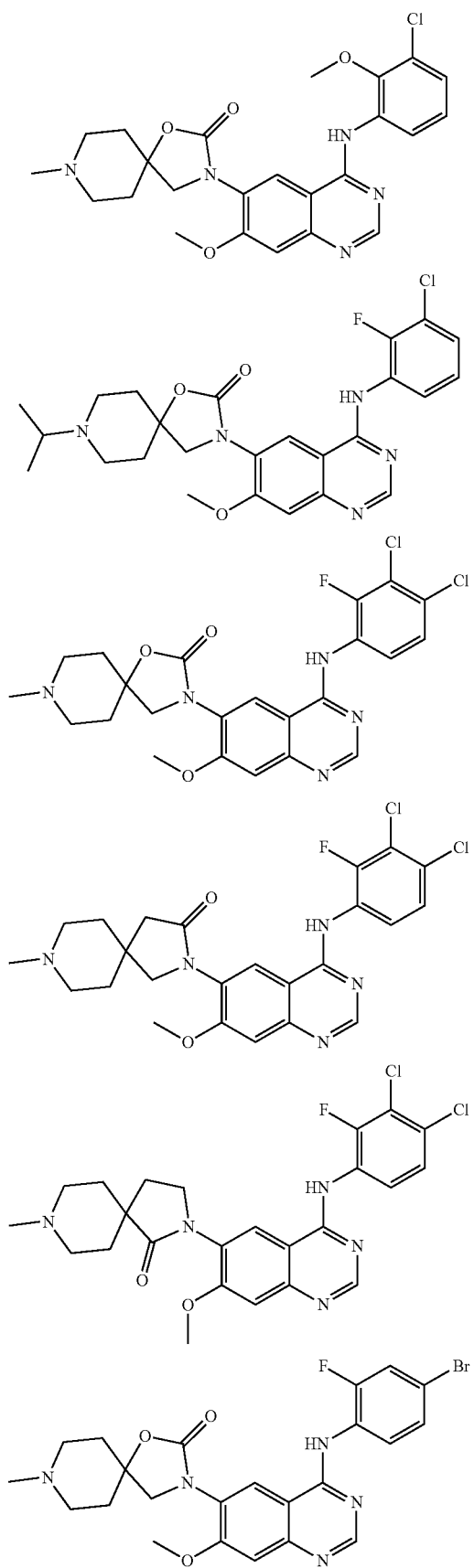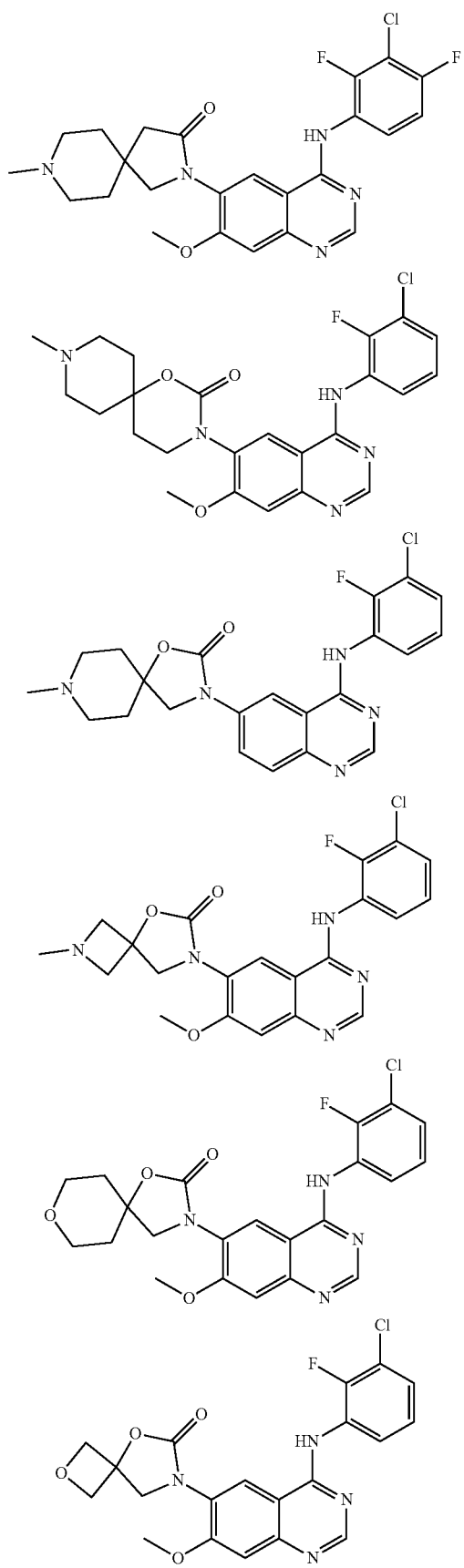

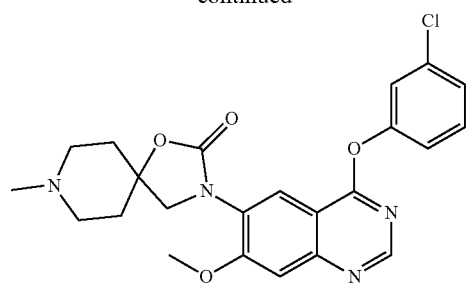
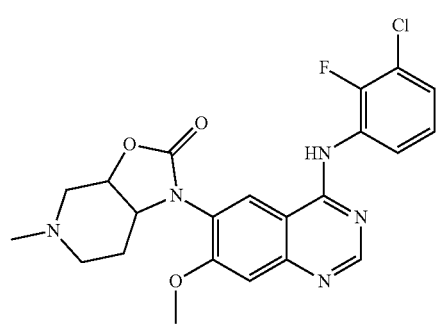
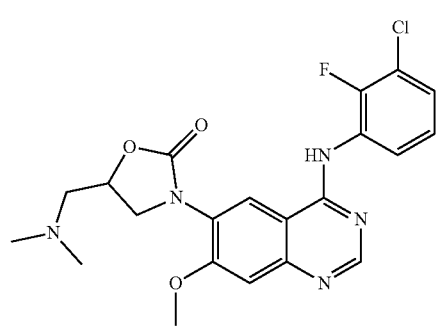
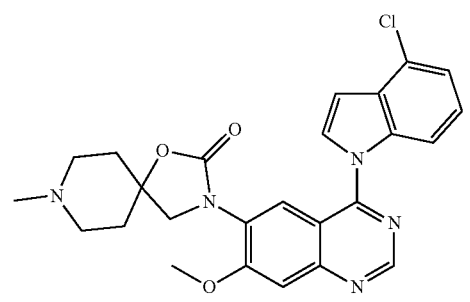
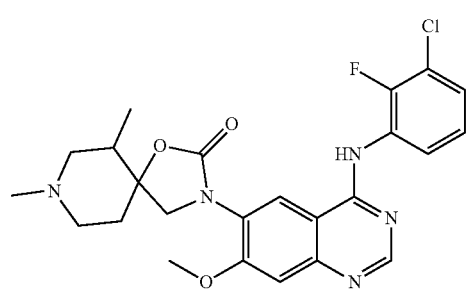
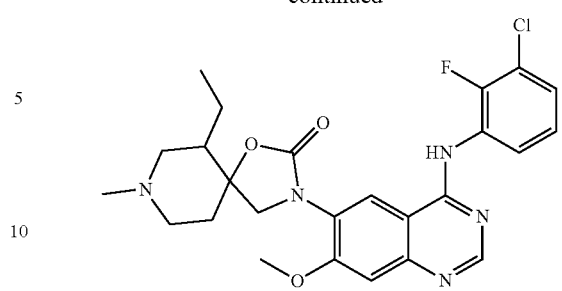
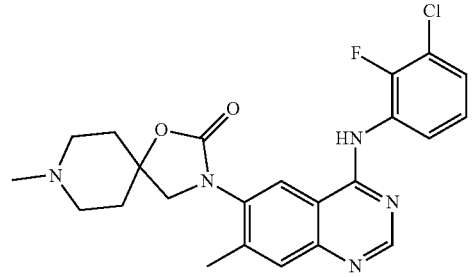
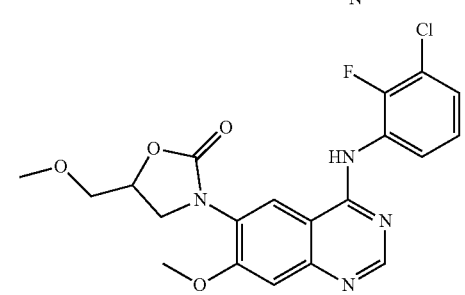
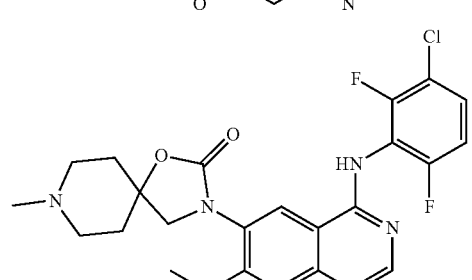
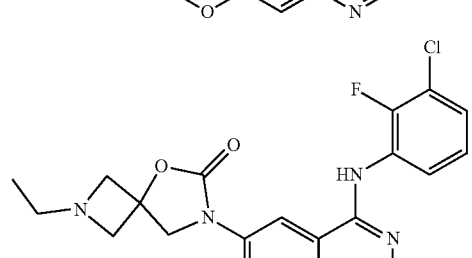
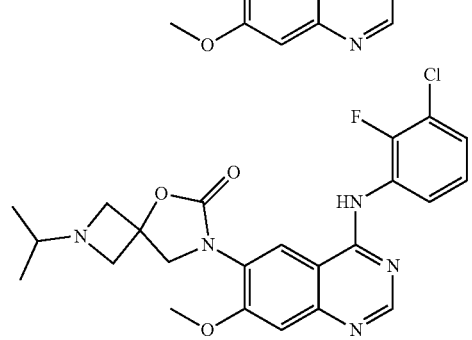
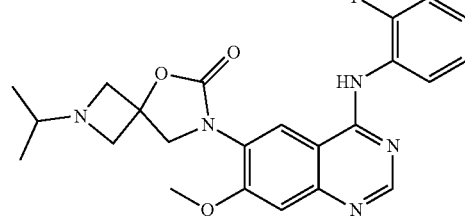

-continued
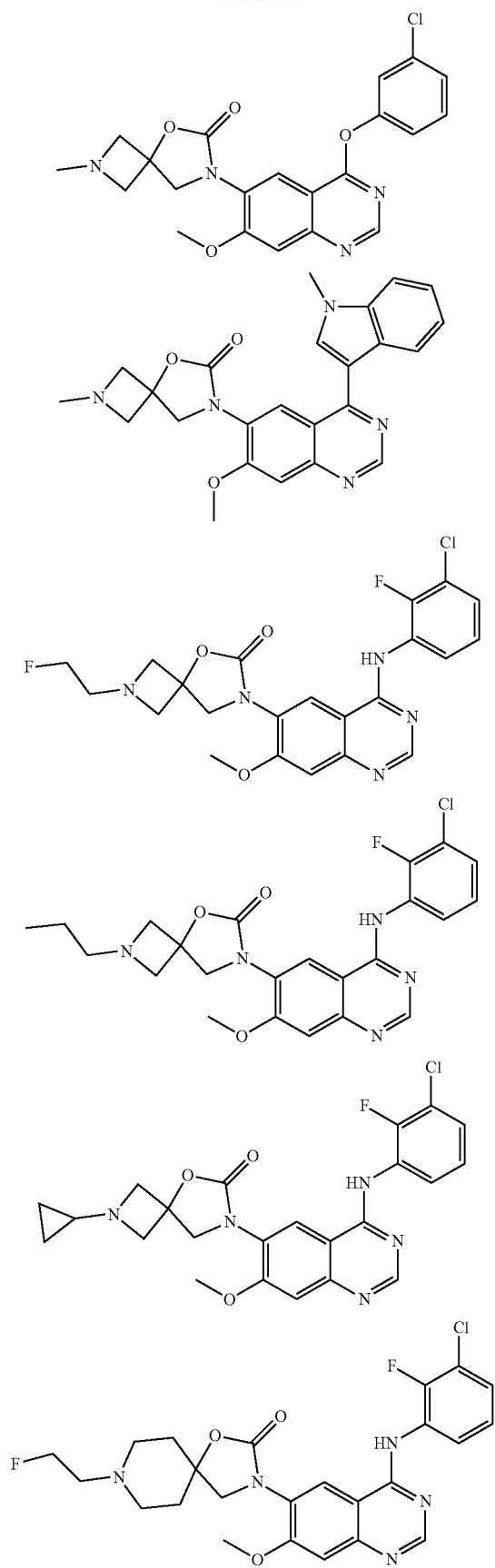
-continued
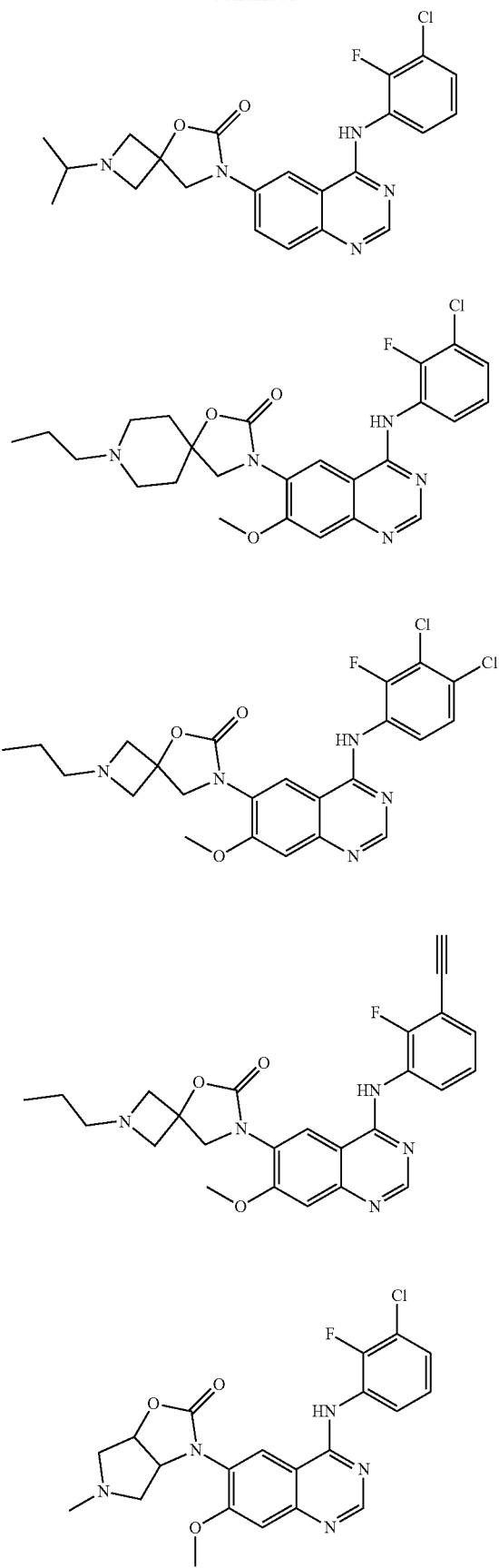

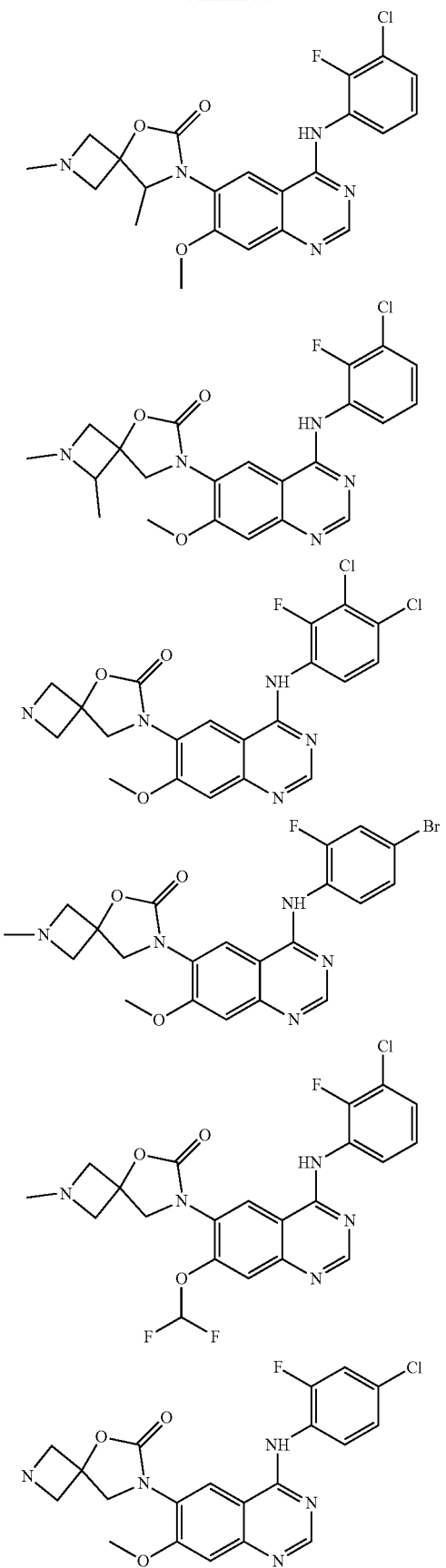
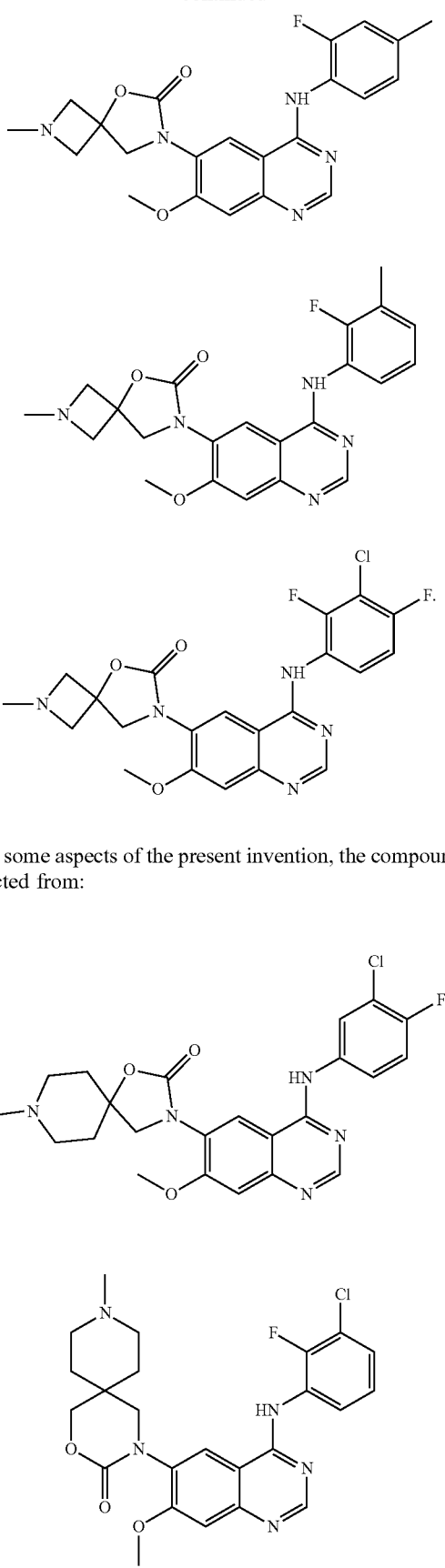
In some aspects of the present invention, the compound is selected from:

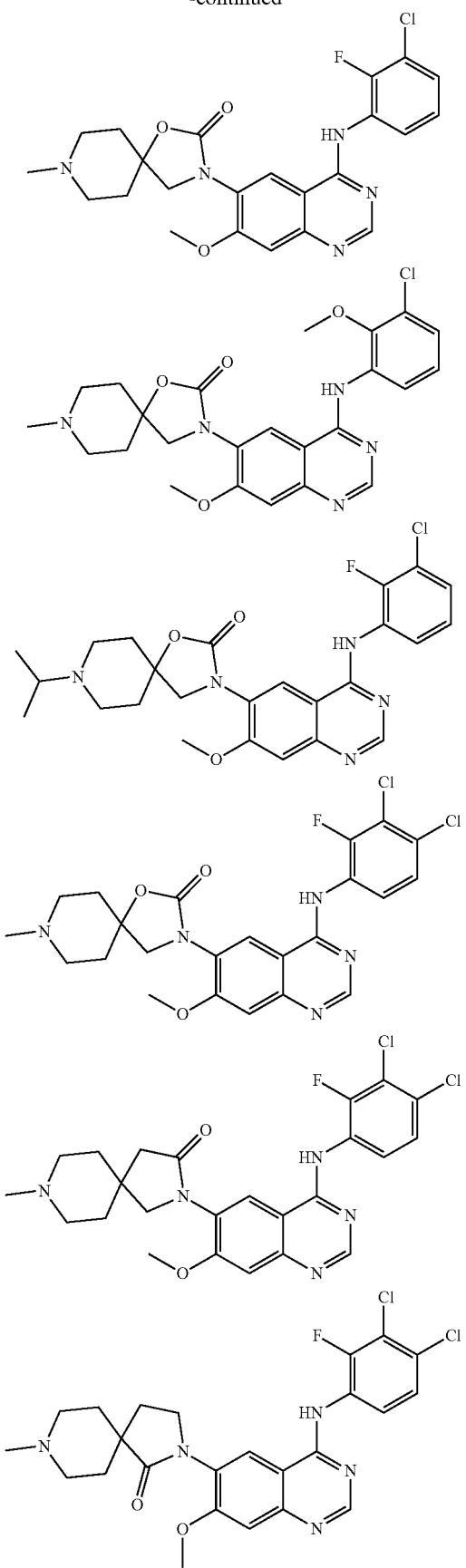
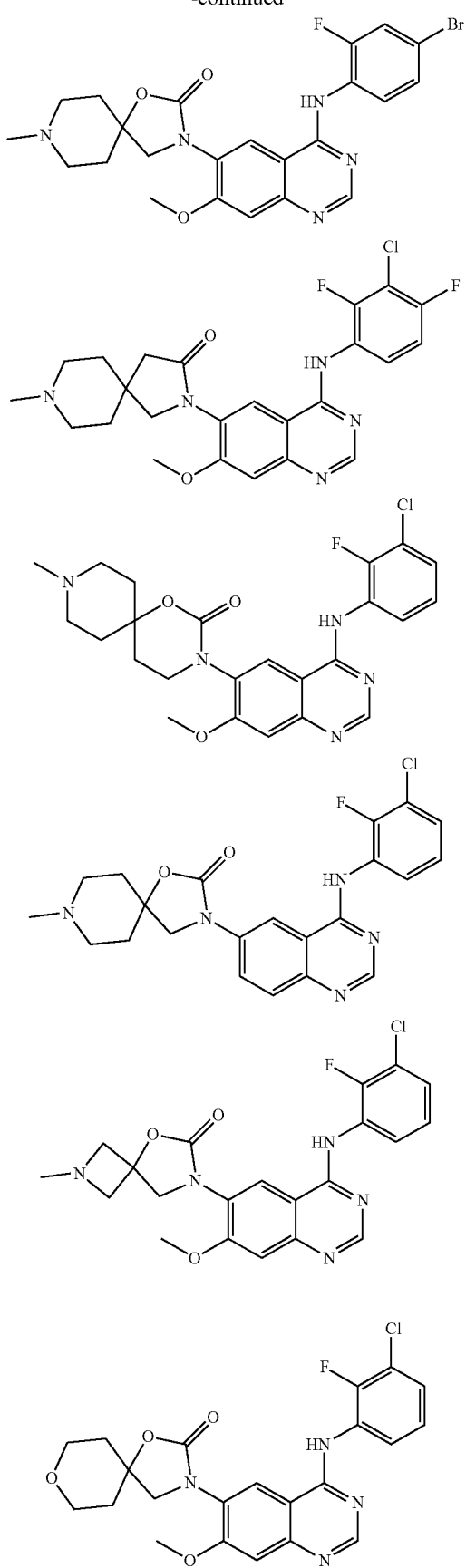

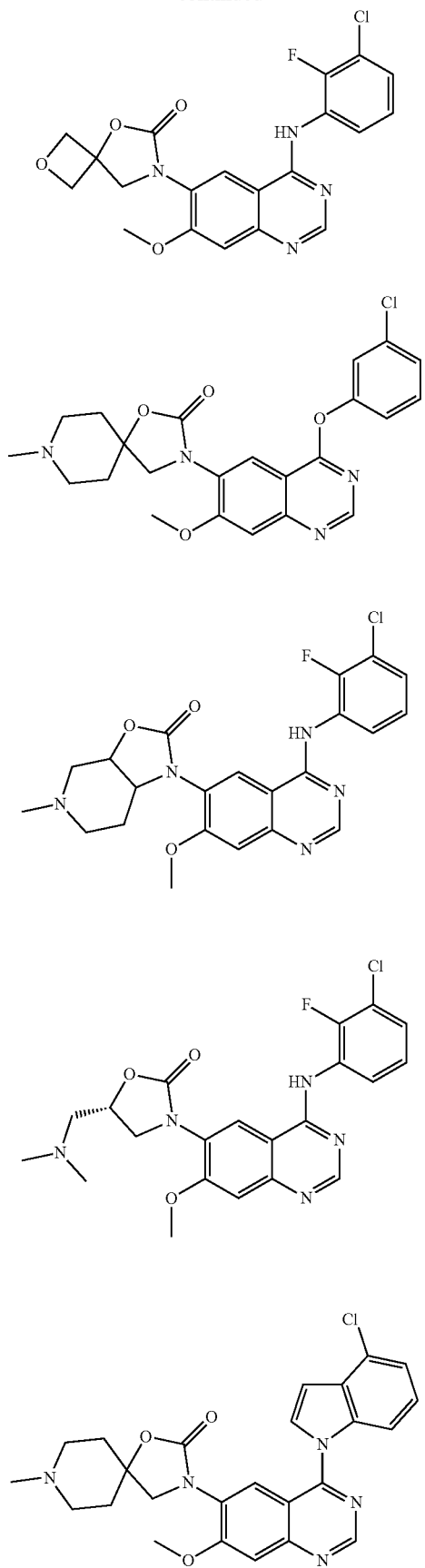
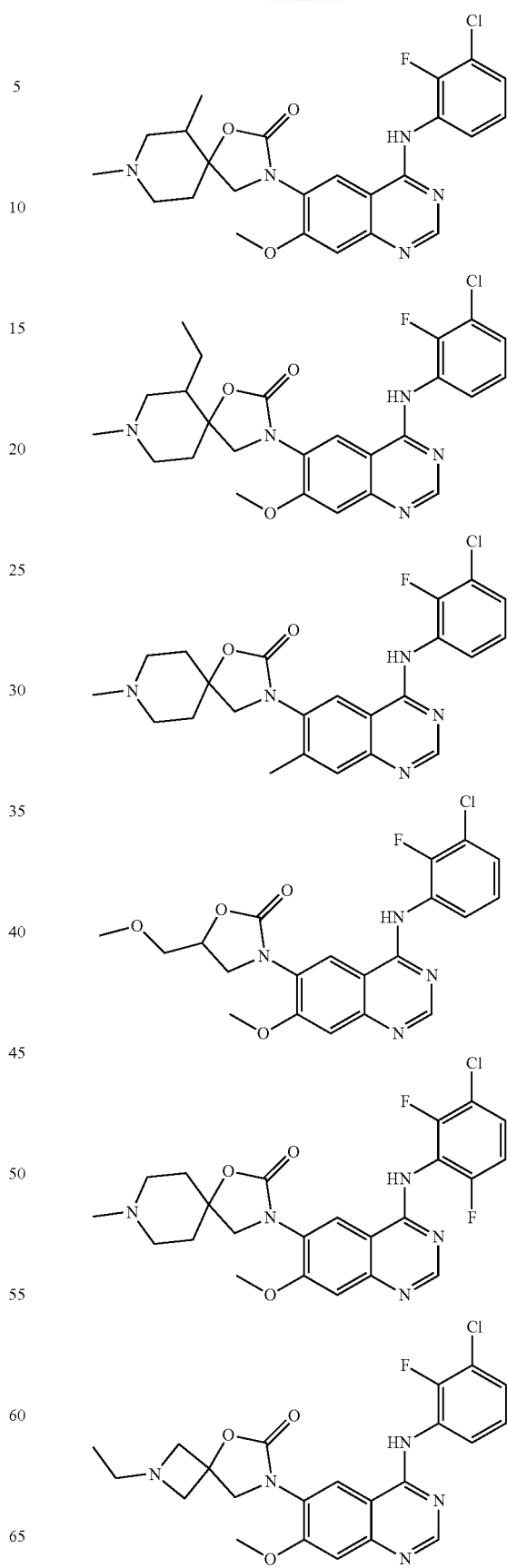

31
-continued
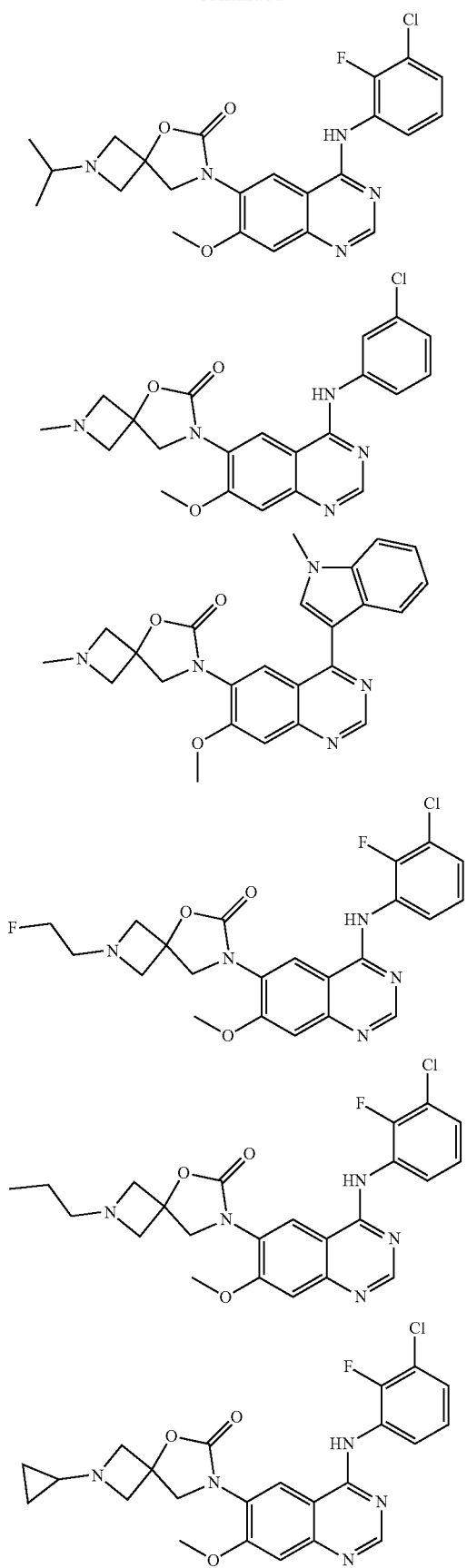
32
-continued
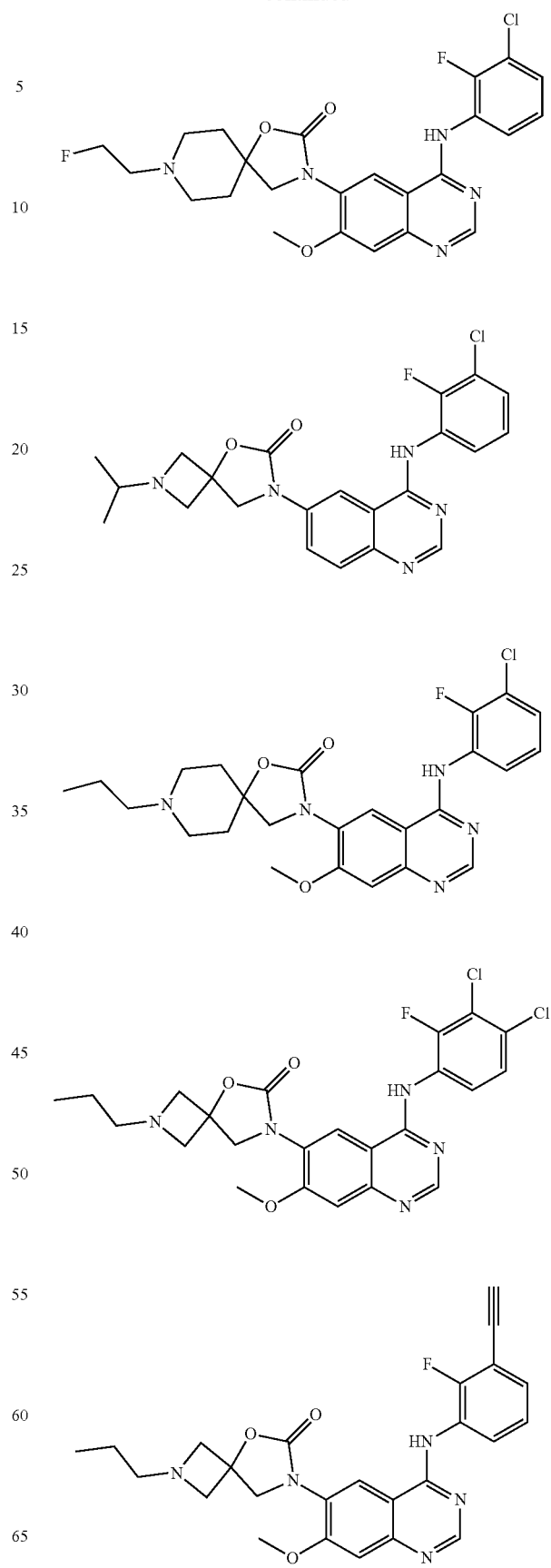

33
-continued
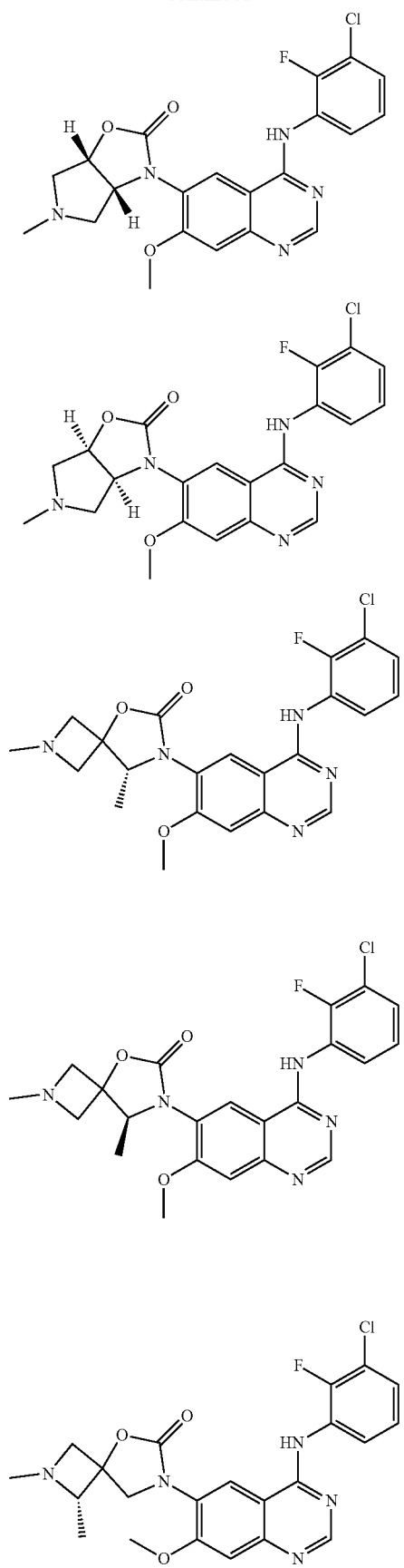
34
-continued
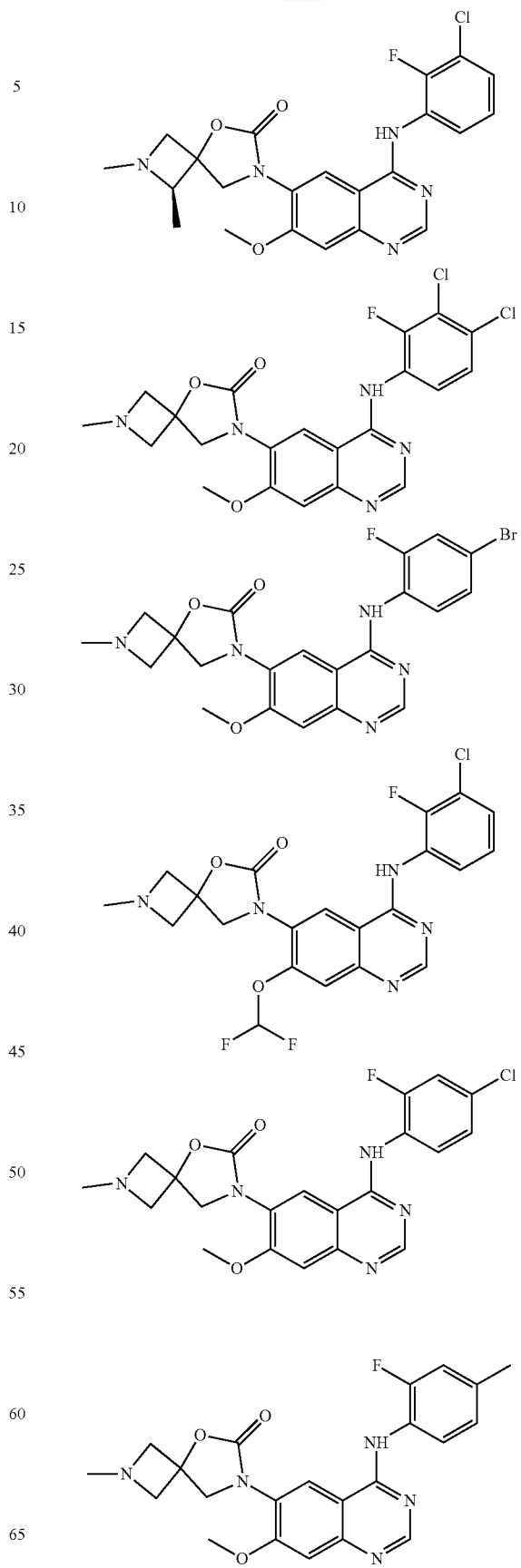

-continued

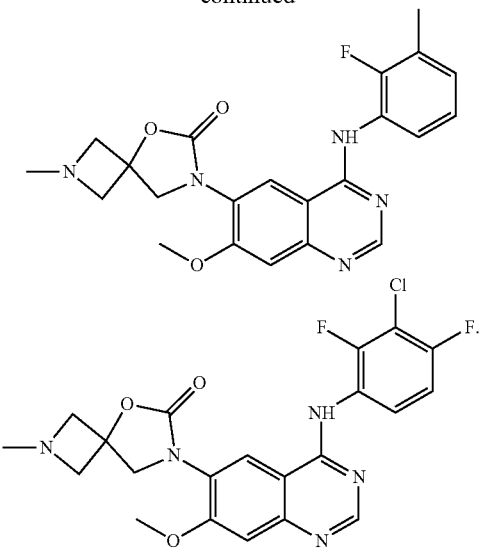

The present invention provides a compound of formula (I) or a pharmaceutically acceptable salt thereof,

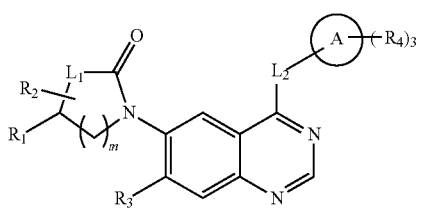

wherein,
$R_1$ and $R_2$ are independently selected from t H, halogen, OH, CN, $NH_2$, respectively, or selected from $C_{1-5}$ alkyl and $C_{1-5}$ heteroalkyl, $C_{1-5}$ alkyl and $C_{1-5}$ heteroalkyl being optionally substituted with one, two or three R;
or, $R_1$ is connected with $R_2$ to form a 4-6-membered ring substituted with two $R_5$;
$L_1$ is selected from a single bond, $—(C(R)_2)_m—$, $—O(C(R)_2)_m—$, $—S(C(R)_2)_m—$;
m is independently selected from 0, 1, or 2, respectively;
$R_5$ is independently selected from H, halogen, OH, CN, $NH_2$, respectively, or independently selected from $C_{1-5}$ alkyl, $C_{1-5}$ heteroalkyl, $C_{3-6}$ cycloalkyl and 3-6-membered heterocycloalkyl, $C_{1-5}$ alkyl, $C_{1-5}$ heteroalkyl, $C_{3-6}$ cycloalkyl and 3-6-membered heterocycloalkyl being optionally substituted with one, two or three R; $R_3$ is H, or selected from $C_{1-3}$ alkyl and $C_{1-3}$ heteroalkyl, $C_{1-3}$ alkyl and $C_{1-3}$ heteroalkyl being optionally substituted with one, two or three R;
$L_2$ is selected from the group consisting of a single bond, $—O—$, $—NH—$;
ring A is selected from the group consisting of phenyl, 5-10-membered heteroaryl;
$R_4$ is independently selected from the group consisting of H, halogen, $C_{1-3}$ alkyl, $C_{1-3}$ heteroalkyl, $C_{2-3}$ alkynyl, respectively;
R is independently selected from H, OH, CN, $NH_2$, halogen, respectively, or selected from $C_{1-3}$ alkyl and $C_{1-3}$ heteroalkyl, $C_{1-3}$ alkyl and $C_{1-3}$ heteroalkyl being optionally substituted with one, two or three R';

the "hetero" of the $C_{1-5}$ heteroalkyl, $C_{1-3}$ heteroalkyl, the 3-6-membered heterocycloalkyl, the 5-9-membered heteroaryl group is selected from the group consisting of $—O—$, $=O$, N, $—NH—$, $—S—$, $=S$, $—S(=O)—$, $—S(=O)_2—$, $—C(=O)O—$, $—C(=O)NH—$, $—S(=O)NH—$;
R' is selected from the group consisting of F, Cl, Br, I, OH, CN, $NH_2$;
in any of the cases, the number of heteroatoms or heteroatom-containing groups is independently selected from 1, 2 or 3, respectively.

In some aspects of the present invention, the R is selected from the group consisting of H, F, Cl, Br, OH, CN, $NH_2$, $CH_3$, $CH_3CH_2$, $CH_3O$, $CF_3$, $CHF_2$, $CH_2F$.

In some aspects of the present invention, the $R_1$ and $R_2$ are independently selected from H, halogen, OH, CN, $NH_2$, respectively, or selected from $CH_3$, $CH_3CH_2$, $CH_3O$, $CH_3NH$, $(CH_3)_2N$, $(CH_3)_2NCH_2$ and $CH_3OCH_2$, $CH_3$, $CH_3CH_2$, $CH_3O$, $CH_3NH$, $(CH_3)_2N$, $(CH_3)_2NCH_2$ and $CH_3OCH_2$ being optionally substituted with one, two or three R.

In some aspects of the present invention, the $R_1$ and $R_2$ are independently selected from the group consisting of H, F, Cl, Br, OH, CN, $NH_2$, $CH_3$, $CH_3CH_2$, $CH_3O$, $CH_3NH$, $(CH_3)_2N$, $(CH_3)_2NCH_2$, $CH_3OCH_2$, respectively.

In some aspects of the present invention, the $L_1$ is selected from a single bond, $—CH_2—$, $—(CH_2)_2—$, $—O—$, $—CH_2O—$ and $—(CH_2)_2O—$.

In some aspects of the present invention, the structural unit

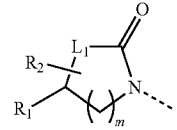

is selected from:

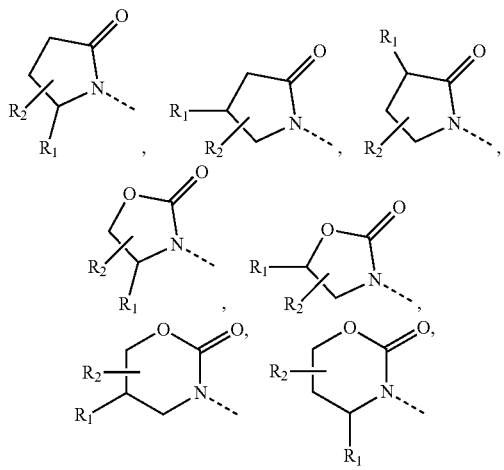

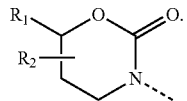

In some aspects of the present invention, the structural unit

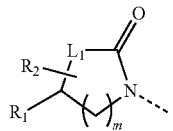

is selected from:

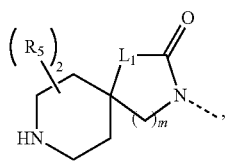 , 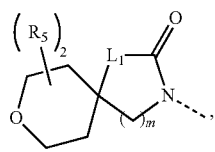 ,

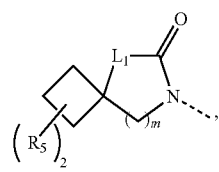 , 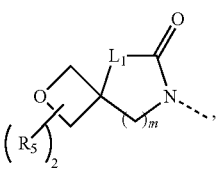 ,

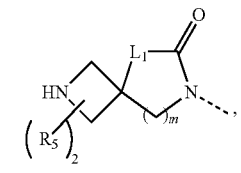 , 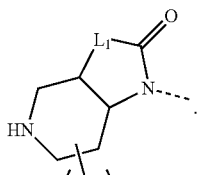 .

In some aspects of the present invention, the structural unit

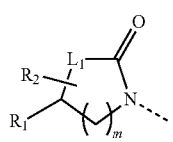

is selected from:

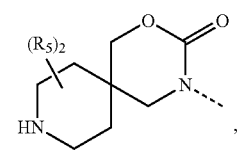 , 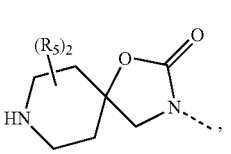 ,

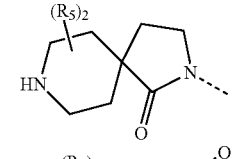 , 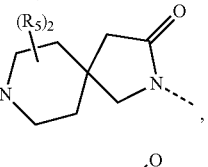 ,

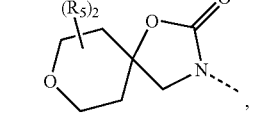 , 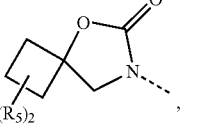 ,

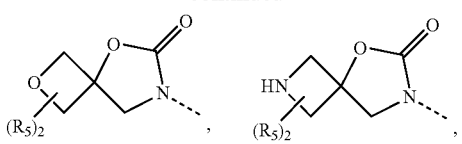

In some aspects of the present invention, the structural unit

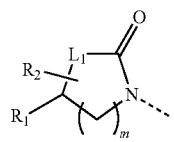

is selected from:

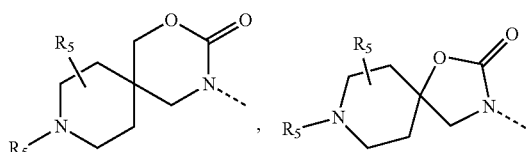

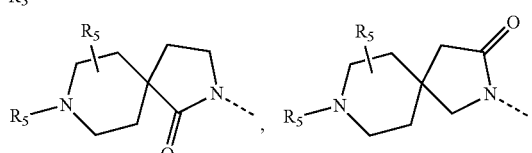

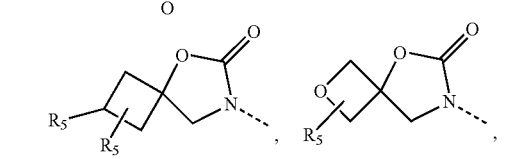

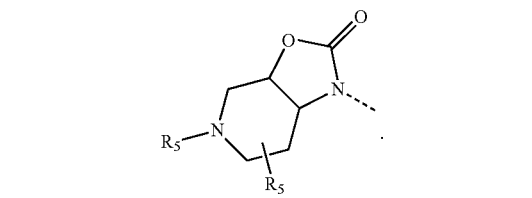

In some aspects of the present invention, the $R_5$ is independently selected from H, F, Cl, Br, OH, CN, $NH_2$, respectively, or selected from $CH_3$, $CH_3CH_2$, $CH_3CH_2CH_2$, $CH_3O$, $CH_3OCH_2$, $N(CH_3)_2$, $NH(CH_3)$,

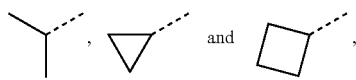 ,

CH₃, CH₃CH₂, CH₃CH₂CH₂, CH₃O, CH₃OCH₂, N(CH₃)₂, NH(CH₃),

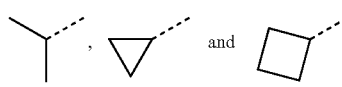

being optionally substituted with one, two or three R.

In some aspects of the present invention, the R₅ is independently selected from the group consisting of F, Cl, Br, OH, CN, NH₂, CH₃, CH₃CH₂, CH₂CH₂F, CH₃CH₂CH₂, CH₃O, CH₃OCH₂, N(CH₃)₂,

respectively.

In some aspects of the present invention, the structural unit

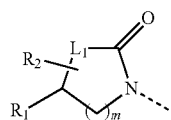

is selected from:

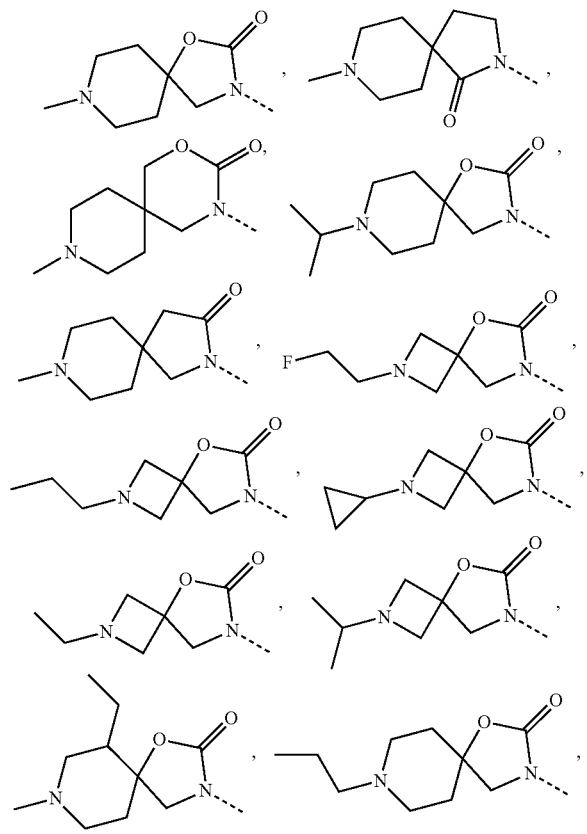

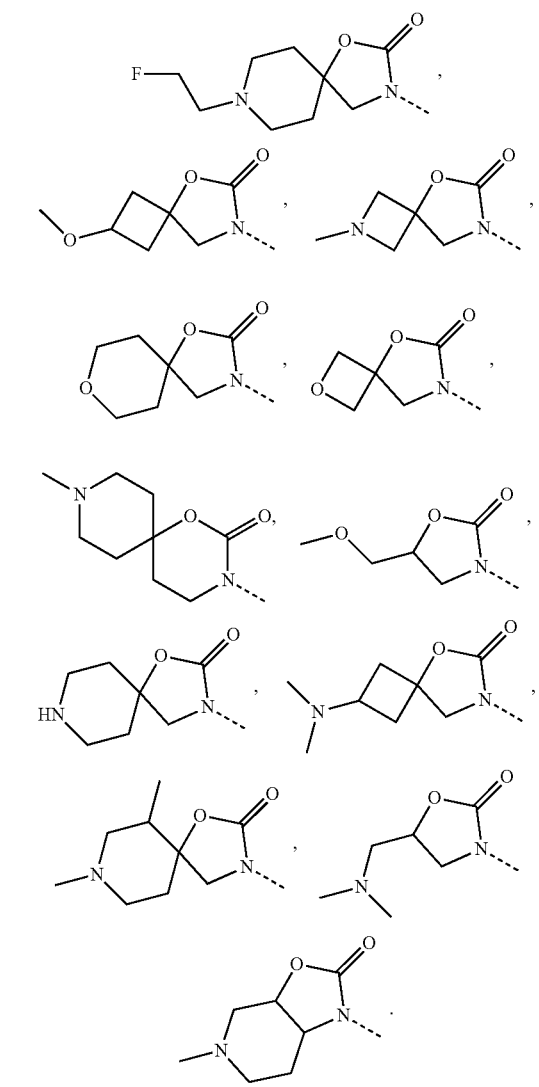

In some aspects of the present invention, the R₃ is H, or selected from CH₃, CH₃CH₂, CH₃CH₂CH₂, CH₃O and CH₃OCH₂, CH₃, CH₃CH₂, CH₃CH₂CH₂, CH₃O and CH₃OCH₂ being optionally substituted with one, two or three R.

In some aspects of the present invention, the R₃ is selected from: H, CH₃, CH₃O.

In some aspects of the present invention, the R₄ is independently selected from: H, F, Cl, Br, I, CH₃, CH₃O and CH≡C—, respectively.

In some aspects of the present invention, the ring A is selected from: phenyl, thienyl, pyrrolyl, furyl, pyridyl, indolyl and benzimidazolyl.

In some aspects of the present invention, the structural unit

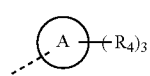

is selected from:

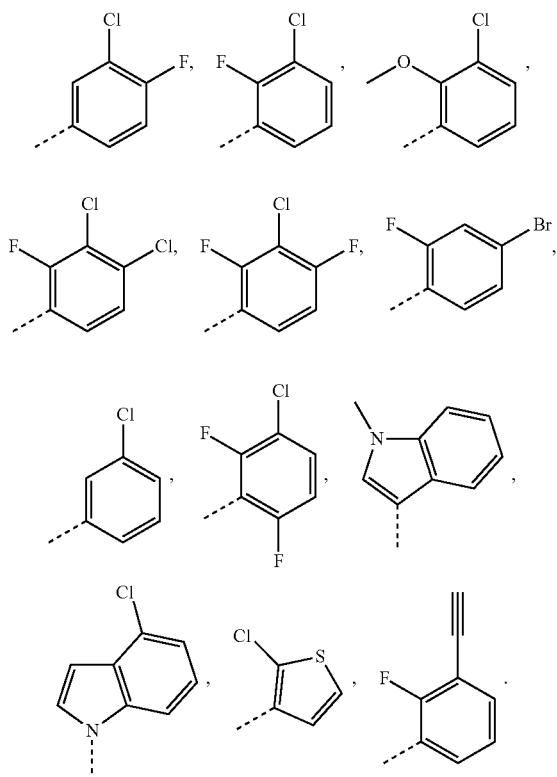

In some aspects of the present invention, the R is selected from the group consisting of H, F, Cl, Br, OH, CN, $NH_2$, $CH_3$, $CH_3CH_2$, $CH_3O$, $CF_3$, $CHF_2$, $CH_2F$, and other variables are as defined above.

In some aspects of the present invention, the $R_1$ and $R_2$ are independently selected from H, halogen, OH, CN, $NH_2$, respectively, or selected from $CH_3$, $CH_3CH_2$, $CH_3O$, $CH_3NH$, $(CH_3)_2N$, $(CH_3)_2NCH_2$ and $CH_3OCH_2$, $CH_3$, $CH_3CH_2$, $CH_3O$, $CH_3NH$, $(CH_3)_2N$, $(CH_3)_2NCH_2$ and $CH_3OCH_2$ being optionally substituted with one, two or three R, and other variables are as defined above.

In some aspects of the present invention, the $R_1$ and $R_2$ are independently selected from the group consisting of H, F, Cl, Br, OH, CN, $NH_2$, $CH_3$, $CH_3CH_2$, $CH_3O$, $CH_3NH$, $(CH_3)_2N$, $(CH_3)_2NCH_2$, $CH_3OCH_2$, respectively, and other variables are as defined above.

In some aspects of the present invention, the $L_1$ is selected from a single bond, —$CH_2$—, —$(CH_2)_2$—, —O—, —$CH_2O$— and —$(CH_2)_2O$—, and other variables are as defined above.

In some aspects of the present invention, the structural unit

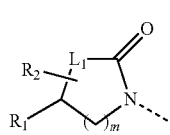

is selected from:

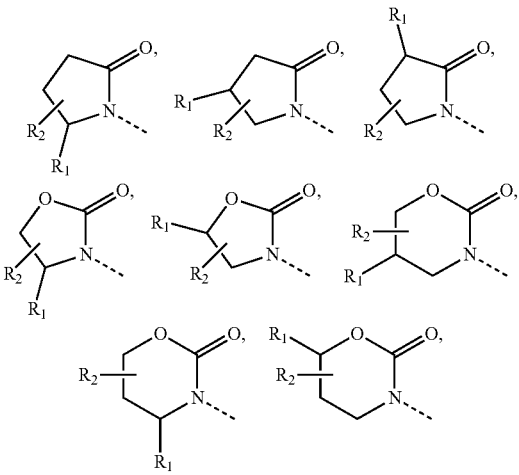

and other variables are as defined above.

In some aspects of the present invention, the structural unit

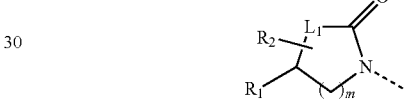

is selected from:

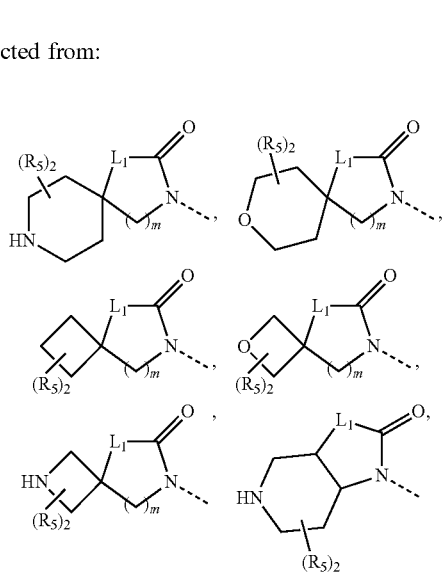

and other variables are as defined above.

In some aspects of the present invention, the structural unit

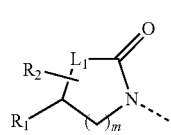

is selected from:

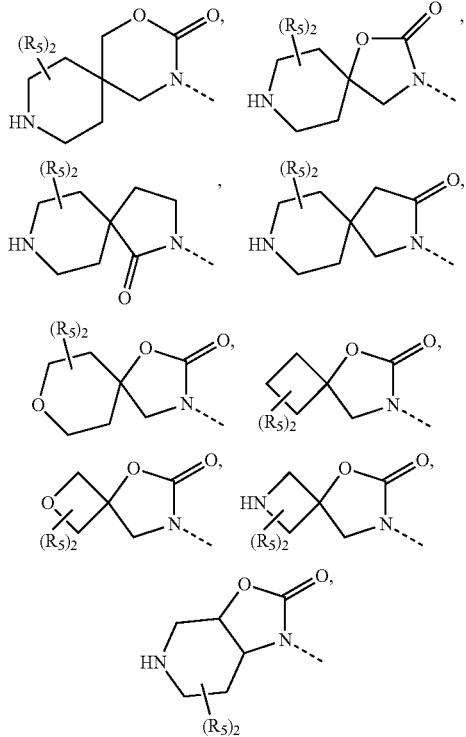

and other variables are as defined above.

In some aspects of the present invention, the structural unit

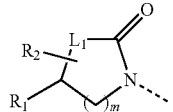

is selected from:

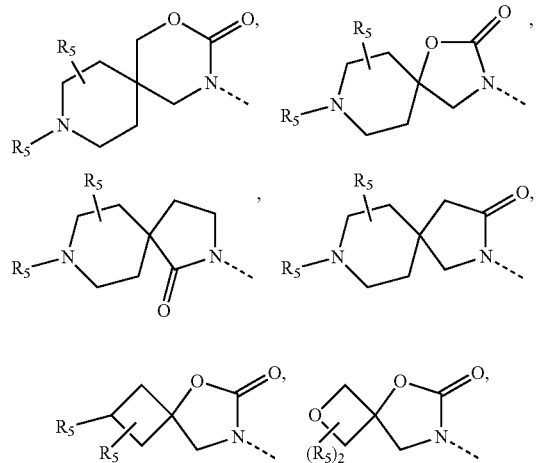

-continued

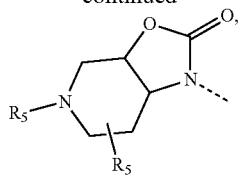

and other variables are as defined above.

In some aspects of the present invention, the $R_5$ is independently selected from H, F, Cl, Br, OH, CN, $NH_2$, respectively, or selected from $CH_3$, $CH_3CH_2$, $CH_3CH_2CH_2$, $CH_3O$, $CH_3OCH_2$, $N(CH_3)_2$, $NH(CH_3)$,

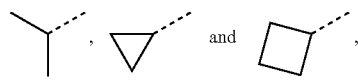

$CH_3$, $CH_3CH_2$, $CH_3CH_2CH_2$, $CH_3O$, $CH_3OCH_2$, $N(CH_3)_2$, $NH(CH_3)$,

being optionally substituted with one, two or three R, and other variables are as defined above.

In some aspects of the present invention, the $R_5$ is independently selected from the group consisting of F, Cl, Br, OH, CN, $NH_2$, $CH_3$, $CH_3CH_2$, $CH_2CH_2F$, $CH_3CH_2CH_2$, $CH_3O$, $CH_3OCH_2$, $N(CH_3)_2$,

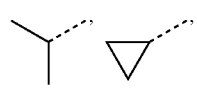

respectively, and other variables are as defined above.

In some aspects of the present invention, the structural unit

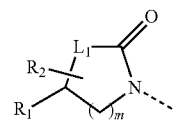

is selected from:

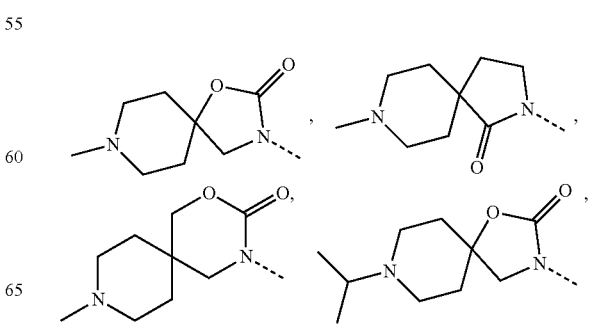

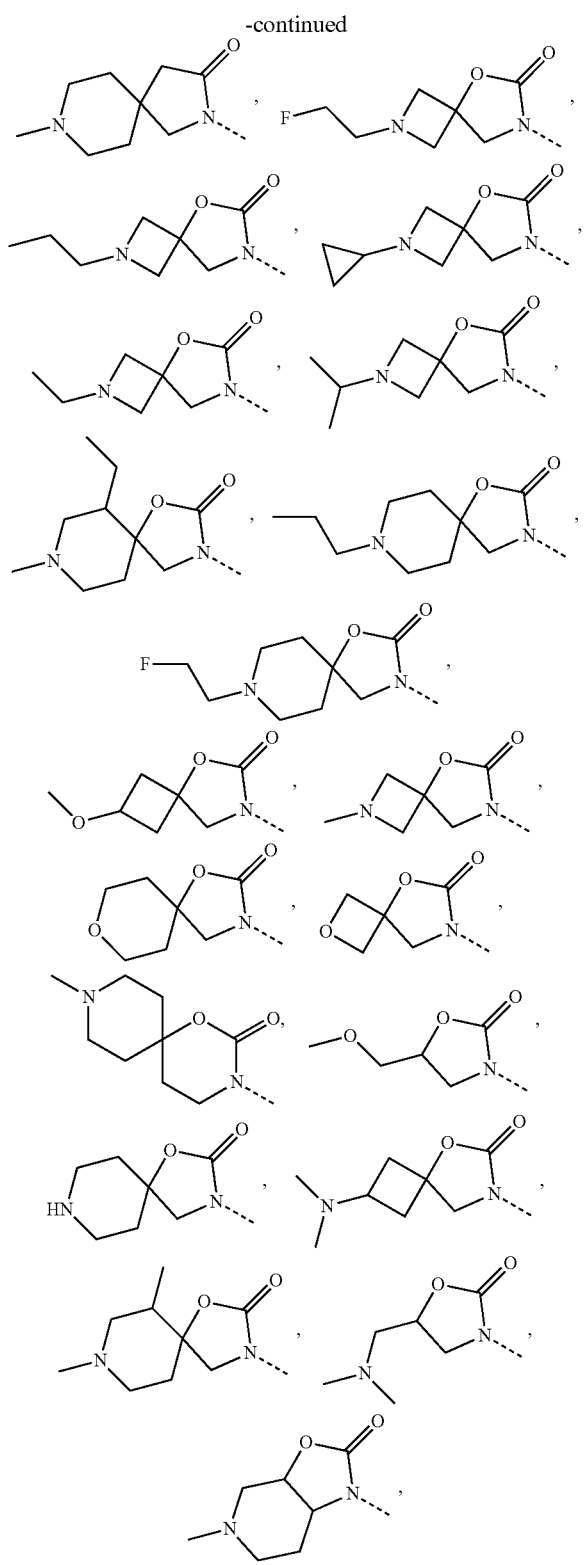

and other variables are as defined above.

In some aspects of the present invention, the $R_3$ is H, or selected from $CH_3$, $CH_3CH_2$, $CH_3CH_2CH_2$, $CH_3O$ and $CH_3OCH_2$, $CH_3$, $CH_3CH_2$, $CH_3CH_2CH_2$, $CH_3O$ and $CH_3OCH_2$ being optionally substituted with one, two or three R, and other variables are as defined above.

In some aspects of the present invention, the $R_3$ is selected from: H, $CH_3$, $CH_3O$, and other variables are as defined above.

In some aspects of the present invention, the $R_4$ is independently selected from: H, F, Cl, Br, I, $CH_3$, $CH_3O$ and $CH\equiv C-$, respectively, and other variables are as defined above.

In some aspects of the present invention, the ring A is selected from: phenyl, thienyl, pyrrolyl, furyl, pyridyl, indolyl and benzimidazolyl.

In some aspects of the present invention, the structural unit

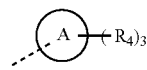

is selected from:

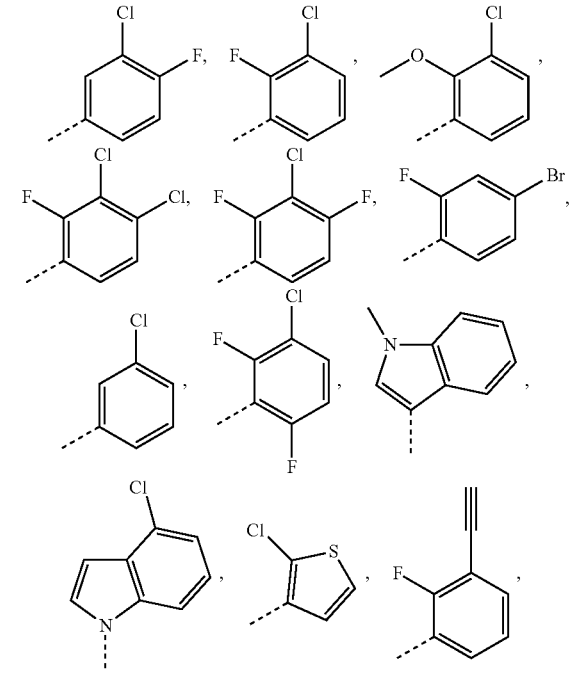

and other variables are as defined above.

In some aspects of the present invention, the compound or pharmaceutically acceptable salt thereof is provided, wherein the compound is selected from:

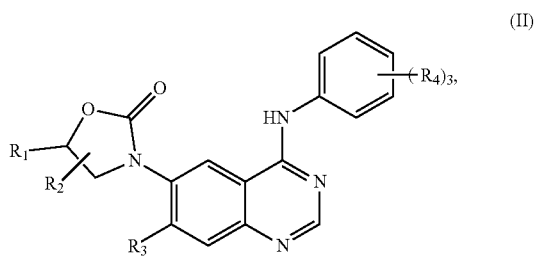

(II)

-continued
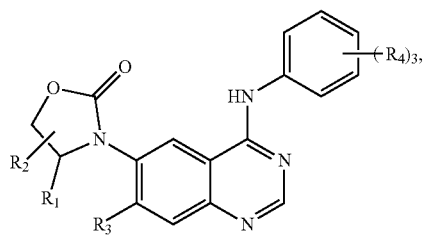
(III)
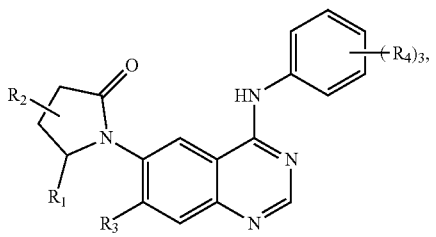
(IV)
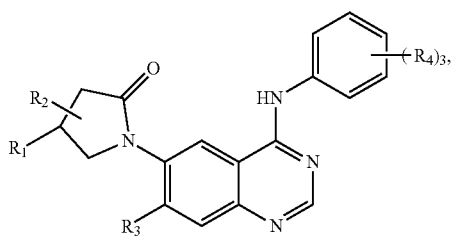
(V)
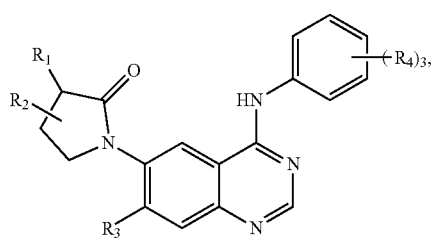
(VI)
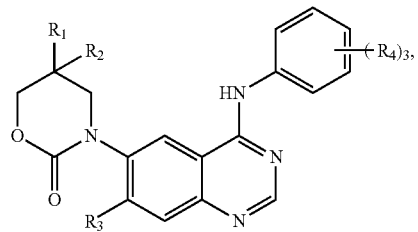
(VII)
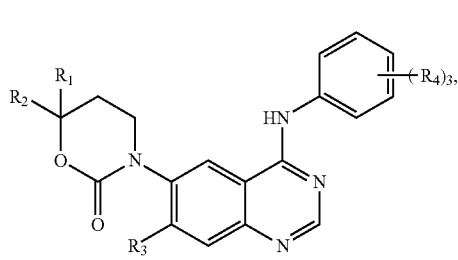
(VIII)
wherein, $R_1$, $R_2$, $R_3$, $R_4$ are as defined above.
In some aspects of the present invention, the compound or pharmaceutically acceptable salt thereof is provided, wherein the compound is selected from:
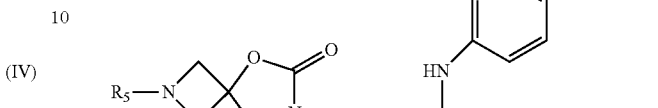
(IX)
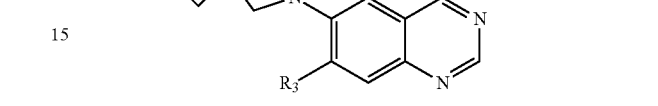
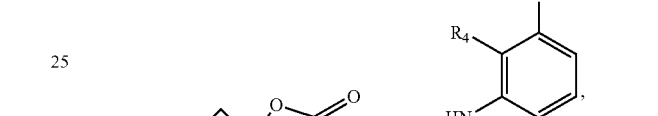
(X)
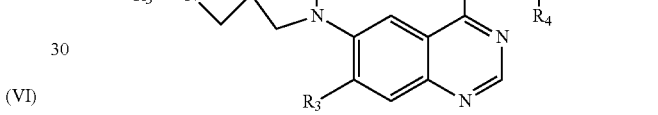
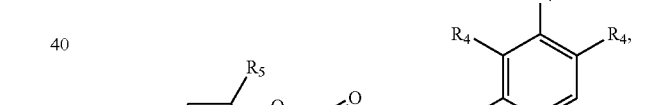
(XI)
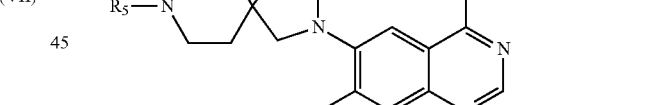
(XII)
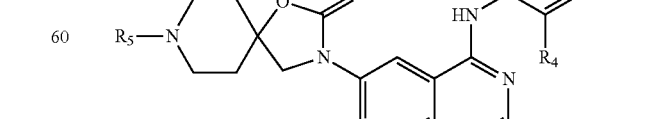
wherein, $R_3$, $R_4$, $R_5$ are as defined above.

The present invention also has some aspects which are derived from arbitrary combinations of the variables
The present invention also provides the following compounds, which are selected from:
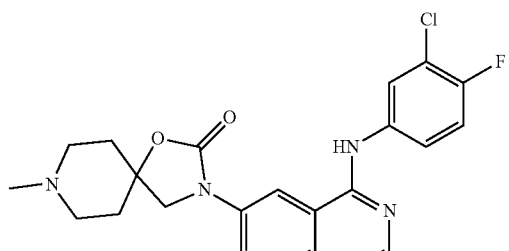
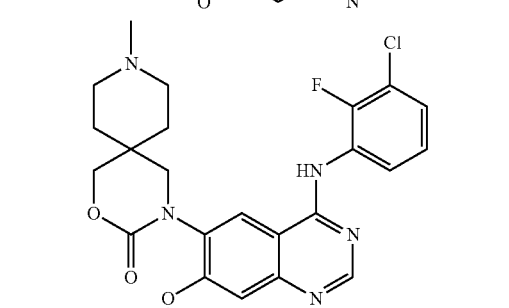
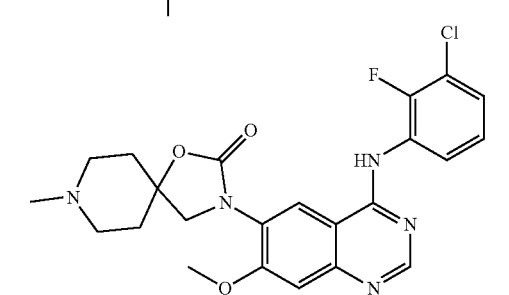
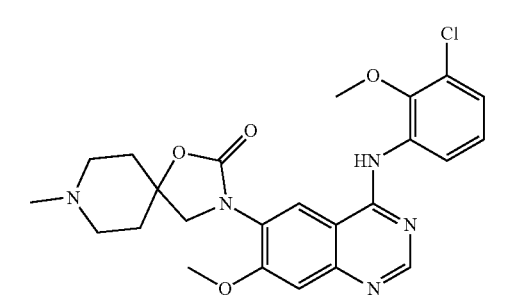
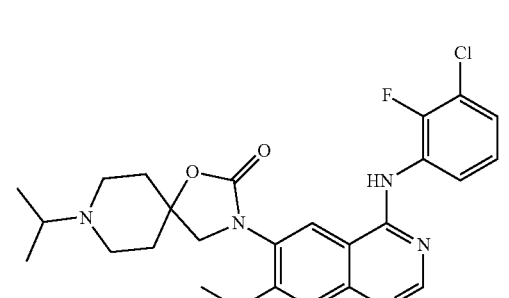
-continued
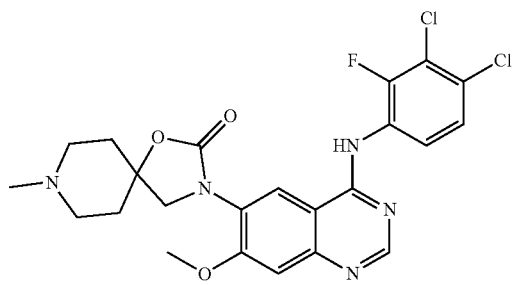
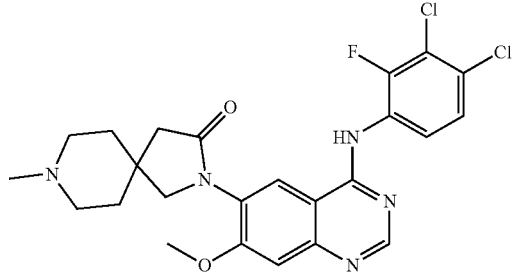
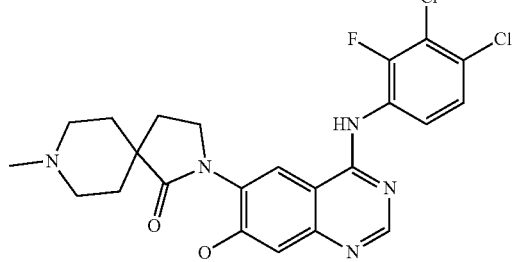
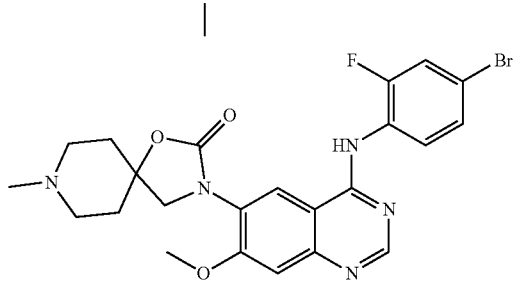
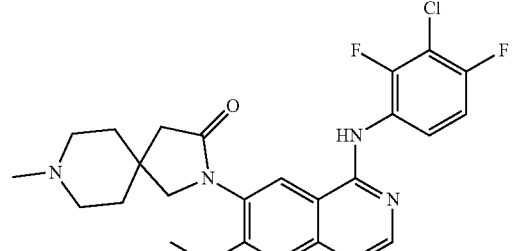
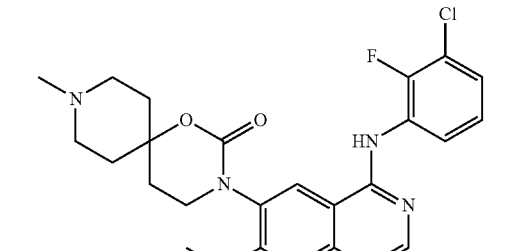

51
-continued
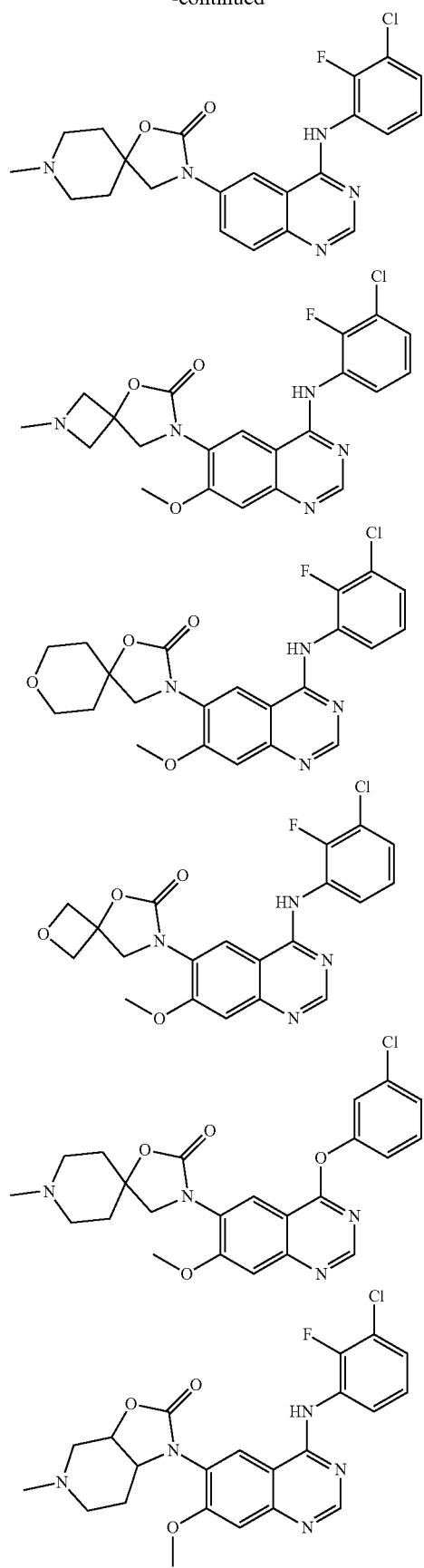
52
-continued
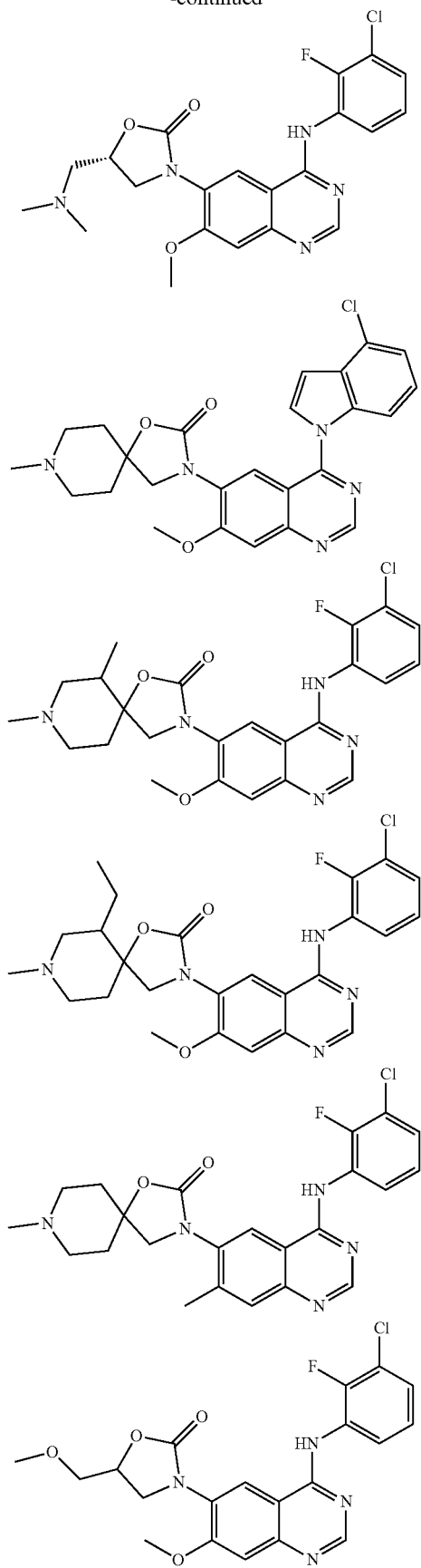

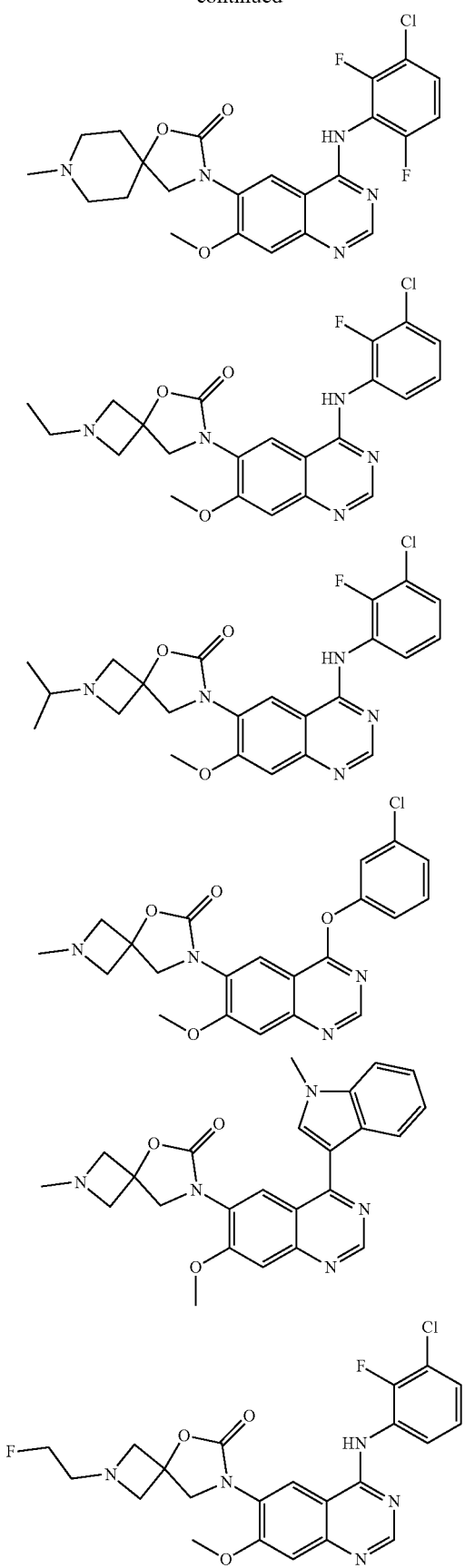
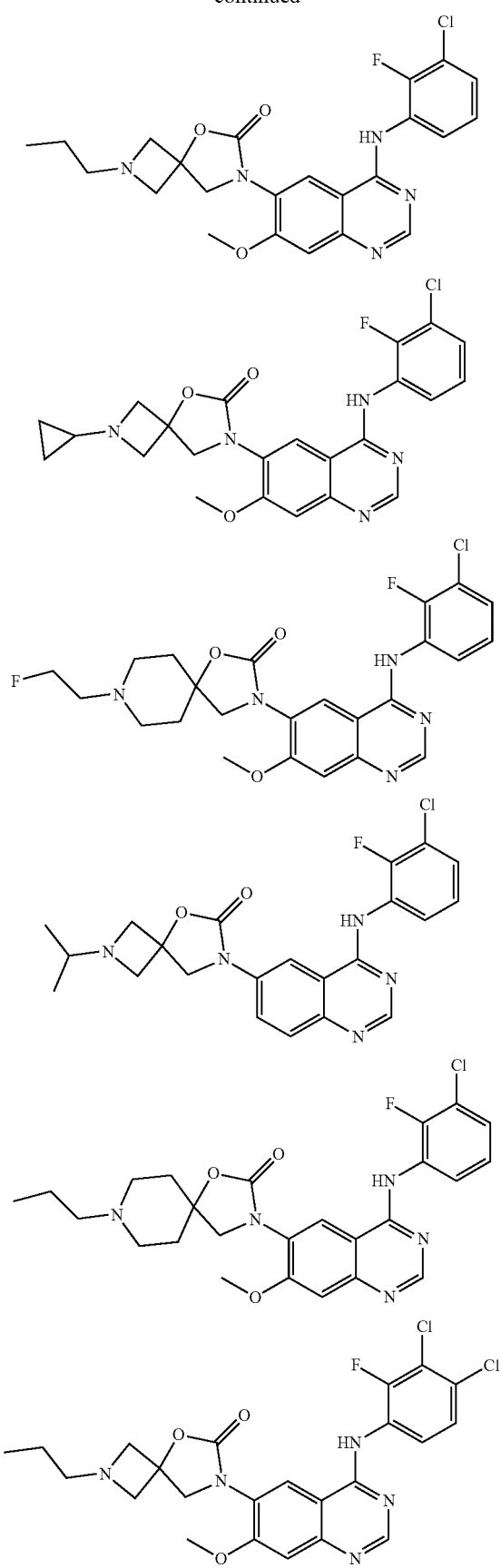

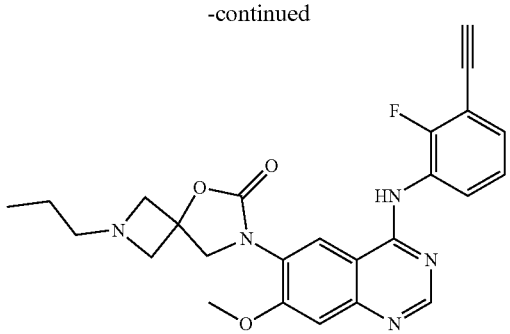

The present invention also provides a pharmaceutical composition, comprising a therapeutically effective amount of the compound or pharmaceutically acceptable salt thereof or pharmaceutically acceptable carriers thereof.

The present invention also provides the use of the compound or pharmaceutically acceptable salt thereof or the pharmaceutical composition in preparing drugs for treatment of cancers.

Technical Effects

The present invention relates to a series of novel quinazoline compounds as EGFR mutation inhibitors, and their use in the treatment of brain metastatases. The novel quinazoline compounds of the present invention have high enzymatic activity and cell line activity against EGFR mutations, as well as good drug-like properties, high permeability and high metabolic stability in vitro. Therefore, these compounds may provide more effective treatment for EGFR mutant brain metastases.

Definitions and Descriptions

Unless otherwise specified, the following terms and phrases used herein are intended to have the following meanings. A particular term or phrase should not be considered uncertain or unclear without a specific definition, but should be understood in the ordinary sense. When a commodity name appears in this article, it is intended to refer to the corresponding commodity or its active ingredients. The term "pharmaceutically acceptable" refers to compounds, materials, compositions and/or formulations that are within a range of reliable medical judgment and are suitable for contact with the tissues of human beings and animals without excessive toxicity, irritation, allergic response or other problems or complications, which are compatible with reasonable benefits/risks.

The term "pharmaceutically acceptable salts" refers to the salts of the compounds of the present invention, which are prepared from the compounds with specific substituents found by the present invention and relatively non-toxic acids or bases. When the compounds of the present invention contain relatively acidic functional groups, basic addition salts can be obtained by contacting such compounds in their neutral forms with sufficient bases in pure solutions or appropriate inert solvents. Pharmaceutically acceptable basic addition salts include sodium salts, potassium salts, calcium salts, ammonium salts, organic ammonium salts, magnesium salts or the like. When the compounds of the present invention contain relatively basic functional groups, acid addition salts can be obtained by contacting such compounds in their neutral forms with sufficient acids in pure solutions or appropriate inert solvents. Examples of pharmaceutically acceptable acid addition salts include inorganic salts, in which the inorganic acids include hydrochloric acid, hydrobromic acid, nitric acid, carbonic acid, bicarbonate, phosphoric acid, monohydrogen phosphate, dihydrogen phosphate, sulfuric acid, bisulfate, hydroiodic acid, phosphorous acid, etc., and organic acid salts, in which the organic acids include acetic acid, propanoic acid, isobutyric acid, maleic acid, propanedioic acid, benzoic acid, succinic acid, octanedioic acid, fumaric acid, lactic acid, mandelic acid, phthalic acid, benzenesulfonic acid, p-toluenesulfonic acid, citric acid, tartaric acid, methanesulfonic acid, or the like; amino acid (such as arginine, etc.) salts and salts of organic acid such as glucuronic acid, etc. are also included (see Berge et al., "Pharmaceutical Salts", Journal of Pharmaceutical Science 66: 1-19 (1977)). Certain specific compounds of the present invention contain basic and acidic functional groups, which can be converted into any base or acid addition salt.

Preferably, the salts are contacted with bases or acids in a conventional manner, and the parent compounds are separated, thereby regenerating the compounds in their neutral forms. The parent forms of the compounds differ from those of various salts in some physical properties, e.g. solubilities in polar solvents.

"Pharmaceutically acceptable salts" used herein belong to derivatives of the compounds of the present invention, wherein the parent compounds are modified by forming salts with acids or bases. Examples of the pharmaceutically acceptable salts include, but are not limited to, mineral or organic acid salts of basic groups such as amines, alkali metal salts or organic salts of acidic groups such as carboxylic acid groups, etc. The pharmaceutically acceptable salts include conventional non-toxic salts or quaternary ammonium salts of the parent compounds, such as salts formed from non-toxic inorganic or organic acids. Conventional non-toxic salts include, but are not limited to, salts derived from inorganic and organic acids. The inorganic or organic acids are selected from the group consisting of 2-(acetoxy) benzoic acid, 2-hydroxyethanesulfonic acid, acetic acid, ascorbic acid, benzenesulfonic acid, benzoic acid, bicarbonate, carbonic acid, citric acid, ethylenediamine tetraacetic acid, ethanedisulfonic acid, ethanesulfonic acid, fumaric acid, glucoheptose, gluconic acid, glutamic acid, glycolic acid, hydrobromic acid, hydrochloric acid, hydroiodic acid, hydroxyl, hydroxynaphthalene, isethionic acid, lactic acid, lactose, dodecyl sulfonic acid, maleic acid, malic acid, mandelic acid, methanesulfonic acid, nitric acid, oxalic acid, dihydroxynaphthalic acid, pantothenic acid, phenylacetic acid, phosphoric acid, polygalactose aldehyde, propionic acid, salicylic acid, stearic acid, subacetate acid, succinic acid, sulfamic acid, p-aminobenzene sulfonic acid, sulfuric acid, tannin, tartaric acid and p-toluenesulfonic acid.

The pharmaceutically acceptable salts of the present invention can be synthesized by conventional chemical methods from the parent compounds containing acidic or basic functional groups. Generally, the preparation method of such salts is: in water, organic solvents, or the mixtures of both, the salts are prepared by reacting these compounds in the form of free acids or bases with stoichiometric appropriate bases or acids. Generally, non-aqueous medium, such as ether, ethyl acetate, ethanol, isopropanol or acetonitrile, etc. is preferred.

In addition to salt forms, the present invention also provides compounds in a prodrug form. The prodrugs of the compounds described herein easily undergo chemical changes under physiological conditions to be converted into the compounds of the present invention. In addition, the prodrugs can be chemically or biochemically converted into the compounds of the present invention in vivo environment.

Certain compounds of the present invention can be in non-solvation or solvation forms, including hydrate forms. Generally speaking, the solvation forms are equivalent to the non-solvation forms, which are all included within the scope of the present invention.

Some compounds of the present invention can contain asymmetric carbon atoms (optical centers) or double bonds. Racemes, diastereoisomers, geometric isomers and single isomers are included within the scope of the present invention.

Unless otherwise specified, the absolute configurations of stereocenters are represented by wedged bonds and dashed bonds (╱ ╲), wave line ∽ represent the wedge bonds or dashed bonds (╱ or ╲), and ╱ ╲ represent the relative configurations of stereocenters. When the compounds described herein contain double bonds in olefins or other geometrically asymmetric centers, unless otherwise specified, they include E and Z geometric isomers. Similarly, all tautomeric forms are included within the scope of the present invention.

The compounds of the present invention can exist in specific geometric or stereoisomeric forms. All of such compounds are conceived in the present invention, including cis- and trans-isomers, (−)- and (+)-enantiomers, (R)- and (S)-enantiomers, diastereomers, (D)-isomers, (L)-isomers, the racemic mixtures thereof, and other mixtures, such as enantiomers or non-enantiomerically enriched mixtures, as falling within the scope of the present invention. Additional asymmetric carbon atoms may be present in a substituent such as an alkyl group. All such isomers and their mixtures are included within the scope of the present invention.

Optically active (R)- and (S)-isomers, D and L isomers can be prepared by chiral synthesis or chiral reagents or other conventional techniques. If an enantiomer of a compound of the present invention is to be obtained, it can be prepared by asymmetric synthesis or by derivatization with chiral auxiliaries, in which the resulting non-enantiomeric mixture is separated and the auxiliary groups are split to provide the pure enantiomers needed. Alternatively, when the molecules contain basic functional groups (such as amino groups) or acidic functional groups (such as carboxyl groups), the non-enantiomeric salts are formed with appropriate optically active acids or bases, then the non-enantiomers are separated by conventional methods known in the art, and the pure enantiomers are recovered. In addition, the separation of the enantiomers and non-enantiomers is usually accomplished by chromatographic methods, which use chiral stationary phases, and are optionally combined with chemical derivatization (e.g., the formation of carbamates from amines).

The compounds of the present invention may contain atomic isotopes in non-natural proportions on one or more atoms constituting the compounds. For example, the compounds can be labeled with radioisotopes, such as tritium ($^3$H), iodine-125 ($^{125}$I) or C-14 ($^{14}$C). The transformation of all isotope compositions of the compounds of the present invention, whether radioactive or not, is included within the scope of the present invention.

The term "pharmaceutically acceptable carrier" refers to a representative carrier for any preparation or carrier medium which can deliver an effective amount of the active substances of the present invention, does not interfere with the effectiveness of the biological activity of the active substances and has no toxic side effects on hosts or patients, including water, oil, vegetable and mineral, paste, lotion matrix, ointment matrix, etc. These matrices include suspensions, tackifiers, penetration enhancers, etc. Their preparations are well known to those skilled in the art of cosmetics or topical pharmaceuticals. For other information about carriers, you can refer to Remington: The Science and Practice of Pharmacy, 21st Ed., Lippincott, Williams & Wilkins (2005), which is incorporated herein by reference.

The term "excipient" usually refers to a carrier, a diluent and/or a medium required for the preparation of an effective pharmaceutical composition.

For pharmaceuticals or pharmacological active agents, the term "effective amount" or "therapeutic effective amount" means a sufficient amount of pharmaceuticals or agents that are non-toxic but can achieve the desired effect. For the oral dosage form in the present invention, the "effective amount" of an active substance in the composition refers to an amount required to achieve the desired effect when combined with another active substance in the composition. The determination of the effective amount varies from person to person, depending on age and general condition of a receptor, and also on a specific active substance. The appropriate effective amount in a case can be determined by those skilled in the art according to routine tests.

The term "active ingredient", "therapeutic agent", "active substance" or "active agent" refers to a chemical entity that can effectively treat target disorders, diseases or illnesses.

"Optional" or "optionally" means that the subsequently described event or circumstance may, but need not, occur, and that the description includes instances where the event or circumstance occurs and instances where it does not.

The term "substituted" refers to any one or more hydrogen atoms on a designated atom is replaced with a substituent, which may include heavy hydrogen and variants of hydrogen, as long as the valence state of the specific atom is normal and the substituted compound is stable. When the substituent is a ketone group (i.e., =O), it means that two hydrogen atoms are substituted. The ketone substitution does not occur on an aromatic group. The term "optionally substituted" means that it may or may not be substituted, unless otherwise specified, the type and number of substituents may be arbitrary on the basis of chemical accessibility.

When any variable (e.g., R) occurs more than once in the composition or structure of a compound, its definition at each occurrence is independent. Thus, for example, if a group is substituted with 0-2 R, the group can be substituted optionally with at most two R, and R has a separate option at each occurrence. Furthermore, combinations of substituents and/or their variables are permissible only if such combinations result in stable compounds.

When the number of bonding groups is zero, such as —(CRR)$_0$—, it means that the bonding groups are single bonds.

When one of the variables is selected from a single bond, the two groups attached directly. For example, when L in A-L-Z presents a single bond, it indicates that the structure is actually A-Z.

When a substituent is absent, it means that the substituent does not exist. For example, when X is absent in A-X, it means that the structure is actually A. When a bond to a substituent can cross a bond connecting two atoms in a ring, then such substituent may be bonded to any atom on the ring. When a substituent is listed without indicating the atom via which such substituent may be bonded to the compound of general formula of chemical structure but not specifically mentioned, the substituents may be bonded via any atom in such substituent. Combinations of substituents and/or their variables are permissible only if such combinations result in stable compounds. For example, a structural unit

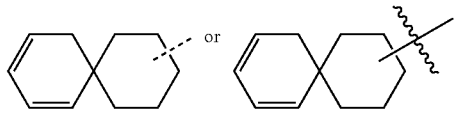

may be substituted at any position on a cyclohexyl group or cyclohexadiene.

Unless otherwise specified, the term "hetero" denotes a heteroatom or a heteroatom-containing group (i.e., a group containing heteroatoms), including atoms other than carbon (C) and hydrogen (H), as well as groups containing these heteroatoms, such as oxygen (O), nitrogen (N), sulfur (S), silicon (Si), germanium (Ge), aluminium (Al), boron (B), —O—, —S—, =O, =S, —C(=O)O—, —C(=O)—, —C(=S)—, —S(=O), —S(=O)$_2$—, and optionally substituted —C(=O)N(H)—, —N(H)—, —C(=NH)—, —S(=O)$_2$N(H)— or —S(=O)N(H)—.

Unless otherwise specified, "ring" means substituted or not substituted cycloalkyl, heterocycloalkyl, cycloalkenyl, heterocycloalkenyl, cycloalkynyl, heterocycloalkynyl, aryl or heteroaryl. The so-called ring includes a single ring, joint ring, spiral ring, parallel ring or bridge ring. The number of atoms in a ring is usually defined as the number of members in a ring. For example, a "5, 6, or 7-membered ring" refers to the arrangement of 5, 6, or 7 atoms in a ring. Unless otherwise specified, the ring optionally contains 1 to 3 heteroatoms. Therefore, a "5, 6, or 7-membered ring" includes, for example, phenyl, pyridyl and piperidinyl; on the other hand, the term "5, 6, or 7-membered heterocycloalkyl ring" includes pyridyl and piperidinyl, but excludes phenyl. The term "ring" also includes a ring system containing at least one ring, each of which independently coincides with the above definition.

Unless otherwise specified, the term "heterocycle" or "heterocyclic group" refers to a stable mono-, bi-, or tri-cyclic ring, containing a heteroatom or heteroatom-containing groups, which may be saturated, partially unsaturated or unsaturated (aromatic), containing carbon atoms and 1, 2, 3 or 4 heteroatoms independently selected from N, O and S, wherein any of the heterocycles may be fused to a benzene ring to form a bicyclic ring. The nitrogen and sulfur heteroatoms may be optionally oxidized (i.e., NO and S(O)p, p is 1 or 2). The nitrogen atom may be substituted or unsubstituted (i.e., N or NR, where R is H or other substituents as already defined herein). The heterocyclic ring may be attached to its pendant group at any heteroatom or carbon atom which results in forming a stable structure. If the formed compound is stable, the heterocycle described herein may be substituted on a carbon or nitrogen atom. A nitrogen atom in heterocycle are optionally quaternized. It is a preferred plan that when the total number of S and O atoms in the heterocycle exceeds 1, these heteroatoms are not adjacent to each other. It is another preferred plan that the total number of S and O atoms in heterocycle is not more than 1. As used herein, the term "aromatic heterocyclic group" or "heteroaryl" refers to a stable 5-, 6- or 7-membered monocyclic or bicyclic or 7-, 8-, 9- or 10-membered bicyclic aromatic heterocyclic group, which contain carbon atoms and 1, 2, 3 or 4 heteroatoms independently selected from N, O and S. The nitrogen atom may be substituted or unsubstituted (i.e., N or NR, where R is H or other substituents as already defined herein). The nitrogen and sulfur heteroatoms may be optionally oxidized (i.e., NO and S(O) p, p is 1 or 2). It is noteworthy that the total number of S and O atoms in the aromatic heterocycle is not more than 1. A bridge ring is also included in the definition of the heterocycle. A bridge ring is formed when one or more atoms (i.e., C, O, N or S) attach two non-adjacent carbon or nitrogen atoms. A preferred bridging ring includes, but is not limited to, one carbon atom, two carbon atoms, one nitrogen atom, two nitrogen atoms and a carbon-nitrogen group. It is noted that a bridge always converts a monocyclic ring into a tricyclic ring. In a bridge ring, substituents on the ring may also be present on the bridge.

Examples of heterocyclic compounds include, but are not limited to, acridinyl, azocinyl, benzimidazolyl, benzofuranyl, benzomercaptofuranyl, benzothiophenyl, benzoxazolyl, benzoxazolinyl, benzothiazolyl, benzotriazolyl, benzotetrazolyl, benzoisoxazolyl, benzoisothiazolyl, benzoimidazolinyl, carbazolyl, 4aH-carbazolyl, carbolinyl, chromanyl, chromone, cinnoline decahydroquinolinyl, 2H,6H-1,5,2-dithiazinyl, dihydrofuro[2,3-b]tetrahydrofuranyl, furanyl, furastanyl, imidazolidinyl, imidazolinyl, imidazolyl, 1H-indazolyl, indole alkenyl, indolinyl, indolizinyl, indolyl, 3H-indolyl, isobenzofuranyl, isoindolyl, isoindolinyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, hydroxyindolyl, pyrimidinyl, phenanthridinyl, phenanthrolinyl, phenazinyl, phenothiazinyl, benzoxanthinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, isothiazolylthiophenyl, thienooxazolyl, thienothiazolyl, thienoimidazolyl, thienyl, triazinyl, 1,2,3-triazolyl, 1,2,4-triazolyl, 1,2,5-triazolyl, 1,3,4-triazolyl, and xanthenyl. Fused rings and spiro compounds are also included.

Unless otherwise specified, the term "hydrocarbyl" or its subordinate concept (e.g., alkyl, alkenyl, alkynyl, aryl, etc.) by itself or a hydrocarbyl group as part of another substituent, representing a straight, branched or cyclic hydrocarbon group, or their combinations, may be fully saturated (e.g., alkyl), monounsaturated or polyunsaturated (e.g., alkenyl, alkynyl, aryl), may be mono-substituted or multi-substituted, may be monovalent (e.g., methyl), divalent (e.g., methylene) or polyvalent (e.g., methine), and may include a divalent or polyvalent group, with a specified number of carbon atoms (e.g., $C_1$-$C_{12}$ for 1 to 12 carbons, $C_{1-12}$ selected from $C_1$, $C_2$, $C_3$, $C_4$, $C_5$, $C_6$, $C_7$, $C_8$, $C_9$, $C_{10}$, $C_{11}$ and $C_{12}$; $C_{3-12}$ were selected from $C_3$, $C_4$, $C_5$, $C_6$, $C_7$, $C_8$, $C_9$, $C_{10}$, $C_{11}$ and $C_{12}$.) "Hydrocarbyl" includes but is not limited to aliphatic and aromatic hydrocarbon, wherein the aliphatic hydrocarbyl group includes a chain and a ring, specifically including but not limited to alkyl, alkene and alkynyl, and the aromatic hydrocarbyl group includes but are not limited to a 6-12-membered aromatic hydrocarbyl group, such as benzene, naphthalene, etc. In some embodiments, the term "hydrocarbyl" denotes a straight or branched group or their combinations, which may be fully saturated, monounsaturated or polyunsaturated, and may include a divalent or polyvalent group. Examples of saturated hydrocarbyl groups include, but are not limited to, methyl, ethyl, n-propyl, isopropyl, n-butyl, tert-butyl, isobutyl, sec-butyl, isobutyl, cyclohexyl, (cyclohexyl) methyl, cyclopropyl methyl, and homologues or isomers of n-pentyl, n-hexyl, n-heptyl, n-octyl, etc. Unsaturated hydrocarbyl groups contain one or more double or triple bonds. Examples include but are not limited to vinyl, 2-propylene, butenyl, crotonyl, 2-isoprenyl, 2-(butadienyl), 2,4-pentadienyl, 3-(1,4-pentadienyl), ethynyl, 1- and 3-propynyl, 3-butynyl, and more advanced homologues and isomers.

Unless otherwise specified, the term "heterohydrocarbyl" or its subordinate concept (e.g., heteroalkyl, heteroalkenyl, heteroalkynyl, heteroaryl, etc.), by itself or in combination with other terms, means a stable straight, branched or cyclic hydrocarbon radical or combinations thereof, consisting of the stated number of carbon atoms and at least one heteroatom. In some embodiments, the term "heteroalkyl", by itself or in combination with other terms, represents a stable straight, branched hydrocarbyl group or their compositions, consisting of a certain number of carbon atoms and at least one heteroatom. In a typical embodiment, a heteroatom is selected from B, O, N and S, where the nitrogen and sulfur atoms are optionally oxidized and the nitrogen heteroatom is optionally quaternized. A heteroatom or heteroatom-containing group may occupy any internal position of a heterohydrocarbyl group, including the position where the hydrocarbyl group is attached to the remainder of the molecule, but the terms "alkoxy", "alkylamino" and "alkylthio" (or thioalkyl) are conventionally expressed, referring to being attached to the remainder of those alkyl groups of a molecule via an oxygen atom, an amino atom or a sulfur atom, respectively. Examples include but are not limited to —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$, —S(O)—CH$_3$, —CH$_2$—CH$_2$—S(O)$_2$—CH$_3$, —CH=CH—O—CH$_3$, —CH$_2$—CH=N—OCH$_3$ and —CH=N(CH$_3$)—CH$_3$. At most two heteroatoms may be adjacent to one another, for example —CH$_2$—NH—OCH$_3$.

Unless otherwise specified, the term "cyclohydrocarbyl", "heterocyclohydrocarbyl" or its subordinate concept (e.g., aryl, heteroaryl, cycloalkyl, heterocycloalkyl, cycloalkenyl, heterocycloalkenyl, cycloalkynyl, heterocycloalkynyl, etc.), by itself or in combination with other terms, represents cyclic "hydrocarbyl" and "heterohydrocarbyl", respectively. Additionally, for heterohydrocarbyl or heterocyclohydrocarbyl (such as heteroalkyl and heterocycloalkyl), a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, etc. Non-limiting examples of heterocycloalkyl moieties include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-indol-3-yl, tetrahydrothien-2-yl, tetrahydrothien-3-yl, 1-piperazinyl and 2-piperazinyl.

Unless otherwise specified, the term "alkyl" is used to denote a straight or branched saturated hydrocarbon chain, which can be mono-substituted (e.g. —CH$_2$F) or poly-substituted (e.g. —CF$_3$), and can be monovalent (e.g. methyl), divalent (e.g. methylene) or polyvalent (e.g. methine). Examples of alkyl include methyl (Me), ethyl (Et), propyl (e.g., n-propyl and isopropyl), butyl (e.g., n-butyl, isobutyl, s-butyl, t-butyl), pentyl (e.g., n-pentyl, isopentyl, neopentyl), etc.

Unless otherwise specified, "alkenyl" refers to an alkyl group containing one or more carbon-carbon double bonds at any point in the chain, which can be mono-substituted or poly-substituted, and can be monovalent, divalent or polyvalent. Examples of alkenyl groups include vinyl, propylene, butenyl, pentenyl, hexenyl, butadienyl, pentadienyl, hexadienyl, etc.

Unless otherwise specified, "alkynyl" refers to an alkyl group containing one or more carbon-carbon triple bonds at any point in the chain, which can be mono-substituted or poly-substituted, and can be monovalent, divalent or polyvalent. Examples of alkynyl groups include acetylene, propynyl, butynyl, pentynyl, etc.

Unless otherwise specified, "cycloalkyl" includes any stable cyclic or polycyclic hydrocarbon groups, and any carbon atom is saturated, which can be mono-substituted or poly-substituted, and can be monovalent, divalent or polyvalent. Examples of these cycloalkyl groups include, but are not limited to, cyclopropyl, norbornyl, bicyclo[2.2.2]octane, bicyclo[4.4.0]decane, etc.

Unless otherwise specified, "cycloalkenyl" includes any stable cyclic or polycyclic hydrocarbon group containing one or more unsaturated carbon-carbon double bonds at any point in the ring, which can be mono-substituted or poly-substituted, and can be monovalent, divalent or polyvalent. Examples of these cycloaklenyl groups include, but are not limited to, cyclopentenyl, cyclohexenyl, etc.

Unless otherwise specified, "cycloalkynyl" includes any stable cyclic or polycyclic hydrocarbon group containing one or more carbon-carbon triple bonds at any point in the ring, which can be mono-substituted or poly-substituted, and can be monovalent, divalent or polyvalent.

Unless otherwise specified, the term "halo" or "halogen", by itself or as part of another substituent, represents a fluorine, chlorine, bromine or iodine atom. Additionally, the term "haloalkyl" is intended to include monohaloalkyl and polyhaloalkyl. For example, the term "halo($C_1$-$C_4$)alkyl" is intended to include, but not limited to, trifluoromethyl, 2,2-trifluoroethyl, 4-chlorobutyl and 3-bromopropyl, etc. Unless otherwise specified, examples of haloalkyl include, but are not limited to, trifluoromethyl, trichloromethyl, pentafluoroethyl, and pentachloroethyl.

"Alkoxy" represents the-mentioned alkyl group with the specified number of carbon atoms attached via an oxygen bridge. Unless otherwise specified, $C_{1-6}$ alkoxy groups include $C_1$, $C_2$, $C_3$, $C_4$, $C_5$ and $C_6$ alkoxy groups. Examples of the alkoxy groups include, but are not limited to, methoxy, ethoxy, n-propoxy, isopropoxy, n-butoxy, sec-butoxy, tert-butoxy, n-pentyloxy and S-pentyloxy.

Unless otherwise specified, the term "aryl" means a polyunsaturated aromatic hydrocarbon substitute, which can be mono-substituted or poly-substituted, can be monovalent, divalent or polyvalent, and can be a single ring or multiple rings (e.g., one to three rings; at least one of them is aromatic), which are fused together or linked covalently. The term "heteroaryl" refers to an aryl group (or a ring) containing from one to four heteroatoms. In an exemplary embodiment, the heteroatom is selected from B, N, O and S, where the nitrogen and sulfur atoms are optionally oxidized and the nitrogen atoms are optionally quaternized. The heteroaryl groups can be attached to the remainder of the molecule via heteroatoms. Non-limiting examples of aryl or heteroaryl groups include phenyl, naphthyl, biphenyl, pyrrolyl, imidazolyl, pyrazinyl, oxazolyl, phenyl-oxazolyl, isoxazolyl, thiazolyl, furyl, thienyl, pyridyl, pyrimidyl, benzothiazolyl, benzimidazolyl, indolyl, isoquinolyl, quinoxalinyl, quinolyl, 1-naphthyl, 2-naphthyl, 4-biphenyl, 1-pyrrolyl, 2-pyrrolyl, 3-pyrrolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl groups. Substituents for any of the aryl and heteroaryl ring systems are selected from the group of acceptable substituents described below.

Unless otherwise specified, an aryl group in combination with other terms (e.g., aryloxy, arylsulfur, arylalkyl) includes an aryl and heteroaryl ring as defined above. Therefore, the term "arylalkyl" is intended to include those groups (e.g., benzyl, phenylethyl, pyridylmethyl, etc.) where aryl groups are attached to alkyl groups, and include those alkyl groups where carbon atoms (e.g., methylene) have been substituted with oxygen atoms, such as phenoxymethyl, 2-pyridyloxymethyl, 3-(1-naphthoxy)propyl, etc.

The term "leaving group" refers to a functional group or atom that can be replaced by another functional group or atom via a substitution reaction (e.g., nucleophilic substitution reaction). For example, the representative leaving group includes trifluoromethanesulfonate; chlorine, bromine, iodine; a sulfonate group, such as methyl sulfonate, toluene sulfonate, p-bromobenzene sulfonate, p-toluene sulfonate, etc.; an acyloxy group, such as acetoxyl, trifluoroacetoxyl, etc.

The term "protecting group" includes but is not limited to "amino protecting group", "hydroxyl protecting group" or "thiol protecting group". The term "amino protecting group" refers to a protecting group suitable for preventing side reactions on the nitrogen site of amino group. Representative amino protection groups include, but are not limited to, formyl groups; acyl groups, such as alkyl acyl groups (e.g., acetyl, trichloroacetyl or trifluoroacetyl); alkoxycarbonyl groups, such as tert-butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), triphenylmethyl (Tr), 1,1-bis (4'-methoxyphenyl)methyl; methylsilyl, such as trimethylsilyl (TMS) and tert-butyldimethylsilyl (TBS), etc. The term "hydroxyl protecting group" refers to a protecting group suitable for preventing side reactions on a hydroxyl group. Representative hydroxyl protecting groups include, but are not limited to, alkyl groups such as methyl, ethyl and tert-butyl groups; acyl groups such as alkyl acyl groups (e.g., acetyl groups); arylmethyl groups, such as benzyl (Bn), p-methoxybenzyl (PMB), 9-fluorenylmethyl (Fm) and diphenylmethyl (DPM); methylsilyl, such as trimethylsilyl (TMS) and tert-butyldimethylsilyl (TBS), etc.

The compounds of the present invention can be prepared by a variety of synthesis methods known to those skilled in the art, including the specific embodiments listed below, the embodiments formed by their combination with other chemical synthesis methods and the equivalent or alternative methods known to those skilled in the art. The preferred embodiments include but are not limited to the embodiments of the present invention.

The solvent used in the present invention is commercially available. The following abbreviations are used in the present invention: aq stands for water; HATU stands for O-(7-azabenzotriazol-1-yl)-N,N,N',N'-tetramethyluronium hexafluorophosphate; EDC stands for N-(3-dimethylaminopropyl)-N'-ethylcarbodiimide hydrochloride; m-CPBA stands for m-chloroperoxybenzoic acid; eq stands for equivalent or equal; CDI stands for carbonyl diimidazole; DCM stands for dichloromethane; PE stands for petroleum ether; DIAD stands for diisopropyl azodicarboxylate; DMF stands for N, N-dimethylformamide; DMSO stands for dimethylsulfoxide; EtOAc stands for ethyl acetate; EtOH stands for ethanol; MeOH stands for methanol; CBz stands for benzyloxycarbonyl, an amine protecting group; BOC stands for tert-butylcarbonyl, an amine protecting group; HOAc stands for acetic acid; NaCNBH$_3$ stands for sodium cyanoborohydride; r.t. stands for room temperature; O/N stands for overnight; THF stands for tetrahydrofuran; Boc$_2$O stands for di-tert-butyl dicarbonate; TFA stands for trifluoroacetic acid; DIPEA stands for diisopropylethylamine; SOCl$_2$ stands for thionyl chloride; CS$_2$ stands for carbon disulfide; TsOH stands for p-toluenesulfonic acid; NFSI stands for N-fluoro-N-(phenylsulfonyl) benzenesulfonamide; NCS stands for 1-chloropyrrolidine-2,5-dione; n-Bu$_4$NF stands for tetrabutylammonium fluoride; iPrOH stands for 2-propanol; mp stands for melting point; LDA stands for lithium diisopropylamine.

Compounds are named manually or with ChemDraw® software, and commercially available compounds are named as in suppliers' catalogues.

Shimadzu LC$_{20}$AB system with Shimadzu SIL-20A Autosampler and Japanese Shimadzu DAD: SPD-M20A detector was used for high performance liquid chromatography analysis, and Xtimate C18 (3 □m packing material, 2.1×300 mm) column was used. A method of 0-60A B_6 minutes: using linear gradient, the elution started with 100% A (A was a 0.0675% T formate aqueous solution) and ended with 60% B (B was 0.0625% T formate MeCN solution); the whole process was 4.2 minutes, followed by elution with 60% B for 1 minute; the column was rebalanced for 0.8 minutes to 100:0, and the total running time was 6 minutes. A method of 10-80A B_6 minutes: using linear gradient, the elution started with 90% A (A was 0.0675% T formate aqueous solution) and ended with 80% B (B was 0.0625% T formate acetonitrile solution); the whole process was 4.2 minutes, followed by 80% B elution for 1 minute; the column was rebalanced for 0.8 minutes to 90:10, and the total running time was 6 minutes. The column temperature was 50° C. and the flow rate was 0.8 ml/min. The diode array detectors scanned the wavelength range from 200 to 400 nm.

Thin layer chromatography (TLC) was performed on Sanpont silica gel GF254. Usually ultraviolet light was used to observe spots, and in some case, other methods were also adopted to observe the spots, by which iodine (adding about 1 g of iodine into 10 g of silica gel and mixing completely), vanillin (dissolving about 1 g of vanillin in 100 ml of 10% H$_2$SO$_4$), ninhydrin (purchased from Aldrich) or a special chromogenic reagent (prepared by completely mixing (NH$_4$)$_6$Mo$_7$O$_{24}$.4H$_2$O, 5 g (NH$_4$)$_2$Ce(IV)(NO$_3$)$_6$, 450 ml of H$_2$O and 50 ml of concentrated H$_2$SO$_4$) was used to develop the thin layer plate and observe the compounds. By the method similar to that disclosed in Still, W. C., Kahn, M., and Mitra, M. Journal of Organic Chemistry, 1978, 43, 2923-2925, the rapid column chromatography on Silicycle 40-63 μm (230-400 mesh) silica gel was performed. Common solvents used in the rapid column chromatography or TLC were the mixtures of dichloromethane/methanol, ethyl acetate/methanol and hexane/ethyl acetate.

On the Gilson-281 Prep LC 322 system, a Gilson UV/VIS-156 detector was used for chromatographic analysis. The chromatography columns used were Agella Venusil ASB Prep C18, 5 □m, 150×21.2 mm; Phenomenex Gemini C18, 5 □m, 150×30 mm; Bon Symmetrix C18, 5 □m, 150×30 mm; or Phenomenex C18, 4 □m, 150×30 mm. At a flow rate of about 25 ml/min, the compounds were eluted with low gradient acetonitrile/water, which contained 0.05% HCl, 0.25% HCOOH or 0.5% NH$_3$.H$_2$O in the water. The total running time was 8-15 minutes.

EXAMPLES

To illustrate the present invention in more detail, the following examples are given, but the scope of the present invention is not limited thereto.

Process A

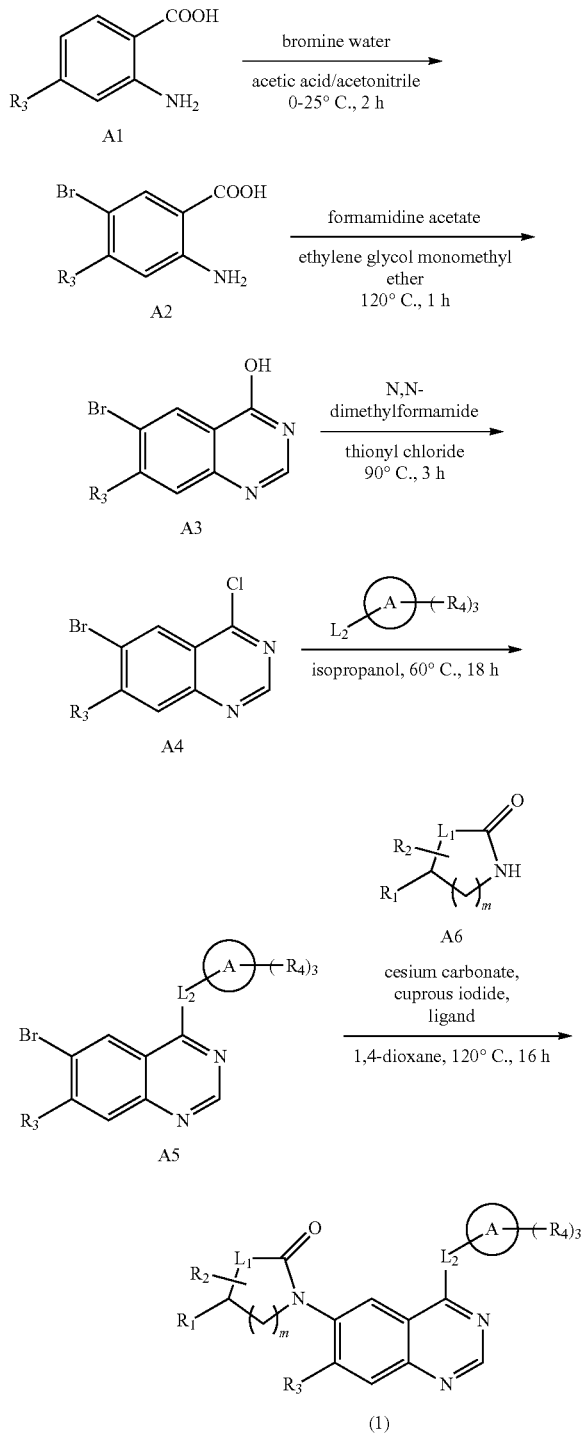

Example 1

Compound 1A

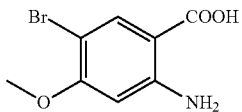

2-Amino-4-methoxybenzoic acid (5.00 g, 29.91 mmol) was dissolved in acetic acid (10 mL) and acetonitrile (100 mL), slowly added dropwise with liquid bromine (4.78 g, 29.91 mmol) at 0° C. and under nitrogen protection, and stirred at 20° C. for 1 hour. TLC showed that the reaction was complete. After the reaction solution was concentrated, water (100 ml) and petroleum ether (100 ml) were successively used for making a slurry, which was vacuum dried to obtain compound 1A. $^1$H NMR (400 MHz, DMSO-$d_6$) δ=7.76 (s, 1H), 6.41 (s, 1H), 3.79 (s, 3H).

Compound 1B

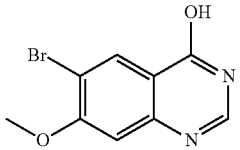

Compound 1A (5.9 g, 18.94 mmol) and formamidine acetate (3.55 g, 34.10 mmol) were dissolved in ethylene glycol monomethyl ether (10 mL), and the reaction mixture was stirred under nitrogen protection at 120° C. for 3 hours. TLC showed that the reaction was complete. The reaction solution was cooled down to room temperature, the solids were precipitated and filtered, and the filter cake was washed with EA (10 mL×2), PE (20 mL×3) and water (50 mL×2), respectively. Compound 1B was obtained after drying. LCMS (ESI) (5-95AB): m/z: 254.9 [M+1].

Compound 1C

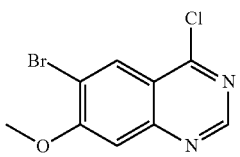

Compound 1B (500 mg, 1.83 mmol) was dissolved in thionyl chloride (6 mL), added with DMF (1.34 g, 18.27 mmol, 1.41 mL), stirred under nitrogen protection at 90° C. for 12 hours. The target compound was detected by LCMS and TLC showed that the reaction was complete. The reaction solution was concentrated, then separated and purified by column chromatography (silica gel, EA:PE=0:1, 1:3), to give compound 1C. LCMS (ESI) (5-95AB): m/z: 273.0 [M+1].

Compound 1D

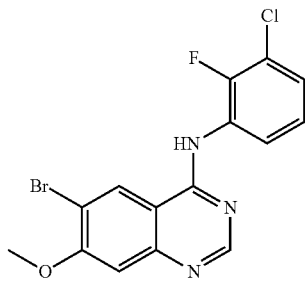 [SMILES: COc1cc2ncnc(Nc3cccc(Cl)c3F)c2cc1Br]

Compound 1C (2.47 g, 9.03 mmol) and 3-chloro-2-fluoroaniline (1.31 g, 9.03 mmol) were dissolved in isopropanol (30 mL), and the reaction mixture was stirred under nitrogen protection at 60° C. for 2 hours. The target compound was detected by liquid chromatography mass spectrometry and TLC showed that the reaction was complete. The reaction liquid was cooled down to room temperature, added with petroleum ether (40 mL) stirred for half an hour filtered to obtain a solid was and washed with petroleum ether (30 mL). The solid was slowly added to a sodium bicarbonate solution (40 mL) and stirred for half an hour, filtered to obtain a solid, which was then washed with water (20 mL) and petroleum ether (30 mL), and dried under vaccum to give the title compound. $^1$H NMR (400 MHz, DMSO-$d_6$) δ=8.78 (s, 1H), 8.43 (s, 1H), 7.46 (td, J=7.4, 19.7 Hz, 2H), 7.29-7.22 (m, 2H), 4.01 (s, 3H). LCMS (ESI) (5-95AB): m/z: 382.1 [M+1].

Compound 1E

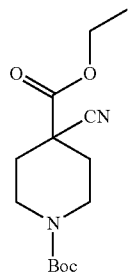 [SMILES: CCOC(=O)C1(C#N)CCN(C(=O)OC(C)(C)C)CC1]

4-Cyanopiperidine-1-formic acid tert-butyl ester (3.00 g, 14.27 mmol) was dissolved in tetrahydrofuran (30.00 mL), slowly added dropwise with lithium hexamethyldisilazide (1M, 28.54 mL) at −78° C. and under nitrogen protection, stirred for 1 hour, slowly added dropwise with ethyl chloroformate (3.10 g, 28.54 mmol), and then stirred under nitrogen protection at −78° C. for 1 hour. TLC showed that the reaction was complete. The reaction solution was quenched with a saturated solution of sodium bicarbonate (15 mL), and extracted with ethyl acetate (20 mL×2), and the combined organic phases were washed with a saturated solution of ammonium chloride (50 mL), dried over anhydrous sodium sulfate (10 g), filtered and concentrated to give 1E. $^1$H NMR (400 MHz, DMSO-$d_6$) δ=4.23 (q, J=7.1 Hz, 2H), 4.00-3.92 (m, 2H), 2.95 (br, 2H), 2.07 (br d, J=13.3 Hz, 2H), 1.89-1.76 (m, 2H), 1.40 (s, 9H), 1.24 (t, J=7.1 Hz, 3H).

Compound 1F

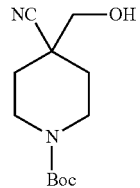

Compound 1E (2.30 g, 8.15 mmol) was dissolved in methanol (15.00 mL), added with sodium borohydride (369.82 mg, 9.78 mmol) at 0° C., and stirred under nitrogen protection at 0-20° C. for 1 hour. TLC showed that the reaction was complete. After the reaction mixture was concentrated, the reaction solution was quenched with a saturated solution of sodium bicarbonate (20 mL), and extracted with ethyl acetate (20 mL×2); the combined organic phases were concentrated, separated and purified by column chromatography (petroleum ether:ethyl acetate=50:1 to 5:1) to give 1F. 1H NMR (400 MHz, deuterated chloroform) δ=4.28-4.06 (m, 2H), 3.67 (s, 2H), 3.04 (br t, J=12.0 Hz, 2H), 1.96 (br dd, J=1.9, 13.4 Hz, 2H), 1.51-1.43 (m, 11H).

Compound 1G

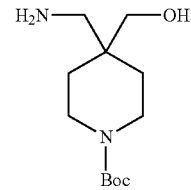

Compound 1F (500.00 mg, 2.08 mmol) was dissolved in methanol (20 mL). Raney nickel (0.2 g) was added into the reaction solution under nitrogen protection, and the gas in the reaction system was displaced with hydrogen gas three times. The reaction mixture was stirred under hydrogen atmosphere (50 psi) at 30° C. for 2 hours. TLC showed that the reaction was complete. The reaction solution was filtered, concentrated and dried on a rotary evaporator to give 1G. 1HNMR (400 MHz, deuterated chloroform) δ=3.71 (s, 2H), 3.57 (br d, J=13.3 Hz, 2H), 3.23 (ddd, J=3.5, 9.7, 13.5 Hz, 2H), 2.84 (s, 2H), 1.59-1.51 (m, 2H), 1.46 (s, 11H), 1.33 (d, J=4.2, 9.5, 13.6 Hz, 3H).

Compound 1H

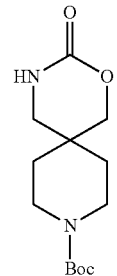

Compounds 1G (1.05 g, 4.30 mmol) and triethylamine (1.09 g, 10.74 mmol) were dissolved in dichloromethane (20 mL), with carbon dioxide gas purged into the reaction solution at −40° C. for 15 minutes, then slowly added dropwise with AcCl (212.64 mg, 4.30 mmol) at −40° C. and stirred for 15 minutes. Finally, the reaction solution was stirred at 20° C. for 39.5 hours. TLC showed that the reaction was partly complete. The reaction solution was concentrated, separated and purified by column chromatography (dichloromethane:methanol=100:1 to 20:1) to give 1H. $^1$H NMR (400 MHz, deuterated chloroform) δ=5.99 (br. s., 1H), 4.07 (s, 2H), 3.54-3.48 (m, 2H), 3.39-3.32 (m, 2H), 3.20 (s, 2H), 1.56 (t, J=5.8 Hz, 4H), 1.47 (s, 9H).

Compound 1I

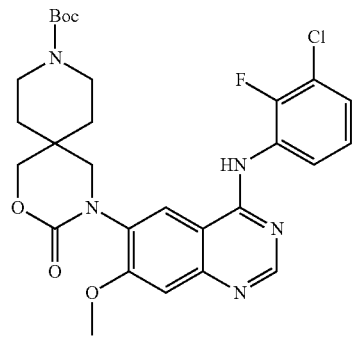 [SMILES: COc1cc2ncnc(Nc3cccc(Cl)c3F)c2cc1N1CC2(CCN(C(=O)OC(C)(C)C)CC2)COC1=O]

Compound 1D (100.0 mg, 261.36 mmol) and Compound 1H (77.72 mg, 287.50 mmol) were dissolved in 1,4-dioxane (2 mL), then added with cesium carbonate (170.31 mg, 522.73 mmol), cuprous iodide (29.87 mg, 156.82 mmol) and N, N'-dimethyl-1,2-ethylenediamine respectively, and stirred under nitrogen protection at 120° C. for 24 hours. The target compound was detected by liquid chromatography mass spectrometry and TLC showed that the raw materials were not completely consumed. The reaction mixture was filtered with dichloromethane:methanol=10:1 (22 mL), then concentrated, separated and purified by TLC (dichloromethane:methanol=20:1) to give 1I. LCMS (ESI) (5-95AB): m/z: 572.2 [M+1].

Compound 1J

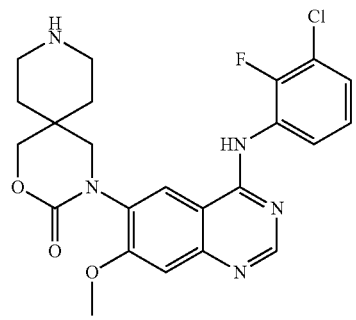 [SMILES: COc1cc2ncnc(Nc3cccc(Cl)c3F)c2cc1N1CC2(CCNCC2)COC1=O]

Compound 1I (96.00 mg, 131.91 mmol) was dissolved in dichloromethane (4 mL), then added with trifluoroacetic acid (1.2 g, 10.55 mmol) and stirred under nitrogen protection at 20° C. for 1 hour. The target compound was detected by liquid chromatography mass spectrometry. The reaction solution was concentrated under vacuum to give Compound 1J, which would be used directly for the next step. $^1$H NMR (400 MHz, METHANOL-d4) δ=8.83 (s, 1H), 8.67 (s, 1H), 7.65-7.51 (m, 3H), 7.35 (br t, J=8.1 Hz, 1H), 4.46 (brs, 2H), 4.23 (s, 4H), 4.17 (s, 3H), 3.76 (br d, J=5.3 Hz, 2H), 2.05 (br d, J=13.2 Hz, 2H), 1.87 (br t, J=5.8 Hz, 7H). LCMS (ESI) (5-95AB): m/z: 472.1 [M+1].

Compound 1

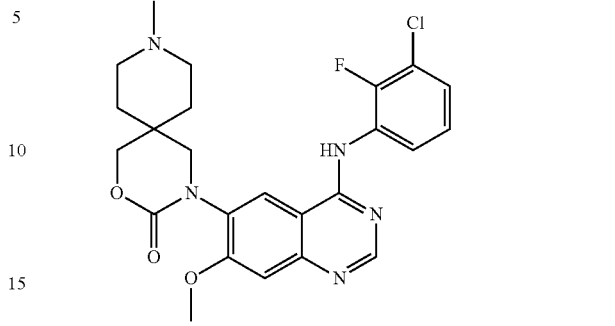

Compound 1J (77.29 mg, 131.91 mmol, trifluoroacetate) was dissolved in methanol (2.00 mL), added with sodium carbonate (13.98 mg, 131.91 mmol), stirred at 40° C. for 0.5 hours, then added with polyformaldehyde (47.53 mg, 527.64 mmol) stirred at 40° C. for 0.5 hours, the added with NaBH$_3$CN (33.16 mg, 527.64 mmol) and stirred at 40° C. for 1 hour. The target compound was detected by liquid chromatography mass spectrometry. The reaction mixture was filtered by DCM:MeOH=10:1 (22 mL), concentrated, separated and purified by high performance liquid chromatography, to give compound 1 finally. The purity was verified by high performance liquid chromatography and liquid chromatography mass spectrometry simultaneously. $^1$H NMR (400 MHz, METHANOL-d4) δ=8.46 (s, 1H), 8.32 (s, 1H), 7.58 (br t, J=7.0 Hz, 1H), 7.41 (t, J=6.7 Hz, 1H), 7.33 (s, 1H), 7.24 (t, J=8.0 Hz, 1H), 4.37 (br d, J=12.7 Hz, 2H), 4.04 (s, 3H), 3.66 (br d, J=15.8 Hz, 2H), 3.28-3.19 (m, 2H), 3.11 (br s, 2H), 2.78 (s, 3H), 1.94 (br d, J=6.0 Hz, 4H). LCMS (ESI) (5-95AB): m/z: 485.9 [M+1].

Example 2

Compound 2A

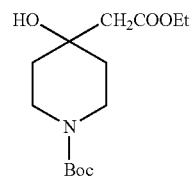

Lithium hexamethyldisilazide (1M, 60.23 mL) was added to tetrahydrofuran (60 mL) under nitrogen protection at −78° C., slowly added dropwise with ethyl acetate (5.84 g, 66.25 mL) under stirring, then added with 4-oxoperidine-1-formic acid tert-butyl ester (10.00 g, 50.19 mmol) dissolved in tetrahydrofuran (40 mL), and stirred at −78-0° C. for 10 hours. TLC showed that the reaction was mostly complete. The reaction solution was concentrated to about 60 mL, added with a saturated solution of ammonium chloride (80 mL), extracted with ethyl acetate (50 mL×3), and the combined organic phases were washed with a saturated solution of ammonium chloride (60 mL), dried over anhydrous sodium sulfate (5 g) and concentrated to give 2A. $^1$HNMR (400 MHz, deuterated chloroform) δ=4.22-4.13 (m, 2H), 3.81 (br. s., 1H), 3.71 (t, J=6.1 Hz, 2H), 3.19 (br. s., 2H), 2.45 (s, 2H), 1.70-1.61 (m, 2H), 1.51 (br. s., 2H), 1.44 (s, 9H), 1.27 (t, J=7.2 Hz, 3H).

Compound 2B

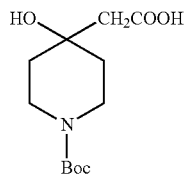

Compound 2A (5.00 g, 17.40 mmol) was dissolved in methanol (15.00 mL) at 25° C., added with sodium hydroxide solution (4 M, 17.40 mL) under stirring and stirred for 3 hours. TLC showed that the reaction was mostly complete. The reaction solution was concentrated, extracted with ethyl acetate (20 mL×2) to give the aqueous phase, which was adjusted to pH=6 with a hydrochloric acid solution (6 N, 20 mL), and extracted with ethyl acetate (20 mL×3). The combined organic phases were washed with a saturated solution of sodium chloride (25 mL), dried over anhydrous sodium sulfate (2 g), and concentrated to give compound 2B. $^1$H NMR (400 MHz, deuterated chloroform) δ=3.95-3.69 (m, 2H), 3.20 (br. s., 2H), 2.52 (s, 2H), 1.72 (d, J=12.8 Hz, 2H), 1.60-1.49 (m, 2H), 1.48-1.38 (m, 9H).

Compound 2C

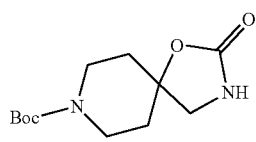

Compound 2B (2 g, 7.71 mmol) and diphenylphosphoryl azide (2.76 g, 10.02 mmol) were dissolved in toluene (30 mL), under nitrogen protection, added with triethylamine (10.95 g, 108.25 mmol), and stirred at 105° C. for 12 hours. TLC showed that the reaction was complete. The reaction solution was quenched with a saturated solution of sodium bicarbonate (30 mL), and extracted with ethyl acetate (20 mL×2). The combined organic phases were washed with a saturated solution of ammonium chloride (30 mL×3), dried over anhydrous sodium sulfate (2 g), concentrated, added with ethyl acetate (10 mL) under stirring, and then added with petroleum ether (30 mL) to precipitate a solid. The solid was filtered, and the filter cake was washed with petroleum ether (30 mL) and dried under vacuum to give compound 2C. $^1$H NMR (400 MHz, deuterated chloroform) δ=5.74 (br. s., 1H), 3.82 (br. s., 2H), 3.34-3.16 (m, 4H), 1.93 (d, J=13.3 Hz, 2H), 1.71-1.61 (m, 2H), 1.46 (s, 9H).

Compound 2D

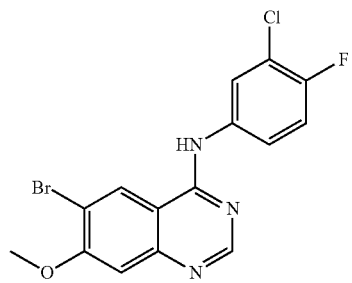 [SMILES: COc1cc2ncnc(Nc3ccc(F)c(Cl)c3)c2cc1Br]

N4-(3-chloro-4-fluorophenyl)-7-methoxyquinazolin-4,6-diamine (100.00 mg, 304.33 mmol) and isoamyl nitrite (71.31 mg, 608.67 mmol) were dissolved in acetonitrile (3.00 mL), then added with copper bromide (135.95 mg, 608.67 mmol), and stirred under nitrogen protection at 65° C. for 10 hours. The target compound was detected by liquid chromatography mass spectrometry and TLC showed that the raw materials were not completely consumed. The reaction mixture was filtered with DCM:MeOH=10:1 (22 mL), then concentrated, separated and purified by TLC (DCM:MeOH=12:1) to give compound 2D finally. $^1$H NMR (400 MHz, METHANOL-d4) δ=8.71 (s, 1H), 8.53 (br. s., 1H), 8.05 (d, J=4.5 Hz, 1H), 7.75-7.64 (m, 1H), 7.32-7.19 (m, 2H), 4.05 (s, 3H). LCMS (ESI) (5-95AB): m/z: 382.1 [M+1].

Compound 2E

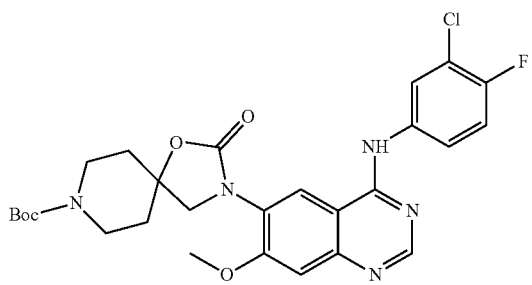 [SMILES: COc1cc2ncnc(Nc3ccc(F)c(Cl)c3)c2cc1N1CC2(CCN(C(=O)OC(C)(C)C)CC2)OC1=O]

According to the preparation method of compound 1I, 3-oxo-2-oxa-4,9-diazaspiro[5.5]undecane-9-formic acid tert-butyl ester was replaced with 2-oxo-1-oxa-3,8-diazaspiro[4.5]decane-8-formic acid tert-butyl ester, and 6-bromo-N-(3-chloro-2-fluorophenyl)-7-methoxyquinazolin-4-amine was replaced with 6-bromo-N-(3-chloro-4-fluorophenyl)-7-methoxyquinazolin-4-amine to give compound 2E. LCMS (ESI) (10-80CD): m/z: 558.2 [M+1].

Compound 2F

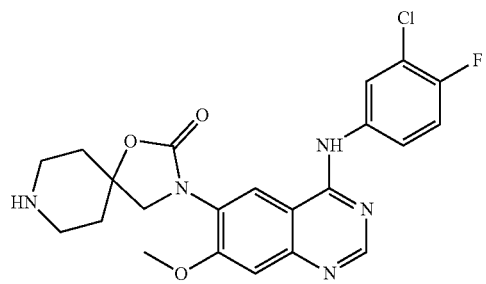 [SMILES: COc1cc2ncnc(Nc3ccc(F)c(Cl)c3)c2cc1N1CC2(CCNCC2)OC1=O]

According to the preparation method of compound 1J, 4-(4-((3-chloro-2-fluorophenyl)amino)-7-methoxyquinazolin-6-yl)-3-oxo-2-oxa-4,9-diazaspiro[5.5]undecane-9-carboxylic acid tert-butyl ester was replaced with 3-(4-((3-chloro-4-fluorophenyl)amino)-7-methoxyquinazolin-6-yl)-2-oxo-1-oxa-3,8-diazaspiro[4.5]decane-8-carboxylic acid tert-butyl ester to give compound 2F. The crude product would be used directly for the next step. LCMS (ESI) (5-95AB): m/z: 458.2 [M+1].

Compound 2

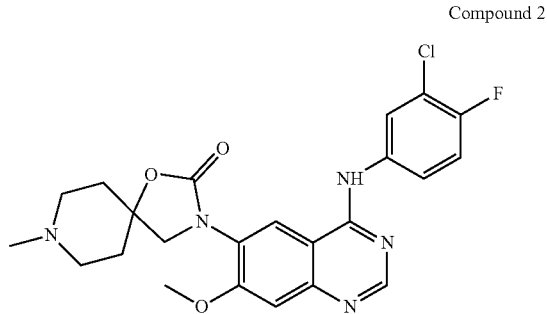 [SMILES: COc1cc2ncnc(Nc3ccc(F)c(Cl)c3)c2cc1N1CC2(CCN(C)CC2)OC1=O]

Compound 2

According to the preparation method of compound 1, (4-((3-chloro-2-fluorophenyl)amino)-7-methoxyquinazolin-6-yl)-2-oxa-4,9-diazaspiro[5.5]undecane-3-one was replaced with 3-(4-((3-chloro-4-fluorophenyl)amino)-7-methoxyquinazolin-6-yl)-1-oxa-3,8-diazaspiro[4.5]decane-2-one to give compound 2. The purity was verified by high performance liquid chromatography and liquid chromatography mass spectrometry simultaneously. $^1$H NMR (400 MHz, METHANOL-d4)=8.61-8.55 (m, 1H), 8.45 (s, 1H), 8.04 (dd, J=2.2, 6.5 Hz, 1H), 7.79-7.56 (m, 1H), 7.45-7.02 (m, 2H), 4.06 (s, 3H), 3.96 (s, 2H), 3.26 (d, J=11.0 Hz, 4H), 2.83 (s, 3H), 2.46-2.17 (m, 4H). LCMS (ESI) (5-95AB): m/z: 472.2 [M+1].

Example 3

Compound 3A

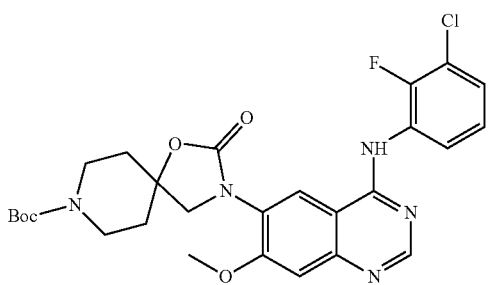 [SMILES: COc1cc2ncnc(Nc3cccc(Cl)c3F)c2cc1N1CC2(CCN(C(=O)OC(C)(C)C)CC2)OC1=O]

According to the preparation method of compound 1I, 3-oxo-2-oxa-4,9-diazaspiro[5.5]undecane-9-formic acid tert-butyl ester was replaced with 2-oxo-1-oxa-3,8-diazaspiro[4.5]decane-8-formic acid tert-butyl ester to give compound 3A. $^1$H NMR (400 MHz, DMSO-d$_6$)=8.72 (br. s., 1H), 8.44 (br. s., 1H), 7.58 (br. s., 1H), 7.47 (br. s., 2H), 7.31 (s, 2H), 3.98 (s, 3H), 3.82 (s, 2H), 3.63-3.50 (m, 4H), 1.87-1.69 (m, 4H), 1.41 (s, 9H). LCMS (ESI) (5-95AB): m/z: 558.2 [M+1].

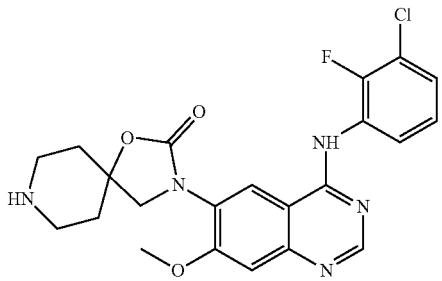 [SMILES: COc1cc2ncnc(Nc3cccc(Cl)c3F)c2cc1N1CC2(CCNCC2)OC1=O]

Compound 3B

According to the preparation method of compound 1J, 4-(4-((3-chloro-2-fluorophenyl)amino)-7-methoxyquinazolin-6-yl)-3-oxo-2-oxa-4,9-diazaspiro[5.5]undecane-9-carboxylic acid tert-butyl ester was replaced with 3-(4-((3-chloro-2-fluorophenyl)amino)-7-methoxyquinazolin-6-yl)-2-oxo-1-oxa-3,8-diazaspiro[4.5]decane-8-carboxylic acid tert-butyl ester to give compound 3B. The crude product would be used directly for the next step. $^1$H NMR (400 MHz, METHANOL-d4)=8.77 (s, 1H), 8.71 (s, 1H), 7.58-7.50 (m, 2H), 7.46 (s, 1H), 7.30 (dt, J=1.2, 8.1 Hz, 1H), 4.15 (s, 3H), 4.01 (s, 2H), 3.43-3.36 (m, 4H), 2.29-2.15 (m, 4H). LCMS (ESI) (5-95AB): m/z: 458.3 [M+1].

Example 3

Compound 3

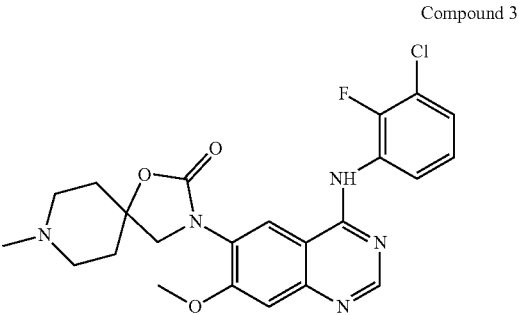 [SMILES: COc1cc2ncnc(Nc3cccc(Cl)c3F)c2cc1N1CC2(CCN(C)CC2)OC1=O]

Compound 3

According to the preparation method of compound 1, (4-((3-chloro-2-fluorophenyl)amino)-7-methoxyquinazolin-6-yl)-2-oxa-4,9-diazaspiro[5.5]undecane-3-one was replaced with 3-(4-((3-chloro-2-fluorophenyl)amino)-7-methoxyquinazolin-6-yl)-1-oxa-3,8-diazaspiro[4.5]decane-2-one to give compound 3. The purity was verified by high performance liquid chromatography and liquid chromatography mass spectrometry simultaneously. $^1$H NMR (400 MHz, METHANOL-d4)=8.46 (br. s., 1H), 8.41 (s, 1H), 7.61-7.53 (m, 1H), 7.46-7.37 (m, 1H), 7.32 (s, 1H), 7.23 (dt, J=1.2, 8.1 Hz, 1H), 4.06 (s, 3H), 3.94 (s, 2H), 3.35-3.32 (m, 2H), 3.25-3.17 (m, 2H), 2.80 (s, 3H), 2.38-2.30 (m, 2H), 2.26-2.16 (m, 2H). LCMS (ESI) (5-95AB): m/z: 472.1 [M+1].

Example 4

Compound 4A

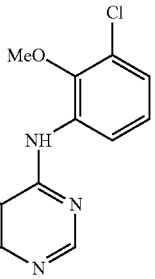

According to the preparation method of compound 1D, 3-chloro-2-fluoroaniline was replaced with 3-chloro-2-methoxyaniline to give compound 4A. $^1$H NMR (400 MHz, DMSO-d6) δ=9.76 (s, 1H), 8.89 (s, 1H), 8.44 (s, 1H), 7.48 (dd, J=1.4, 8.0 Hz, 1H), 7.41 (dd, J=1.5, 8.2 Hz, 1H), 7.31 (s, 1H), 7.23-7.14 (m, 1H), 4.02 (s, 3H), 3.67 (s, 3H). LCMS (ESI) (5-95AB): m/z: 394.0 [M+1].

Compound 4B

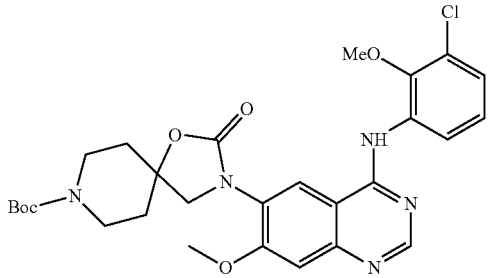 [SMILES: COc1cc2ncnc(Nc3cccc(Cl)c3OC)c2cc1N1CC2(CCN(C(=O)OC(C)(C)C)CC2)OC1=O]

According to the preparation method of compound 1I, 3-oxo-2-oxa-4,9-diazaspiro[5.5]undecane-9-formic acid tert-butyl ester was replaced with 2-oxo-1-oxa-3,8-diazaspiro[4.5]decane-8-formic acid tert-butyl ester, and 6-bromo-N-(3-chloro-2-fluorophenyl)-7-methoxyquinazolin-4-amine was replaced with 6-bromo-N-(3-chloro-2-methoxyphenyl)-7-methoxyquinazolin-4-amine to give compound 4B. ¹HNMR (400 MHz, METHANOL-d4) δ=8.44 (br. s., 2H), 7.70 (d, J=7.0 Hz, 1H), 7.34 (dd, J=1.4, 8.0 Hz, 2H), 7.17 (t, J=8.1 Hz, 1H), 4.59 (s, 2H), 4.05 (s, 3H), 3.89 (s, 2H), 3.88-3.82 (m, 2H), 3.79 (s, 3H), 2.08 (d, J=13.7 Hz, 2H), 1.95-1.87 (m, 2H), 1.49 (s, 9H). LCMS (ESI) (5-95AB): m/z: 570.4 [M+1].

Compound 4C

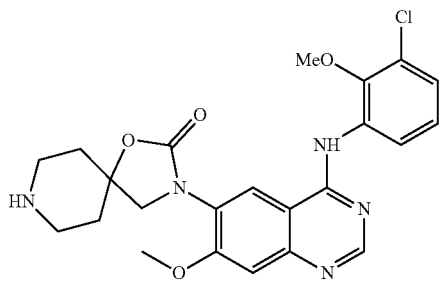 [SMILES: COc1cc2ncnc(Nc3cccc(Cl)c3OC)c2cc1N1CC2(CCNCC2)OC1=O]

According to the preparation method of compound 1J, 4-(4-((3-chloro-2-fluorophenyl)amino)-7-methoxyquinazolin-6-yl)-3-oxo-2-oxa-4,9-diazaspiro[5.5]undecane-9-carboxylic acid tert-butyl ester was replaced with 3-(4-((3-chloro-2-methoxyphenyl)amino)-7-methoxyquinazolin-6-yl)-2-oxo-1-oxa-3,8-diazaspiro[4.5]decane-8-carboxylic acid tert-butyl ester to give compound 4C. The crude product would be used directly for the next step. ¹H NMR (400 MHz, METHANOL-d4)=8.73 (s, 1H), 8.67 (s, 1H), 7.50 (ddd, J=1.5, 6.8, 8.2 Hz, 2H), 7.40 (s, 1H), 7.24 (t, J=8.1 Hz, 1H), 4.15 (s, 3H), 4.00 (s, 2H), 3.80 (s, 3H), 3.49-3.38 (m, 4H), 2.42-2.33 (m, 2H), 2.25-2.17 (m, 2H). LCMS (ESI) (5-95AB): m/z: 470.1 [M+1].

Compound 4

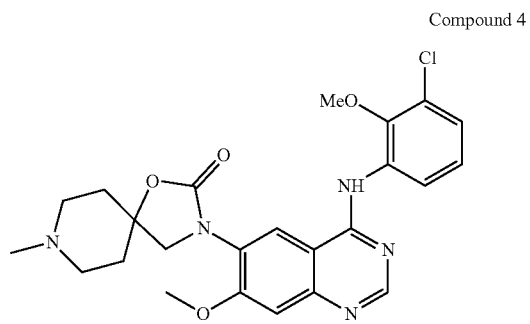 [SMILES: COc1cc2ncnc(Nc3cccc(Cl)c3OC)c2cc1N1CC2(CCN(C)CC2)OC1=O]

According to the preparation method of compound 1, (4-((3-chloro-2-fluorophenyl)amino)-7-methoxyquinazolin-6-yl)-2-oxa-4,9-diazaspiro[5.5]undecane-3-one was replaced with 3-(4-((3-chloro-2-methoxyphenyl)amino)-7-methoxyquinazolin-6-yl)-1-oxa-3,8-diazaspiro[4.5]decane-2-one to give compound 4. The purity was verified by high performance liquid chromatography and liquid chromatography mass spectrometry simultaneously. ¹H NMR (400 MHz, METHANOL-d4) δ=8.46 (br s, 2H), 7.72 (d, J=7.9 Hz, 1H), 7.42-7.28 (m, 2H), 7.21-7.14 (m, 1H), 4.06 (s, 3H), 3.94 (s, 2H), 3.79 (s, 3H), 3.26-3.07 (m, 4H), 2.73 (s, 3H), 2.38-2.26 (m, 2H), 2.24-2.10 (m, 2H). LCMS (ESI) (5-95AB): m/z: 484.1 [M+1].

Example 5

Compound 5

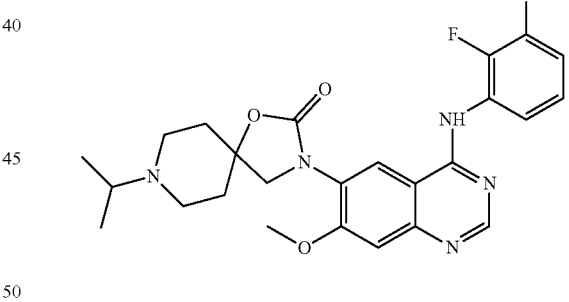

According to the preparation method of compound 1, (4-((3-chloro-2-fluorophenyl)amino)-7-methoxyquinazolin-6-yl)-2-oxa-4,9-diazaspiro[5.5]undecane-3-one was replaced with 3-(4-((3-chloro-2-methoxyphenyl)amino)-7-methoxyquinazolin-6-yl)-1-oxa-3,8-diazaspiro[4.5]decane-2-one, and polyformaldehyde was replaced with acetone to give compound 5. The purity was verified by high performance liquid chromatography and liquid chromatography mass spectrometry simultaneously. 1H NMR (400 MHz, METHANOL-d4) δ=8.45 (s, 1H), 8.41 (s, 1H), 7.62-7.54 (m, 1H), 7.40 (dt, J=1.4, 7.4 Hz, 1H), 7.32 (s, 1H), 7.22 (dt, J=1.4, 8.1 Hz, 1H), 4.06 (s, 3H), 3.95 (s, 2H), 3.59-3.51 (m, 1H), 3.50-3.40 (m, 2H), 3.40-3.32 (m, 2H), 2.48-2.36 (m, 2H), 2.34-2.22 (m, 2H), 1.39 (d, J=6.5 Hz, 6H). LCMS (ESI) (5-95AB): m/z: 500.1 [M+1].

Example 6

Compound 6A

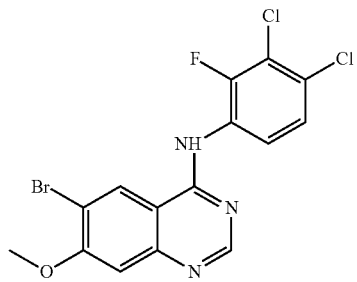 [SMILES: COc1cc2ncnc(Nc3ccc(Cl)c(Cl)c3F)c2cc1Br]

According to the preparation method of compound 1D, 3-chloro-2-fluoroaniline was replaced with 3,4-dichloro-2-fluoroaniline to give compound 6A. $^1$H NMR (400 MHz, METHANOL-d4) δ=8.65 (s, 1H), 8.46 (s, 1H), 7.59 (t, J=8.2 Hz, 1H), 7.44 (dd, J=1.7, 8.8 Hz, 1H), 7.26 (s, 1H), 4.06 (s, 3H). LCMS (ESI) (5-95AB): m/z: 415.9 [M+1].

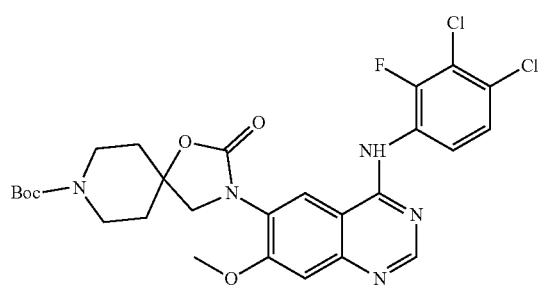 [SMILES: COc1cc2ncnc(Nc3ccc(Cl)c(Cl)c3F)c2cc1N1CC2(CCN(C(=O)OC(C)(C)C)CC2)OC1=O]

Compound 6B

According to the preparation method of compound 1I, 3-oxo-2-oxa-4,9-diazaspiro[5.5]undecane-9-formic acid tert-butyl ester was replaced with 2-oxo-1-oxa-3,8-diazaspiro[4.5]decane-8-formic acid tert-butyl ester, and 6-bromo-N-(3-chloro-2-fluorophenyl)-7-methoxyquinazolin-4-amine was replaced with 6-bromo-N-(3,4-dichloro-2-fluorophenyl)-7-methoxyquinazolin-4-amine to give compound 6B. LCMS (ESI) (5-95AB): m/z: 592.0 [M+1].

Compound 6C

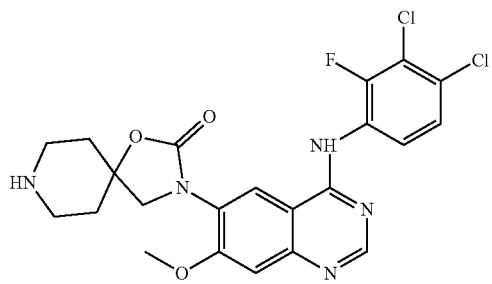 [SMILES: COc1cc2ncnc(Nc3ccc(Cl)c(Cl)c3F)c2cc1N1CC2(CCNCC2)OC1=O]

According to the preparation method of compound 1J, 4-(4-((3-chloro-2-fluorophenyl)amino)-7-methoxyquinazolin-6-yl)-3-oxo-2-oxa-4,9-diazaspiro[5.5]undecane-9-carboxylic acid tert-butyl ester was replaced with 3-(4-((3,4-dichloro-2-fluorophenyl)amino)-7-methoxyquinazolin-6-yl)-2-oxo-1-oxa-3,8-diazaspiro[4.5]decane-8-carboxylic acid tert-butyl ester to give compound 6C. The crude product would be used directly for the next step. LCMS (ESI) (5-95AB): m/z: 492.0 [M+1].

Compound 6

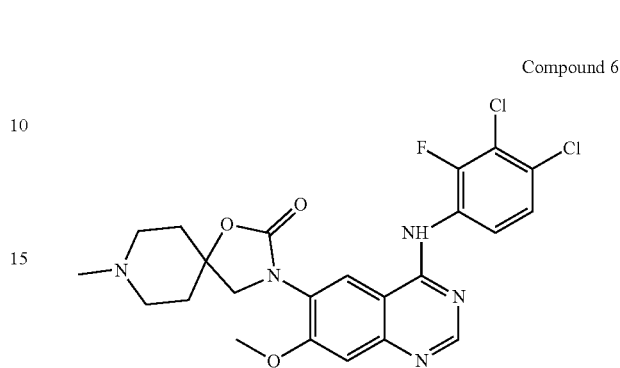

According to the preparation method of compound 1, (4-((3-chloro-2-fluorophenyl)amino)-7-methoxyquinazolin-6-yl)-2-oxa-4,9-diazaspiro[5.5]undecane-3-one was replaced with 3-(4-((3,4-dichloro-2-fluorophenyl)amino)-7-methoxyquinazolin-6-yl)-1-oxa-3,8-diazaspiro[4.5]decane-2-one to give compound 6. The purity was verified by high performance liquid chromatography and liquid chromatography mass spectrometry simultaneously. $^1$H NMR (400 MHz, METHANOL-d4) δ=8.47 (s, 1H), 8.39 (s, 1H), 7.61 (br t, J=8.3 Hz, 1H), 7.44 (dd, J=1.9, 8.8 Hz, 1H), 7.33 (s, 1H), 4.06 (s, 3H), 3.93 (s, 2H), 3.28-3.10 (m, 4H), 2.75 (s, 3H), 2.34-2.14 (m, 4H). LCMS (ESI) (5-95AB): m/z: 506.1 [M+1].

Example 7

Compound 7A

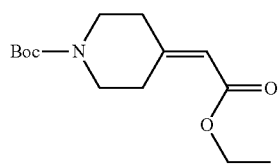

4-oxypiperidine-1-formic acid tert-butyl ester (10.00 g, 50.19 mmol) and ethyl 2-(diethoxyphosphoryl)acetate (11.25 g, 50.19 mmol) were dissolved in N, N-dimethylformamide (50.00 mL), then added with potassium carbonate (13.87 g, 100.38 mmol) and stirred under nitrogen protection at 80° C. for 2 hours. TLC showed that the reaction was complete. The reaction mixture was added with water (600 mL), extracted with ethyl acetate (100 mL×2), washed with saturated brine (100 mL×2), dried over anhydrous sodium sulfate (15 g), concentrated, separated and purified by column chromatography (PE:EA=20:1, 10:1) to give compound 7A. $^1$HNMR (400 MHz, deuterated chloroform) δ ppm 5.71 (s, 1H), 4.16 (q, J=7.15 Hz, 2H), 3.49 (dt, J=11.14, 5.79 Hz, 4H), 2.94 (t, J=5.58 Hz, 2H), 2.28 (t, J=5.65 Hz, 2H), 1.47 (s, 9H), 1.28 (t, J=7.09 Hz, 3H).

Compound 7B

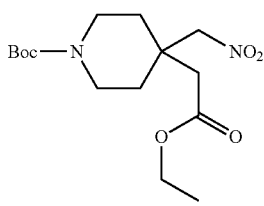 [SMILES: CCOC(=O)CC1(C[N+](=O)[O-])CCN(C(=O)OC(C)(C)C)CC1]

Potassium carbonate (256.57 mg, 1.86 mmol) and dimethyl sulfoxide (6 mL) were added to a 50 mL round-bottom flask, and the mixture was stirred and heated to 80° C. Compound 7A (1.00 g, 3.71 mmol) was then added and nitromethane (1.13 g, 18.56 mmol, 1.00 mL) was added slowly. The reaction mixture was stirred under nitrogen protection at 80° C. for 2 hours. TLC showed that the reaction was complete. The reaction liquid was cooled down to 28° C., poured into 100 mL water and extracted with ethyl acetate (30 mL×2). The organic phase was washed with saturated sodium chloride solution (30 mL×2), dried over anhydrous sodium sulfate (5.0 g), and concentrated to give compound 7B.

Compound 7C

The compound 4-(2-ethoxy-2-oxo-ethyl)-4-(nitromethyl) piperidine-1-formic acid tert-butyl ester (1.10 g, 3.15 mmol) was dissolved in methanol (10.00 mL). Raney nickel (1.00 g) was added to the solution, and after the removal of oxygen by vacuum, the gas in the reactor was displaced with hydrogen gas several times. The reaction liquid was stirred under hydrogen atmosphere (50 Psi) at 40° C. for 24 hours. TLC showed that the reaction was complete. The reaction solution was filtered through Celite, concentrated, separated and purified by column chromatography (silica gel, DCM: MeOH=10:1) to give compound 7C. $^1$H NMR (400 MHz, deuterated chloroform) δ ppm 5.78 (br s, 1H), 3.49-3.6 (m, 2H), 3.26-3.38 (m, 2H), 3.21 (s, 2H), 2.24 (s, 2H), 1.58-1.65 (m, 4H), 1.46 (s, 9H).

Compound 7D

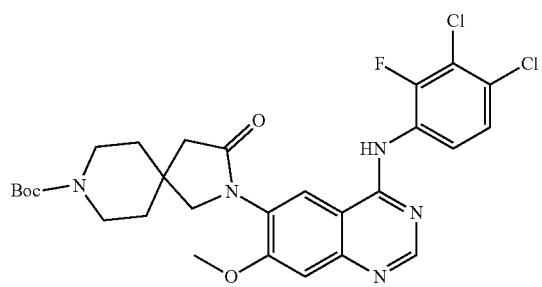 [SMILES: COc1cc2ncnc(Nc3ccc(Cl)c(Cl)c3F)c2cc1N1CC2(CCN(C(=O)OC(C)(C)C)CC2)CC1=O]

According to the preparation method of compound 1I, 3-oxo-2-oxa-4,9-diazaspiro[5.5]undecane-9-formic acid tert-butyl ester was replaced with 3-oxo-2,8-diazaspiro[4.5] decane-8-formic acid tert-butyl ester, and 6-bromo-N-(3-chloro-2-fluorophenyl)-7-methoxyquinazolin-4-amine was replaced with 6-bromo-N-(3,4-dichloro-2-fluorophenyl)-7-methoxyquinazolin-4-amine to give compound 7D. $^1$H NMR (400 MHz, deuterated chloroform) δ ppm 8.63 (br s, 1H), 8.18 (br s, 1H), 8.10 (br s, 1H), 7.94 (br s, 1H), 7.15 (br s, 1H), 3.88 (s, 3H), 3.71 (s, 2H), 3.50 (br s, 4H), 2.54 (s, 2H), 1.49 (s, 9H), 1.42-1.47 (m, 4H). LCMS (ESI) (5-95AB): m/z: 590.1 [M+1].

Compound 7E

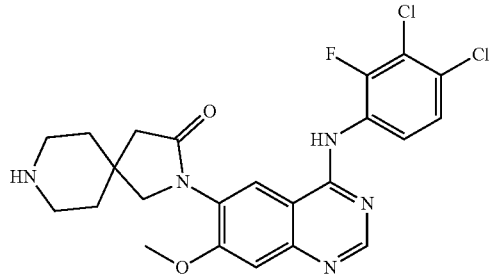 [SMILES: COc1cc2ncnc(Nc3ccc(Cl)c(Cl)c3F)c2cc1N1CC2(CCNCC2)CC1=O]

According to the preparation method of compound 1J, 4-(4-((3-chloro-2-fluorophenyl)amino)-7-methoxyquinazolin-6-yl)-3-oxo-2-oxa-4,9-diazaspiro[5.5]undecane-9-carboxylic acid tert-butyl ester was replaced with 2-(4-((3,4-dichloro-2-fluorophenyl)amino)-7-methoxyquinazolin-6-yl)-3-oxo-2,8-diazaspiro[4.5]decane-8-carboxylic acid tert-butyl ester to give compound 7E. The crude product would be used directly for the next step. LCMS (ESI) (5-95AB): m/z: 490.1 [M+1].

Compound 7

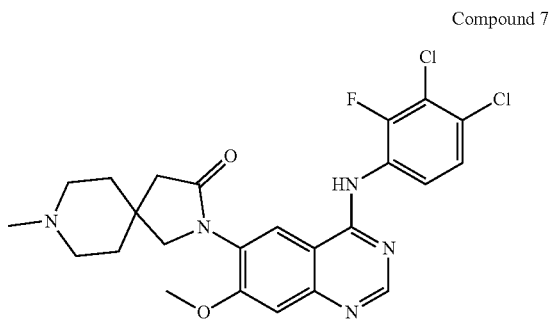 [SMILES: COc1cc2ncnc(Nc3ccc(Cl)c(Cl)c3F)c2cc1N1CC2(CCN(C)CC2)CC1=O]

According to the preparation method of compound 1, (4-((3-chloro-2-fluorophenyl)amino)-7-methoxyquinazolin-6-yl)-2-oxa-4,9-diazaspiro[5.5]undecane-3-one was replaced with 2-(4-((3,4-dichloro-2-fluorophenyl)amino)-7-methoxyquinazolin-6-yl)-2,8-diazaspiro[4.5]decane-2-one to give compound 7. The purity was verified by high performance liquid chromatography and liquid chromatography mass spectrometry simultaneously. $^1$H NMR (400 MHz, METHANOL-d4) δ ppm 8.46 (br s, 3H), 8.30 (s, 1H), 7.61 (br t, J=8.16 Hz, 1H), 7.45 (dd, J=8.85, 1.82 Hz, 1H), 7.33 (s, 1H), 4.03 (s, 3H), 3.80 (s, 2H), 3.15-3.29 (m, 3H), 2.84 (s, 3H), 2.57-2.69 (m, 2H), 2.08 (br s, 4H). LCMS (ESI) (5-95AB): m/z: 504.0 [M+1].

Example 8

Compound 8A

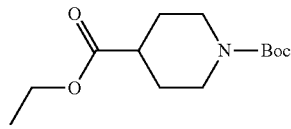 [SMILES: CCOC(=O)C1CCN(C(=O)OC(C)(C)C)CC1]

Ethyl 4-piperidinecarboxylate (5.00 g, 31.80 mmol) and diisopropylethylamine (8.22 g, 63.60 mmol) were dissolved in tetrahydrofuran (50.00 mL), then added with Boc$_2$O (6.94 g, 31.80 mmol) and stirred under nitrogen protection at 30° C. for 5 hours. TLC showed that the reaction was complete. After the reaction solution was concentrated, dichloride methane (30 mL) was added and washed twice with potassium carbonate solution (15 mL). The organic phase was dried over anhydrous sodium sulfate (1 g), concentrated, separated and purified by column chromatography (DCM:MeOH=20:1 to 10:1) to give compound 8A. $^1$H NMR (400 MHz, deuterated chloroform) δ=4.14 (q, J=7.1 Hz, 2H), 4.02 (d, J=8.9 Hz, 2H), 2.83 (t, J=11.7 Hz, 2H), 2.47-2.39 (m, 1H), 1.87 (d, J=10.9 Hz, 2H), 1.69-1.59 (m, 2H), 1.46 (s, 9H), 1.26 (t, J=7.2 Hz, 3H).

Compound 8B

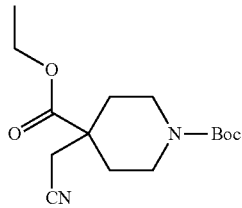 [SMILES: CCOC(=O)C1(CC#N)CCN(C(=O)OC(C)(C)C)CC1]

O1-tert-butyl O4-ethyl piperidine-1,4-dicarboxylate (4.00 g, 15.54 mmol) was dissolved in tetrahydrofuran (20 mL), then added with lithium diisopropylamide (2 M, 10.88 mL) under nitrogen protection at −65° C., and stirred at −65° C. for 1.5 hours. Then bromoacetonitrile (2.80 g, 23.32 mmol) diluted with tetrahydrofuran (5 mL) was added to the reaction solution, and the reaction mixture was stirred at −65° C. for 1.5 hours. Then the reaction mixture was stirred at 20° C. for 12 hours. TLC showed that new products appeared but the raw materials were not completely consumed. Ammonium chloride solution (50 mL) was added to the reaction solution and extracted four times with ethyl acetate (50 mL). The combined organic phases were dried over anhydrous sodium sulfate (3 g), concentrated, separated and purified by column chromatography (PE:EA=10:1 to 3:1) to give compound 8B. $^1$HNMR (400 MHz, deuterated chloroform) δ=4.26 (d, J=7.1 Hz, 2H), 3.83 (d, J=10.8 Hz, 2H), 3.08 (br. s., 2H), 2.60 (s, 2H), 2.23-2.11 (m, 2H), 1.60-1.52 (m, 2H), 1.46 (s, 9H), 1.32 (t, J=7.2 Hz, 3H).

Compound 8C

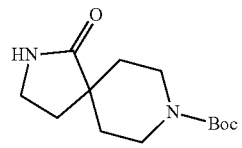

4-(Cyanomethyl)piperidine-1,4-dicarboxylic acid O1-tert-butyl O4-ethyl ester (1.80 g, 6.07 mmol) and ammonia water (2.00 mL) were dissolved in methanol (40.00 mL), then added with Raney nickel (1.80 g) in nitrogen atmosphere. The reaction system was vacuumed, displaced with nitrogen gas three times and with hydrogen gas three times. The reaction mixture was stirred under hydrogen atmosphere (50 psi) at 60° C. for 15 hours. TLC showed that new products appeared and the raw materials were completely consumed. The reaction solution was filtered with methanol (20 mL), concentrated, added with water (20 mL) and extracted with ethyl acetate (25 mL) three times. The combined organic phases were dried over anhydrous sodium sulfate (1 g) and concentrated to give compound 8C. $^1$HNMR (400 MHz, deuterated chloroform) δ=6.01 (br s, 1H), 3.99 (br s, 2H), 3.35 (t, J=6.8 Hz, 2H), 2.99 (br t, J=11.3 Hz, 2H), 2.13-2.01 (m, 2H), 1.91-1.79 (m, 2H), 1.46 (s, 11H).

Compound 8D

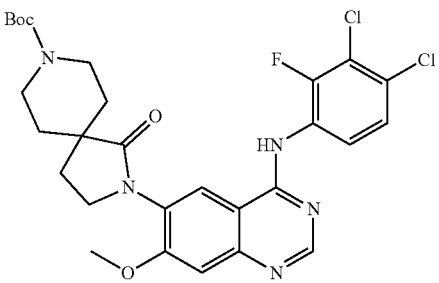 [SMILES: COc1cc2ncnc(Nc3ccc(Cl)c(Cl)c3F)c2cc1N1CCC2(CCN(C(=O)OC(C)(C)C)CC2)C1=O]

According to the preparation method of compound 1I, 3-oxo-2-oxa-4,9-diazaspiro[5.5]undecane-9-formic acid tert-butyl ester was replaced with 1-oxo-2,8-diazaspiro[4.5]decane-8-formic acid tert-butyl ester, and 6-bromo-N-(3-chloro-2-fluorophenyl)-7-methoxyquinazolin-4-amine was replaced with 6-bromo-N-(3,4-dichloro-2-fluorophenyl)-7-methoxyquinazolin-4-amine to give compound 8D. The crude produce would be used directly for the next step. LCMS (ESI) (5-95AB): m/z: 590.1 [M+1].

Compound 8E

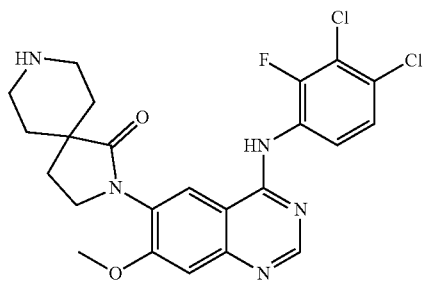

According to the preparation method of compound 1J, 4-(4-((3-chloro-2-fluorophenyl)amino)-7-methoxyquinazolin-6-yl)-3-oxo-2-oxa-4,9-diazaspiro[5.5]undecane-9-carboxylic acid tert-butyl ester was replaced with 2-(4-((3,4-dichloro-2-fluorophenyl)amino)-7-methoxyquinazolin-6-yl)-1-oxo-2,8-diazaspiro[4.5]decane-8-carboxylic acid tert-butyl ester to give compound 8E. The crude product would be used directly for the next step. LCMS (ESI) (5-95AB): m/z: 490.0 [M+1].

Compound 8

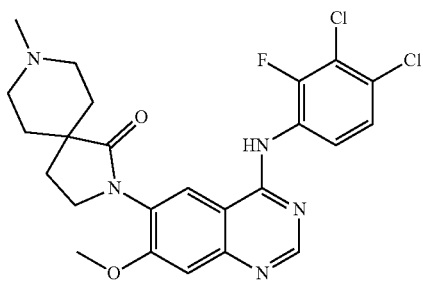 [SMILES: COc1cc2ncnc(Nc3ccc(Cl)c(Cl)c3F)c2cc1N1CCC2(CCNCC2)C1=O]

Compound 8

According to the preparation method of compound 1, (4-((3-chloro-2-fluorophenyl)amino)-7-methoxyquinazolin-6-yl)-2-oxa-4,9-diazaspiro[5.5]undecane-3-one was replaced with 2-(4-((3,4-dichloro-2-fluorophenyl)amino)-7-methoxyquinazolin-6-yl)-2,8-diazaspiro[4.5]decane-2-one to give compound 8. The purity was verified by high performance liquid chromatography and liquid chromatography mass spectrometry simultaneously. $^1$H NMR (400 MHz, METHANOL-d4) δ=8.47 (br s, 1H), 8.30 (s, 1H), 7.61 (br t, J=8.0 Hz, 1H), 7.45 (dd, J=1.9, 8.8 Hz, 1H), 7.33 (s, 1H), 4.02 (s, 3H), 3.87 (t, J=6.9 Hz, 2H), 3.53 (br dd, J=4.3, 11.6 Hz, 2H), 3.23-3.10 (m, 2H), 2.86 (s, 3H), 2.34-2.17 (m, 4H), 1.97 (br d, J=15.1 Hz, 2H). LCMS (ESI) (5-95AB): m/z: 504.1 [M+1].

Example 9

Compound 9A

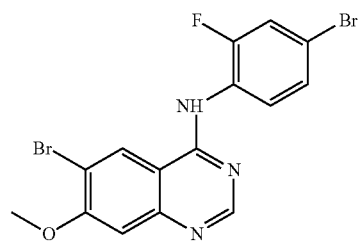 [SMILES: COc1cc2ncnc(Nc3ccc(Br)cc3F)c2cc1Br]

According to the preparation method of compound 1D, 3-chloro-2-fluoroaniline was replaced with 4-bromo-2-fluoroaniline to give 9A. $^1$HNMR (400 MHz, METHANOL-d4) δ=8.62 (s, 1H), 8.43 (s, 1H), 7.59 (t, J=8.3 Hz, 1H), 7.51-7.38 (m, 2H), 7.22 (s, 1H), 4.05 (s, 3H). LCMS (ESI) (5-95AB): m/z: 425.9 [M+1].

Compound 9B

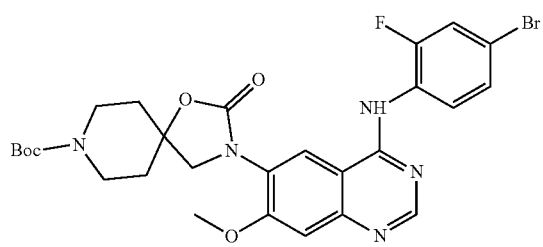 [SMILES: COc1cc2ncnc(Nc3ccc(Br)cc3F)c2cc1N1CC2(CCN(C(=O)OC(C)(C)C)CC2)OC1=O]

According to the preparation method of compound 1I, 3-oxo-2-oxa-4,9-diazaspiro[5.5]undecane-9-formic acid tert-butyl ester was replaced with 2-oxo-1-oxa-3,8-diazaspiro[4.5]decane-8-formic acid tert-butyl ester, and 6-bromo-N-(3-chloro-2-fluorophenyl)-7-methoxyquinazolin-4-amine was replaced with 6-bromo-N-(4-bromo-2-fluorophenyl)-7-methoxyquinazolin-4-amine to give compound 9B. LCMS (ESI) (5-95AB): m/z: 602.1 [M+1].

Compound 9C

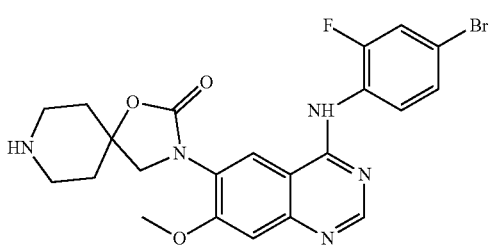 [SMILES: COc1cc2ncnc(Nc3ccc(Br)cc3F)c2cc1N1CC2(CCNCC2)OC1=O]

According to the preparation method of compound 1J, 4-(4-((3-chloro-2-fluorophenyl)amino)-7-methoxyquinazolin-6-yl)-3-oxo-2-oxa-4,9-diazaspiro[5.5]undecane-9-carboxylic acid tert-butyl ester was replaced with 3-(4-((4-bromo-2-fluorophenyl)amino)-7-methoxyquinazolin-6-yl)-2-oxo-1-oxa-3,8-diazaspiro[4.5]decane-8-carboxylic acid tert-butyl ester to give compound 9C. The crude product would be used directly for the next step. LCMS (ESI) (10-80CD): m/z: 502.1[M+1].

Compound 9

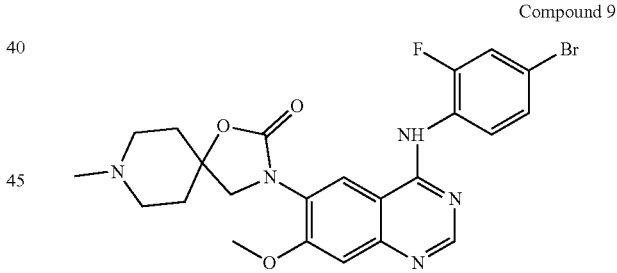

Compound 9

According to the preparation method of compound 1, (4-((3-chloro-2-fluorophenyl)amino)-7-methoxyquinazolin-6-yl)-2-oxa-4,9-diazaspiro[5.5]undecane-3-one was replaced with 3-(4-((4-bromo-2-fluorophenyl)amino)-7-methoxyquinazolin-6-yl)-1-oxa-3,8-diazaspiro[4.5]decane-2-one to give compound 9. The purity was verified by high performance liquid chromatography and liquid chromatography mass spectrometry simultaneously. $^1$H NMR (400 MHz, METHANOL-d4) δ=8.45 (s, 1H), 8.39 (s, 1H), 7.61 (t, J=8.3 Hz, 1H), 7.50-7.41 (m, 2H), 7.32 (s, 1H), 4.06 (s, 3H), 3.93 (s, 2H), 3.20 (br s, 2H), 3.14-3.07 (m, 2H), 2.73 (s, 3H), 2.35-2.26 (m, 2H), 2.22-2.11 (m, 2H). LCMS (ESI) (5-95AB): m/z: 516.0 [M+1].

Example 10

Compound 10A

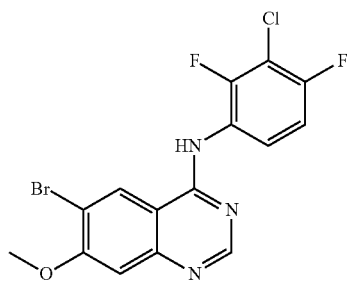 [SMILES: COc1cc2ncnc(Nc3ccc(F)c(Cl)c3F)c2cc1Br]

According to the preparation method of compound 1D, 3-chloro-2-fluoroaniline was replaced with 3-chloro-2,4-difluoroaniline to give compound 10A. $^1$H NMR (400 MHz, METHANOL-d4) δ=8.63 (s, 1H), 8.43 (s, 1H), 7.54 (dt, J=5.6, 8.6 Hz, 1H), 7.25 (s, 1H), 7.20 (dt, J=2.0, 8.8 Hz, 1H), 4.06 (s, 3H). LCMS (ESI) (5-95AB): m/z: 399.9 [M+1].

Compound 10B

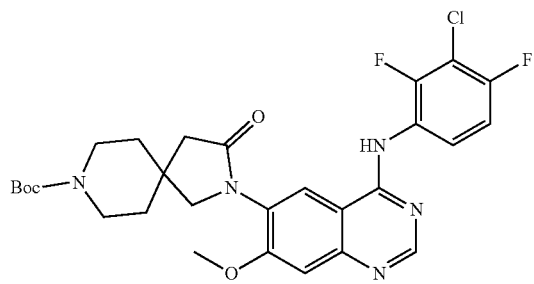 [SMILES: COc1cc2ncnc(Nc3ccc(F)c(Cl)c3F)c2cc1N1CC2(CCN(C(=O)OC(C)(C)C)CC2)CC1=O]

According to the preparation method of compound 1I, 3-oxo-2-oxa-4,9-diazaspiro[5.5]undecane-9-formic acid tert-butyl ester was replaced with 3-oxo-3,8-diazaspiro[4.5]decane-8-formic acid tert-butyl ester, and 6-bromo-N-(3-chloro-2-fluorophenyl)-7-methoxyquinazolin-4-amine was replaced with 6-bromo-N-(3-chloro-2,4-difluorophenyl)-7-methoxyquinazolin-4-amine to give compound 10B. $^1$H NMR (400 MHz, METHANOL-d4) δ=8.43 (br s, 1H), 8.38 (s, 1H), 7.59-7.49 (m, 1H), 7.31 (s, 1H), 7.25-7.16 (m, 1H), 4.06 (s, 3H), 3.88 (s, 2H), 2.07 (br d, J=13.6 Hz, 2H), 1.97-1.85 (m, 4H), 1.81-1.67 (m, 2H), 1.48 (s, 9H).

Compound 10C

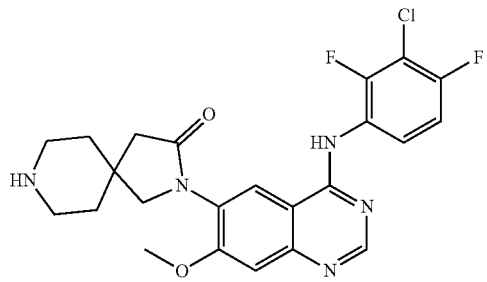 [SMILES: COc1cc2ncnc(Nc3ccc(F)c(Cl)c3F)c2cc1N1CC2(CCNCC2)CC1=O]

According to the preparation method of compound 1J, 4-(4-((3-chloro-2-fluorophenyl)amino)-7-methoxyquinazolin-6-yl)-3-oxo-2-oxa-4,9-diazaspiro[5.5]undecane-9-carboxylic acid tert-butyl ester was replaced with 2-(4-((3-chloro-2,4-difluorophenyl)amino)-7-methoxyquinazolin-6-yl)-3-oxo-2,8-diazaspiro[4.5]decane-8-carboxylic acid tert-butyl ester to give compound 10C. The crude product would be used directly for the next step. $^1$HNMR (400 MHz, METHANOL-d4) δ=8.79 (br s, 1H), 8.64 (s, 1H), 7.62-7.52 (m, 1H), 7.43 (s, 1H), 7.29 (dt, J=1.9, 8.8 Hz, 1H), 4.15 (s, 3H), 4.00 (s, 2H), 2.37 (br d, J=14.1 Hz, 2H), 2.28-2.15 (m, 4H), 2.05-1.96 (m, 2H). LCMS (ESI) (5-95AB): m/z: 475.9 [M+1].

Compound 10

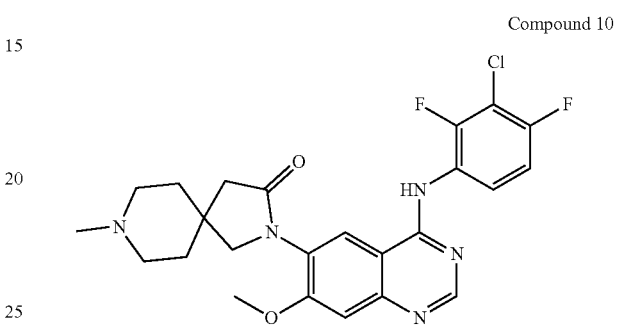

According to the preparation method of compound 1, (4-((3-chloro-2-fluorophenyl)amino)-7-methoxyquinazolin-6-yl)-2-oxa-4,9-diazaspiro[5.5]undecane-3-one was replaced with 2-(4-((3-chloro-2,4-difluorophenyl)amino)-7-methoxyquinazolin-6-yl)-2,8-diazaspiro[4.5]decane-3-one to give compound 10. The purity was verified by high performance liquid chromatography and liquid chromatography mass spectrometry simultaneously. $^1$H NMR (400 MHz, METHANOL-d4) δ=8.46 (br s, 1H), 8.40 (s, 1H), 7.54 (dt, J=5.7, 8.6 Hz, 1H), 7.33 (br s, 1H), 7.20 (dt, J=1.9, 8.8 Hz, 1H), 4.06 (s, 3H), 3.93 (s, 2H), 3.26 (br s, 2H), 3.20-3.12 (m, 2H), 2.76 (s, 3H), 2.37-2.27 (m, 2H), 2.26-2.15 (m, 2H). LCMS (ESI) (5-95AB): m/z: 490.0 [M+1].

Example 11

Compound 11A

Acetonitrile (2.06 g, 50.18 mmol) was added to tetrahydrofuran (30.00 mL); added dropwise with n-butyl lithium (2.5 M, 20.07 mL) at −78° C. and under nitrogen protection, and stirred at −78° C. for 1 hour. 4-oxoperidine-1-formic acid tert-butyl ester (5.00 g, 25.09 mmol) was added to the reaction solution under nitrogen protection at −78-25° C., and the reaction mixture was stirred at −78-25° C. for 9 hours. TLC showed that new products appeared but the raw materials were not completely consumed. The reaction solution was concentrated, added with ethyl acetate (10 mL) and water (20 mL), and then extracted with ethyl acetate (20 mL) three times. The combined organic phases were dried over anhydrous sodium sulfate (5 g), concentrated, separated and purified by column chromatography (PE:EA=5:1 to 2:1) to give compound 11A. $^1$H NMR (400 MHz, deuterated chloroform) δ=3.91 (br s, 2H), 3.15 (br t, J=11.6 Hz, 2H), 2.54 (s, 2H), 1.77-1.70 (m, 2H), 1.67-1.60 (m, 2H), 1.46 (s, 9H).

Compound 11B

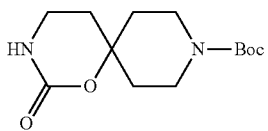

4-(Cyanomethyl)-4-hydroxy-piperidine-1-formic acid tert-butyl ester (800.00 mg, 3.33 mmol) was dissolved in methanol (20 mL), added with Boc$_2$O (2.91 g, 13.32 mmol) and then added with Raney nickel (0.1 g). The reaction system was vacuumed, displaced with nitrogen gas three times and with hydrogen gas three times. The reaction mixture was stirred under hydrogen atmosphere (50 psi) at 40° C. for 10 hours. TLC showed that new products appeared and the raw materials were completely consumed. The reaction solution was filtered with methanol (20 mL), concentrated, separated and purified by column chromatography (PE:EA=5:1 to 2:1) to give compound 11B. $^1$H NMR (400 MHz, deuterated chloroform) δ=4.92 (br s, 1H), 3.79 (br s, 2H), 3.30 (q, J=6.4 Hz, 2H), 3.18 (br t, J=11.4 Hz, 2H), 1.65-1.57 (m, 4H), 1.52 (br dd, J=4.4, 11.4 Hz, 2H), 1.44 (s, 9H).

Compound 11C

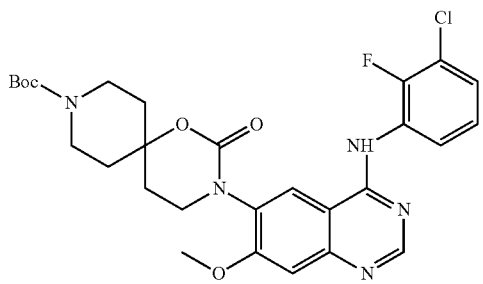 [SMILES: COc1cc2ncnc(Nc3cccc(Cl)c3F)c2cc1N1CCC2(CCN(C(=O)OC(C)(C)C)CC2)OC1=O]

According to the preparation method of compound 1I, 3-oxo-2-oxa-4,9-diazaspiro[5.5]undecane-9-formic acid tert-butyl ester was replaced with 2-oxo-1-oxa-3,9-diazaspiro[5.5]undecane-9-formic acid tert-butyl ester to give compound 11C. $^1$H NMR (400 MHz, METHANOL-d4) δ=8.46 (br s, 1H), 8.36 (br s, 1H), 7.59 (br s, 1H), 7.40 (br t, J=7.2 Hz, 1H), 7.31 (br s, 1H), 7.22 (br t, J=7.8 Hz, 1H), 4.03 (s, 3H), 3.95 (br d, J=13.3 Hz, 2H), 3.88-3.82 (m, 2H), 3.77-3.70 (m, 2H), 1.89-1.82 (m, 4H), 1.68-1.61 (m, 2H), 1.46 (s, 9H). LCMS (ESI) (5-95AB): m/z: 572.1 [M+1].

Compound 11D

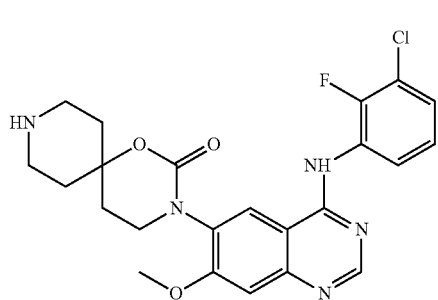 [SMILES: COc1cc2ncnc(Nc3cccc(Cl)c3F)c2cc1N1CCC2(CCNCC2)OC1=O]

According to the preparation method of compound 1J, 4-(4-((3-chloro-2-fluorophenyl)amino)-7-methoxyquinazolin-6-yl)-3-oxo-2-oxa-4,9-diazaspiro[5.5]undecane-9-carboxylic acid tert-butyl ester was replaced with 3-(4-((3-chloro-2-fluorophenyl)amino)-7-methoxyquinazolin-6-yl)-2-oxo-1-oxa-3,9-diazaspiro[5.5]undecane-9-carboxylic acid tert-butyl ester to give compound 11D. The crude product would be used directly for the next step. $^1$H NMR (400 MHz, METHANOL-d4) δ=8.78 (br s, 1H), 8.70 (br s, 1H), 7.51 (br t, J=7.0 Hz, 3H), 7.32-7.23 (m, 1H), 4.10 (s, 3H), 3.78 (br t, J=5.6 Hz, 2H), 3.44 (br s, 2H), 2.29 (br d, J=7.5 Hz, 2H), 2.18-2.08 (m, 4H), 1.95 (br t, J=6.1 Hz, 2H). LCMS (ESI) (5-95AB): m/z: 472.1 [M+1].

Compound 11

Compound 11

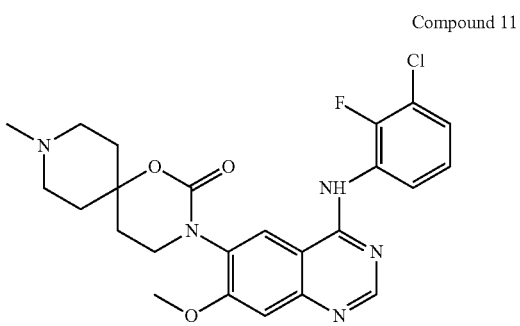 [SMILES: COc1cc2ncnc(Nc3cccc(Cl)c3F)c2cc1N1CCC2(CCN(C)CC2)OC1=O]

According to the preparation method of compound 1, (4-((3-chloro-2-fluorophenyl)amino)-7-methoxyquinazolin-6-yl)-2-oxa-4,9-diazaspiro[5.5]undecane-3-one was replaced with 3-(4-((3-chloro-2-fluorophenyl)amino)-7-methoxyquinazolin-6-yl)-1-oxa-3,9-diazaspiro[4.5]undecane-2-one to give compound 11. The purity was verified by high performance liquid chromatography and liquid chromatography mass spectrometry simultaneously. $^1$HNMR (400 MHz, METHANOL-d4) δ=8.46 (s, 1H), 8.36 (s, 1H), 7.64-7.54 (m, 1H), 7.41 (ddd, J=1.6, 6.7, 8.2 Hz, 1H), 7.33 (s, 1H), 7.27-7.19 (m, 1H), 4.03 (s, 3H), 3.76 (br s, 2H), 3.40 (br s, 2H), 3.30-3.17 (m, 2H), 2.86 (s, 3H), 2.26 (br s, 4H), 2.19-2.06 (m, 2H). LCMS (ESI) (5-95AB): m/z: 486.1 [M+1].

Example 12

Compound 12A

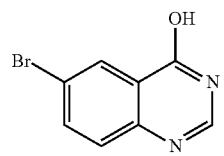 [SMILES: Oc1ncnc2ccc(Br)cc12]

According to the preparation method of compound 1B, 2-amino-5-bromo-4-methoxybenzoic acid was replaced with 2-amino-5-bromo-benzoic acid to give compound 12A. $^1$H NMR (400 MHz, DMSO-d6) δ=8.19 (d, J=2.3 Hz, 1H), 8.15-8.11 (s, 1H), 7.95 (dd, J=2.4, 8.7 Hz, 1H), 7.62 (d, J=8.7 Hz, 1H).

Compound 12B

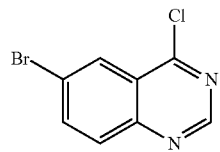

According to the preparation method of compound 1C, 6-bromo-7-methoxyquinazolin-4-ol was replaced with 6-bromo-quinazolin-4-ol to give compound 12B. The crude product would be used directly for the next step. LCMS (ESI) (5-95AB): m/z: 242.9 [M+1].

Compound 12C

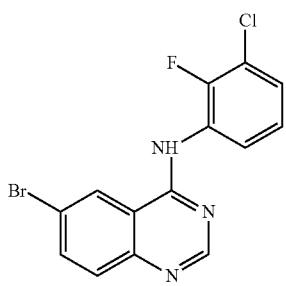 [SMILES: Fc1c(Cl)cccc1Nc1ncnc2ccc(Br)cc12]

According to the preparation method of compound 1D, 6-bromo-4-chloro-7-methoxyquinazoline was replaced with 6-bromo-4-chloroquinazoline to give 12C. $^1$H NMR (400 MHz, METHANOL-d4) δ=8.62 (d, J=2.0 Hz, 1H), 8.51 (s, 1H), 8.00 (dd, J=2.1, 8.9 Hz, 1H), 7.74 (d, J=8.9 Hz, 1H), 7.62-7.52 (m, 1H), 7.47-7.39 (m, 1H), 7.28-7.21 (m, 1H). LCMS (ESI) (5-95AB): m/z: 351.9.

Compound 12D

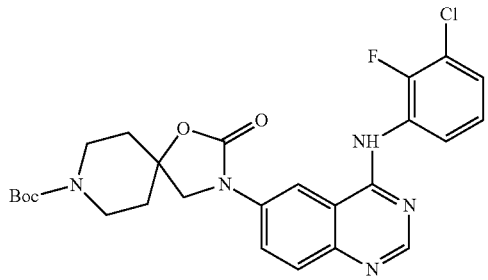 [SMILES: CC(C)(C)OC(=O)N1CCC2(CC1)CN(c1ccc3ncnc(Nc4cccc(Cl)c4F)c3c1)C(=O)O2]

According to the preparation method of compound 1I, 3-oxo-2-oxa-4,9-diazaspiro[5.5]undecane-9-formic acid tert-butyl ester was replaced with 2-oxo-1-oxa-3,8-diazaspiro[4.5]decane-8-formic acid tert-butyl ester, and 6-bromo-N-(3-chloro-2-fluorophenyl)-7-methoxyquinazolin-4-amine was replaced with 6-bromo-N-(3-chloro-2,4-difluorophenyl)quinazolin-4-amine to give compound 12D. $^1$H NMR (400 MHz, METHANOL-d4) δ=8.50-8.34 (m, 2H), 8.14 (d, J=1.8 Hz, 1H), 7.79 (br d, J=9.2 Hz, 1H), 7.59 (br s, 1H), 7.40 (br t, J=7.2 Hz, 1H), 7.28-7.19 (m, 1H), 4.04 (s, 2H), 3.83-3.73 (m, 4H), 1.92-1.86 (m, 4H), 1.48 (s, 9H). LCMS (ESI) (5-95AB): m/z: 528.1 [M+1].

Compound 12E

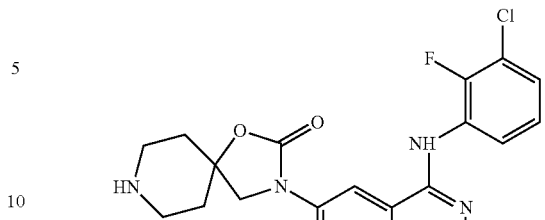

According to the preparation method of compound 1J, 4-(4-((3-chloro-2-fluorophenyl)amino)-7-methoxyquinazolin-6-yl)-3-oxo-2-oxa-4,9-diazaspiro[5.5]undecane-9-carboxylic acid tert-butyl ester was replaced with 3-(4-((3-chloro-2-fluorophenyl)amino)-quinazolin-6-yl)-2-oxo-1-oxa-3,8-diazaspiro[4.5]decane-8-carboxylic acid tert-butyl ester to give compound 12E. The crude product would be used directly for the next step. $^1$H NMR (400 MHz, METHANOL-d4) δ=8.81 (s, 1H), 8.76 (dd, J=2.4, 9.3 Hz, 1H), 8.50 (d, J=2.3 Hz, 1H), 7.99 (d, J=9.3 Hz, 1H), 7.58 (dddd, J=1.6, 6.7, 8.1, 16.0 Hz, 2H), 7.35 (dt, J=1.4, 8.1 Hz, 1H), 4.19 (s, 2H), 3.42-3.37 (m, 4H), 2.28-2.19 (m, 4H). LCMS (ESI) (5-95AB): m/z: 428.1 [M+1].

Compound 12

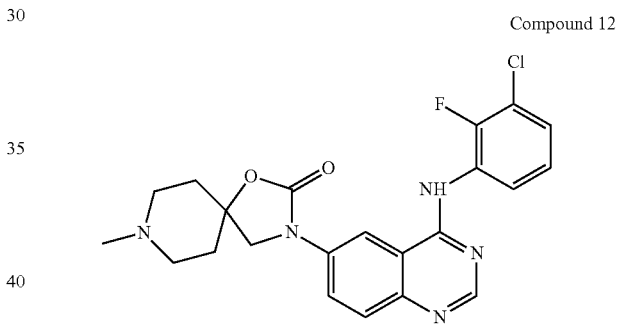

According to the preparation method of compound 1, (4-((3-chloro-2-fluorophenyl)amino)-7-methoxyquinazolin-6-yl)-2-oxa-4,9-diazaspiro[5.5]undecane-3-one was replaced with 3-(4-((3-chloro-2-fluorophenyl)amino)-quinazolin-6-yl)-1-oxa-3,8-diazaspiro[4.5]decane-2-one to give compound 12. The purity was verified by high performance liquid chromatography and liquid chromatography mass spectrometry simultaneously. $^1$H NMR (400 MHz, METHANOL-d4) δ=8.43 (s, 1H), 8.41 (br d, J=2.3 Hz, 1H), 8.18 (d, J=2.2 Hz, 1H), 7.83 (d, J=9.2 Hz, 1H), 7.62-7.53 (m, 1H), 7.47-7.37 (m, 1H), 7.24 (dt, J=1.2, 8.1 Hz, 1H), 4.12 (s, 2H), 3.40 (br d, J=12.0 Hz, 2H), 3.30-3.18 (m, 2H), 2.85 (s, 3H), 2.37-2.17 (m, 4H). LCMS (ESI) (5-95AB): m/z: 442.1 [M+1].

Example 13

Compound 13A

3-Oxoazetidin-1-carboxylic acid tert-butyl ester (9.00 g, 52.57 mmol) was dissolved in ethanol (30.00 mL) at 20° C., and added with nitromethane (33.90 g, 555.37 mmol) and triethylamine (730.00 mg, 7.21 mmol). The mixture was stirred at 20° C. for 16 hours. TLC (PE:EA=5:1) showed that the reaction was complete. The reaction mixture was concentrated under vacuum to give compound 13A. $^1$HNMR (400 MHz, DMSO-d6) δ=6.44 (s, 1H), 4.86 (s, 2H), 4.04 (br d, J=8.9 Hz, 2H), 3.74 (br d, J=9.2 Hz, 2H), 1.38 (s, 9H).

Compound 13B

3-Hydroxy-3-(nitromethyl)azetidin-1-carboxylic acid tert-butyl ester (6.00 g, 25.84 mmol) was dissolved in methanol (60.00 mL) at 20° C., and added with wet palladium on carbon (10%, 0.6 g) under nitrogen protection. The suspension was degassed, displaced, and purified with hydrogen gas four times, and then stirred under hydrogen atmosphere (15 psi) at 20° C. for 16 hours. TLC (petroleum ether:ethyl acetate=): 1) showed that the reaction was complete. The reaction mixture was filtered and concentrated under vacuum to give compound 13B. $^1$H NMR (400 MHz, DMSO-d6) δ=5.55 (br s, 1H), 3.87 (br d, J=7.9 Hz, 1H), 3.73 (br d, J=7.8 Hz, 1H), 3.63-3.51 (m, 2H), 2.90 (s, 1H), 2.59 (s, 1H), 1.36 (s, 9H).

Compound 13C

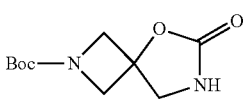

3-(Aminomethyl)-3-hydroxy-azetidin-1-carboxylic acid tert-butyl ester (2.00 g, 9.89 mmol) was dissolved in dichloromethane (40.00 mL) at 20° C., added with triethylamine (3.00 g, 29.67 mmol) and triphosgene (3.23 g, 10.88 mmol), and then stirred for 3 hours. TLC (DCM:MeOH=10:1) showed that the reaction was complete. The reaction was quenched with saturated ammonium chloride solution (60 mL) and stirred for 10 minutes. The aqueous phase was separated, and the organic phase was washed with water (2*60 mL). The combined water phases were extracted with dichloromethane (3*30 mL). The combined organic phases were dried over anhydrous sodium sulfate (20 g), filtered and concentrated under vacuum. The residue was separated and purified by column chromatography (silica gel, dichloromethane/methanol=100/1 to 50/1) to give compound 13C. $^1$H NMR (400 MHz, deuterated chloroform) δ=4.38-4.22 (m, 2H), 4.11-3.98 (m, 2H), 3.84-3.58 (m, 2H), 1.68 (br s, 1H), 1.47 (s, 9H).

Compound 13D

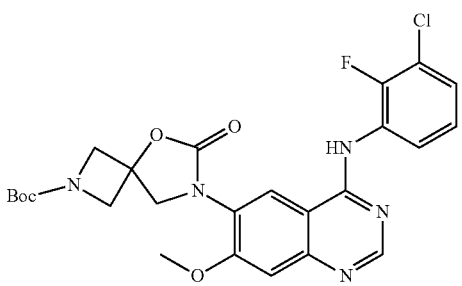 [SMILES: COc1cc2ncnc(Nc3cccc(Cl)c3F)c2cc1N1CC2(CN(C(=O)OC(C)(C)C)C2)OC1=O]

According to the preparation method of compound 1I, 3-oxo-2-oxa-4,9-diazaspiro[5.5]undecane-9-formic acid tert-butyl ester was replaced with 6-oxo-5-oxa-2,7-diazaspiro[3.4]octane-2-carboxylic acid tert-butyl ester to give compound 13D. LCMS (ESI) (5-95AB): m/z:530.0 [M+1].

Compound 13E

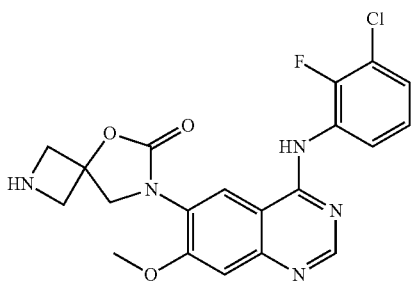 [SMILES: COc1cc2ncnc(Nc3cccc(Cl)c3F)c2cc1N1CC2(CNC2)OC1=O]

According to the preparation method of compound 1J, 4-(4-((3-chloro-2-fluorophenyl)amino)-7-methoxyquinazolin-6-yl)-3-oxo-2-oxa-4,9-diazaspiro[5.5]undecane-9-carboxylic acid tert-butyl ester was replaced with 7-(4-((3-chloro-2-fluorophenyl)amino)-7-methoxyquinazolin-6-yl)-6-oxo-5-oxa-2,7-diazaspiro[3.4]octane-2-carboxylic acid tert-butyl ester to give compound 13E. The crude product would be used directly for the next step.

Compound 13

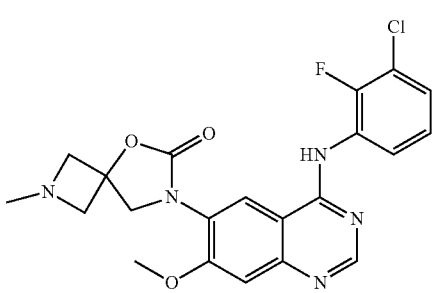

According to the preparation method of compound 1, (4-((3-chloro-2-fluorophenyl)amino)-7-methoxyquinazolin-6-yl)-2-oxa-4,9-diazaspiro[5.5]undecane-3-one was replaced with 7-(4-((3-chloro-2-fluorophenyl)amino)-7-methoxyquinazolin-6-yl)-5-oxa-2,7-diazaspiro[3.4]octane-6-one to give compound 13. The purity was verified by high performance liquid chromatography and liquid chromatography mass spectrometry simultaneously. $^1$H NMR (400

MHz, DMSO-d6) δ=9.91 (br s, 1H), 8.47 (s, 2H), 8.21 (s, 1H), 7.49 (br t, J=7.2 Hz, 2H), 7.34 (s, 1H), 7.31-7.23 (m, 1H), 4.19 (s, 2H), 3.99 (s, 3H), 3.55-3.54 (m, 2H), 3.40 (br d, J=8.8 Hz, 3H), 2.31 (s, 3H). LCMS (ESI) (5-95CD): m/z:444.0 [M+1].

Example 14

Compound 14A

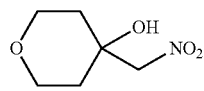

According to the preparation method of compound 13A, 3-oxoazetidin-1-carboxylic acid tert-butyl ester was replaced with tetrahydropyran-4-one to give compound 14A. $^1$H NMR (400 MHz, deuterated chloroform) δ ppm 4.45 (s, 2H), 3.82 (t, J=2.6 Hz, 2H), 3.80 (d, J=2.6 Hz, 2H), 2.76-3.20 (m, 1H), 1.71-1.82 (m, 2H), 1.59-1.67 (m, 2H).

Compound 14B

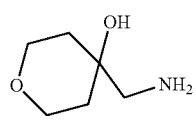

According to the preparation method of compound 13B, 3-hydroxy-3-(nitromethyl)azetidin-1-carboxylic acid tert-butyl ester was replaced with 4-(nitromethyl)tetrahydro-2H-pyran-4-ol to give compound 14B. $^1$H NMR (400 MHz, deuterated chloroform) δ ppm 3.75-3.82 (m, 4H), 3.48 (s, 1H), 3.00 (s, 1H), 2.63 (s, 2H), 1.53-1.60 (m, 2H), 1.45-1.51 (m, 2H).

Compound 14C

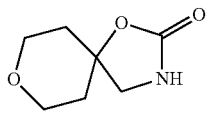 [SMILES: O=C1NCC2(CCOCC2)O1]

According to the preparation method of compound 13C, 3-(aminomethyl)-3-hydroxy-azetidin-1-carboxylic acid tert-butyl ester was replaced with 4-(aminomethyl)tetrahydro-2H-pyran-4-ol to give compound 14C. $^1$H NMR (400 MHz, deuterated chloroform) δ ppm 3.71-3.94 (m, 7H), 1.83-2.04 (m, 3H), 1.83-2.04 (m, 1H).

Compound 14

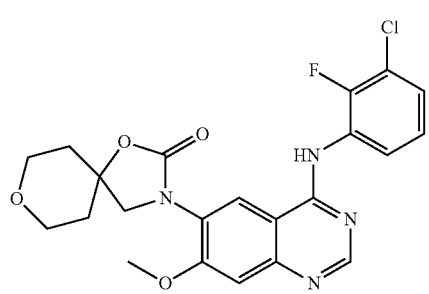

According to the preparation method of compound 1I, 3-oxo-2-oxa-4,9-diazaspiro[5.5]undecane-9-formic acid tert-butyl ester was replaced with 1,8-dioxa-3-azaspiro[4.5]decane-2-one to give compound 14. $^1$HNMR (400 MHz, deuterated chloroform) δ ppm 8.72 (s, 1H), 8.24-8.34 (m, 1H), 8.06 (s, 1H), 7.62 (br s, 1H), 7.30 (s, 1H), 7.10-7.22 (m, 2H), 4.00 (s, 3H), 3.95 (br d, J=9.9 Hz, 2H), 3.83-3.90 (m, 4H), 2.13 (br d, J=13.8 Hz, 2H), 1.95-2.02 (m, 2H). LCMS (ESI) (5-95AB): m/z: 459.0 [M+1].

Example 15

Compound 15A

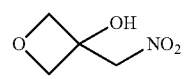

According to the preparation method of compound 13A, 3-oxoazetidin-1-carboxylic acid tert-butyl ester was replaced with oxetan-3-one to give title compound 15A. $^1$HNMR (400 MHz, deuterated chloroform) δ ppm 4.84 (s, 2H), 4.73 (d, J=7.7 Hz, 2H), 4.62 (d, J=8.1 Hz, 2H).

Compound 15B

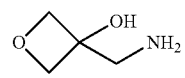

According to the preparation method of compound 13B, 3-hydroxy-3-(nitromethyl)azetidin-1-carboxylic acid tert-butyl ester was replaced with 3-(nitromethyl)oxetan-3-ol to give compound 15B. $^1$H NMR (400 MHz, deuterated chloroform) δ ppm 4.65 (d, J=7.0 Hz, 2H), 4.43 (d, J=7.3 Hz, 2H), 3.09 (s, 2H).

Compound 15C

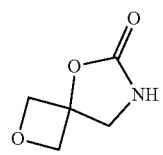

According to the preparation method of compound 13C, 3-(aminomethyl)-3-hydroxy-azetidin-1-carboxylic acid tert-butyl ester was replaced with 3-(aminomethyl)oxetan-3-ol to give compound 15C. $^1$H NMR (400 MHz, deuterated chloroform) δ ppm 4.99 (d, J=8.9 Hz, 2H), 4.59 (d, J=8.1 Hz, 2H), 4.29 (s, 2H).

Compound 15

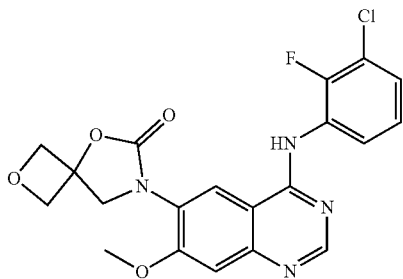

Compound 15

According to the preparation method of compound 1I, 3-oxo-2-oxa-4,9-diazaspiro[5.5]undecane-9-formic acid tert-butyl ester was replaced with 2,5-dioxa-7-azaspiro[3.4]octane-6-one to give compound 15. 1H NMR (400 MHz, deuterated chloroform) δ ppm 8.74 (s, 1H), 8.33-8.41 (m, 1H), 8.01 (s, 1H), 7.56 (br s, 1H), 7.35 (s, 1H), 7.13-7.22 (m, 2H), 5.15 (d, J=8.4 Hz, 2H), 4.80 (d, J=8.3 Hz, 2H), 4.37 (s, 2H), 4.03 (s, 3H). LCMS (ESI) (5-95AB): m/z: 431.0 [M+1].

Example 16

Compound 16A

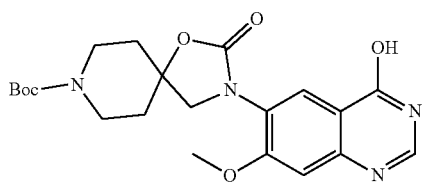 [SMILES: COc1cc2ncnc(O)c2cc1N1CC2(CCN(C(=O)OC(C)(C)C)CC2)OC1=O]

According to the preparation method of compound 1I, 3-oxo-2-oxa-4,9-diazaspiro[5.5]undecane-9-formic acid tert-butyl ester was replaced with 2-oxo-1-oxa-3,8-diazaspiro[4.5]decane-8-formic acid tert-butyl ester, and 6-bromo-N-(3-chloro-2-fluorophenyl)-7-methoxyquinazolin-4-amine was replaced with 6-bromo-7-methoxyquinazolin-4-ol to give compound 16A. $^1$H NMR (400 MHz, deuterated chloroform) δ ppm 8.23 (s, 1H), 8.05 (s, 1H), 7.22 (s, 1H), 3.99 (s, 3H), 3.78-3.91 (m, 2H), 3.73 (s, 2H), 3.33-3.41 (m, 2H), 2.08 (br d, J=13.43 Hz, 2H), 1.74-1.85 (m, 2H), 1.48 (s, 9H). LCMS (ESI) (5-95AB): m/z: 431.3 [M+1].

Compound 16B

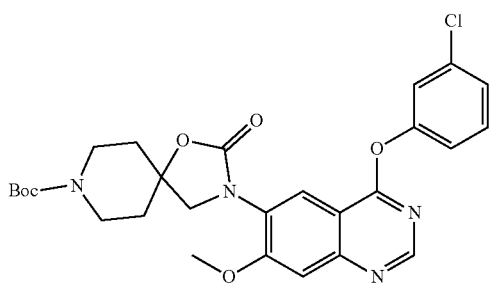 [SMILES: COc1cc2ncnc(Oc3cccc(Cl)c3)c2cc1N1CC2(CCN(C(=O)OC(C)(C)C)CC2)OC1=O]

3-(4-Hydroxy-7-methoxy-quinazolin-6-yl)-2-oxo-1-oxa-3,8-diazaspiro[4.5]decane-8-formic acid tert-butyl ester (500.00 mg, 847.95 mmol) was dissolved in acetonitrile (10 mL), then added with BOP (450.04 mg, 1.02 mmol) and DBU (180.73 mg, 1.19 mmol), and reacted at 26° C. for 1 hour. LCMS showed that the raw materials were completely consumed to obtain intermediates. Then DBU (180.73 mg, 1.19 mmol) and m-chlorophenol (163.52 mg, 1.27 mmol) were added successively, and the reaction solution was stirred at 26° C. for 1 hour. LCMS showed that the intermediates were completely consumed and the target compound was detected. The reaction mixture was filtered, concentrated, separated and purified by column chromatography (silica gel, PE/EA=1:1) to give compound 16B. $^1$H NMR (400 MHz, deuterated chloroform) δ ppm 8.71 (s, 1H), 8.32-8.39 (m, 1H), 7.38-7.48 (m, 2H), 7.28-7.33 (m, 2H), 7.16 (ddd, J=8.16, 2.20, 0.94 Hz, 1H), 4.06 (s, 3H), 3.81 (s, 2H), 3.24-3.48 (m, 4H), 2.08-2.17 (m, 2H), 1.78-1.86 (m, 2H), 1.49 (s, 9H). LCMS (ESI) (5-95AB): m/z: 541.0 [M+1].

Compound 16C

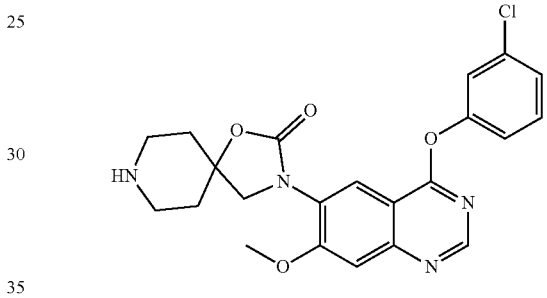

According to the preparation method of compound 1J, 4-(4-((3-chloro-2-fluorophenyl)amino)-7-methoxyquinazolin-6-yl)-3-oxo-2-oxa-4,9-diazaspiro[5.5]undecane-9-carboxylic acid tert-butyl ester was replaced with 3-(4-(3-chlorophenoxy)-7-methoxyquinazolin-6-yl)-2-oxo-1-oxa-3,8-diazaspiro[4.5]decane-8-carboxylic acid tert-butyl ester to give compound 16C. The crude product would be used directly for the next step. LCMS (ESI) (5-95AB): m/z: 441.3 [M+1].

Compound 16

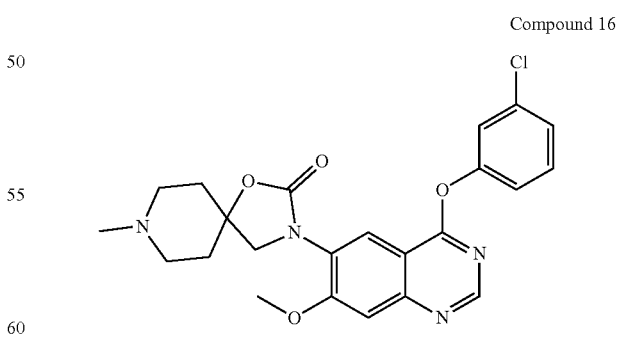

Compound 16

According to the preparation method of compound 1, (4-((3-chloro-2-fluorophenyl)amino)-7-methoxyquinazolin-6-yl)-2-oxa-4,9-diazaspiro[5.5]undecane-3-one was replaced with 3-(4-(3-chlorophenoxy)-7-methoxyquinazolin-6-yl)-1-oxa-3,8-diazaspiro[4.5]decane-2-one to give compound 16. The purity was verified by high performance liquid chromatography and liquid chromatography mass spectrometry simultaneously. ¹H NMR (400 MHz, deuterated chloroform) δ ppm 8.71 (s, 1H), 8.35 (s, 1H), 7.39-7.46 (m, 2H), 7.28-7.33 (m, 2H), 7.17 (dd, J=8.03, 1.25 Hz, 1H), 4.06 (s, 3H), 3.81 (s, 2H), 2.61 (br s, 4H), 2.36 (s, 3H), 2.17 (br d, J=13.43 Hz, 2H), 1.87-2.01 (m, 2H). LCMS (ESI) (5-95AB): m/z: 455.1 [M+1].

Example 17

Compound 17A

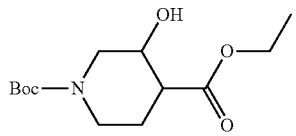

3-Oxoperidine-1,4-dicarboxylic acid 1-tert-butyl-4-ethyl ester (4.50 g, 16.59 mmol) was dissolved in ethanol (30 mL), added with sodium borohydride (313.73 mg, 8.30 mmol) in nitrogen atmosphere, and stirred at 30° C. for 1 hour. TLC showed that new products appeared and the raw materials were completely consumed. The reaction solution was concentrated, added with ethyl acetate (20 mL) and water (20 mL), and then extracted with ethyl acetate (20 mL) three times. The combined organic phases were washed with brine (40 mL) one time, then dried over anhydrous sodium sulfate (1 g), concentrated, separated and purified by column chromatography (PE:EA=10:1 to 3:1) to give compound 17A. ¹H NMR (400 MHz, deuterated chloroform) δ=4.26-3.99 (m, 5H), 2.97 (br s, 1H), 2.90-2.78 (m, 1H), 2.60-2.48 (m, 1H), 2.11-2.03 (m, 1H), 1.79-1.67 (m, 1H), 1.46 (s, 9H), 1.32-1.25 (m, 3H).

Compound 17B

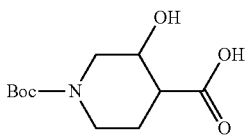 [SMILES: CC(C)(C)OC(=O)N1CCC(C(=O)O)C(O)C1]

3-Hydroxyperidine-1,4-dicarboxylic acid 1-tert-butyl-4-ethyl ester (3.3 g, 12.07 mmol) was dissolved in methanol (20 mL), added with sodium hydroxide solution (4 M, 12.07 mL) and stirred at 30° C. for 1 hour. TLC showed that new products appeared and the raw materials were completely consumed. The reaction solution was concentrated, added with water (20 mL) and washed with ethyl acetate (20 mL) three times. The obtained aqueous phase was adjusted to be acidic with hydrochloric acid (2 M, 5 mL), extracted with ethyl acetate (25 mL) three times. Then the combined organic phases were washed with brine (40 mL) three times, then dried over anhydrous sodium sulfate (1 g), concentrated to give compound 17B. ¹H NMR (400 MHz, deuterated chloroform) δ=4.40-3.96 (m, 3H), 3.12-2.37 (m, 3H), 2.09-1.97 (m, 3H), 1.83-1.56 (m, 1H), 1.48-1.44 (s, 9H).

Compound 17C

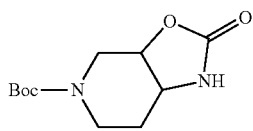 [SMILES: CC(C)(C)OC(=O)N1CCC2NC(=O)OC2C1]

According to the preparation method of compound 2C, 2-(1-(tert-butoxycarbonyl)-4-hydroxypiperidin-4-yl) acetic acid was replaced with 1-tert-butoxycarbonyl-3-hydroxypiperidine-4-carboxylic acid to give compound 17C. ¹H NMR (400 MHz, deuterated chloroform) δ=5.71 (br s, 1H), 4.16-4.05 (m, 1H), 3.96 (dd, J=4.1, 14.9 Hz, 1H), 3.44 (br d, J=11.5 Hz, 2H), 3.35-3.13 (m, 1H), 2.82-2.75 (m, 1H), 1.99-1.82 (m, 2H), 1.47 (s, 9H).

Compound 17D

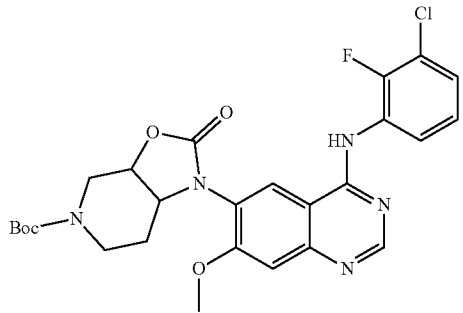 [SMILES: COc1cc2ncnc(Nc3cccc(Cl)c3F)c2cc1N1C(=O)OC2CN(C(=O)OC(C)(C)C)CCC21]

According to the preparation method of compound 1I, 3-oxo-2-oxa-4,9-diazaspiro[5.5]undecane-9-formic acid tert-butyl ester was replaced with 2-oxo-hexahydrooxazo[5,4-c]pyridine-5(2H)-formic acid tert-butyl ester to give compound 17D. ¹H NMR (400 MHz, METHANOL-d4) δ=8.45 (br s, 1H), 8.37 (s, 1H), 7.61-7.50 (m, 1H), 7.41 (br t, J=7.2 Hz, 1H), 7.32 (s, 1H), 7.27-7.20 (m, 1H), 4.05 (s, 3H), 4.01-3.81 (m, 2H), 3.63 (s, 2H), 3.55-3.42 (m, 2H), 2.00-1.91 (m, 1H), 1.81-1.73 (m, 1H), 1.45 (s, 9H). LCMS (ESI) (5-95AB): m/z: 544.3 [M+1].

Compound 17E

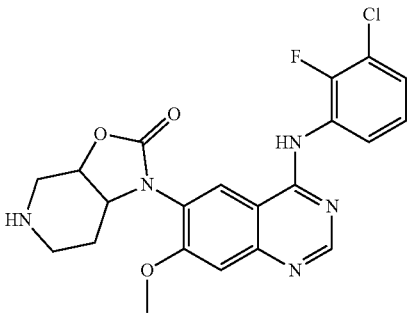 [SMILES: COc1cc2ncnc(Nc3cccc(Cl)c3F)c2cc1N1C(=O)OC2CNCCC21]

According to the preparation method of compound 1J, 4-(4-((3-chloro-2-fluorophenyl)amino)-7-methoxyquinazolin-6-yl)-3-oxo-2-oxa-4,9-diazaspiro[5.5]undecane-9-carboxylic acid tert-butyl ester was replaced with 1-(4-((3-chloro-2-fluorophenyl)amino)-7-methoxyquinazolin-6-yl)-2-oxo-hexahydrooxazo[5,4-c]pyridine-5(2H)-carboxylic acid tert-butyl ester to give compound 17E. The crude product would be used directly for the next step. ¹H NMR (400 MHz, METHANOL-d4) δ=8.78 (s, 1H), 8.74 (s, 1H), 7.57-7.46 (m, 3H), 7.33-7.25 (m, 1H), 4.14 (s, 3H), 3.77-3.43 (m, 6H), 2.23-2.13 (m, 1H), 1.91-1.70 (m, 1H). LCMS (ESI) (5-95AB): m/z: 444.2 [M+1].

Compound 17

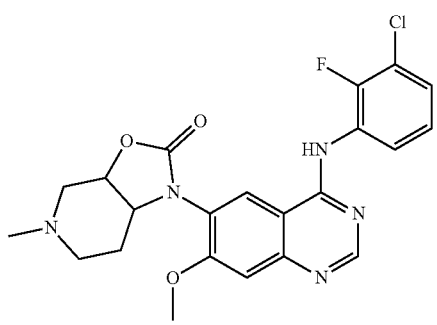

Compound 17

According to the preparation method of compound 1, (4-((3-chloro-2-fluorophenyl)amino)-7-methoxyquinazolin-6-yl)-2-oxa-4,9-diazaspiro[5.5]undecane-3-one was replaced with 1-(4-((3-chloro-2-fluorophenyl)amino)-7-methoxyquinazolin-6-yl)-hexahydrooxazo[5,4-c]pyridin-2(1H)-one to give compound 17. The purity was verified by high performance liquid chromatography and liquid chromatography mass spectrometry simultaneously. $^1$H NMR (400 MHz, METHANOL-d4) δ=8.46 (s, 1H), 8.40 (s, 1H), 8.21 (br s, 1H), 7.60-7.50 (m, 1H), 7.48-7.37 (m, 1H), 7.33 (s, 1H), 7.27-7.15 (m, 1H), 5.11-4.94 (m, 1H), 4.65-4.51 (m, 1H), 4.05 (s, 3H), 3.28-3.16 (m, 1H), 3.09 (dd, J=5.6, 13.1 Hz, 1H), 2.91-2.78 (m, 1H), 2.76-2.65 (m, 1H), 2.59 (s, 3H), 2.06 (tdd, J=4.6, 9.5, 14.5 Hz, 1H), 1.95-1.80 (m, 1H). LCMS (ESI) (5-95AB): m/z: 458.1 [M+1].

Example 18

Compound 18A

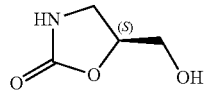

Triphosgene (9.77 g, 32.93 mmol, 1.00 eq.) and sodium bicarbonate (12.25 g, 145.88 mmol, 5.67 mL, 4.43 eq.) were added to a solution of (2S)-3-aminopropane-1,2-diol (3.00 g, 32.93 mmol, 1.00 eq.) in water (35.00 mL). The mixture was stirred at 25° C. for 16 hours. TLC (DCM:MeOH=5:1) showed that the reaction was complete. The mixture was extracted by DCM (25 mL×2). The aqueous phase was neutralized with HCl and then concentrated under vacuum. The solid residue was suspended in anhydrous ethanol and the inorganic salt was filtered off. The filtrate was concentrated under vacuum to give compound 18A.

Compound 18B

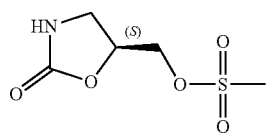

Methylsulfonyl chloride (4.20 g, 36.67 mmol, 2.84 mL, 1.13 eq.) was added drop by drop to a solution of (5S)-5-(hydroxymethyl)oxazolidin-2-one (3.80 g, 32.45 mol, 1.00 eq.) and pyridine (37.24 g, 470.85 mmol, 38.00 mL, 14.51 eq.) in dichloromethane (60.00 mL) under N$_2$ protection at 0° C. The mixture was stirred for 3 hours at 0° C. and in nitrogen atmosphere. TLC (DCM:MeOH=10:1) showed that the reaction was complete. The reaction mixture was concentrated under vacuum, the residue was purified by column chromatography (DCM/MeOH=200/1 to 100:1) to give compound 18B. $^1$H NMR (400 MHz, DMSO-d6) δ ppm 7.65 (br s, 1H), 3.94-3.76 (m, 1H), 4.43-4.37 (m, 1H), 4.35-4.28 (m, 1H), 3.58 (t, J=9.2 Hz, 1H), 3.24 (s, 3H).

Compound 18C

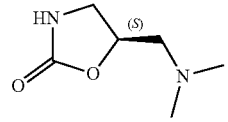

N-methylmethylamine (2 M, tetrahydrofuran solution, 30.00 mL) was added to the mixture of ((5S)-2-oxazolidin-5-yl) methyl sulfonate (450.00 mg, 2.31 mmol, 1.00 eq.) in ethanol (5.00 mL), and the obtained reaction solution was stirred in a sealed tank at 120° C. for 20 hours. TLC (DCM:MeOH=10:1, PMA) test indicated no residual raw materials. The mixture was concentrated. The residue was added with ethyl acetate (30 mL), washed with saturated sodium bicarbonate solution (30 mL×1), dried over anhydrous sodium sulfate (10 g) and concentrated to give compound 18C. $^1$H NMR (400 MHz, DMSO-d6) δ ppm 6.42-6.25 (m, 0.4H), 4.07-3.92 (m, 0.3H), 3.66-3.57 (m, 0.4H), 3.48-3.34 (m, 0.7H), 3.20-3.07 (m, 0.6H), 3.02-2.86 (m, 1H), 2.78 (s, 3H), 2.33-2.25 (m, 1H), 2.20 (s, 3H), 2.18-2.12 (m, 1H).

Compound 18

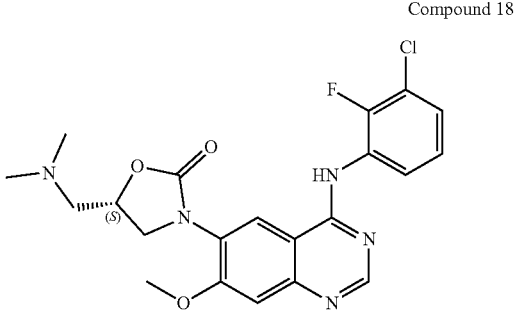

Compound 18

According to the preparation method of compound 1I, 3-oxo-2-oxa-4,9-diazaspiro[5.5]undecane-9-formic acid tert-butyl ester was replaced with (5S)-5-[(dimethylamino)methyl]oxazolidin-2-one to give compound 18. $^1$H NMR (400 MHz, METHANOL-d$_4$) δ ppm 8.47 (s, 1H), 8.40 (s, 1H), 7.60 (dd, J=6.8 6.8 Hz, 1H), 7.48-7.36 (m, 1H), 7.31 (s, 1H), 7.28-7.19 (m, 1H), 5.16-5.02 (m, 1H), 4.28-4.19 (m, 1H), 4.07 (s, 3H), 3.86-3.77 (m, 1H), 3.19-3.06 (m, 1H), 3.02-2.90 (m, 1H), 2.60 (s, 6H). LCMS (ESI) (5-95AB): m/z: 446.1 [M+1].

Example 19

Compound 19A

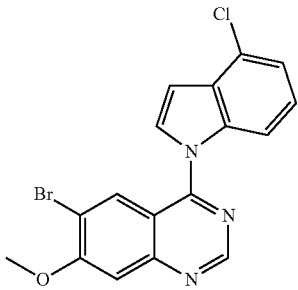 [SMILES: COc1cc2ncnc(-n3ccc4c(Cl)cccc43)c2cc1Br]

According to the preparation method of compound 16B, 3-(4-hydroxy-7-methoxyquinazolin-6-yl)-2-oxo-1-oxa-3,8-diazaspiro[3.4]octane-2-carboxylic acid tert-butyl ester was replaced with 6-bromo-7-methoxyquinazolin-4-ol, and 4-chlorophenol was replaced with 4-chloro-1H-indole to give compound 19A. $^1$H NMR (400 MHz, deuterated chloroform) δ=9.19 (s, 1H), 8.33 (s, 1H), 7.73 (d, J=8.2 Hz, 1H), 7.68 (d, J=3.5 Hz, 1H), 7.49 (s, 1H), 7.33-7.24 (m, 2H), 7.01 (d, J=3.5 Hz, 1H), 4.14 (s, 3H). LCMS (ESI) (5-95AB): m/z: 390.1 [M+1].

Compound 19B

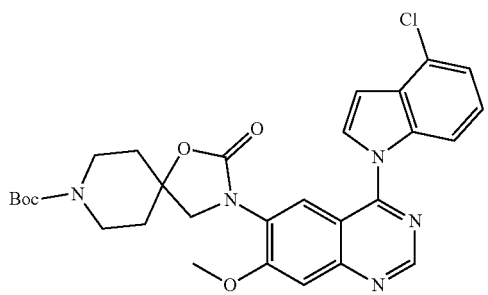 [SMILES: COc1cc2ncnc(-n3ccc4c(Cl)cccc43)c2cc1N1CC2(CCN(C(=O)OC(C)(C)C)CC2)OC1=O]

At 25° C. and under nitrogen protection, trans-cyclohexanediamine (11.75 mg, 102.92 mmol, 12.64 mL), cuprous iodide (49.00 mg, 257.30 mmol) and potassium carbonate (213.37 mg, 1.54 mmol) were added to a solution of compound 19A (200.00 mg, 514.60 mmol) and compound 2C (131.89 mg, 514.60 mmol) in 1,4-dioxane (2.00 mL). The reaction solution was stirred at 120° C. for 18 hours. LCMS detected product generation in the reaction. The reaction liquid was filtered and the filter cake was washed with dichloromethane 80 mL (40 mL*2). The filtrate was concentrated to give a crude product. The crude product was purified by TLC (dichloromethane:methanol=20:1) to give compound 19B. $^1$H NMR (400 MHz, deuterated chloroform) δ=9.16 (s, 1H), 8.15 (s, 1H), 7.82 (d, J=7.8 Hz, 1H), 7.74 (d, J=3.5 Hz, 1H), 7.53 (s, 1H), 7.29-7.23 (m, 2H), 6.98 (d, J=3.5 Hz, 1H), 4.10 (s, 3H), 3.97-3.83 (m, 2H), 3.76 (s, 2H), 3.42-3.25 (m, 2H), 2.10-1.99 (m, 2H), 1.76 (br s, 2H), 1.48 (s, 9H). LCMS (ESI) (5-95AB): m/z: 564.4[M+1].

Compound 19C

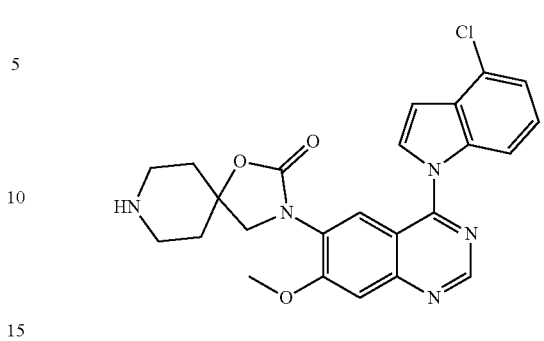

According to the preparation method of compound 1J, 4-(4-((3-chloro-2-fluorophenyl)amino)-7-methoxyquinazolin-6-yl)-3-oxo-2-oxa-4,9-diazaspiro[5.5]undecane-9-carboxylic acid tert-butyl ester was replaced with 3-(4-(4-chloro-1H-indol-1-yl)-7-methoxyquinazolin-6-yl)-2-oxo-1-oxa-3,8-diazaspiro[4.5]decane-8-carboxylic acid tert-butyl ester to give compound 19C. The crude product would be used directly for the next step. LCMS (ESI) (5-95AB): m/z: 464.0 [M+1].

Compound 19

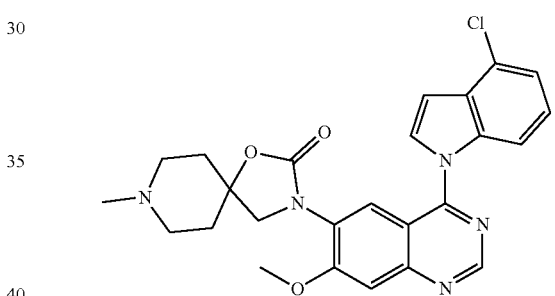

According to the preparation method of compound 1, (4-((3-chloro-2-fluorophenyl)amino)-7-methoxyquinazolin-6-yl)-2-oxa-4,9-diazaspiro[5.5]undecane-3-one was replaced with 3-(4-(4-chloro-1H-indol-1-yl)-7-methoxyquinazolin-6-yl)-1-oxa-3,8-diazaspiro[4.5]decane-2-one to give compound 19. $^1$H NMR (400 MHz, METHANOL-d4) δ=9.15 (s, 1H), 8.20 (s, 1H), 7.90 (d, J=3.4 Hz, 1H), 7.85-7.79 (m, 1H), 7.64 (s, 1H), 7.30-7.23 (m, 2H), 6.97 (d, J=3.4 Hz, 1H), 4.17 (s, 3H), 3.93 (s, 2H), 3.20 (br d, J=6.5 Hz, 2H), 3.11 (br s, 2H), 2.74 (br s, 3H), 2.34-2.25 (m, 2H), 2.21-2.04 (m, 2H). LCMS (ESI) (5-95AB): m/z: 478.1 [M+1].

Example 20

Compound 20A

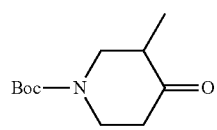

1-Benzyl-3-methyl-piperidin-4-one (4.50 g, 22.14 mmol) and Boc$_2$O (6.28 g, 28.78 mmol) were dissolved in ethanol (20.00 mL), and then added with Pd—C (10%, 1 g) in nitrogen atmosphere. The reaction system was vacuumed, displaced with nitrogen gas three times and with hydrogen gas three times, and the reaction solution was stirred under hydrogen atmosphere (50 psi) at 30° C. for 5 hours. TLC showed that new products appeared and the raw materials were completely consumed. The reaction solution was filtered by DCM:MeOH=10:1 (22 mL), concentrated, separated and purified by column chromatography (PE:EA=3:1) to give compound 20A. $^1$H NMR (400 MHz, deuterated chloroform) δ=4.48-4.14 (m, 2H), 3.35-3.17 (m, 1H), 2.85 (br s, 1H), 2.59-2.35 (m, 3H), 1.51-1.47 (m, 9H), 1.05 (d, J=6.8 Hz, 3H).

Compound 20B

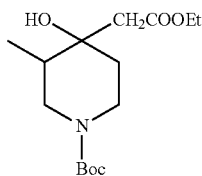

According to the preparation method of compound 2A, 4-oxoperidine-1-formic acid tert-butyl ester was replaced with 3-methyl-4-oxoperidine-1-formic acid tert-butyl ester to give compound 20B. $^1$H NMR (400 MHz, deuterated chloroform) δ=4.20-4.17 (m, 2H), 3.45 (s, 2H), 2.77-2.55 (m, 2H), 2.52-2.37 (m, 2H), 2.34-1.79 (m, 3H), 1.45 (s, 9H), 1.29-1.27 (m, 3H), 0.95-0.88 (m, 3H).

Compound 20C

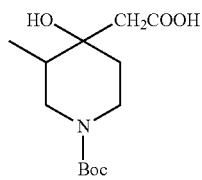

According to the preparation method of compound 2B, 4-(2-ethoxy-2-oxoethyl)-4-hydroxyperidine-1-formic acid tert-butyl ester was replaced with 4-(2-ethoxy-2-oxoethyl)-4-hydroxy-3-methylpiperidine-1-formic acid tert-butyl ester to give compound 20C. $^1$H NMR (400 MHz, deuterated chloroform) δ=3.98-3.63 (m, 1H), 3.43-3.03 (m, 1H), 2.91-2.52 (m, 2H), 2.39-2.23 (m, 1H), 2.11 (s, 2H), 1.89-1.69 (m, 1H), 1.86-1.57 (m, 1H), 1.45 (s, 9H), 0.99-0.88 (m, 3H).

Compound 20D

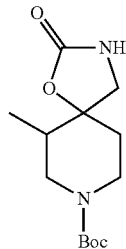

According to the preparation method of compound 2C, 2-(1-(tert-butoxycarbonyl)-4-hydroxypiperidin-4-yl)acetic acid was replaced with 2-(1-(tert-butoxycarbonyl)-4-hydroxy-3-methylpiperidin-4-yl)acetic acid to give compound 20D. $^1$H NMR (400 MHz, deuterated chloroform) δ=5.74 (br s, 1H), 3.53-3.44 (m, 1H), 3.33-3.18 (m, 2H), 2.87-2.77 (m, 1H), 2.09-1.79 (m, 2H), 1.75-1.63 (m, 2H), 1.46 (s, 9H), 1.13 (t, J=7.2 Hz, 1H), 1.01-0.93 (m, 3H).

Compound 20E

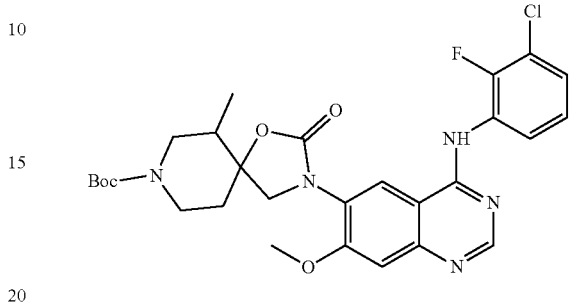

According to the preparation method of compound 1I, 3-oxo-2-oxa-4,9-diazaspiro[5.5]undecane-9-formic acid tert-butyl ester was replaced with 6-methyl-2-oxo-1-oxa-3,8-diazaspiro[4.5]decane-8-formic acid tert-butyl ester to give compound 20E. $^1$H NMR (400 MHz, METHANOL-d4) δ=8.52-8.31 (m, 2H), 7.52 (br t, J=6.7 Hz, 1H), 7.43-7.36 (m, 1H), 7.28 (s, 1H), 7.24-7.16 (m, 1H), 4.04 (s, 3H), 3.52-3.49 (m, 1H), 3.28-3.21 (m, 3H), 1.97-1.90 (m, 2H), 1.77-1.69 (m, 2H), 1.46 (s, 9H), 1.13 (d, J=5.7 Hz, 1H), 0.97-0.95 (m, 3H). LCMS (ESI) (5-95AB): m/z: 572.2 [M+1].

Compound 20F

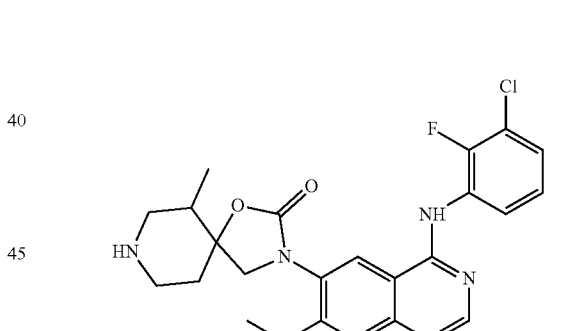

According to the preparation method of compound 1J, 4-(4-((3-chloro-2-fluorophenyl)amino)-7-methoxyquinazolin-6-yl)-3-oxo-2-oxa-4,9-diazaspiro[5.5]undecane-9-carboxylic acid tert-butyl ester was replaced with 3-(4-((3-chloro-2-fluorophenyl)amino)-7-methoxyquinazolin-6-yl)-6-methyl-2-oxo-1-oxa-3,8-diazaspiro[4.5]decane-8-carboxylic ester to give compound 20F. The crude product would be used directly for the next step. $^1$H NMR (400 MHz, METHANOL-d4) δ=8.78 (s, 1H), 8.66 (s, 1H), 7.63-7.48 (m, 2H), 7.44 (s, 1H), 7.31 (dt, J=1.4, 8.1 Hz, 1H), 4.15 (s, 3H), 3.28-2.87 (m, 4H), 2.46-2.16 (m, 4H), 1.21 (d, J=2.3 Hz, 1H), 1.13-1.01 (m, 3H). LCMS (ESI) (5-95AB): m/z: 472.1 [M+1].

Compound 20

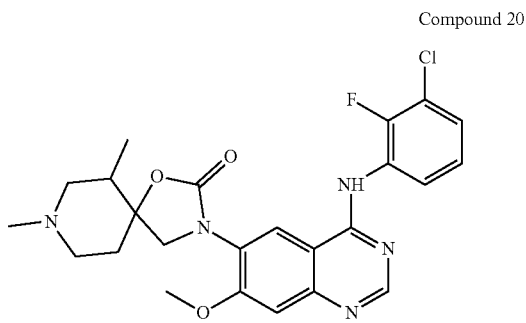 [SMILES: COc1cc2ncnc(Nc3cccc(Cl)c3F)c2cc1N1CC2(CCN(C)CC2C)OC1=O]

Compound 20

According to the preparation method of compound 1, (4-((3-chloro-2-fluorophenyl)amino)-7-methoxyquinazolin-6-yl)-2-oxa-4,9-diazaspiro[5.5]undecane-3-one was replaced with 3-(4-((3-chloro-2-fluorophenyl)amino)-7-methoxyquinazolin-6-yl)-6-methyl-1-oxa-3,8-diazaspiro[4.5]decane-2-one to give compound 20. The purity was verified by high performance liquid chromatography and liquid chromatography mass spectrometry simultaneously. ¹H NMR (400 MHz, METHANOL-d4) δ=8.45 (s, 1H), 8.41 (s, 1H), 7.60-7.49 (m, 1H), 7.41 (dt, J=1.5, 7.4 Hz, 1H), 7.32 (s, 1H), 7.22 (dt, J=1.3, 8.1 Hz, 1H), 4.11-4.07 (m, 1H), 4.06 (s, 3H), 3.85-3.77 (m, 1H), 3.41-3.32 (m, 1H), 3.28-3.02 (m, 2H), 2.83 (br t, J=12.3 Hz, 1H), 2.77 (s, 2H), 2.61 (s, 1H), 2.42-2.13 (m, 3H), 1.24-1.15 (m, 3H). LCMS (ESI) (5-95AB): m/z: 486.1 [M+1].

Example 21

Compound 21A

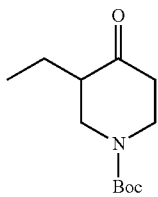 [SMILES: CCC1CN(C(=O)OC(C)(C)C)CCC1=O]

Under nitrogen protection at −70° C., LDA (2 M, 158.09 mL, 2.52 eq.) was added dropwise to a solution of 4-oxoperidine-1-formic acid tert-butyl ester (25.00 g, 125.47 mmol, 1.00 eq.) in THF (200.00 mL). Thirty minutes later, ethylene iodide (78.27 g, 501.88 mmol, 40.14 mL, 4.00 eq.) was added to the above solution at −70° C., and then the mixture was stirred at room temperature (30° C.) for 16 hours. TLC showed that there were still raw materials left. The reaction solution was quenched with saturated ammonium chloride solution (100 mL) and partitioned between ethyl acetate (100 mL) and water (200 mL). The aqueous solution was extracted with ethyl acetate (100 mL×1). The combined organic layers were washed with brine (100 mL×2), dried over anhydrous sodium sulfate (50 g), and concentrated to a light yellow oily substance. The residue was purified by silica gel column chromatography (petroleum ether:ethyl acetate=20:1) to give compound 21A. LCMS (ESI) (5-95AB): m/z: 128.1 [M+1-100].

Compound 21B

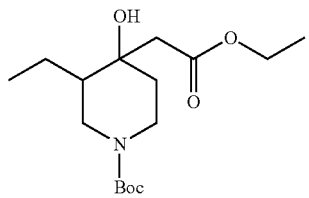 [SMILES: CCOC(=O)CC1(O)CCN(C(=O)OC(C)(C)C)CC1CC]

According to the preparation method of compound 2A, 4-oxoperidine-1-formic acid tert-butyl ester was replaced with 3-ethyl-4-oxoperidine-1-formic acid tert-butyl ester to give compound 21B. LCMS (ESI) (5-95AB): m/z: 216.1 [M+1-100].

Compound 21C

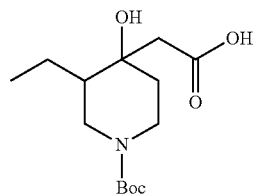 [SMILES: CCC1CN(C(=O)OC(C)(C)C)CCC1(O)CC(=O)O]

According to the preparation method of compound 2B, 4-(2-ethoxy-2-oxoethyl)-4-hydroxyperidine-1-formic acid tert-butyl ester was replaced with 4-(2-ethoxy-2-oxoethyl)-4-hydroxy-3-ethylpiperidine-1-formic acid tert-butyl ester to give compound 21C. ¹H NMR (400 MHz, deuterated chloroform) δ=3.90-2.94 (m, 3H), 2.89-2.50 (m, 1H), 2.46-2.11 (m, 1H), 2.19 (d, J=15.6 Hz, 1H), 1.95 (s, 2H), 1.68-1.49 (m, 1H), 1.46-1.36 (m, 1H), 1.30 (s, 9H), 1.19-0.97 (m, 2H), 0.85-0.76 (m, 2H).

Compound 21D

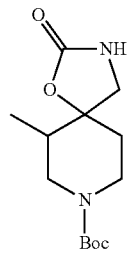 [SMILES: CC1CN(C(=O)OC(C)(C)C)CCC12CNC(=O)O2]

According to the preparation method of compound 2C, 2-(1-(tert-butoxycarbonyl)-4-hydroxypiperidin-4-yl)acetic acid was replaced with 2-(1-(tert-butoxycarbonyl)-4-hydroxy-3-ethylpiperidin-4-yl)acetic acid to give compound 21D. ¹H NMR (400 MHz, deuterated chloroform) δ=5.79 (br s, 1H), 3.96-3.76 (m, 1H), 3.56-3.18 (m, 4H), 2.03-1.85 (m, 1H), 1.75-1.60 (m, 3H), 1.46 (s, 9H), 1.34-1.10 (m, 2H), 1.07-0.95 (m, 3H).

Compound 21E

Compound 21

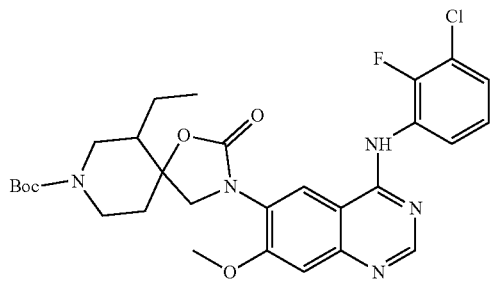 [SMILES: CCC1CN(C(=O)OC(C)(C)C)CCC12CN(c1cc3c(Nc4cccc(Cl)c4F)ncnc3cc1OC)C(=O)O2]

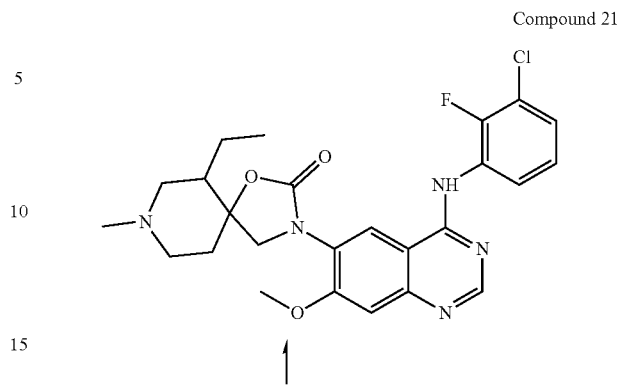

Compound 21

According to the preparation method of compound 1I, 3-oxo-2-oxa-4,9-diazaspiro[5.5]undecane-9-formic acid tert-butyl ester was replaced with 6-ethyl-2-oxo-1-oxa-3,8-diazaspiro[4.5]decane-8-formic acid tert-butyl ester to give compound 21E. ¹H NMR (400 MHz, METHANOL-d4) δ=8.61-8.25 (m, 2H), 7.55 (br s, 1H), 7.41 (br t, J=7.3 Hz, 1H), 7.32 (br s, 1H), 7.27-7.19 (m, 1H), 4.06 (s, 3H), 3.81-3.75 (m, 2H), 3.53 (br d, J=9.3 Hz, 2H), 1.97-1.86 (m, 3H), 1.75-1.64 (m, 4H), 1.48 (s, 9H), 1.03-1.01 (m, 3H). LCMS (ESI) (5-95AB): m/z: 586.3 [M+1].

Compound 21F

According to the preparation method of compound 1, (4-((3-chloro-2-fluorophenyl)amino)-7-methoxyquinazolin-6-yl)-2-oxa-4,9-diazaspiro[5.5]undecane-3-one was replaced with 3-(4-((3-chloro-2-fluorophenyl)amino)-7-methoxyquinazolin-6-yl)-6-ethyl-1-oxa-3,8-diazaspiro[4.5]decane-2-one to give compound 21. The purity was verified by high performance liquid chromatography and liquid chromatography mass spectrometry simultaneously. ¹H NMR (400 MHz, METHANOL-d4) δ=8.48-8.37 (m, 3H), 7.59-7.49 (m, 1H), 7.39 (br t, J=7.4 Hz, 1H), 7.32-7.26 (m, 1H), 7.24-7.16 (m, 1H), 4.15-4.08 (m, 1H), 4.07-4.00 (m, 3H), 3.90-3.76 (m, 1H), 3.62-3.40 (m, 2H), 3.23 (br t, J=11.8 Hz, 1H), 2.95 (br t, J=12.4 Hz, 1H), 2.79-2.89 (m, 3H), 2.49-2.00 (m, 4H), 1.48-1.30 (m, 1H), 1.10 (br t, J=7.4 Hz, 3H). LCMS (ESI) (5-95AB): m/z: 500.1 [M+1].

Example 22

Compound 22A

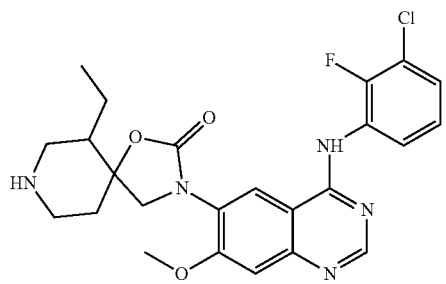 [SMILES: CCC1CNCCC12CN(c1cc3c(Nc4cccc(Cl)c4F)ncnc3cc1OC)C(=O)O2]

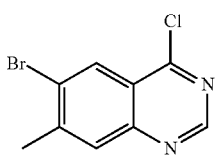

According to the preparation method of compound 1B, 2-amino-5-bromo-4-methoxybenzoic acid was replaced with 2-amino-5-bromo-4-methylbenzoic acid to give compound 22A. ¹H NMR (400 MHz, DMSO-d6) δ=8.21-8.19 (m, 1H), 8.10 (s, 1H), 7.68 (s, 1H), 2.48 (s, 3H), 2.18 (s, 1H), 1.75 (s, 1H). LCMS (ESI) (5-95AB): m/z:238.9 [M+1].

Compound 22B

According to the preparation method of compound 1J, 4-(4-((3-chloro-2-fluorophenyl)amino)-7-methoxyquinazolin-6-yl)-3-oxo-2-oxa-4,9-diazaspiro[5.5]undecane-9-carboxylic acid tert-butyl ester was replaced with 3-(4-((3-chloro-2-fluorophenyl)amino)-7-methoxyquinazolin-6-yl)-6-ethyl-2-oxo-1-oxa-3,8-diazaspiro[4.5]decane-8-carboxylic acid tert-butyl ester to give compound 21F. The crude product would be used directly for the next step. ¹H NMR (400 MHz, METHANOL-d4) δ=8.78 (s, 1H), 8.71-8.61 (m, 1H), 7.61-7.48 (m, 2H), 7.43 (s, 1H), 7.36-7.27 (m, 1H), 4.15 (s, 3H), 3.85-3.37 (m, 5H), 3.24-2.86 (m, 2H), 2.47-2.08 (m, 4H), 1.14-1.04 (m, 3H). LCMS (ESI) (5-95AB): m/z: 486.1 [M+1].

According to the preparation method of compound 1C, 6-bromo-7-methoxyquinazolin-4-ol was replaced with 6-bromo-7-methoxyquinazolin-4-ol to give compound 22B. ¹H NMR (400 MHz, DMSO-d6) δ=8.30 (s, 1H), 8.22 (s, 1H), 7.70 (s, 1H), 3.28 (s, 1H), 3.20-3.16 (m, 1H), 2.93 (s, 1H), 2.34-2.25 (m, 2H). LCMS (ESI) (5-95CD): m/z:258.8 [M+1].

Compound 22C

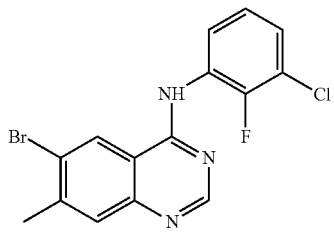 [SMILES: Cc1cc2ncnc(Nc3cccc(Cl)c3F)c2cc1Br]

According to the preparation method of compound 1D, 6-bromo-4-chloro-7-methoxyquinazoline was replaced with 6-bromo-4-chloro-7-methylquinazoline to give 22C. 1H NMR (400 MHz, deuterated chloroform) δ=8.79 (s, 1H), 8.53-8.47 (m, 1H), 8.11 (s, 1H), 7.82 (s, 1H), 7.55 (br s, 1H), 7.20-7.16 (m, 2H), 2.61 (s, 3H). LCMS (ESI) (5-95AB): m/z:367.8 [M+1].

Compound 22D

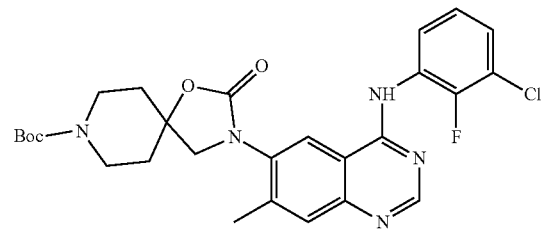 [SMILES: Cc1cc2ncnc(Nc3cccc(Cl)c3F)c2cc1N1CC2(CCN(C(=O)OC(C)(C)C)CC2)OC1=O]

According to the preparation method of compound 1I, 3-oxo-2-oxa-4,9-diazaspiro[5.5]undecane-9-formic acid tert-butyl ester was replaced with 2-oxo-1-oxa-3,8-diazaspiro[4.5]decane-8-formic acid tert-butyl ester, and 6-bromo-N-(3-chloro-2-fluorophenyl)-7-methoxyquinazolin-4-amine was replaced with 6-bromo-N-(3-chloro-2-fluorophenyl)-7-methoxyquinazolin-4-amine to give compound 22D. $^1$H NMR (400 MHz, deuterated chloroform) δ=8.76 (s, 1H), 8.45-8.36 (m, 1H), 7.87 (s, 1H), 7.76 (s, 1H), 7.58 (br s, 1H), 7.20-7.16 (m, 2H), 3.94 (br s, 2H), 3.76 (s, 2H), 3.49 (d, J=4.4 Hz, 1H), 3.45-3.33 (m, 2H), 2.46 (s, 3H), 2.15 (br d, J=13.8 Hz, 2H), 1.91-1.80 (m, 2H), 1.49 (s, 9H), 1.46 (s, 1H). LCMS (ESI) (5-95AB): m/z:542.0 [M+1].

Compound 22E

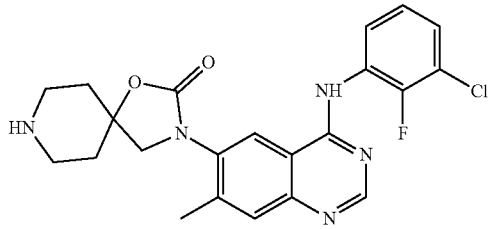 [SMILES: Cc1cc2ncnc(Nc3cccc(Cl)c3F)c2cc1N1CC2(CCNCC2)OC1=O]

According to the preparation method of compound 1J, 4-(4-((3-chloro-2-fluorophenyl)amino)-7-methoxyquinazolin-6-yl)-3-oxo-2-oxa-4,9-diazaspiro[5.5]undecane-9-carboxylic acid tert-butyl ester was replaced with 3-(4-((3-chloro-2-fluorophenyl)amino)-7-methoxyquinazolin-6-yl)-2-oxo-1-oxa-3,8-diazaspiro[4.5]decane-8-carboxylic acid tert-butyl ester to give compound 22E. The crude product would be used directly for the next step. LCMS (ESI) (5-95AB): m/z:442.1 [M+1].

Compound 22

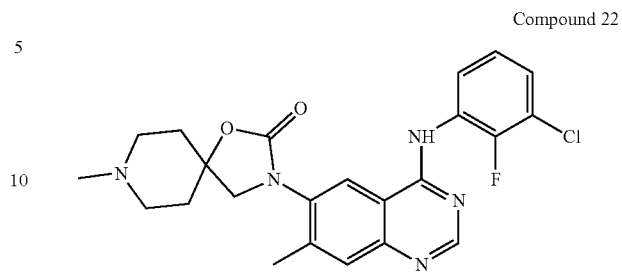

Compound 22

According to the preparation method of compound 1, (4-((3-chloro-2-fluorophenyl)amino)-7-methoxyquinazolin-6-yl)-2-oxa-4,9-diazaspiro[5.5]undecane-3-one was replaced with 3-(4-((3-chloro-2-fluorophenyl)amino)-7-methoxyquinazolin-6-yl)-1-oxa-3,8-diazaspiro[3.4]decane-2-one to give compound 22. The purity was verified by high performance liquid chromatography and liquid chromatography mass spectrometry simultaneously. $^1$H NMR (400 MHz, DMSO-d6) δ=9.98 (br s, 1H), 8.53-8.48 (m, 1H), 8.46 (br s, 1H), 8.20 (s, 1H), 7.74 (br s, 1H), 7.50 (br s, 2H), 7.32-7.26 (m, 1H), 3.88 (s, 2H), 2.52 (br d, J=1.8 Hz, 4H), 2.43 (s, 3H), 2.26 (s, 3H), 2.06-1.90 (m, 4H). LCMS (ESI) (5-95CD): m/z:456.1 [M+1].

Example 23

Compound 23A

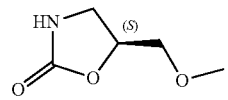

Sodium (117.71 mg, 5.12 mmol,) was added to methanol (20.00 mL) at 25° C. and stirred for 10 minutes. After the solid was dissolved, the mixture was added with (((5S)-2-oxazolidin-2-yl)pyridin-5-yl) methylsulfonate (500.00 mg, 2.56 mmol), and stirred at 65° C. for 16 hours. TLC (DCM:MeOH=10:1) showed that the reaction was complete and new points appeared. The mixture was concentrated, and the residue was added with water (20 mL) and extracted with dichloromethane (20 mL×2). The organic substance was discarded. The aqueous layer was adjusted to pH=6 with 1N HCl and extracted with dichloromethane (20 mL×3). The combined organic layers were washed with water (30 mL×1), dried over anhydrous sodium sulfate (5 g) and concentrated to give compound 23A. $^1$H NMR (400 MHz, DMSO-d6) δ ppm 7.48 (s, 1H), 7.60-7.45 (m, 1H), 3.53-3.51 (m, 1H), 3.49-3.44 (m, 2H), 3.34 (s, 1H), 3.30 (s, 3H), 3.20 (s, 1H).

Compound 23

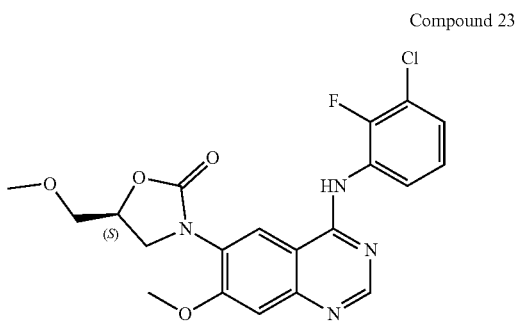

Compound 23

According to the preparation method of compound 1I, 3-oxo-2-oxa-4,9-diazaspiro[5.5]undecane-9-formic acid tert-butyl ester was replaced with (S)-5-(methoxymethyl)oxazolidin-2-one to give compound 23. $^1$H NMR (400 MHz, METHANOL-$d_4$) δ ppm 8.52-8.42 (m, 1H), 8.38 (s, 1H), 7.62-7.51 (m, 1H), 7.47-7.37 (m, 1H), 7.31 (s, 1H), 7.25-7.20 (m, 1H), 5.00-4.94 (m, 1H), 4.25-4.14 (m, 1H), 4.06 (s, 3H), 3.95-3.87 (m, 1H), 3.79-3.64 (m, 2H), 3.50 (s, 3H). LCMS (ESI) (5-95AB): m/z: 433.0 [M+1].

Example 24

Compound 24A

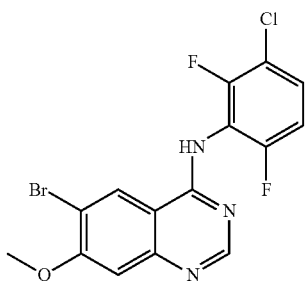 [SMILES: COc1cc2ncnc(Nc3c(F)ccc(Cl)c3F)c2cc1Br]

According to the preparation method of compound 1D, 3-chloro-2-fluoroaniline was replaced with 3-chloro-2,6-difluoroaniline to give compound 24A. LCMS (ESI) (5-95AB): m/z: 401.9 [M+1].

Compound 24B

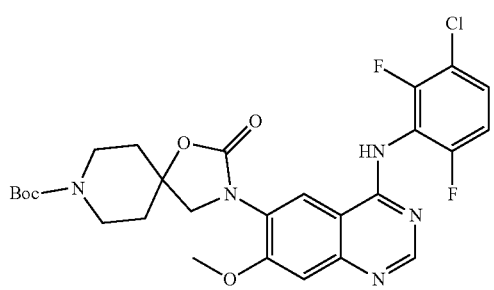 [SMILES: COc1cc2ncnc(Nc3c(F)ccc(Cl)c3F)c2cc1N1CC2(CCN(C(=O)OC(C)(C)C)CC2)OC1=O]

According to the preparation method of compound 1I, 3-oxo-2-oxa-4,9-diazaspiro[5.5]undecane-9-formic acid tert-butyl ester was replaced with 2-oxo-1-oxa-3,8-diazaspiro[4.5]decane-8-formic acid tert-butyl ester, and 6-bromo-N-(3-chloro-2-fluorophenyl)-7-methoxyquinazolin-4-amine was replaced with 6-bromo-N-(3-chloro-2,6-difluorophenyl)-7-methoxyquinazolin-4-amine to give compound 24B. LCMS (ESI) (5-95AB): m/z: 576.3 [M+1].

Compound 24C

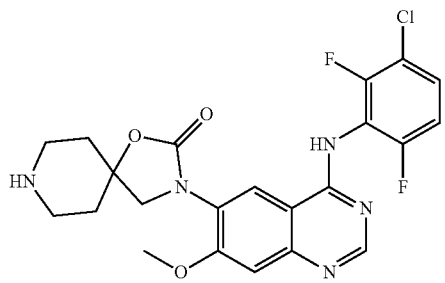 [SMILES: COc1cc2ncnc(Nc3c(F)ccc(Cl)c3F)c2cc1N1CC2(CCNCC2)OC1=O]

Compound 24B (50 mg, 49.91 mmol) was added to ethyl acetate hydrochloride (10 mL, 4 M) and stirred at 20° C. for 1 hour. LCMS detection showed that the reaction was complete. The reaction solution was concentrated, added into 5 mL water, adjusted to 8 of the pH value with 0.5 mol/L sodium carbonate solution, and extracted with dichloromethane (5 mL×2). The organic phase was dried over anhydrous sodium sulfate (0.5 g), filtered, concentrated, and purified by using preparated silica gel chromatography plates to give compound 24C.

Compound 24

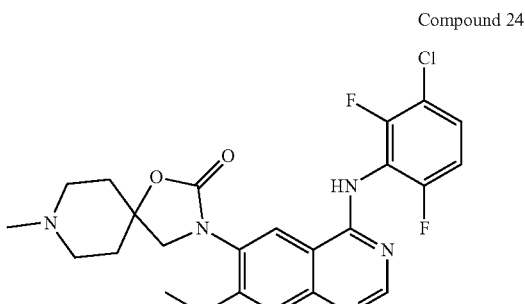

Compound 24

According to the preparation method of compound 1, (4-((3-chloro-2-fluorophenyl)amino)-7-methoxyquinazolin-6-yl)-2-oxa-4,9-diazaspiro[5.5]undecane-3-one was replaced with 3-(4-((3-chloro-2,6-difluorophenyl)amino)-7-methoxyquinazolin-6-yl)-1-oxa-3,8-diazaspiro[4.5]detane-2-one to give compound 24. $^1$H NMR (400 MHz, METHANOL-$d_4$) δ ppm 8.46 (br s, 3H), 8.43 (s, 2H), 7.47-7.61 (m, 1H), 7.37 (s, 1H), 7.18 (td, J=9.1, 1.9 Hz, 1H), 4.09 (s, 3H), 3.95 (s, 2H), 2.93-3.28 (m, 4H), 2.71 (br s, 3H), 2.25-2.40 (m, 2H), 2.19 (br d, J=10.0 Hz, 2H). LCMS (ESI) (5-95AB): m/z: 490.3 [M+1].

Example 25

Compound 25

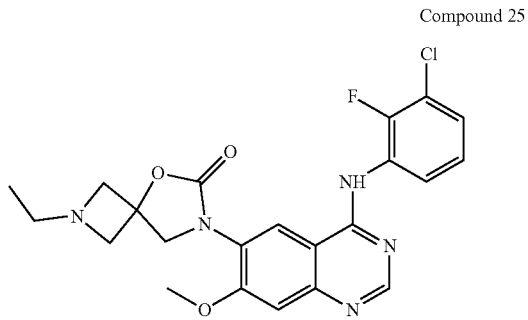 [SMILES: CCN1CC2(C1)CN(c1cc3c(Nc4cccc(Cl)c4F)ncnc3cc1OC)C(=O)O2]

Compound 25

According to the preparation method of compound 1, (4-((3-chloro-2-fluorophenyl)amino)-7-methoxyquinazolin-6-yl)-2-oxa-4,9-diazaspiro[5.5]undecane-3-one was replaced with 7-(4-((3-chloro-2-fluorophenyl)amino)-7-methoxyquinazolin-6-yl)-5-oxa-2,7-diazaspiro[3.4]octane-6-one, and polyformaldehyde was replaced with acetaldehyde to give compound 25. $^1$H NMR (400 MHz, METHANOL-$d_4$) δ=8.47 (s, 1H), 8.39 (s, 1H), 8.58-8.24 (m, 1H), 7.65-7.55 (m, 1H), 7.47-7.39 (m, 1H), 7.34 (s, 1H), 7.30-7.20 (m, 1H), 4.33 (s, 2H), 4.19-4.09 (m, 4H), 3.02 (q, J=7.2 Hz, 2H), 1.18 (t, J=7.2 Hz, 3H). LCMS (ESI) (5-95AB): m/z: 458.1 [M+1].

Example 26

Compound 26

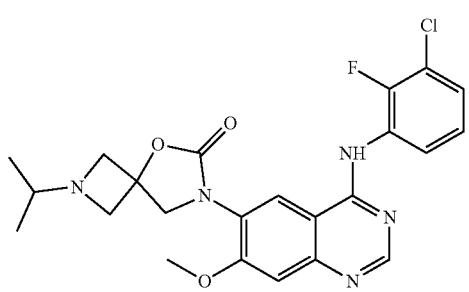

Compound 26

According to the preparation method of compound 1, (4-((3-chloro-2-fluorophenyl)amino)-7-methoxyquinazolin-6-yl)-2-oxa-4,9-diazaspiro[5.5]undecane-3-one was replaced with 7-(4-((3-chloro-2-fluorophenyl)amino)-7-methoxyquinazolin-6-yl)-5-oxa-2,7-diazaspiro[3.4]octane-6-one, and polyformaldehyde was replaced with acetone to give compound 26. $^1$H NMR (400 MHz, METHANOL-$d_4$) δ=8.47 (s, 1H), 8.39 (s, 1H), 7.65-7.54 (m, 1H), 7.47-7.38 (m, 1H), 7.33 (s, 1H), 7.28-7.19 (m, 1H), 4.30 (s, 2H), 4.07 (s, 3H), 3.95-3.84 (m, 4H), 2.89-2.76 (m, 1H), 1.12 (d, J=6.4 Hz, 6H). LCMS (ESI) (5-95AB): m/z: 472.0 [M+1].

Example 27

Compound 27A

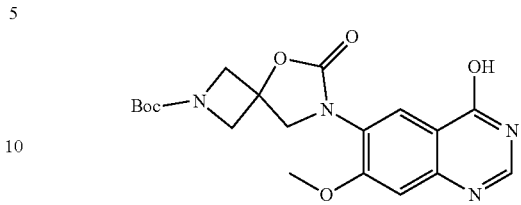

According to the preparation method of compound 1I, 3-oxo-2-oxa-4,9-diazaspiro[5.5]undecane-9-formic acid tert-butyl ester was replaced with 6-oxo-5-oxa-2,7-diazaspiro[3.4]octane-2-carboxylic acid tert-butyl ester, and 6-bromo-N-(3-chloro-2-fluorophenyl)-7-methoxyquinazolin-4-amine was replaced with 6-bromo-7-methoxyquinazolin-4-ol to give compound 27A. LCMS (ESI) (5-95AB): m/z: 403.1 [M+1].

Compound 27B

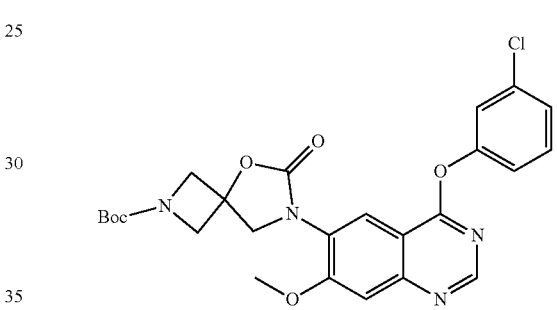

According to the preparation method of compound 16B, 3-(4-hydroxy-7-methoxyquinazolin-6-yl)-2-oxo-1-oxa-3,8-diazaspiro[3.4]octane-2-carboxylic acid tert-butyl ester was replaced with 7-(4-hydroxy-7-methoxyquinazolin-6-yl)-6-oxo-5-oxa-2,7-diazaspiro[3.4]octane-2-carboxylic acid tert-butyl ester to give compound 27B. LCMS (ESI) (5-95AB): m/z: 513.2 [M+1].

Compound 27C

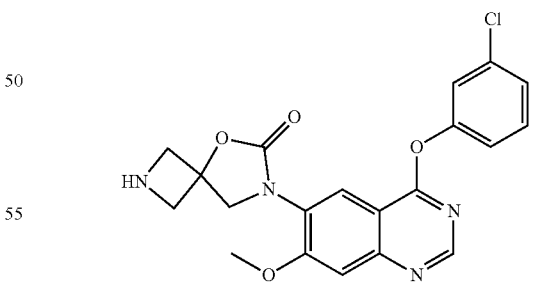

According to the preparation method of compound 24C, 3-(4-((3-chloro-2,6-difluorophenyl)amino)-7-methoxyquinazolin-6-yl)-2-oxo-1-oxa-3,8-diazaspiro[4.5]-8-methyl formate was replaced with 7-(4-(3-chlorophenoxy)-7-methoxyquinazolin-6-yl)-6-oxo-5-oxa-2,7-diazaspiro[3.4]octane-2-carboxylic acid tert-butyl ester to give compound 27C. The crude product would be used directly for the next step.

Compound 27

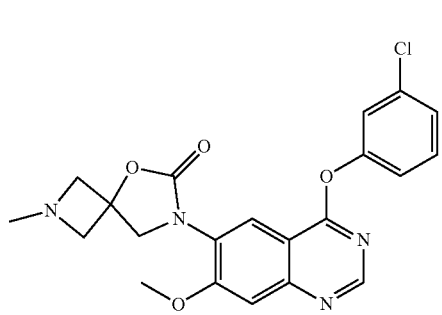

According to the preparation method of compound 1, (4-((3-chloro-2-fluorophenyl)amino)-7-methoxyquinazolin-6-yl)-2-oxa-4,9-diazaspiro[5.5]undecane-3-one was replaced with 7-(4-(3-chlorophenoxy)-7-methoxyquinazolin-6-yl)-5-oxa-2,7-diazaspiro[3.4]octane-6-one to give compound 27. The purity was verified by high performance liquid chromatography and liquid chromatography mass spectrometry simultaneously. $^1$H NMR (400 MHz, deuterated chloroform) δ=8.63 (s, 1H), 8.40 (s, 1H), 7.51-7.42 (m, 2H), 7.41-7.31 (m, 2H), 7.28-7.18 (m, 1H), 4.26 (s, 2H), 4.08 (s, 3H), 3.68-3.59 (m, 4H), 2.44 (s, 3H), LCMS (ESI) (5-95AB): m/z: 427.1 [M+1].

Example 28

Compound 28A

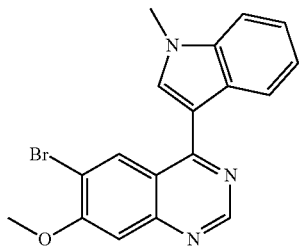 [SMILES: COc1cc2ncnc(-c3cn(C)c4ccccc34)c2cc1Br]

The mixture of 6-bromo-4-chloro-7-methoxy-quinazoline (100.00 mg, 345.54 mmol) and anhydrous aluminium trichloride (150.00 mg, 1.12 mmol, 61.48 µL, 3.26 eq.) in ethylene glycol dimethyl ether (1.50 mL) was heated up to 80° C., then added with a solution of 1-methylindole (100.00 mg, 762.37 mmol) in ethylene glycol dimethyl ether (500.00 µL) and stirred at 80° C. for 2 hours. TLC (PE:EA=1:1) showed that the reaction was complete. LCMS showed products were formed. The mixture was cooled down to 20° C., and added with water (10 mL) to form a suspension. The mixture was filtered. The filter cake was washed with water (5 mL×1) and then dried on a rotary evaporator. The residue was purified by silica gel (PE:EA=10:1 to 1:1 to DCM:MeOH=50:1) to give compound 28A. $^1$H NMR (400 MHz, deuterated chloroform) δ=9.15 (s, 1H), 8.51 (s, 1H), 8.04 (d, J=8.0 Hz, 1H), 7.62 (s, 1H), 7.40-7.21 (m, 4H), 4.02 (s, 3H), 3.89 (s, 3H). LCMS (ESI) (5-95AB): m/z: 367.9 [M+1].

Compound 28B

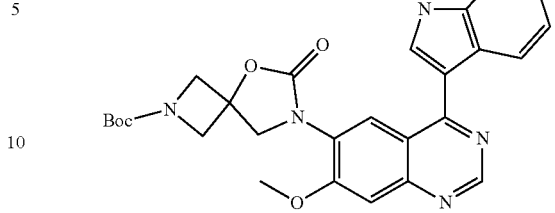

According to the preparation method of compound 1I, 3-oxo-2-oxa-4,9-diazaspiro[5.5]undecane-9-formic acid tert-butyl ester was replaced with 6-oxo-5-oxa-2,7-diazaspiro[3.4]decane-2-carboxylic acid tert-butyl ester, and 6-bromo-N-(3-chloro-2-fluorophenyl)-7-methoxyquinazolin-4-amine was replaced with 6-bromo-7-methoxy-4-(1-methyl-1H-indol-3-yl) quinazoline to give compound 28B. $^1$H NMR (400 MHz, deuterated chloroform) δ=9.16 (s, 1H), 8.36 (s, 1H), 8.23 (d, J=7.6 Hz, 1H), 7.72 (s, 1H), 7.40-7.23 (m, 4H), 4.38-4.28 (m, 2H), 4.17 (s, 2H), 4.06-3.98 (m, 5H), 3.88 (s, 3H), 1.39 (s, 9H). LCMS (ESI) (5-95AB): m/z: 516.1 [M+1].

Compound 28C

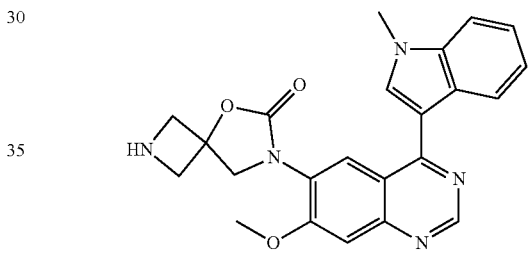

According to the preparation method of compound 24C, 3-(4-((3-chloro-2,6-difluorophenyl)amino)-7-methoxyquinazolin-6-yl)-2-oxo-1-oxa-3,8-diazaspiro[4.5]-8-carboxylic acid tert-butyl ester was replaced with 7-(7-methoxy-4-(1-methyl-1H-indol-3-yl)quinazolin-6-yl)-6-oxo-5-oxa-2,7-diazaspiro[3.4]octane-2-carboxylic acid tert-butyl ester to give compound 28C. The crude product would be used directly for the next step.

Compound 28

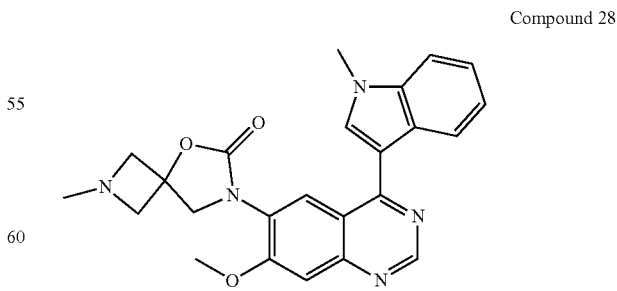

According to the preparation method of compound 1, (4-((3-chloro-2-fluorophenyl)amino)-7-methoxyquinazolin-6-yl)-2-oxa-4,9-diazaspiro[5.5]undecane-3-one was replaced with 7-(7-methoxy-4-(1-methyl-1H-indol-3-yl)

quinazolin-6-yl)-5-oxa-2,7-diazaspiro[3.4]octane-6-one to give compound 28. ¹HNMR (400 MHz, METHANOL-d4) δ ppm 9.09 (s, 1H), 8.60-8.40 (m, 2H), 8.20 (d, J=8.0 Hz, 1H), 7.98 (s, 1H), 7.55 (d, J=8.4 Hz, 1H), 7.47 (s, 1H), 7.40-7.30 (m, 1H), 7.30-7.20 (m, 1H), 4.30 (s, 2H), 4.13 (s, 3H), 3.99 (s, 3H), 3.89 (s, 4H), 2.61 (s, 3H). LCMS (ESI) (5-95AB): m/z: 430.1 [M+1].

Example 29

Compound 29

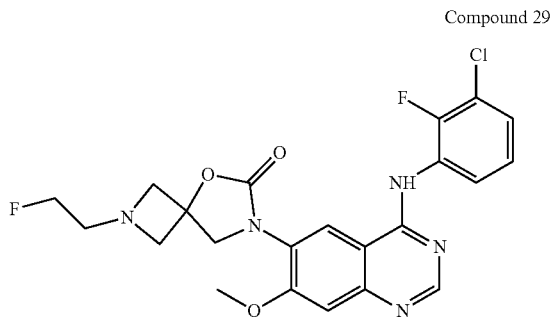 [SMILES: COc1cc2ncnc(Nc3cccc(Cl)c3F)c2cc1N1CC2(CN(CCF)C2)OC1=O]

Compound 29

The mixture of 13E and 1-fluoro-2-iodo-ethane in methanol (1.0 mL) was added with triethylamine (100.00 mg, 988.24 mmol) and then heated up to 70° C. for 4 hours. LCMS detection showed that the reaction was complete. The reaction solution was cooled down to 15° C., diluted with methanol (4 mL) and filtered. The filtrate was purified by high-performance liquid chromatography and then by thin-layer chromatography. The obtained product was dissolved in methanol (5 mL) and water (30 mL), added with 2 M hydrochloric acid (1 mL), and then freeze dried to give compound 29. ¹H NMR (400 MHz, METHANOL-d4) δ=8.76-8.55 (m, 2H), 7.62-7.46 (m, 2H), 7.42-7.36 (m, 1H), 7.34-7.26 (m, 1H), 4.86-4.83 (m, 1H), 4.82-4.64 (m, 5H), 4.47 (s, 2H), 4.13 (s, 3H), 3.81-3.68 (m, 2H). LCMS (ESI) (5-95AB): m/z: 476.0 [M+1].

Example 30

Compound 30

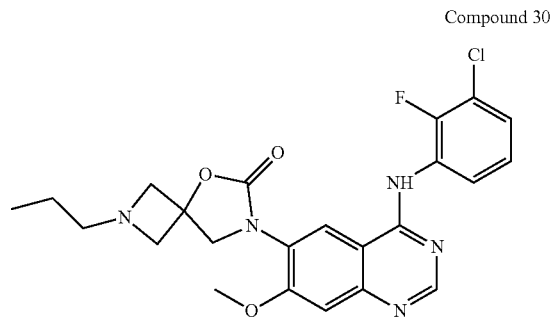 [SMILES: CCCN1CC2(C1)CN(c1cc3c(Nc4cccc(Cl)c4F)ncnc3cc1OC)C(=O)O2]

Compound 30

13E (90.00 mg, 209.39 mmol) and 1-iodopropane (355.94 mg, 2.09 mmol) were dissolved in methanol (4.00 mL), added with triethylamine (423.76 mg, 4.19 mmol) was added to the solution and stirred at 70-80° C. in nitrogen atmosphere for 16 hours. The target compound was detected by liquid chromatography mass spectrometry and the raw materials were not completely consumed. The reaction mixture was filtered with DCM:MeOH=10:1 (22 mL), concentrated, separated and purified by high-performance liquid chromatography, to give compound 30 finally. The purity was verified by high performance liquid chromatography and liquid chromatography mass spectrometry simultaneously.

Example 31

Compound 31

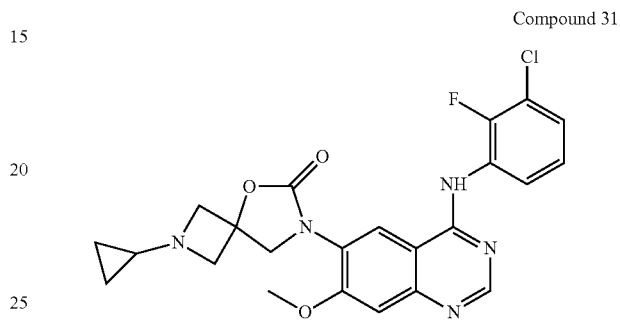

Compound 31

Compound 13E (90.00 mg, 209.39 mmol) and (1-ethoxy-cyclopropoxy)trimethylsilane (145.99 mg, 837.54 mmol) were dissolved in methanol (2.00 mL) and tetrahydrofuran (2.00 mL), added with acetic acid (50.29 mg, 837.54 mmol) then added with sodium cyanoborohydride (52.63 mg, 837.54 mmol) and stirred at 70-80° C. in nitrogen atmosphere for 16 hours. The target compound was detected by liquid chromatography mass spectrometry and the raw materials were not completely consumed. The reaction mixture was filtered by DCM:MeOH=10:1 (22 mL), concentrated, separated and purified by high performance liquid chromatography (HCl condition), to give compound 31 finally. ¹H NMR (400 MHz, METHANOL-d4) δ=8.76 (s, 1H), 8.66 (s, 1H), 7.63-7.48 (m, 2H), 7.39 (s, 1H), 7.36-7.27 (m, 1H), 4.80-4.71 (m, 4H), 4.46 (s, 2H), 4.16 (s, 3H), 3.24-3.18 (m, 1H), 1.09-0.89 (m, 4H). LCMS (ESI) (5-95AB): m/z: 470.1 [M+1].

Example 32

Compound 32

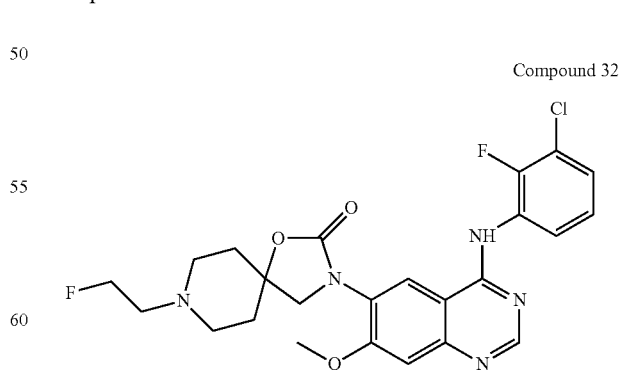

Compound 32

According to the preparation method of compound 29, 7-(4-((3-chloro-2-fluorophenyl)amino)-7-methoxyquinazolin-6-yl)-5-oxa-2,7-diazaspiro[3.4]octane-6-one was replaced with 3-(4-((3-chloro-2-fluorophenyl)amino)-7- methoxyquinazolin-6-yl)-1-oxa-3,8-diazaspiro[4.5]decane-2-one to give compound 32. 1H NMR (400 MHz, METHANOL-d4) δ ppm 8.85-8.71 (m, 2H), 7.71-7.53 (m, 2H), 7.43 (s, 1H), 7.29-7.18 (m, 1H), 5.00 (s, 2H), 4.16 (s, 3H), 4.03 (s, 2H), 3.74-3.56 (m, 4H), 3.53-3.41 (m, 2H). 2.65-2.30 (m, 4H). LCMS (ESI) (5-95AB): m/z: 504.2 [M+1].

Example 33

Compound 33A

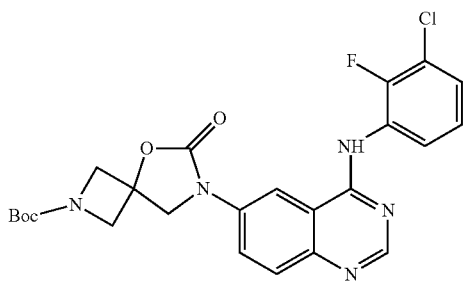 [SMILES: CC(C)(C)OC(=O)N1CC2(C1)CN(c1ccc3ncnc(Nc4cccc(Cl)c4F)c3c1)C(=O)O2]

According to the preparation method of compound 1I, 3-oxo-2-oxa-4,9-diazaspiro[5.5]undecane-9-formic acid tert-butyl ester was replaced with 6-oxo-5-oxa-2,7-diazaspiro[3.4]decane-2-carboxylic acid tert-butyl ester, and 6-bromo-N-(3-chloro-2-fluorophenyl)-7-methoxyquinazolin-4-amine was replaced with 6-bromo-N-(3-chloro-2-fluorophenyl)quinazolin-4-amine to give compound 33A. ¹H NMR (400 MHz, deuterated chloroform) δ=8.78 (s, 1H), 8.42-8.33 (m, 1H), 8.26 (s, 1H), 8.01-7.96 (m, 1H), 7.93-7.87 (m, 1H), 7.23-7.16 (m, 2H), 4.48-4.42 (m, 2H), 4.38 (s, 2H), 4.22-4.15 (m, 2H), 1.50 (s, 9H). LCMS (ESI) (5-95AB): m/z: 500.1 [M+1].

Compound 33B

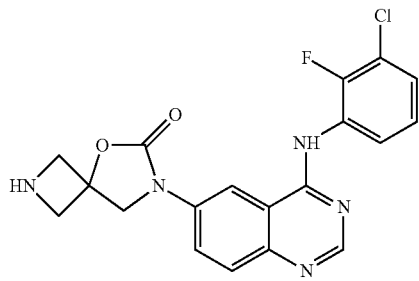 [SMILES: O=C1OC2(CNC2)CN1c1ccc2ncnc(Nc3cccc(Cl)c3F)c2c1]

According to the preparation method of compound 24C, 3-(4-((3-chloro-2,6-difluorophenyl)amino)-7-methoxyquinazolin-6-yl)-2-oxo-1-oxa-3,8-diazaspiro[4.5]decane-8-carboxylic acid tert-butyl ester was replaced with 7-(4-(3-chloro-2-fluorophenyl)amino)quinazolin-6-yl)-6-oxo-5-oxa-2,7-diazaspiro[3.4]octane-2-carboxylic acid tert-butyl ester to give compound 33B. The crude product would be used directly for the next step. LCMS (ESI) (5-95AB): m/z: 400.0 [M+1].

Compound 33

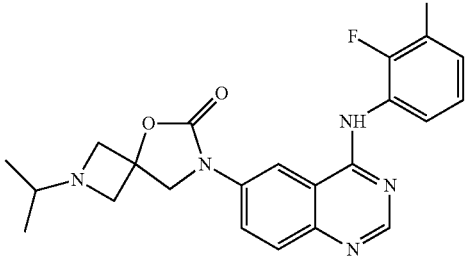

According to the preparation method of compound 1, (4-((3-chloro-2-fluorophenyl)amino)-7-methoxyquinazolin-6-yl)-2-oxa-4,9-diazaspiro[5.5]undecane-3-one was replaced with 7-(4-((3-chloro-2-fluorophenyl)amino)quinazolin-6-yl)-5-oxa-2,7-diazaspiro[3.4]octane-6-one, and polyformaldehyde was replaced with acetone to give compound 33. The purity was verified by high performance liquid chromatography and liquid chromatography mass spectrometry simultaneously. ¹H NMR (400 MHz, METHANOL-d4) δ=8.95-8.77 (m, 2H), 8.54 (br s, 1H), 8.05-7.95 (m, 1H), 7.63-7.53 (m, 2H), 7.38-7.28 (m, 1H), 4.77-4.55 (m, 6H), 3.70-3.60 (m, 1H), 1.43-1.25 (m, 6H). LCMS (ESI) (5-95AB): m/z: 442.0 [M+1].

Example 34

Compound 34

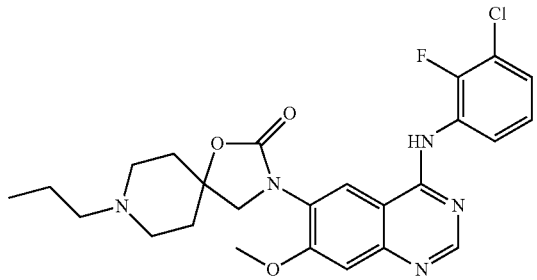

According to the preparation method of compound 1, (4-((3-chloro-2-fluorophenyl)amino)-7-methoxyquinazolin-6-yl)-2-oxa-4,9-diazaspiro[5.5]undecane-3-one was replaced with 3-(4-((3-chloro-2-fluorophenyl)amino)-7-methoxyquinazolin-6-yl)-1-oxa-3,8-diazaspiro[4.5]decane-2-one, and polyformaldehyde was replaced with propanal to give compound 34. ¹H NMR (400 MHz, METHANOL-d4) δ=8.45 (s, 1H), 8.41 (s, 1H), 8.39 (br s, 1H), 7.63-7.54 (m, 1H), 7.44-7.36 (m, 1H), 7.30 (s, 1H), 7.25-7.15 (m, 1H), 4.05 (s, 3H), 3.94 (s, 2H), 3.54-3.43 (m, 2H), 3.30-3.23 (m, 2H), 3.11-3.01 (m, 2H), 2.43-2.18 (m, 4H), 1.88-1.72 (m, 2H), 1.03 (t, J=7.2 Hz, 3H). LCMS (ESI) (5-95AB): m/z: 500.2 [M+1].

Example 35

Compound 35A

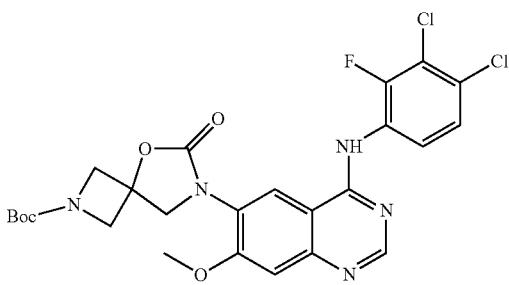 [SMILES: COc1cc2ncnc(Nc3ccc(Cl)c(Cl)c3F)c2cc1N1CC2(CN(C(=O)OC(C)(C)C)C2)OC1=O]

According to the preparation method of compound 1I, 3-oxo-2-oxa-4,9-diazaspiro[5.5]undecane-9-formic acid tert-butyl ester was replaced with 6-oxo-5-oxa-2,7-diazaspiro[3.4]decane-2-carboxylic acid tert-butyl ester, and 6-bromo-N-(3-chloro-2-fluorophenyl)-7-methoxyquinazolin-4-amine was replaced with 6-bromo-N-(3,4-dichloro-2-fluorophenyl)-7-methoxyquinazolin-4-amine to give compound 35A. LCMS (ESI) (5-95AB): m/z: 564.1 [M+1].

Compound 35B

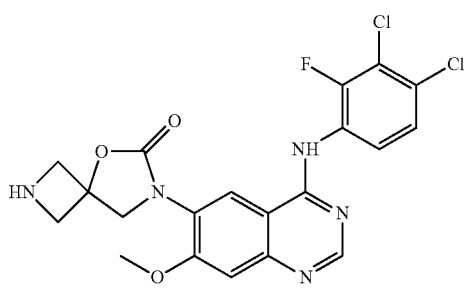 [SMILES: COc1cc2ncnc(Nc3ccc(Cl)c(Cl)c3F)c2cc1N1CC2(CNC2)OC1=O]

According to the preparation method of compound 1J, 4-(4-((3-chloro-2-fluorophenyl)amino)-7-methoxyquinazolin-6-yl)-3-oxo-2-oxa-4,9-diazaspiro[5.5]undecane-9-carboxylic acid tert-butyl ester was replaced with 7-(4-((3,4-dichloro-2-fluorophenyl)amino)-7-methoxyquinazolin-6-yl)-6-oxo-5-oxa-2,7-diazaspiro[4.5]octane-2-carboxylic acid tert-butyl ester to give compound 35B. LCMS (ESI) (5-95AB): m/z: 464.1 [M+1].

Compound 35

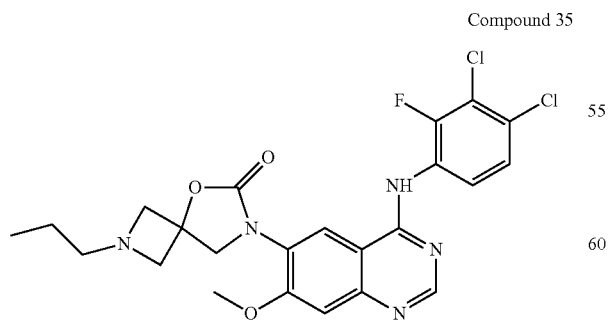

According to the preparation method of compound 1, (4-((3-chloro-2-fluorophenyl)amino)-7-methoxyquinazolin-6-yl)-2-oxa-4,9-diazaspiro[5.5]undecane-3-one was replaced with 7-(4-((3,4-dichloro-2-fluorophenyl)amino)-7-methoxyquinazolin-6-yl)-5-oxa-2,7-diazaspiro[3.4]octane-6-one to give compound 35. ¹H NMR (400 MHz, METHANOL-d4) δ=8.46 (s, 1H), 8.35 (s, 1H), 8.31 (br s, 1H), 7.61 (dd, J=8.0 8.0 Hz, 1H), 7.43 (dd, J=2.0, 8.8 Hz, 1H), 7.31 (s, 1H), 4.32 (s, 2H), 4.18-4.13 (m, 2H), 4.05 (s, 3H), 2.99-2.88 (m, 2H), 1.59-1.51 (m, 2H), 1.04-0.96 (m, 5H). LCMS (ESI) (5-95AB): m/z: 506.1 [M+1].

Example 36

Compound 36A

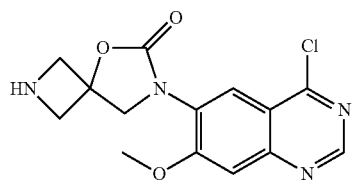 [SMILES: COc1cc2ncnc(Cl)c2cc1N1CC2(CNC2)OC1=O]

According to the preparation method of compound 1C, 6-bromo-7-methoxyquinazolin-4-ol was replaced with 7-(4-hydroxy-7-methoxyquinazolin-6-yl)-6-oxo-5-oxa-2,7-diazaspiro[3.4]octane-2-carboxylic acid tert-butyl ester to give compound 36A. The crude product would be used directly for the next step.

Compound 36B

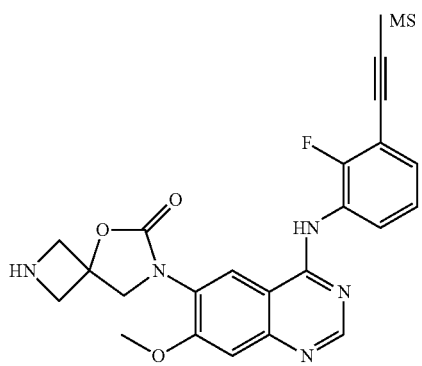 [SMILES: CC#Cc1cccc(Nc2ncnc3cc(OC)c(N4CC5(CNC5)OC4=O)cc23)c1F]

According to the preparation method of compound 1D, 6-bromo-4-chloro-7-methoxyquinazoline was replaced with 7-(4-chloro-7-methoxyquinazolin-6-yl)-5-oxa-2,7-diazaspiro[3.4]octane-6-one, and 3-chloro-2-fluoroaniline was replaced with 2-fluoro-3-((trimethylsilyl)acetylene)aniline to give compound 36B. LCMS (ESI) (5-95AB): m/z: 492.1 [M+1].

Compound 36

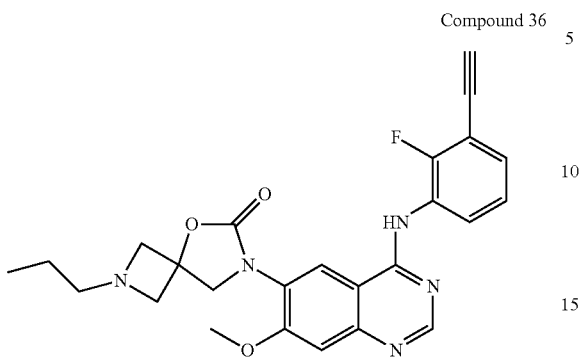

Compound 36

A solution of compound 36B (40.00 mg, 81.37 umol, 1.00 eq.) in methanol (2.00 mL) was added with aldehyde (20.00 mg, 344.20 umol, 25.00 uL, 4.23 eq.), stirred at 40° C. for 0.5 hours, added with NaBH₃CN (20.00 mg, 318.16 umol, 3.91 eq.), and stirred at 40° C. for another 1 hour. The detection results indicated that the reductive amination reaction was complete. After potassium carbonate (45.00 mg, 325.48 umol) was added to the reaction solution, the solution was stirred at room temperature for 0.5 hours. The product was detected by LCMS. The pH value of the reaction solution was adjusted to pH=6 with 2N hydrochloric acid, and the solution was concentrated. The residue was diluted with methanol (2 mL), and then separated and purified by high performance liquid chromatography to give compound 36. $^1$H NMR (400 MHz, METHANOL-d4) δ=8.79 (s, 1H), 8.72 (s, 1H), 7.68-7.53 (m, 1H), 7.68-7.53 (m, 1H), 7.41 (s, 1H), 7.36-7.27 (m, 1H), 4.83-4.73 (m, 2H), 4.70-4.58 (m, 2H), 4.56-4.41 (m, 2H), 4.20 (s, 3H), 3.93 (s, 1H), 3.42-3.34 (m, 2H), 1.80-1.61 (m, 2H), 1.11-1.02 (m, 3H). LCMS (ESI) (5-95AB): m/z: 462.1 [M+1].

Examples 37,38

Compound 37A

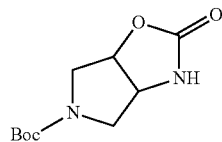

A tetrahydrofuran solution of compound (3R, 4S)-3-(benzyloxycarbonyl amino)-4-hydroxy-pyrrolidine-1-formic acid tert-butyl ester (200 mg, 594.56 mmol, 1.00 eq.) was added with potassium tert-butanol (80.06 mg, 713.47 mmol, 1.20 eq.), and stirred at 20° C. for 2 hours. TLC detection showed that the reaction was complete. The reaction solution was concentrated, and the residue was separated by column chromatography to give compound 37A.

Compound 37B

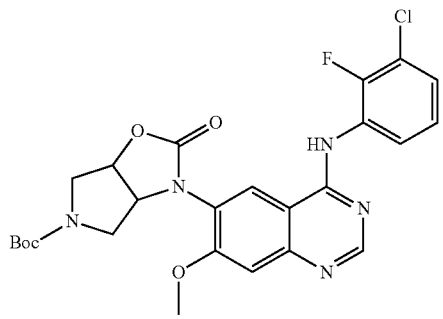 [SMILES: COc1cc2ncnc(Nc3cccc(Cl)c3F)c2cc1N1C(=O)OC2CN(C(=O)OC(C)(C)C)CC21]

Compound 1D (200.0 mg, 522.72 mmol) and compound 37B (119.31 mg, 522.72 mmol) were dissolved in 1,4-dioxane (3 mL), then added with cesium carbonate (510.94 mg, 1.57 mmol), cuprous iodide (298.66 mg, 1.57 mmol) and N, N'-dimethyl-1,2-ethylenediamine (138.2 mg, 1.57 mmol), respectively and stirred under nitrogen protection at 120° C. for 12 hours. TLC showed that the raw materials were not completely consumed. The reaction solution was concentrated, then separated and purified by thin-layer chromatography to give compound 37B. $^1$H NMR (400 MHz, deuterated chloroform) δ=8.75 (s, 1H), 8.33 (br s, 1H), 8.04 (br s, 1H), 7.82 (br d, J=9.3 Hz, 1H), 7.36 (s, 1H), 7.23-7.11 (m, 2H), 5.25 (t, J=6.1 Hz, 1H), 4.85 (br s, 1H), 4.16 (br d, J=12.7 Hz, 1H), 4.02 (s, 3H), 3.58-3.29 (m, 2H), 3.18-2.96 (m, 1H), 1.47 (s, 9H).

Compound 37C

According to the preparation method of compound 1J, 4-(4-((3-chloro-2-fluorophenyl)amino)-7-methoxyquinazolin-6-yl)-3-oxo-2-oxa-4,9-diazaspiro[5.5]undecane-9-carboxylic acid tert-butyl ester was replaced with (3aR, 6aS)-3-(4-((3-chloro-2-fluorophenyl)amino)-7-methoxyquinazolin-6-yl)-2-oxotetrahydro-2H-pyrrol[3,4-d]oxazol-5(3H)-carboxylic acid tert-butyl ester to give compound 37C, which did not require purification. The crude product would be used directly for the next step.

Compound 37D

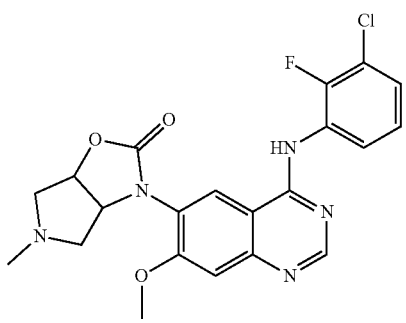 [SMILES: COc1cc2ncnc(Nc3cccc(Cl)c3F)c2cc1N1C(=O)OC2CN(C)CC21]

According to the preparation method of compound 1, (4-((3-chloro-2-fluorophenyl)amino)-7-methoxyquinazolin-6-yl)-2-oxa-4,9-diazaspiro[5.5]undecane-3-one was replaced with (3AR, 6AS)-3-(4-((3-chloro-2-fluorophenyl)amino)-7-methoxyquinazolin-6-yl)hexahydro-2H-pyrrol[3,4-d]oxazol-2-one to give compound 37D. SFC of the compound showed two peaks, which indicated that it was a mixture. $^1$H NMR (400 MHz, METHANOL-d4) δ=8.47 (br s, 1H), 8.33 (s, 1H), 7.56 (t, J=7.4 Hz, 1H), 7.45-7.38 (m, 1H), 7.33 (s, 1H), 7.27-7.19 (m, 1H), 5.31 (dd, J=4.5, 8.0 Hz, 1H), 4.97 (dd, J=5.0, 8.0 Hz, 1H), 4.07 (s, 3H), 3.43 (d, J=11.8 Hz, 1H), 3.12 (d, J=11.3 Hz, 1H), 2.51 (dd, J=4.6, 11.9 Hz, 1H), 2.47 (s, 3H), 2.23 (dd, J=5.0, 11.3 Hz, 1H). LCMS (ESI) (5-95AB): m/z: 444.3 [M+1].

Compounds 37 and 38

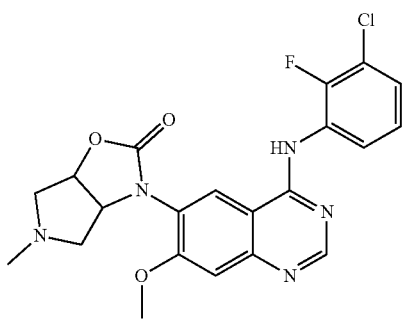 [SMILES: COc1cc2ncnc(Nc3cccc(Cl)c3F)c2cc1N1C(=O)OC2CN(C)CC21]

Compound 37D (21 mg) was weighed and separated by SFC (conditions: Daicel chiral column (250 mm*30 mm, 5 □m), mobile phase (methanol solution containing 0.1% ammonia water)) to give compound 37 (ee value: 100%, retention time (min): 1.142) and compound 38 (ee value: 95.98%, retention time (min): 1.209).

Compound 37: $^1$H NMR (400 MHz, METHANOL-d4) δ=8.45 (s, 1H), 8.30 (s, 1H), 7.59-7.49 (m, 1H), 7.46-7.39 (m, 1H), 7.33 (s, 1H), 7.24 (dt, J=1.5, 8.1 Hz, 1H), 5.28 (dd, J=4.5, 7.9 Hz, 1H), 4.96 (br d, J=4.9 Hz, 1H), 4.07 (s, 3H), 3.37 (br d, J=11.7 Hz, 1H), 3.04 (br d, J=10.3 Hz, 1H), 2.44-2.39 (m, 4H), 2.18-2.09 (m, 1H). LCMS (ESI) (5-95AB): m/z: 444.3 [M+1].

Compound 38: $^1$H NMR (400 MHz, METHANOL-d4) δ=8.45 (s, 1H), 8.30 (s, 1H), 7.55 (br t, J=7.0 Hz, 1H), 7.43 (t, J=6.7 Hz, 1H), 7.33 (s, 1H), 7.24 (dt, J=1.1, 8.1 Hz, 1H), 5.28 (dd, J=4.5, 7.9 Hz, 1H), 4.99-4.94 (m, 1H), 4.07 (s, 3H), 3.36 (d, J=12.0 Hz, 1H), 3.03 (d, J=11.0 Hz, 1H), 2.44-2.38 (m, 4H), 2.12 (dd, J=5.0, 11.1 Hz, 1H). LCMS (ESI) (5-95AB): m/z: 444.3 [M+1].

Examples 39, 40

Compound 39A

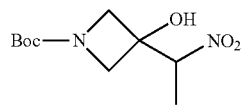 [SMILES: CC([N+](=O)[O-])C1(O)CN(C(=O)OC(C)(C)C)C1]

According to the preparation method of compound 13A, nitromethane was replaced with 1-nitroethane to give compound 39A. 1H NMR (400 MHz, deuterated chloroform) δ=4.82 (q, J=7.0 Hz, 1H), 4.03-3.95 (m, 2H), 3.95-3.86 (m, 2H), 1.67 (d, J=7.0 Hz, 3H), 1.47 (s, 9H).

Compound 39B

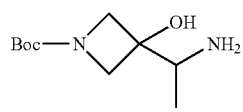

According to the preparation method of compound 13B, 3-hydroxy-3-(nitromethyl)azacyclobutane-1-formic acid tert-butyl ester was replaced with 3-hydroxy-3-(1-nitroethyl)azacyclobutane-1-carboxylic acid tert-butyl ester to give compound 39B. 1HNMR (400 MHz, deuterated chloroform) δ=3.97-3.83 (m, 4H), 3.35-3.28 (m, 1H), 1.46 (s, 9H), 1.10 (d, J=6.8 Hz, 3H).

Compound 39C

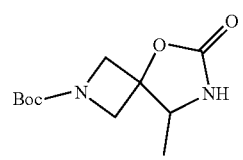 [SMILES: CC1NC(=O)OC12CN(C(=O)OC(C)(C)C)C2]

According to the preparation method of compound 13C, compound 13B was replaced with compound 39B to give compound 39C.

Compound 39D

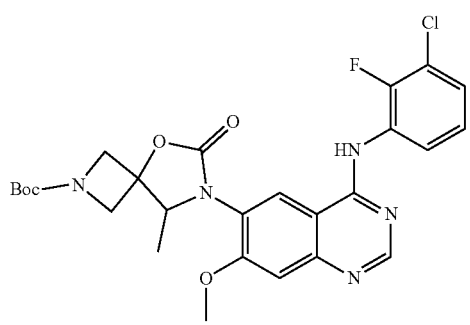 [SMILES: COc1cc2ncnc(Nc3cccc(Cl)c3F)c2cc1N1C(=O)OC2(CN(C(=O)OC(C)(C)C)C2)C1C]

According to the preparation method of compound 1I, compound 1H was replaced with compound 39C to give compound 39D. LCMS (ESI) (5-95AB): m/z: 444.1 [M+1-Boc].

Compound 39E

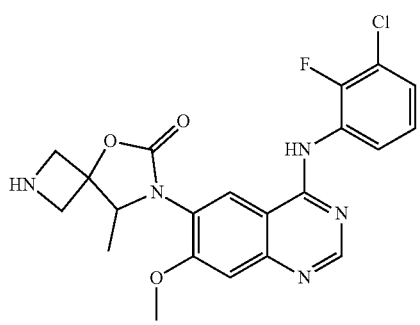 [SMILES: COc1cc2ncnc(Nc3cccc(Cl)c3F)c2cc1N1C(=O)OC2(CNC2)C1C]

According to the preparation method of compound 1J, compound 1I was replaced with compound 39D to give compound 39E.

Compound 39F

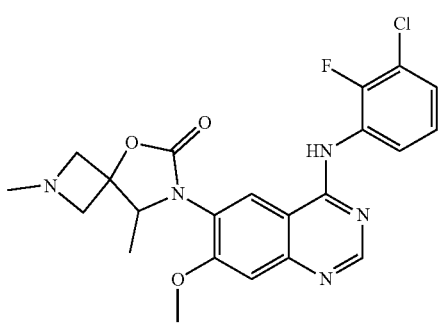 [SMILES: COc1cc2ncnc(Nc3cccc(Cl)c3F)c2cc1N1C(=O)OC2(CN(C)C2)C1C]

According to the preparation method of compound 1, compound 1J was replaced with 39E to give compound 39F. SFC showed two peaks, which indicated that it was a mixture.

Compounds 39 and 40

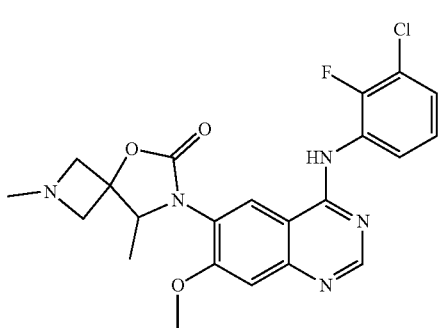 [SMILES: COc1cc2ncnc(Nc3cccc(Cl)c3F)c2cc1N1C(=O)OC2(CN(C)C2)C1C]

Compound 39F (75 mg) was weighed and separated by SFC (condition: Daicel chiral column (250 mm*30 mm, 10 □m), mobile phase (ethanol solution containing 0.1% ammonia water, flow rate: 70 ml/min)) to give compound 39 (ee value: 100%, retention time (min): 0.826).

$^1$H NMR (400 MHz, METHANOL-d4) δ=8.42-8.31 (m, 1H), 8.23 (s, 1H), 7.45 (br t, J=7.0 Hz, 1H), 7.36-7.26 (m, 1H), 7.22 (s, 1H), 7.16-7.06 (m, 1H), 4.48 (br s, 1H), 4.40 (q, J=6.4 Hz, 1H), 3.94 (s, 3H), 3.70 (d, J=9.3 Hz, 1H), 3.57-3.46 (m, 3H), 3.41-3.31 (m, 1H), 2.36 (s, 3H), 1.28-1.15 (m, 4H).

Compound 40 (ee value: 100%, retention time (min): 1.098). $^1$H NMR (400 MHz, METHANOL-d4) δ=8.42-8.31 (m, 1H), 8.23 (s, 1H), 7.45 (br t, J=7.0 Hz, 1H), 7.36-7.26 (m, 1H), 7.22 (s, 1H), 7.16-7.06 (m, 1H), 4.48 (br s, 1H), 4.40 (q, J=6.4 Hz, 1H), 3.94 (s, 3H), 3.70 (d, J=9.3 Hz, 1H), 3.57-3.46 (m, 3H), 3.41-3.31 (m, 1H), 2.36 (s, 3H), 1.28-1.15 (m, 4H).

Examples 41, 42

Compound 41A

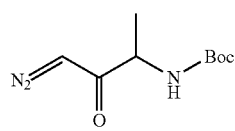

DIEA (69.67 g, 539.09 mmol, 1.70 eq.) and isobutyl chloroformate (64.97 g, 475.67 mmol, 1.5 eq.) were added to a tetrahydrofuran solution (400 mL) of compound 2-(tert-butoxycarbonyl amino) propionic acid (60 g, 317.11 mmol, 1.00 eq.) at 0° C. and stirred for 4 hours, then added with diazomethyl(trimethyl)silane (2 mol, 317.11 mL, 2 eq.), stirred at 0° C. for 2 hours, heated up to 250° C. and stirred for further 6 hours. The reaction solution was concentrated, and the residue was separated by column chromatography to give compound 41A.

Compound 41B

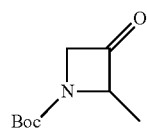

Rhodium acetate (525.32 mg, 1.88 mmol, 0.02 eq.) and triethylamine (189.82 mg, 1.88 mmol, 0.02 eq.) were added to a dichloromethane solution (200 mL) of compound 41A (20 g, 93.79 mmol, 1.00 eq.), and stirred at 0° C. for 1 hour. The reaction solution was concentrated to give a green oily substance, and the residue was separated by column chromatography to compound 41B.

Compound 41C

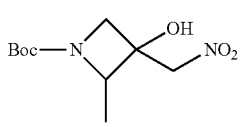

Nitromethane (16.48 g, 269.95 mmol, 5.00 eq.) and triethylamine (273.16 mg, 2.70 mmol, 0.05 eq.) were added to an ethanol solution of compound 41B (10 g, 53.99 mmol, 1.00 eq.), and stirred at 250° C. for 12 hours. The reaction solution was concentrated to give a green oily substance, and the crude product was separated by column chromatography to give compound 41C.

Compound 41D

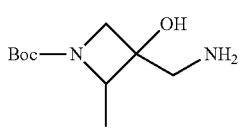

According to the preparation method of compound 13B, 3-hydroxy-3-(nitromethyl)azacyclobutane-1-formic acid tert-butyl ester was replaced with 41C to give compound 41D. ¹HNMR (400 MHz, DMSO-d6) δ=3.90-3.69 (m, 1H), 3.66-3.37 (m, 2H), 3.35-3.13 (m, 2H), 1.20-1.10 (m, 9H), 1.01-0.92 (m, 3H).

Compound 41E

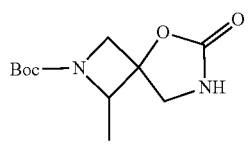 [SMILES: CC1N(C(=O)OC(C)(C)C)CC12CNC(=O)O2]

According to the preparation method of compound 13C, compound 13B was replaced with compound 41D to give compound 41E. ¹H NMR (400 MHz, deuterated chloroform) δ=4.05-3.96 (m, 1H), 3.47-3.30 (m, 4H), 3.47-3.30 (m, 1H), 1.38 (s, 9H), 1.37 (br s, 2H).

Compound 41F

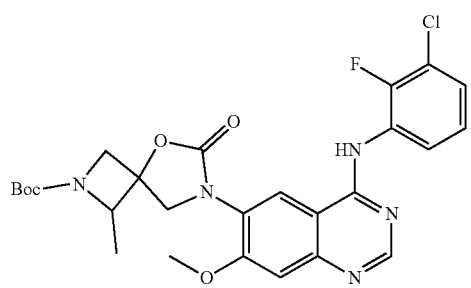 [SMILES: COc1cc2ncnc(Nc3cccc(Cl)c3F)c2cc1N1CC2(CN(C(=O)OC(C)(C)C)C2C)OC1=O]

According to the preparation method of compound 1I, 1H was replaced with 41E to give compound 41F. 1H NMR (400 MHz, deuterated chloroform) δ=8.60 (s, 1H), 8.12-7.99 (m, 2H), 7.80 (br s, 1H), 7.24-7.16 (m, 2H), 7.14-7.01 (m, 1H), 4.38-4.29 (m, 1H), 4.25 (d, J=10.3 Hz, 1H), 4.02 (s, 3H), 1.49 (d, J=6.6 Hz, 3H), 1.41 (s, 9H).

Compound 41G

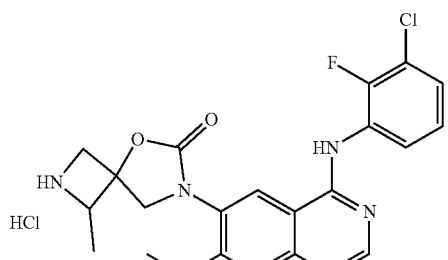

According to the preparation method of compound 1J, compound 1I was replaced with 41F to give compound 41G.

Compound 41H

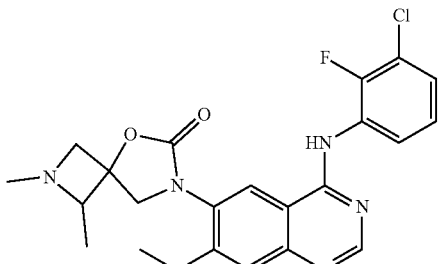

According to the preparation method of compound 1, compound 1J was replaced with compound 41G. SFC showed two peaks, which indicated that it was a mixture.

Compounds 41 and 42

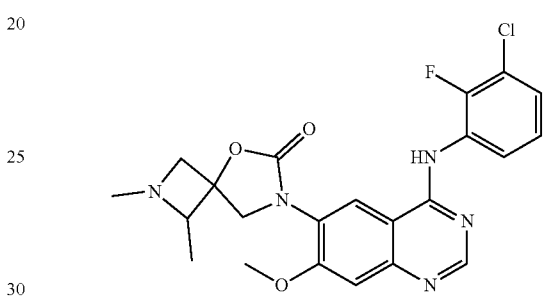

Compound 41H was weighed and separated by SFC (condition: Daicel chiral column (250 mm*30 mm, 10 □m), mobile phase (ethanol solution of 0.1% ammonia water)) to give compound 41 (ee value: 100%, retention time (min): 2.368). ¹HNMR (400 MHz, METHANOL-d4) δ=8.36 (s, 1H), 8.23 (s, 1H), 7.44 (br t, J=7.1 Hz, 1H), 7.31 (br t, J=6.8 Hz, 1H), 7.21 (s, 1H), 7.16-7.09 (m, 1H), 4.76 (s, 16H), 4.39 (q, J=6.5 Hz, 1H), 3.93 (s, 3H), 3.70 (d, J=9.3 Hz, 1H), 3.57-3.48 (m, 2H), 3.36 (d, J=9.3 Hz, 1H), 2.36 (s, 3H), 1.42-1.24 (m, 1H), 1.24-1.14 (m, 5H), 1.08 (br t, J=7.1 Hz, 1H), 0.79 (br d, J=7.1 Hz, 1H).

Compound 42 (ee value: 95.528%, retention time (min): 2.529). ¹H NMR (400 MHz, METHANOL-d4) 8.36 (s, 1H), 8.23 (s, 1H), 7.44 (br t, J=7.1 Hz, 1H), 7.31 (br t, J=6.8 Hz, 1H), 7.21 (s, 1H), 7.16-7.09 (m, 1H), 4.76 (s, 16H), 4.39 (q, J=6.5 Hz, 1H), 3.93 (s, 3H), 3.70 (d, J=9.3 Hz, 1H), 3.57-3.48 (m, 2H), 3.36 (d, J=9.3 Hz, 1H), 2.36 (s, 3H), 1.42-1.24 (m, 1H), 1.24-1.14 (m, 5H), 1.08 (br t, J=7.1 Hz, 1H), 0.79 (br d, J=7.1 Hz, 1H).

Example 43

Compound 43A

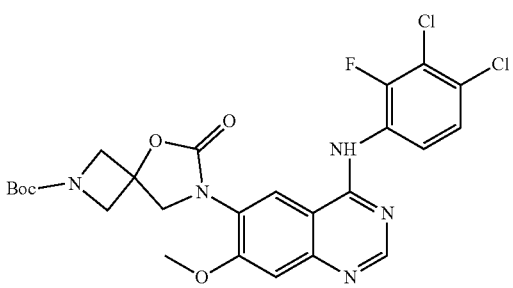 [SMILES: COc1cc2ncnc(Nc3ccc(Cl)c(Cl)c3F)c2cc1N1CC2(CN(C(=O)OC(C)(C)C)C2)OC1=O]

According to the preparation method of compound 1I, compound 1D was replaced with compound 6A to give compound 43A. 1H NMR (400 MHz, deuterated chloroform) δ 8.74-8.62 (m, 1H), 8.20-8.13 (m, 1H), 8.11 (s, 1H), 7.75 (br s, 1H), 7.32-7.27 (m, 2H), 4.48-4.41 (m, 2H), 4.26 (s, 2H), 4.17 (d, J=10.0 Hz, 2H), 3.97 (s, 3H), 1.49 (s, 9H).

Compound 43B

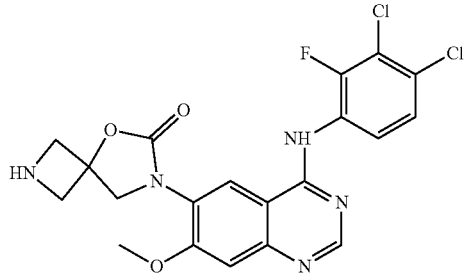 [SMILES: COc1cc2ncnc(Nc3ccc(Cl)c(Cl)c3F)c2cc1N1CC2(CNC2)OC1=O]

According to the preparation method of compound 1J, compound 1I was replaced with 43A to give compound 43B.

Compound 43

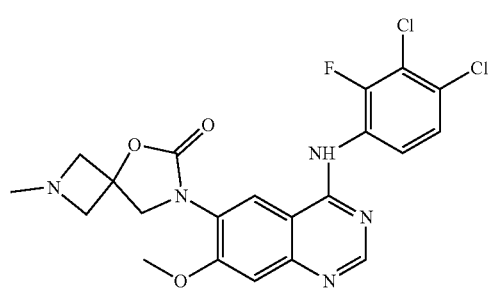 [SMILES: COc1cc2ncnc(Nc3ccc(Cl)c(Cl)c3F)c2cc1N1CC2(CN(C)C2)OC1=O]

According to the preparation method of compound 1, compound 1J was replaced with compound 43B to give compound 43. $^1$HNMR (400 MHz, DMSO-d$_6$) δ 9.97 (br s, 1H), 8.48 (br d, J=14.8 Hz, 1H), 8.13 (s, 1H), 7.66-7.49 (m, 2H), 7.37 (s, 1H), 4.21 (s, 2H), 4.00 (s, 3H), 3.87-3.60 (m, 4H), 2.52 (s, 3H).

Example 44

Compound 44A

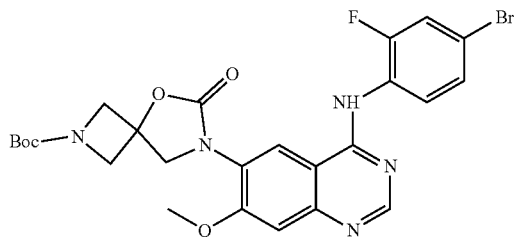 [SMILES: COc1cc2ncnc(Nc3ccc(Br)cc3F)c2cc1N1CC2(CN(C(=O)OC(C)(C)C)C2)OC1=O]

According to the preparation method of compound 1I, compound 1D was replaced with compound 9A to give compound 44A. 1H NMR (400 MHz, deuterated chloroform) δ=8.76-8.68 (m, 1H), 8.23 (t, J=8.5 Hz, 1H), 8.09 (s, 1H), 7.38-7.36 (m, 1H), 7.38-7.35 (m, 1H), 7.35-7.33 (m, 1H), 7.32-7.30 (m, 1H), 4.44 (d, J=10.3 Hz, 2H), 4.27 (s, 2H), 4.18 (d, J=10.2 Hz, 2H), 4.01 (s, 3H), 1.49 (s, 9H).

Compound 44B

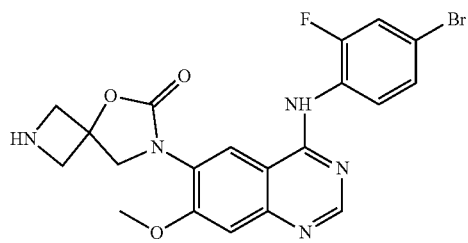 [SMILES: COc1cc2ncnc(Nc3ccc(Br)cc3F)c2cc1N1CC2(CNC2)OC1=O]

According to the preparation method of compound 1J, compound 1I was replaced with 44A to give compound 44B. LCMS (ESI) (5-95AB): m/z: 473.9 [M+1].

Compound 44

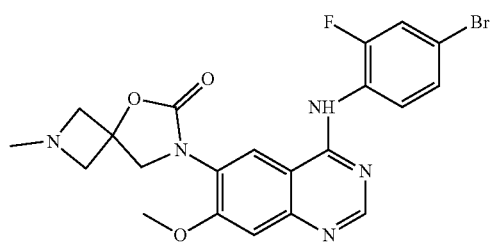 [SMILES: COc1cc2ncnc(Nc3ccc(Br)cc3F)c2cc1N1CC2(CN(C)C2)OC1=O]

According to the preparation method of compound 1, compound 1J was replaced with compound 44B to give compound 44. $^1$H NMR (400 MHz, METHANOL-d$_4$) δ=8.46 (s, 1H), 8.43-8.28 (m, 2H), 7.62 (t, J=8.4 Hz, 1H), 7.49 (d, J=9.8 Hz, 1H), 7.43 (d, J=8.7 Hz, 1H), 7.32 (s, 1H), 4.32 (s, 2H), 4.20-4.11 (m, 4H), 4.09-3.96 (m, 3H), 2.77 (s, 3H). LCMS (ESI) (5-95AB): m/z: 487.9 [M+1].

Example 45

Compound 45A

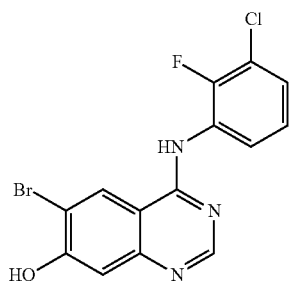 [SMILES: Oc1cc2ncnc(Nc3cccc(Cl)c3F)c2cc1Br]

Pyridine hydrochloride (3.02 g, 26.14 mmol, 5.00 eq.) was added to compound 1D (2 g, 5.23 mmol, 1.00 eq.), heated up to 170° C. and stirred for 2 hours. The reaction solution was concentrated, and saturated sodium bicarbonate solution was added to adjust the solution to PH=9. The residue was extracted with mixed solvent (DCM:MeOH=10:1), and the organic layer was separated, dried over anhydrous sodium sulfate, and concentrated. The crude product was separated by column chromatography to give compound 45A. 1H NMR (400 MHz, DMSO-d6) δ=9.86 (s, 1H), 8.75 (s, 1H), 8.41 (s, 1H), 7.50 (q, J=6.9 Hz, 2H), 7.33-7.25 (m, 1H), 7.20 (s, 1H).

Compound 45B

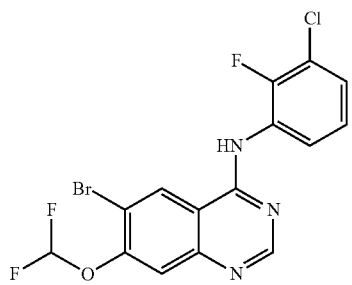 [SMILES: Fc1c(Cl)cccc1Nc1ncnc2cc(OC(F)F)c(Br)cc12]

Potassium hydroxide (4.26 g, 75.97 mmol, 20.0 eq.) and diethyl (bromodifluoromethyl)phosphonate (2.03 g, 7.60 mmol, 2.0 eq.) were added to the mixture of acetonitrile (5 mL) and water (5 mL) of compound 45A (1.4 g, 3.80 mmol, 1.00 eq.), and stirred at 20° C. for 12 hours. The reaction solution was concentrated to give compound 45B. ¹H NMR (400 MHz, METHANOL-d4) δ=8.82 (s, 1H), 8.53 (s, 1H), 7.61-7.55 (m, 2H), 7.50-7.36 (m, 2H), 7.30-7.20 (m, 2H).

Compound 45C

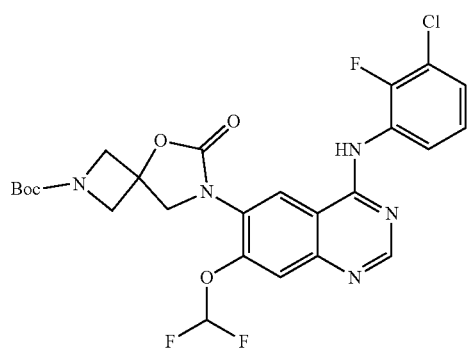 [SMILES: CC(C)(C)OC(=O)N1CC2(C1)CN(c1cc3c(Nc4cccc(Cl)c4F)ncnc3cc1OC(F)F)C(=O)O2]

According to the preparation method of compound 1I, compound 1D was replaced with compound 45B to give compound 45C. ¹H NMR (400 MHz, METHANOL-d4) δ=8.63-8.48 (m, 2H), 7.68-7.55 (m, 2H), 7.49-7.43 (m, 1H), 7.38 (s, 1H), 7.26 (t, J=8.1 Hz, 1H), 7.20 (s, 1H), 7.02 (s, 1H), 4.35-4.19 (m, 4H), 1.50 (s, 9H), 1.47 (s, 2H).

Compound 45D

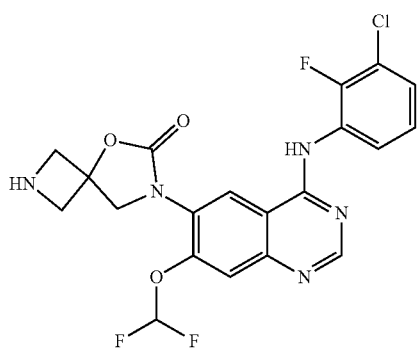 [SMILES: O=C1OC2(CNC2)CN1c1cc2c(Nc3cccc(Cl)c3F)ncnc2cc1OC(F)F]

According to the preparation method of compound 1J, compound 1I was replaced with compound 45C to give compound 45D.

Compound 45

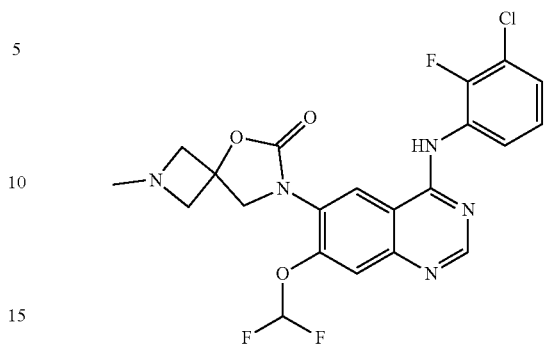

According to the preparation method of compound 1, compound 1J was replaced with compound 45D to give compound 45. 1H NMR (400 MHz, METHANOL-d4) δ=8.53 (s, 2H), 7.67-7.55 (m, 2H), 7.45 (br t, J=7.5 Hz, 1H), 7.38 (s, 1H), 7.31-7.22 (m, 1H), 7.20 (s, 1H), 7.02 (s, 1H), 4.32 (s, 2H), 3.73-3.61 (m, 4H), 2.48 (s, 3H).

Example 46

Compound 46A

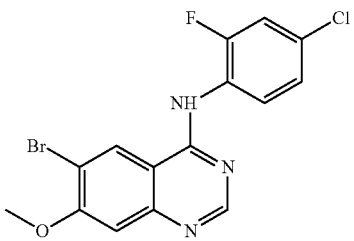 [SMILES: COc1cc2ncnc(Nc3ccc(Cl)cc3F)c2cc1Br]

According to the preparation method of compound 1D, 3-chloro-2-fluoroaniline was replaced with 4-chloro-2-fluoroaniline to give compound 46A. ¹HNMR (400 MHz, DMSO-d6) δ=9.15 (s, 1H), 8.71 (s, 1H), 7.58 (dt, J=6.1, 8.8 Hz, 1H), 7.49-7.41 (m, 2H), 7.25-7.16 (m, 1H), 4.05 (s, 3H).

Compound 46B

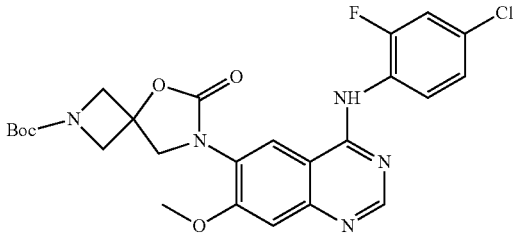 [SMILES: COc1cc2ncnc(Nc3ccc(Cl)cc3F)c2cc1N1CC2(CN(C(=O)OC(C)(C)C)C2)OC1=O]

According to the preparation method of compound 1I, compound 1D was replaced with compound 46A to give compound 46B. ¹H NMR (400 MHz, CHLOROFORM-d) δ=8.70 (s, 1H), 8.30-8.21 (m, 1H), 8.09 (s, 1H), 7.30 (s, 1H), 7.23-7.21 (m, 1H), 7.21-7.18 (m, 1H), 4.45 (d, J=10.5 Hz, 2H), 4.27 (s, 2H), 4.18 (d, J=10.3 Hz, 2H), 4.00 (s, 3H), 1.50 (s, 9H). LCMS (ESI) (5-95AB): m/z: 530.0 [M+1].

Compound 46C

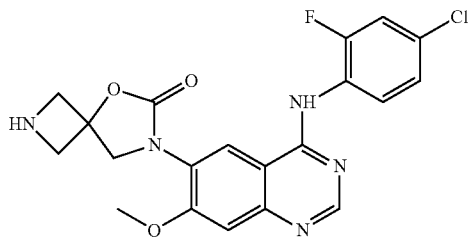 [SMILES: COc1cc2ncnc(Nc3ccc(Cl)cc3F)c2cc1N1CC2(CNC2)OC1=O]

According to the preparation method of compound 1J, compound 1I was replaced with compound 46B to give compound 46C. LCMS (ESI) (5-95AB): m/z: 430.0 [M+1].

Compound 46

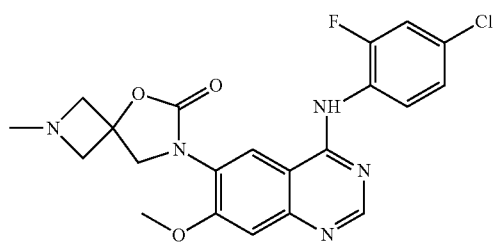 [SMILES: COc1cc2ncnc(Nc3ccc(Cl)cc3F)c2cc1N1CC2(CN(C)C2)OC1=O]

According to the preparation method of compound 1, compound 1J was replaced with compound 46C to give compound 46. $^1$HNMR (400 MHz, METHANOL-d4) δ=8.46 (s, 1H), 8.37 (s, 1H), 7.67 (t, J=8.4 Hz, 1H), 7.39-7.25 (m, 3H), 4.30 (s, 2H), 4.09-4.02 (m, 4H), 4.07 (s, 3H), 2.71 (s, 3H). LCMS (ESI) (5-95AB): m/z: 444.0 [M+1].

Example 47

Compound 47A

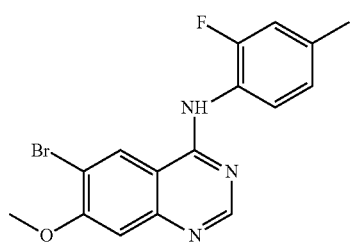

According to the preparation method of compound 1D, 3-chloro-2-fluoroaniline was replaced with 2-fluoro-4-methylaniline to give compound 47A. $^1$H NMR (400 MHz, DMSO-d6) δ=9.08 (s, 1H), 8.71 (s, 1H), 7.45-7.37 (m, 2H), 7.21 (d, J=11.4 Hz, 1H), 7.12 (d, J=8.3 Hz, 1H), 4.06 (s, 3H), 2.38 (s, 3H).

Compound 47B

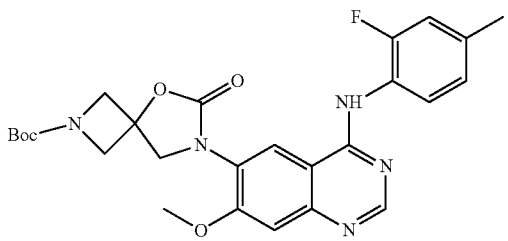 [SMILES: COc1cc2ncnc(Nc3ccc(C)cc3F)c2cc1N1CC2(CN(C(=O)OC(C)(C)C)C2)OC1=O]

According to the preparation method of compound 1I, compound 1D was replaced with compound 47A to give compound 47B. $^1$H NMR (400 MHz, deuterated chloroform) δ=8.73 (s, 1H), 8.19 (t, J=8.3 Hz, 1H), 7.99 (s, 1H), 7.37 (s, 1H), 7.06-7.01 (t, 2H), 4.45 (d, J=10.3 Hz, 2H), 4.27 (s, 2H), 4.17 (d, J=10.0 Hz, 2H), 4.04 (s, 3H), 2.39 (s, 3H), 1.50 (s, 9H). LCMS (ESI) (5-95AB): m/z: 510.1 [M+1].

Compound 47C

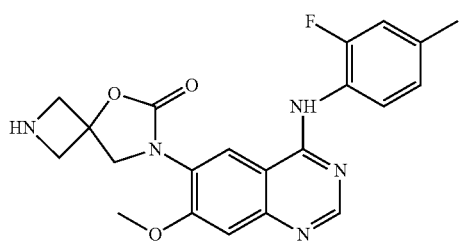 [SMILES: COc1cc2ncnc(Nc3ccc(C)cc3F)c2cc1N1CC2(CNC2)OC1=O]

According to the preparation method of compound 1J, compound 1I was replaced with compound 47B to give compound 47C. LCMS (ESI) (5-95AB): m/z: 410.3 [M+1].

Compound 47

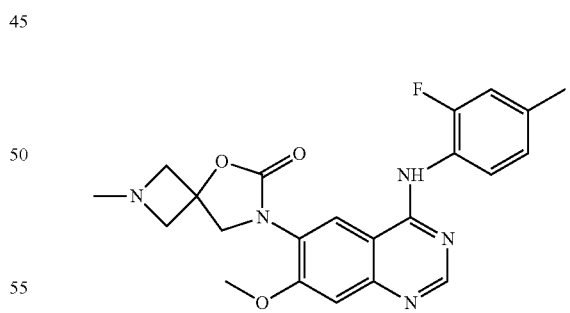

According to the preparation method of compound 1, compound 1J was replaced with 47C to give compound 47. 1H NMR (400 MHz, METHANOL-d4) δ=8.41 (s, 1H), 8.37 (s, 1H), 7.47 (t, J=8.2 Hz, 1H), 7.32 (s, 1H), 7.12-7.04 (m, 2H), 4.28 (s, 2H), 4.07 (s, 3H), 3.92-3.79 (m, 4H), 2.62-2.55 (m, 3H), 2.42 (s, 3H). LCMS (ESI) (5-95AB): m/z: 424.1 [M+1].

Example 48

Compound 48A

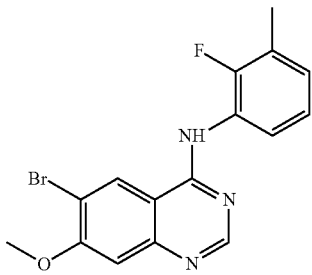 [SMILES: COc1cc2ncnc(Nc3cccc(C)c3F)c2cc1Br]

According to the preparation method of compound 1D, 3-chloro-2-fluoroaniline was replaced with 2-fluoro-3-methylaniline to give compound 48A. $^1$H NMR (400 MHz, DMSO-d6) δ=11.77 (br s, 1H), 9.29 (s, 1H), 8.87 (s, 1H), 7.53 (s, 1H), 7.41-7.28 (m, 2H), 7.28-7.15 (m, 1H), 4.07 (s, 3H), 2.31 (s, 3H).

Compound 48B

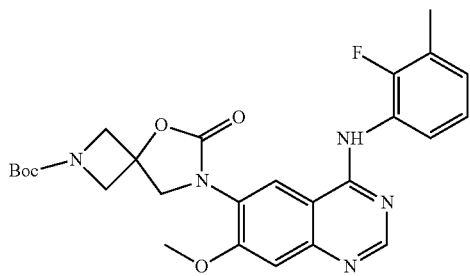 [SMILES: COc1cc2ncnc(Nc3cccc(C)c3F)c2cc1N1CC2(CN(C(=O)OC(C)(C)C)C2)OC1=O]

According to the preparation method of compound 1I, compound 1D was replaced with compound 48A to give compound 48B. $^1$H NMR (400 MHz, deuterated chloroform) δ=8.63 (s, 1H), 8.10 (t, J=7.5 Hz, 1H), 7.94 (s, 1H), 7.53-7.43 (m, 1H), 7.21 (s, 1H), 7.02 (t, J=7.9 Hz, 1H), 6.94-6.86 (m, 1H), 4.36 (d, J=10.9 Hz, 2H), 4.17 (s, 2H), 4.11-4.06 (m, 2H), 3.90 (s, 3H), 2.26 (d, J=2.0 Hz, 3H), 1.41 (s, 9H). LCMS (ESI) (5-95AB): m/z: 510.1 [M+1].

Compound 48C

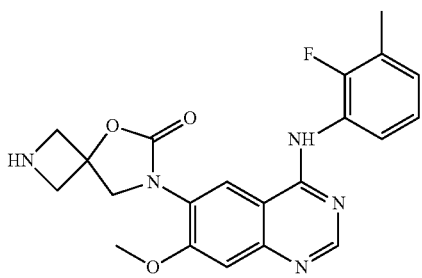 [SMILES: COc1cc2ncnc(Nc3cccc(C)c3F)c2cc1N1CC2(CNC2)OC1=O]

According to the preparation method of compound 1J, compound 1I was replaced with compound 48B to give compound 48C. LCMS (ESI) (5-95AB): m/z: 410.1 [M+1].

Compound 48

According to the preparation method of compound 1, compound 1J was replaced with compound 48C to give compound 48. 1HNMR (400 MHz, METHANOL-d4) δ=8.42 (s, 1H), 8.38 (s, 1H), 8.33 (br s, 1H), 7.47-7.40 (m, 1H), 7.30 (s, 1H), 7.23-7.17 (m, 1H), 7.16-7.10 (m, 1H), 4.39-4.28 (m, 2H), 4.25-4.13 (m, 4H), 4.06 (s, 3H), 2.79 (s, 3H), 2.34 (d, J=1.7 Hz, 3H). LCMS (ESI) (5-95AB): m/z: 424.2 [M+1].

Example 49

Compound 49A

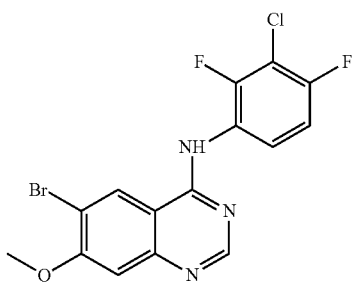 [SMILES: COc1cc2ncnc(Nc3ccc(F)c(Cl)c3F)c2cc1Br]

According to the preparation method of compound 1D, 3-chloro-2-fluoroaniline was replaced with 2,4-dichloro-3-methylaniline to give compound 49A. $^1$H NMR (400 MHz, DMSO-d$_6$) δ=9.03 (s, 1H), 8.61 (s, 1H), 7.62-7.54 (m, 1H), 7.48-7.38 (m, 2H), 4.04 (s, 3H).

Compound 49B

According to the preparation method of compound 1I, compound 1D was replaced with 49A to give compound 49B. $^1$HNMR (400 MHz, deuterated chloroform) δ=8.63 (s, 1H), 8.20 (s, 1H), 7.95-7.66 (m, 2H), 7.21 (s, 1H), 4.44 (d, J=10.3 Hz, 2H), 4.26 (s, 2H), 4.18 (d, J=10.4 Hz, 2H), 3.95 (s, 3H), 1.50 (s, 9H). LCMS (ESI) (5-95AB): m/z: 548.0 [M+1].

Compound 49C

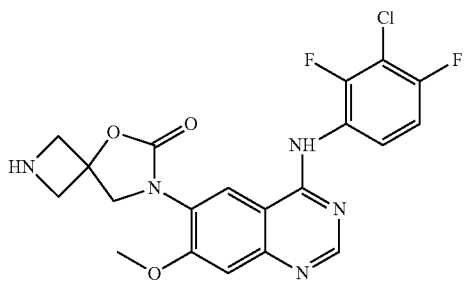 [SMILES: COc1cc2ncnc(Nc3ccc(F)c(Cl)c3F)c2cc1N1CC2(CNC2)OC1=O]

According to the preparation method of compound 1J, compound 1I was replaced with 49B to give compound 49C. LCMS (ESI) (5-95AB): m/z: 448.1 [M+1].

Compound 49

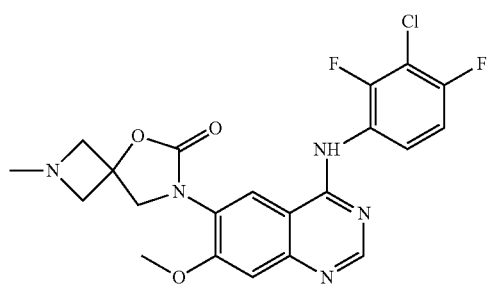 [SMILES: COc1cc2ncnc(Nc3ccc(F)c(Cl)c3F)c2cc1N1CC2(CN(C)C2)OC1=O]

According to the preparation method of compound 1, compound 1J was replaced with 49C to give compound 49. 1H NMR (400 MHz, deuterated chloroform) δ=8.64 (s, 1H), 8.17 (s, 1H), 7.87 (dt, J=5.6, 8.8 Hz, 1H), 7.80 (br s, 1H), 7.22 (s, 1H), 7.05-6.97 (m, 1H), 4.30 (s, 2H), 3.96 (s, 3H), 3.69 (d, J=9.2 Hz, 2H), 3.51 (d, J=9.2 Hz, 2H), 2.48 (s, 3H). LCMS (ESI) (5-95AB): m/z: 462.2 [M+1]

Biochemical Experiments:

The Purpose of the Experiment is:

Detection of inhibitory effects of compounds on enzymatic activities of EGFR WT, EGFR [L858R] and EGFR [d746-750]

Examperimental Materials:

EGFR WT (Invitrogen, Cat. No PR7295B), EGFR [L858R] (Invitrogen, Cat. No PR7447A), EGFR [d746-750] (Invitrogen, Cat. No PV6179), ATP (Sigma, Cat. No. A7699-1G), DMSO (Sigma, Cat. No. D2650), DTT (Sigma, Cat. No. 43815), 384-well plates compound dilution plates (Greiner, Cat. No. 781280), 384-well plates_test plates (Perkin Elmer, Cat. No. 6007299), HTRF KinEASE TK Kit (Cisbio, Cat. No. 62TKOPEB), MgCl$_2$ (Sigma, Cat. No. M1028), Orthovanadate (Sigma, Cat. No. S6508), BSA (Sigma, Cat. No. A7030), HEPES (Life technology, Cat. No. 11344-041)

Experimental Methods:

Final Test Concentrations of Compounds:

The final test concentrations of the test compounds ranged from 10 μM to 0.17 nM, with serial 3-fold dilutions and 11 gradient concentrations.

Kinase Assay:

Buffer formulation: a buffer consisted of 50 mM HEPES (pH 7.5), 0.01% BSA, 5 mM MgCl$_2$, 0.1 mM Orthovanadate. After the buffer was formulated, an enzyme and a substrate were mixed with pre-diluted compounds of varying concentrations, and placed at room temperature for 15 minutes. The reaction was initiated by adding ATP and incubated at room temperature for 60 minutes (wherein negative and positive controls were set up). The 10 μL reaction system consisted of a 2.5 μL compound, a 5 μL mixture of enzyme and substrate, and 2.5 μL ATP. After the reaction was complete, antibodies were added to test, the detection was performed with Evnvision after incubation at room temperature for 60 minutes, and data were collected. Data analysis and simulation were performed using XLfit5 software.

Cell Experiment:

Experimental Materials

RPMI 1640 medium, FBS fetal bovine serum and trypsin-EDTA were purchased from Giboco. DPBS was purchased from Corning, penicillin/streptomycin solution from Hyclone, Cell-Titer Glo reagent from Promega (1 kit, Cat. No. G7571). PC-9 was built by WuXi itself. Plate reader: Envision (Perkin Elmer).

Experimental Methods:

45 μL Culture media was added to columns 1, 2, 24 of a 384-well plate, repectively. The cell suspension was separated by Multi-drop, 45 μL (1000 cells) per well, which was placed and cultured in an incubator overnight. A compound was added to the source plate according to the requirement of Echo liquid-separation. The compound in the source plate was added to the interplate and diluted to an intermediate concentration, then the compound in the source plate and the interplate was added to the cell plate, and the cells were further cultured in the incubator for 72 hours. After 72 hours, Cell-Titer Glo reagent and cells were taken out and equilibrated at room temperature for 30 minutes. 25 μL Cell-Titer Glo reagent was separated into the cells in 384-well plate by Multi-drop, shaken at medium speed for 3 minutes, centrifuged at 1000 rpm for 2 minutes, and kept for 10 minutes. Envision was used to read the plate (Luminescence).

IC 50 values of wild-type EGFR enzyme, EGFR exon 19 deletion enzyme, EGFR L858R enzyme, anti-PC-9 cell proliferative activity, anti-HCC827 cell proliferative activity and anti-A431 cell proliferative activity of the compounds of the present invention are shown in the following table.

| Compounds | Wild-type EGFR enzyme IC$_{50}$ (nM) | EGFR exon 19 deletion enzyme IC$_{50}$ (nM) | EGFR L858R enzyme IC$_{50}$ (nM) | Anti-PC-9 (Δ19del) cell proliferative activity IC$_{50}$ (nM) | Anti-A431 cell proliferative activity IC$_{50}$ (nM) |
|---|---|---|---|---|---|
| Formate of compound 2 | — | 16.5 | 48.1 | 165 | — |
| Formate of compound 3 | — | 0.02 | 0.1 | 3 | 96 |
| Formate of compound 4 | — | 55.4 | 30.1 | 396 | — |
| Formate of compound 5 | — | — | — | 2.725 | — |
| Formate of compound 6 | <0.015 | 0.070 | — | 4.900 | — |
| Formate of compound 10 | — | — | — | 6.012 | 73.0 |
| Formate of compound 12 | 0.017 | 0.085 | — | 9.113 | 46.0 |
| Formate of compound 13 | 0.016 | 0.052 | — | 5.340 | — |
| Formate of compound 15 | — | — | — | 23.020 | — |
| Compound 16 | — | — | — | 539.587 | — |

-continued

| Compounds | Wild-type EGFR enzyme IC$_{50}$ (nM) | EGFR exon 19 deletion enzyme IC$_{50}$ (nM) | EGFR L858R enzyme IC$_{50}$ (nM) | Anti-PC-9 (Δ19del) cell proliferative activity IC$_{50}$ (nM) | Anti-A431 cell proliferative activity IC$_{50}$ (nM) |
| --- | --- | --- | --- | --- | --- |
| Formate of compound 17 | — | — | — | 29.385 | — |
| Compound 18 | <0.015 | 0.050 | — | 12.534 | 59.0 |
| Formate of compound 19 | — | — | — | 1280.181 | — |
| Formate of compound 20 | — | — | — | 2.166 | — |
| Formate of compound 21 | — | — | — | 2.961 | — |
| Formate of compound 22 | — | — | — | 41.401 | — |
| Compound 23 | 0.038 | 0.170 | — | 23.961 | — |
| Formate of compound 24 | — | — | — | 7.534 | — |
| Compound 25 | 0.022 | 0.069 | — | 6.756 | 64.0 |
| Compound 26 | — | — | — | 7.202 | 98.0 |
| Compound 27 | — | — | — | 84.027 | — |
| Formate of compound 28 | — | — | — | 249.975 | — |
| Compound 29 | — | — | — | 14.662 | — |
| Hydrochloride of compound 30 | 0.021 | 0.052 | — | 11.177 | 71.0 |
| Hydrochloride of compound 31 | — | — | — | 15.279 | — |
| Formate of compound 33 | 0.114 | 0.290 | — | — | — |
| Compound 37 | — | — | — | 21.2 | — |
| Compound 38 | — | — | — | 24.9 | — |
| Compound 39 | — | — | — | 16.8 | — |
| Compound 41 | — | — | — | 5.74 | — |
| Compound 45 | — | — | — | 8.86 | — |
| Formate of compound 46 | — | — | — | 29.8 | — |
| Formate of compound 48 | — | — | — | 8.55 | — |
| Compound 49 | — | — | — | 4.20 | — |

Note:
"—" means not tested

Conclusion: Since EGFR autophosphorylation, i.e. dimerization, can activate the kinase pathway in cells, the autophosphorylation can lead to downstream phosphorylation and induce cell proliferation. There is high or abnormal expression of EGFR in many tumors, which plays an important role in the progression of malignant tumors. Inhibition of PC-9 (19del) cell activity can most intuitively reflect the anti-proliferative effect of compounds on an exon 19 deletion cell model, so as to screen compounds in vitro. It can be seen from the table that the compounds of the invention show very high anti-proliferative activity against PC-9 (19del) cells.

The invention claimed is:

1. A compound of formula (I) or a pharmaceutically acceptable salt thereof,

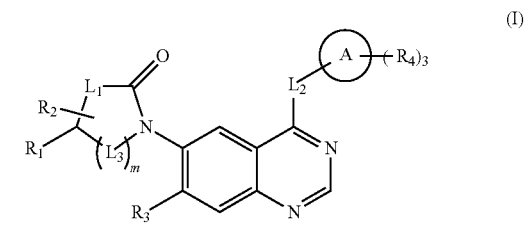

wherein,
R$_1$ and R$_2$ are independently selected from H, halogen, OH, CN, and NH$_2$, or
R$_1$ and R$_2$ are C$_{1-5}$ alkyl and C$_{1-5}$ heteroalkyl, or C$_{1-5}$ alkyl and C$_{1-5}$ heteroalkyl being optionally substituted with one, two or three R,
or, R$_1$ is connected with R$_2$ to form a 4-6-membered ring substituted with two R$_5$;
L$_1$ is —O(C(R)$_2$)$_m$— or —S(C(R)$_2$)$_m$—;
m is independently selected from 0, 1, and 2;
R$_5$ is independently selected from H, halogen, OH, CN, and NH$_2$, or independently selected from C$_{1-5}$ alkyl, C$_{1-5}$ heteroalkyl, C$_{3-6}$ cycloalkyl, 3-6-membered heterocycloalkyl, C$_{1-5}$ alkyl, C$_{1-5}$ heteroalkyl, C$_{3-6}$ cycloalkyl optionally substituted with one, two or three R, and 3-6-membered heterocycloalkyl optionally substituted with one, two or three R;
R$_3$ is selected from H, or selected from C$_{1-3}$ alkyl, C$_{1-3}$ heteroalkyl, C$_{1-3}$ alkyl optionally substituted with one, two or three R, and C$_{1-3}$ heteroalkyl being optionally substituted with one, two or three R;
L$_2$ is a single bond, —O—, or —NH—;
L$_3$ is —C(R)$_2$—;
ring A is phenyl or 5-10-membered heteroaryl;
R$_4$ is independently selected from H, halogen, C$_{1-3}$ alkyl, C$_{1-3}$ heteroalkyl, and C$_{2-3}$ alkynyl;
R is independently selected from H, OH, CN, NH$_2$, halogen, or independently selected from C$_{1-3}$ alkyl, C$_{1-3}$ heteroalkyl, C$_{1-3}$ alkyl optionally substituted with one, two or three R', and C$_{1-3}$ heteroalkyl optionally substituted with one, two or three R';
wherein said C$_{1-5}$ heteroalkyl, said C$_{1-3}$ heteroalkyl, said 3-6-membered heterocycloalkyl, said 5-9-membered heteroaryl comprises 1, 2, or 3 heteroatoms or heteroatom-containing groups independently selected from —O—, =O, N, —NH—, —S—, =S, —S(=O)—, —S(=O)$_2$—, —C(=O)O—, —C(=O)NH—, and —S(=O)NH—; and
R' is selected from F, Cl, Br, I, OH, CN, and NH$_2$.

2. The compound or pharmaceutically acceptable salt thereof according to claim 1, wherein, R is selected from H, F, Cl, Br, OH, CN, NH$_2$, CH$_3$, CH$_3$CH$_2$, CH$_3$O, CF$_3$, CHF$_2$, and CH$_2$F.

3. The compound or pharmaceutically acceptable salt thereof according to claim 1, wherein, R$_1$ and R$_2$ are independently selected from H, halogen, OH, CN, and NH$_2$, or independently selected from CH$_3$, CH$_3$CH$_2$, CH$_3$O, CH$_3$NH, (CH$_3$)$_2$N, (CH$_3$)$_2$NCH$_2$ and CH$_3$OCH$_2$, and, CH$_3$, CH$_3$CH$_2$, CH$_3$O, CH$_3$NH, (CH$_3$)$_2$N, (CH$_3$)$_2$NCH$_2$, and CH$_3$OCH$_2$ that are substituted with one, two or three R.

4. The compound or pharmaceutically acceptable salt thereof according to claim 3, wherein, R$_1$ and R$_2$ are independently selected from H, F, Cl, Br, OH, CN, NH₂, CH₃, CH₃CH₂, CH₃O, CH₃NH, (CH₃)₂N, (CH₃)₂NCH₂, and CH₃OCH₂.

5. The compound or pharmaceutically acceptable salt thereof according to claim 1, wherein, L₁ is —OC(R)₂— or —O(C(R)₂)₂—.

6. The compound or pharmaceutically acceptable salt thereof according to claim 5, wherein, L₁ is selected from —CH₂O— and —(CH₂)₂O—.

7. The compound or pharmaceutically acceptable salt thereof according to claim 1, wherein, the structural unit

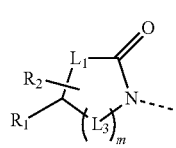

is selected from:

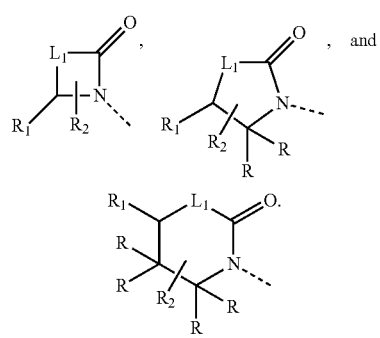

8. The compound or pharmaceutically acceptable salt thereof according to claim 7, wherein, the structural unit

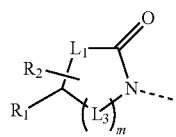

is selected from:

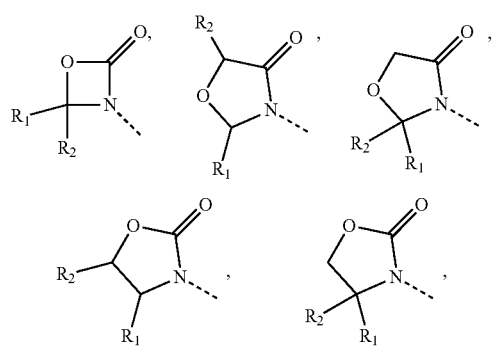

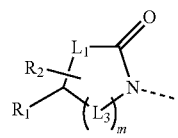

9. The compound or pharmaceutically acceptable salt thereof according to claim 1, wherein, the structural unit

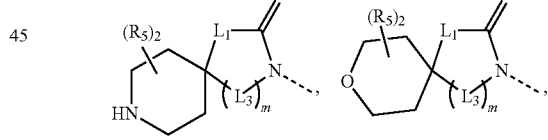

is selected from:

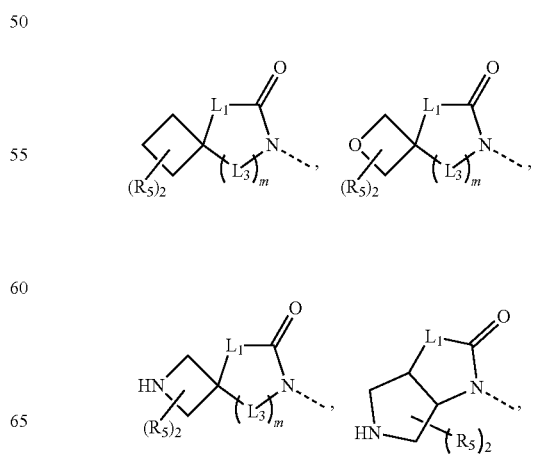

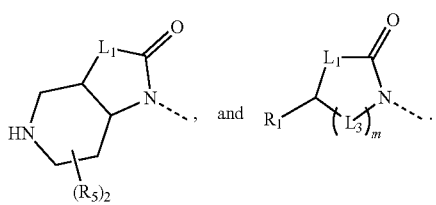

10. The compound or pharmaceutically acceptable salt thereof according to claim 1, wherein, the structural unit

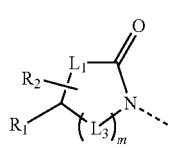

is selected from:

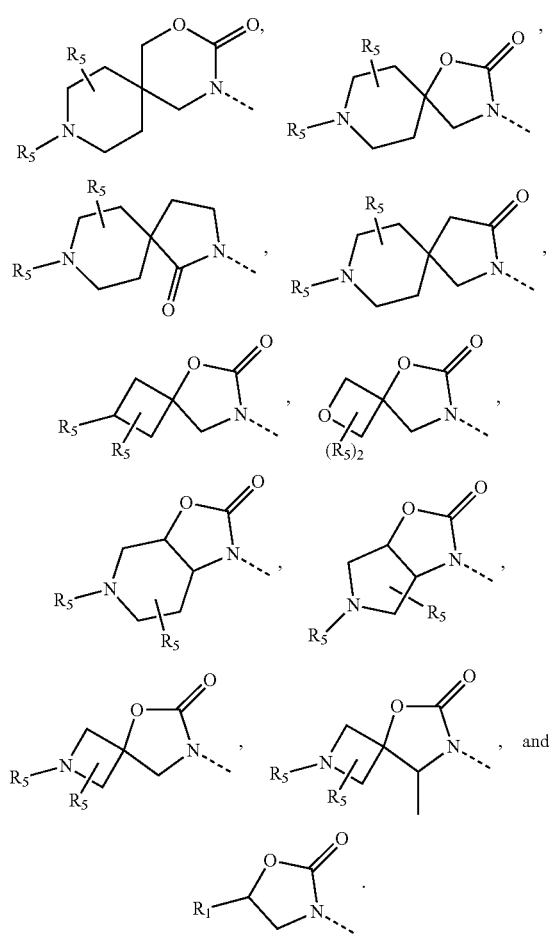

11. The compound or pharmaceutically acceptable salt thereof according to claim 1, wherein, $R_5$ is independently selected from H, F, Cl, Br, OH, CN, and $NH_2$, respectively, or selected from substituted or unsubstituted $CH_3$, $CH_3CH_2$, $CH_3CH_2CH_2$, $CH_3O$, $CH_3OCH_2$, $N(CH_3)_2$, $NH(CH_3)$,

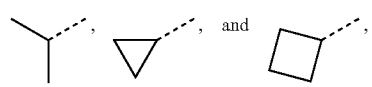

wherein the substitutes are one, two, or three R.

12. The compound or pharmaceutically acceptable salt thereof according to claim 11, wherein, $R_5$ is independently selected from F, Cl, Br, OH, CN, $NH_2$, $CH_3$, $CH_3CH_2$, $CH_2CH_2F$, $CH_3CH_2CH_2$, $CH_3O$, $CH_3OCH_2$, $N(CH_3)_2$,

13. The compound or pharmaceutically acceptable salt thereof according to claim 10, wherein, the structural unit

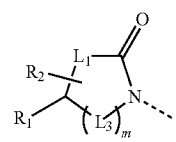

is selected from:

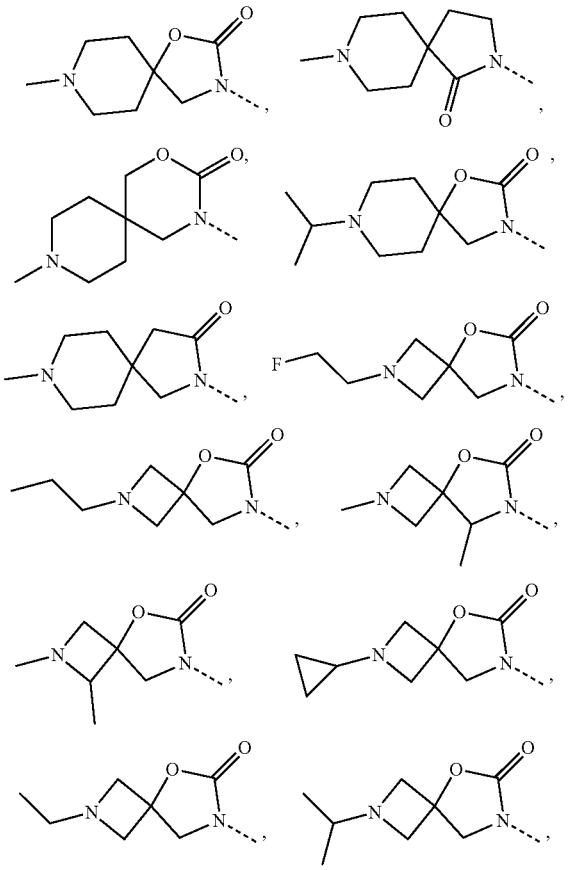

-continued

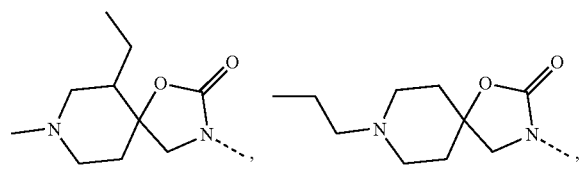

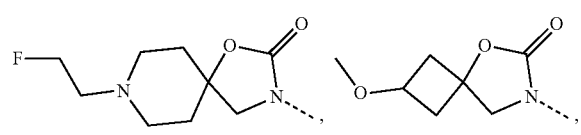

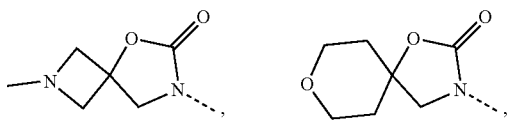

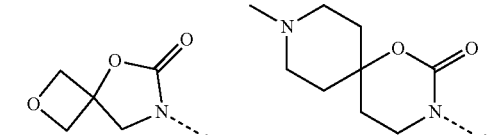

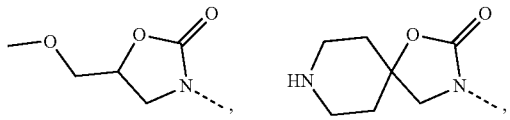

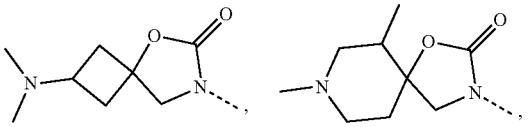

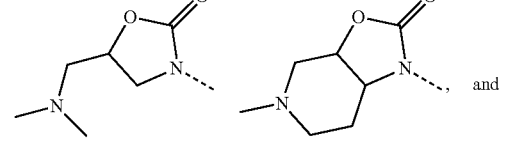

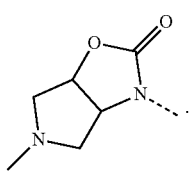

14. The compound or pharmaceutically acceptable salt thereof according to claim 1, wherein, $R_3$ is selected from H, $CH_3$, $CH_3CH_2$, $CH_3CH_2CH_2$, $CH_3O$, and $CH_3OCH_2$, or selected from $CH_3$, $CH_3CH_2$, $CH_3CH_2CH_2$, $CH_3O$, and $CH_3OCH_2$ that are substituted with one, two or three R.

15. The compound or pharmaceutically acceptable salt thereof according to claim 14, wherein, $R_3$ is selected from H, $CH_3$, $CH_3CH_2$, $CH_3CH_2CH_2$, $CH_3O$, $CHF_2O$, and $CH_3OCH_2$.

16. The compound or pharmaceutically acceptable salt thereof according to claim 1, wherein, $R_4$ is independently selected from H, F, Cl, Br, I, $CH_3$, $CH_3O$, and $CH\equiv C$—.

17. The compound or pharmaceutically acceptable salt thereof according to claim 1, wherein, ring A is selected from phenyl, thienyl, pyrrolyl, furyl, pyridyl, indolyl, and benzimidazolyl.

18. The compound or pharmaceutically acceptable salt thereof according to claim 1, wherein

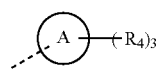

is selected from:

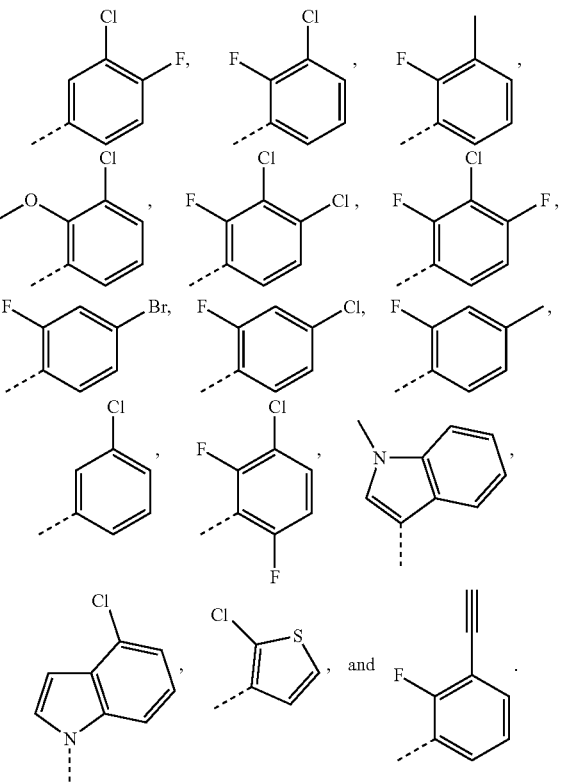

19. The compound or pharmaceutically acceptable salt thereof according to claim 1, wherein the compound is selected from:

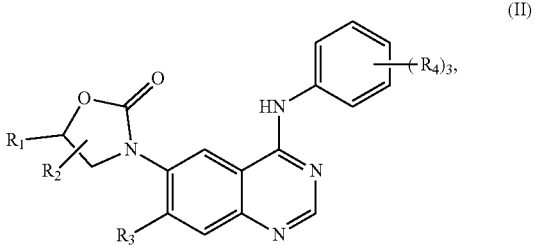

(II)

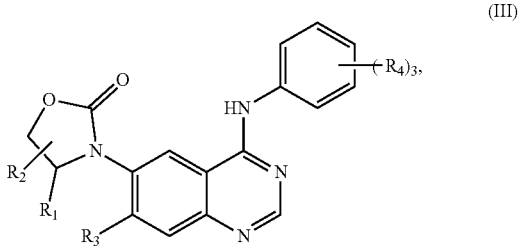

(III)

-continued

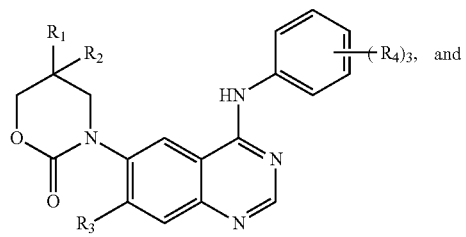

(VII)

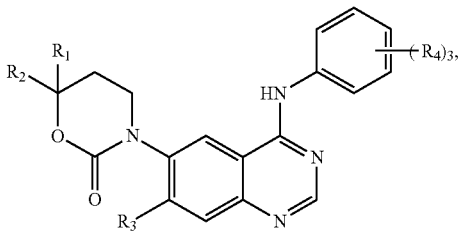

(VIII)

wherein R₁, R₂, R₃, R₄ are as defined in claim 1, or the compound is selected from:

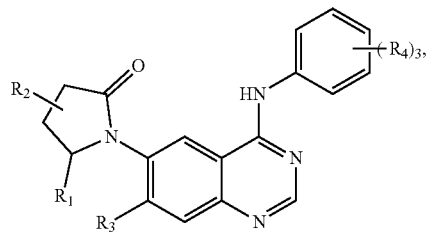

(IV)

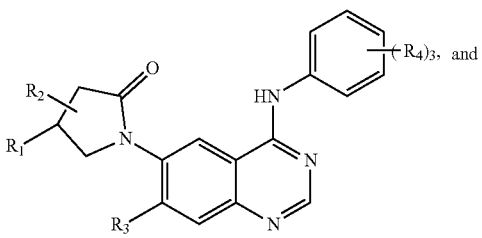

(V)

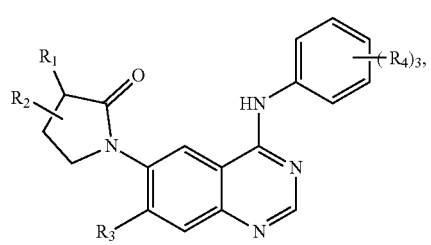

(VI)

wherein R₁, R₂, R₃, R₄ are as defined in claim 1, with the proviso that R₁ is connected with R₂ to form a 4-6-membered ring substituted with two R₅.

20. The compound or pharmaceutically acceptable salt thereof according to claim 19, wherein the compound is selected from:

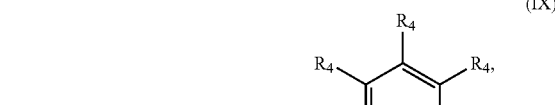

(IX)

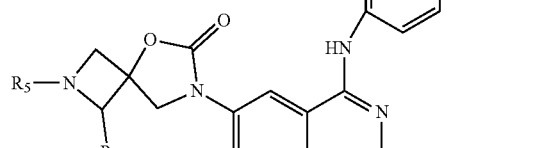

(X)

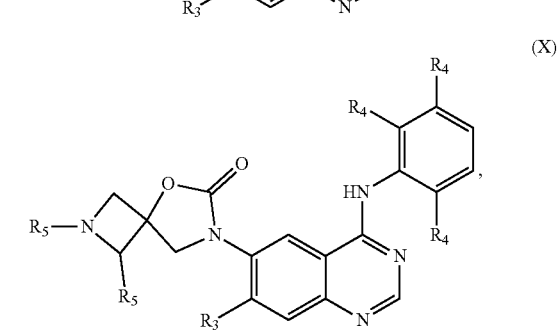

(XI)

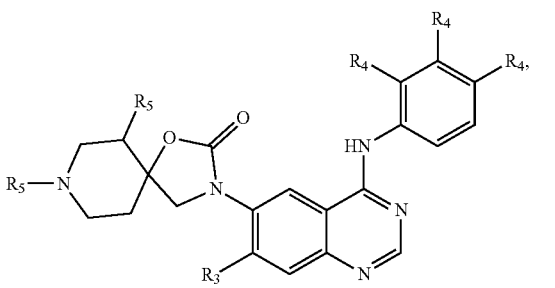

(XII)

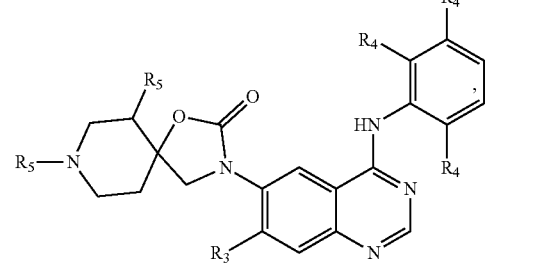

(XIII)

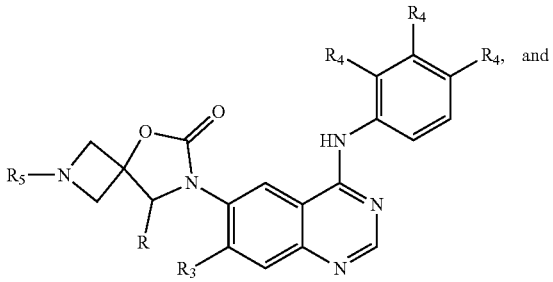

(XIV)
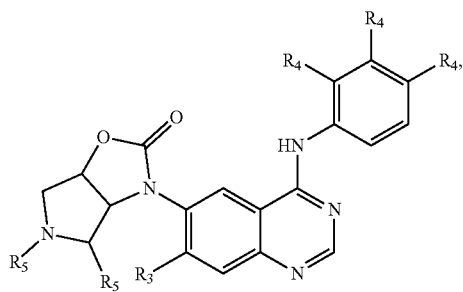
wherein, R, R₃, R₄, R₅ are as defined in claim 19.
21. The compound of claim 1, selected from:
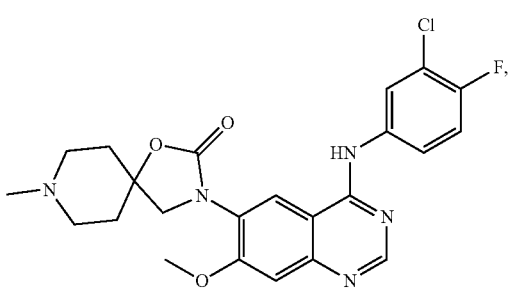
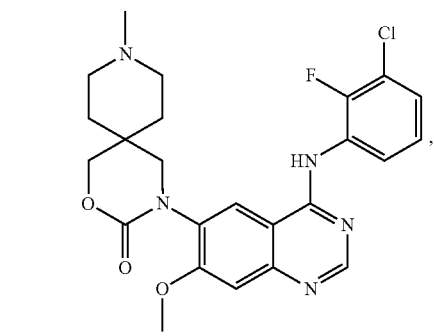
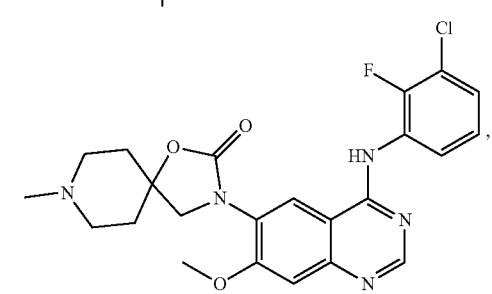
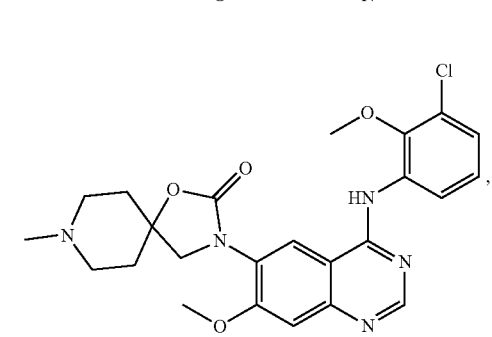
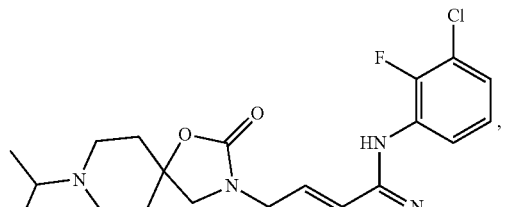
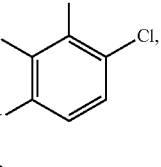
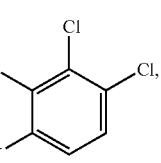
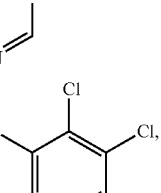
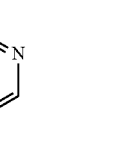
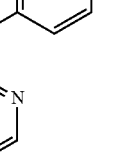
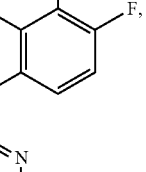

153
-continued
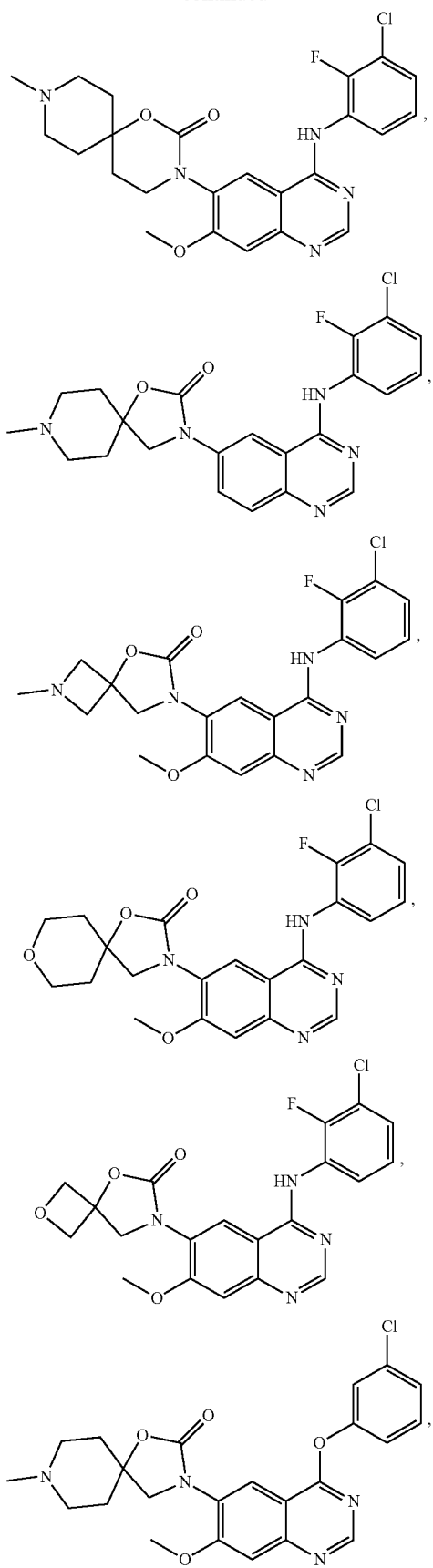
154
-continued
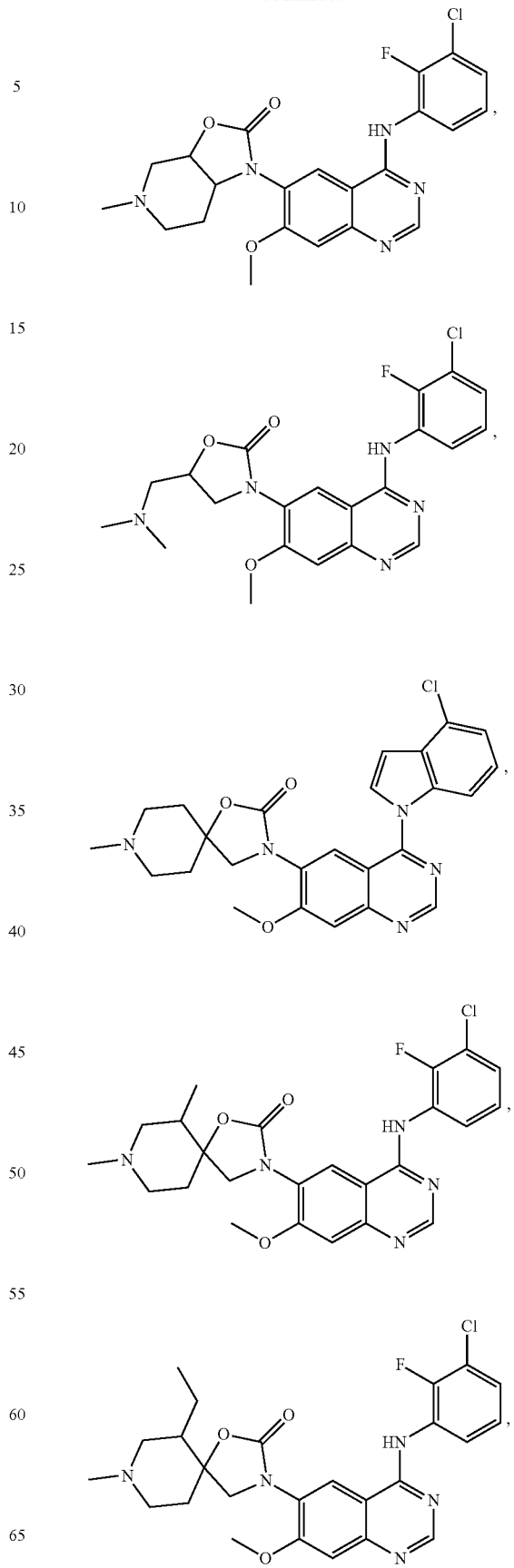

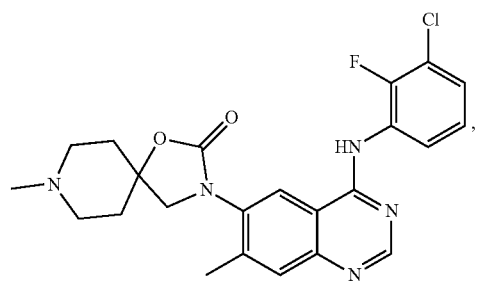
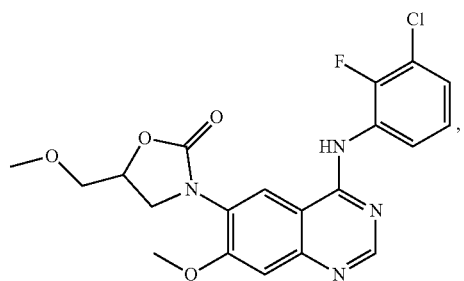
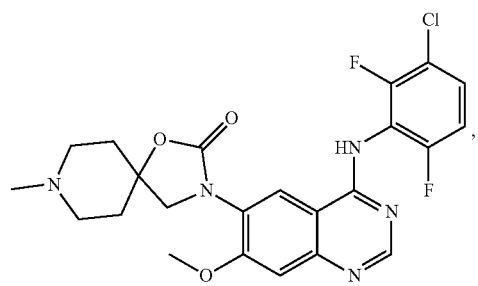
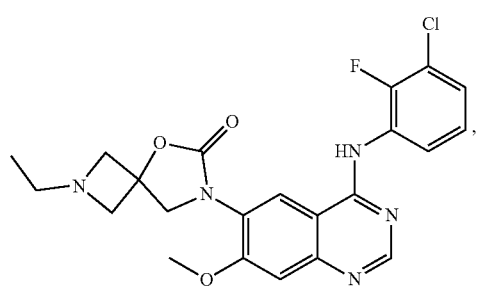
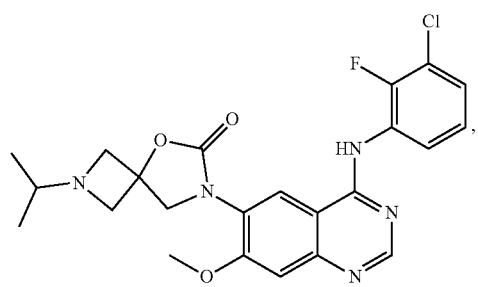
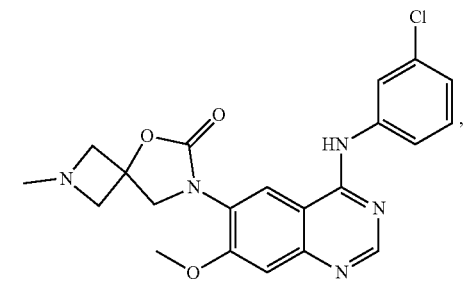
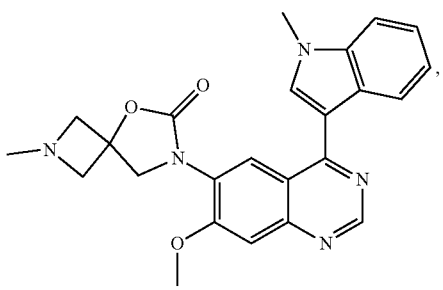
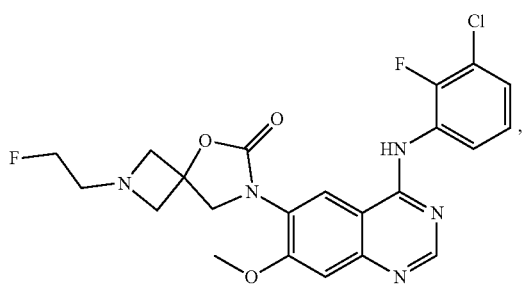
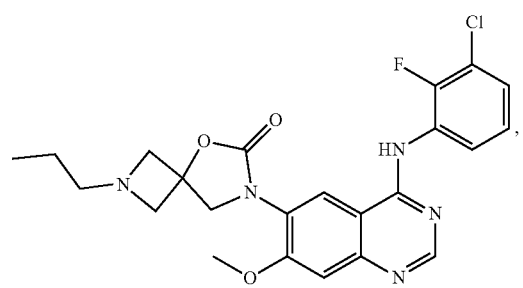
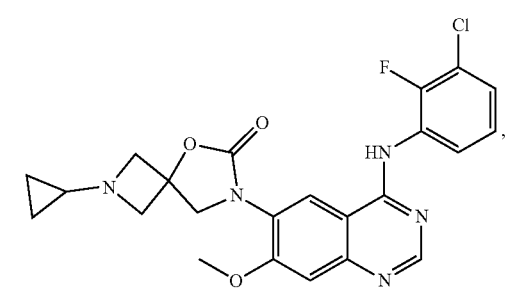
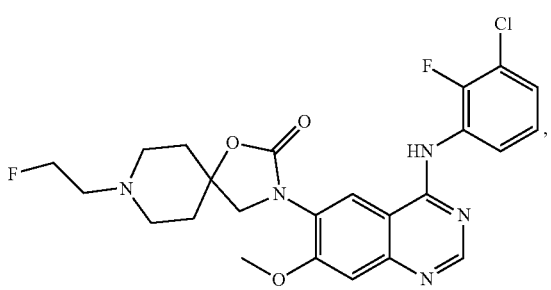
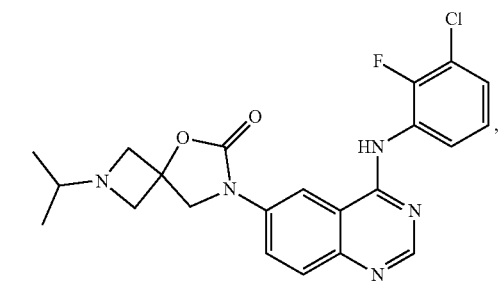

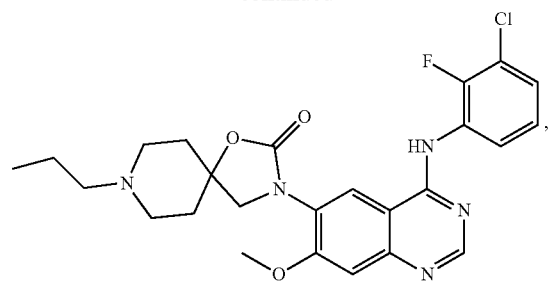
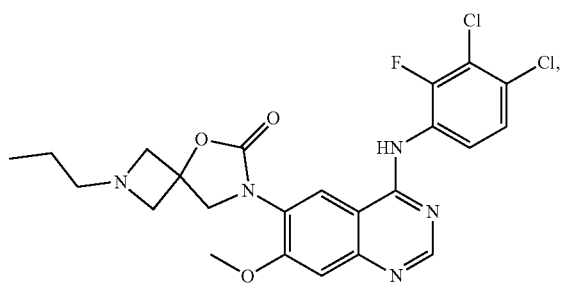
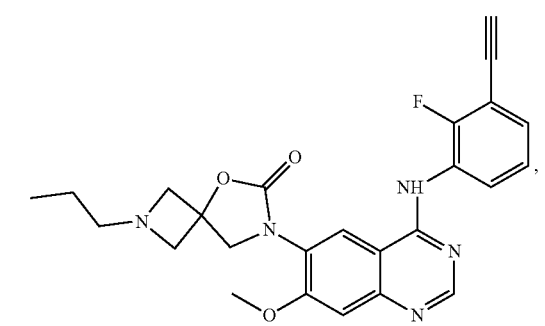
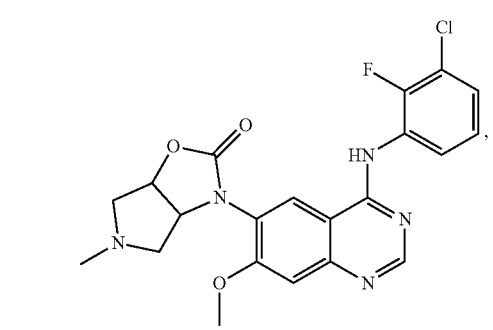
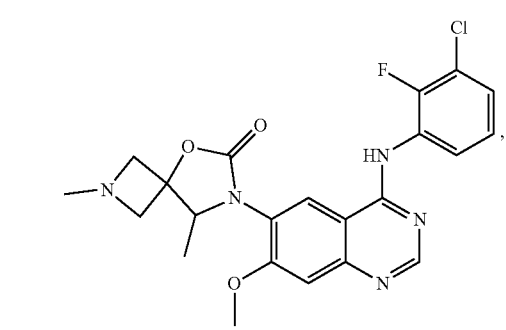
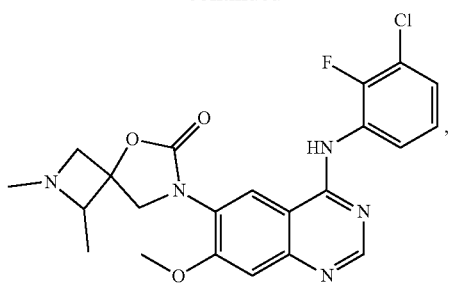
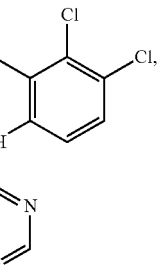
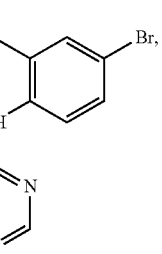
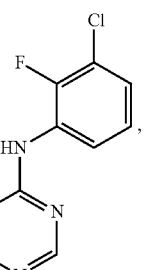
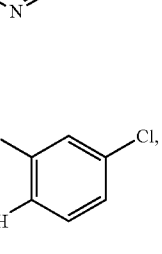

-continued
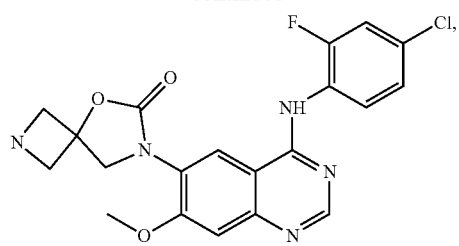
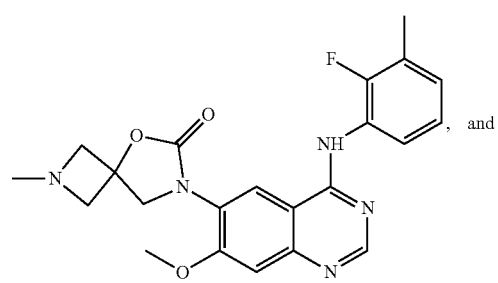
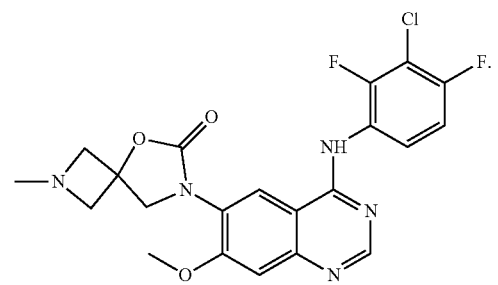
22. The compound according to claim 21, which is selected from:
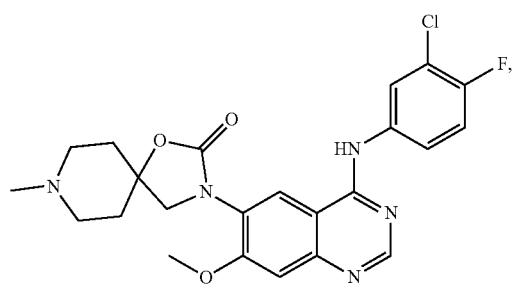
-continued
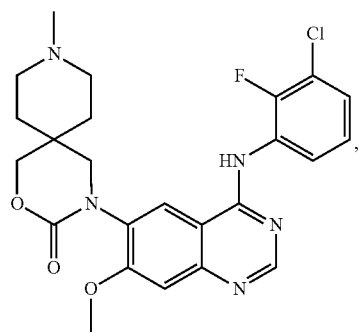
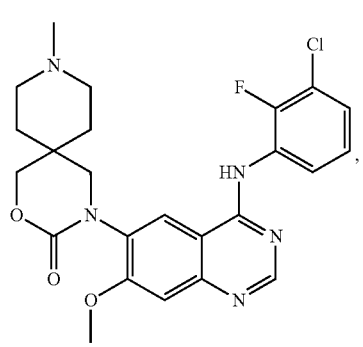
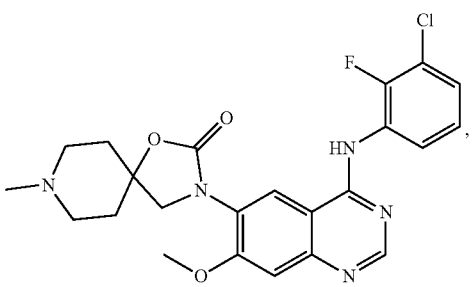

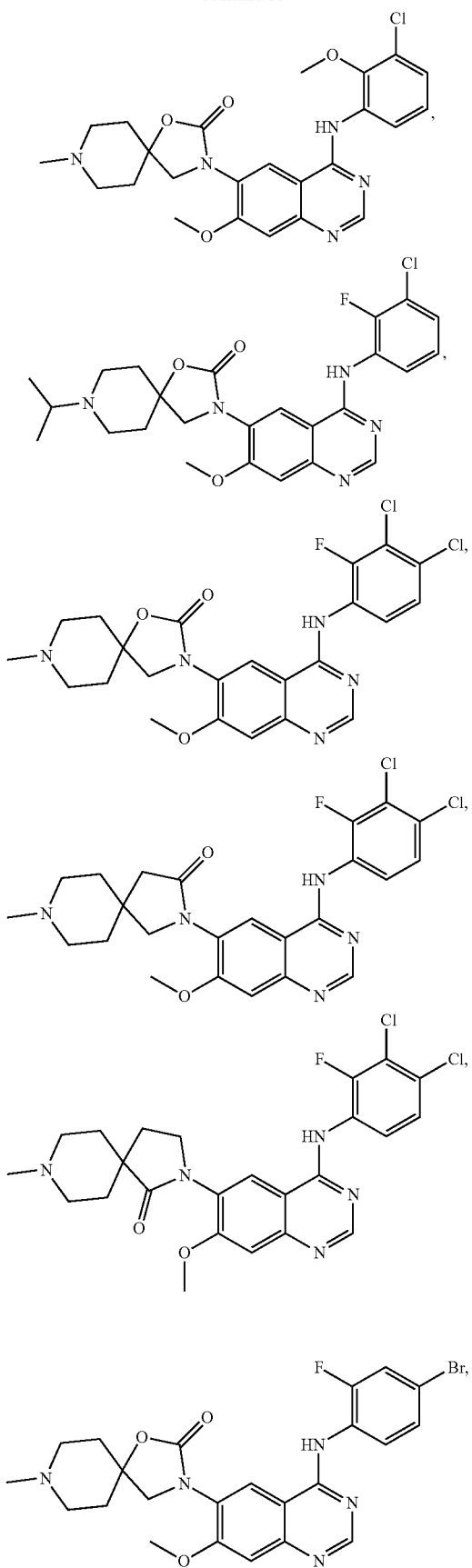
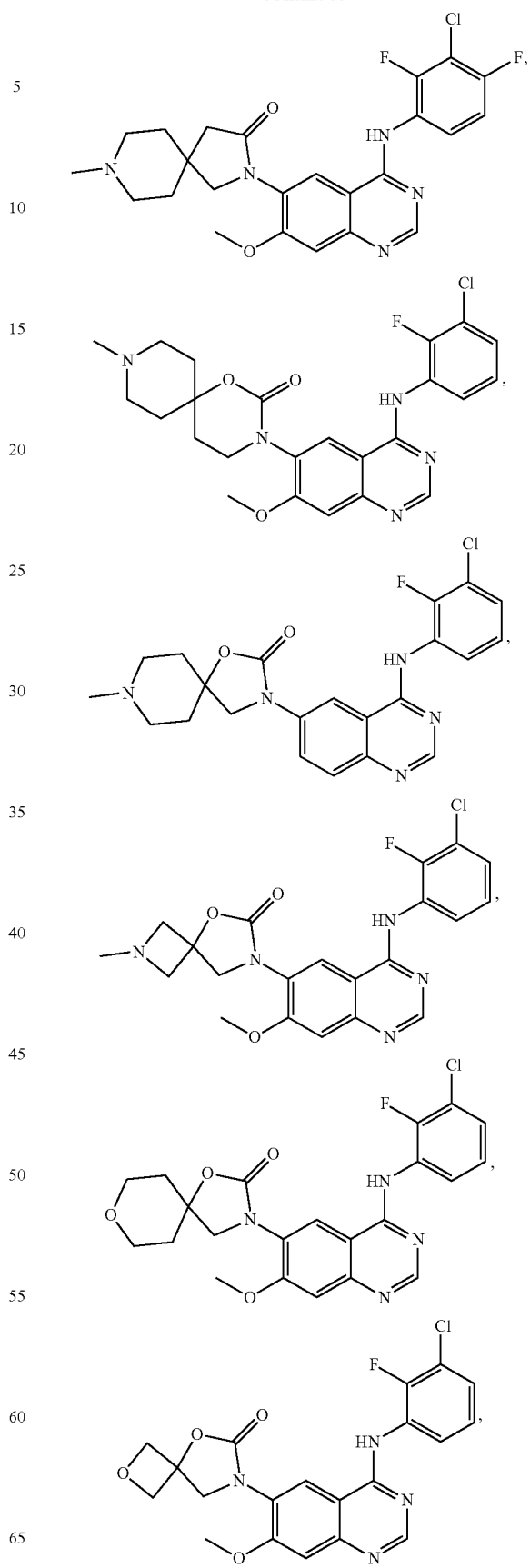

163
-continued
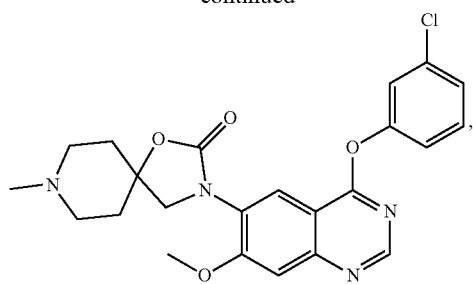
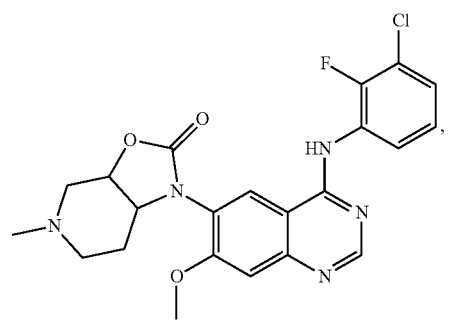
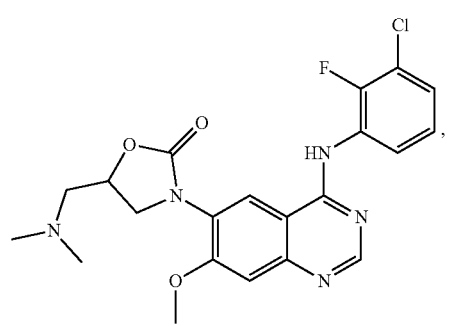
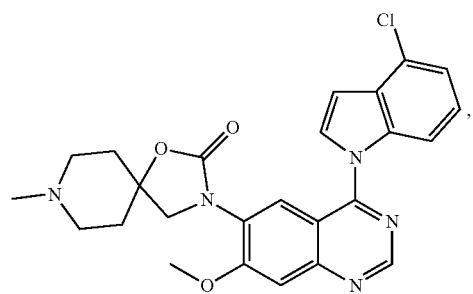
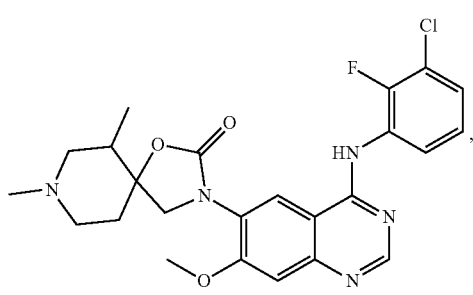
164
-continued
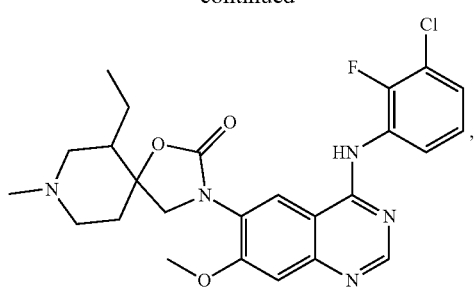
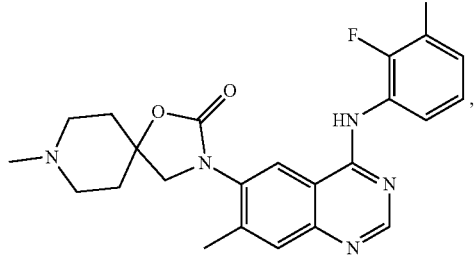
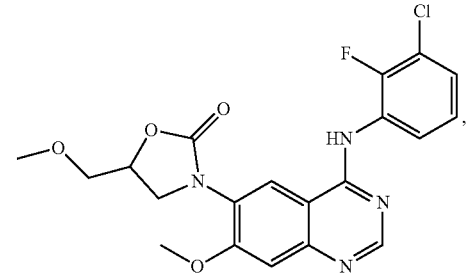
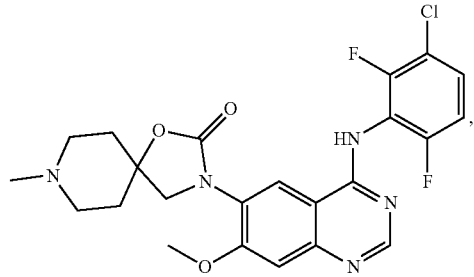
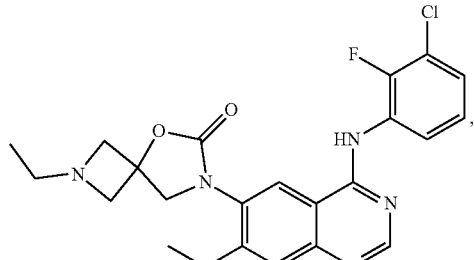
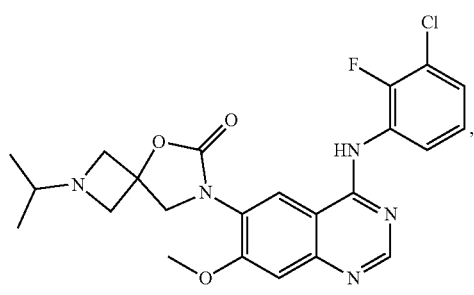

165
-continued
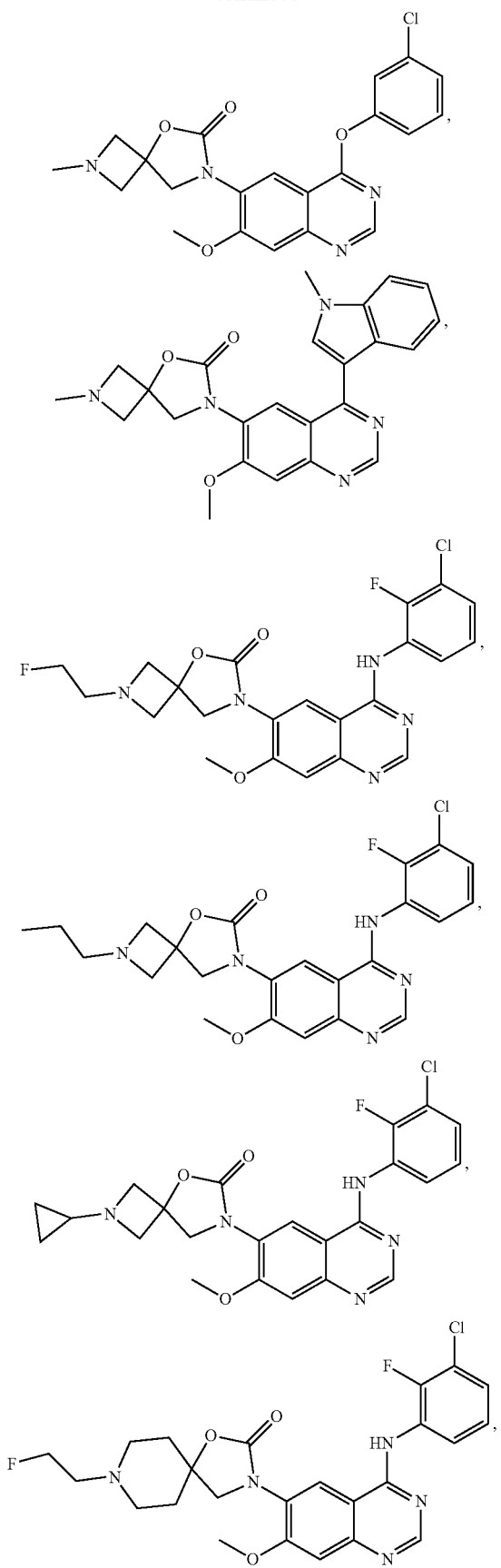
166
-continued
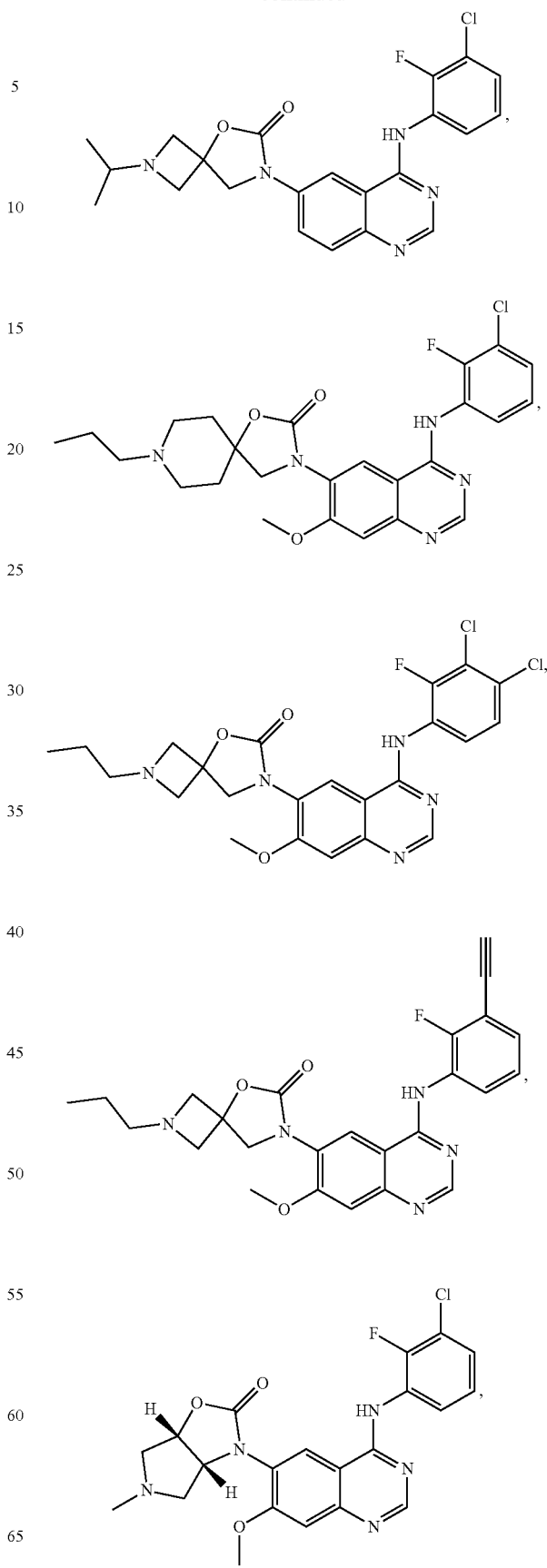

167
-continued
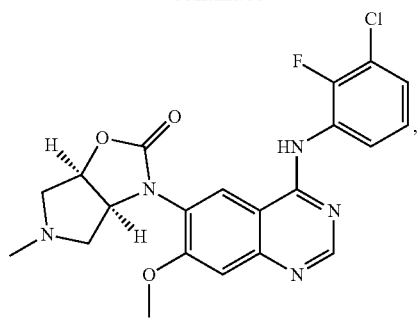
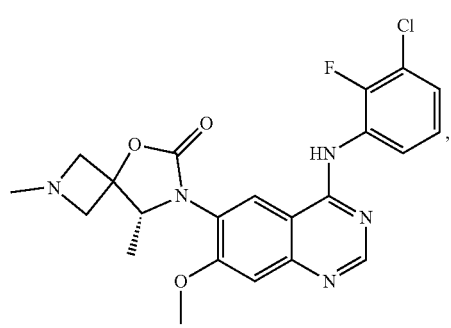
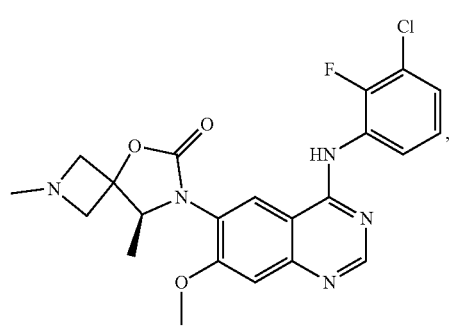
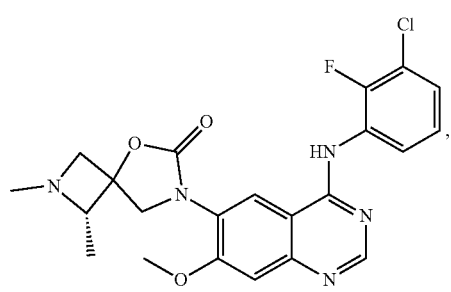
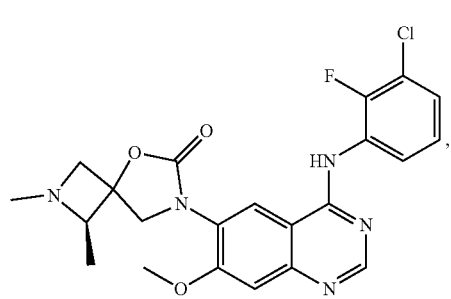
168
-continued
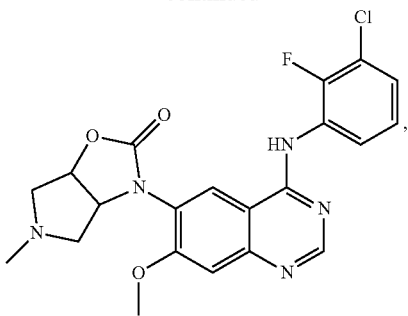
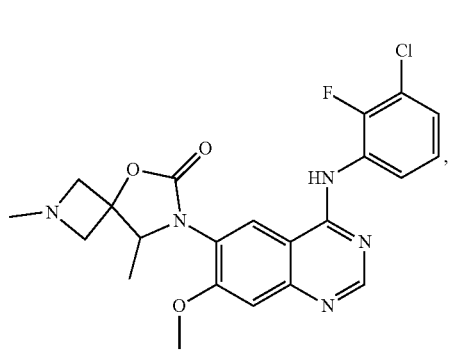
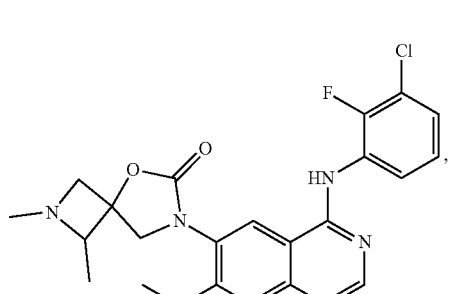
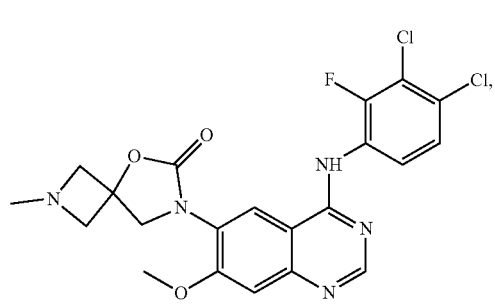
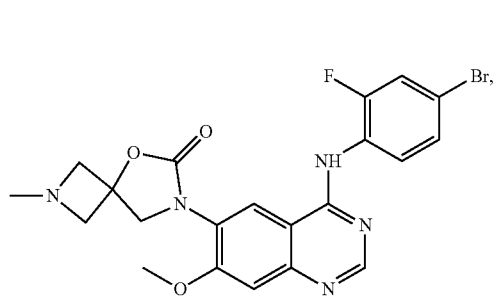

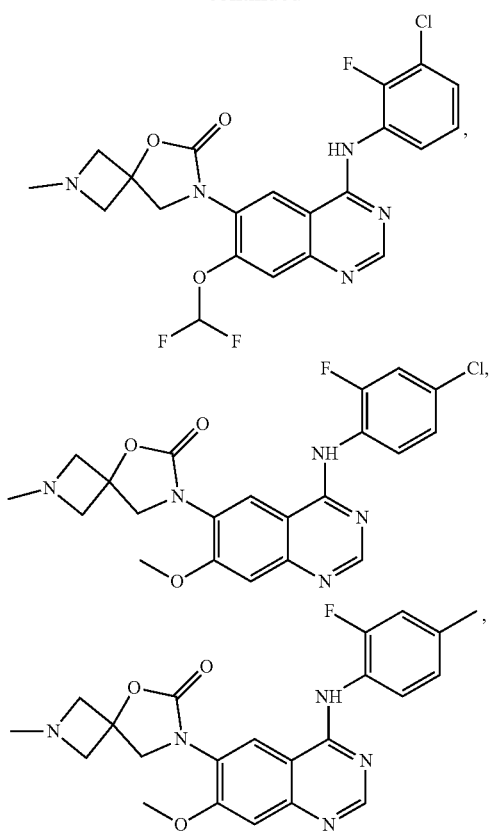

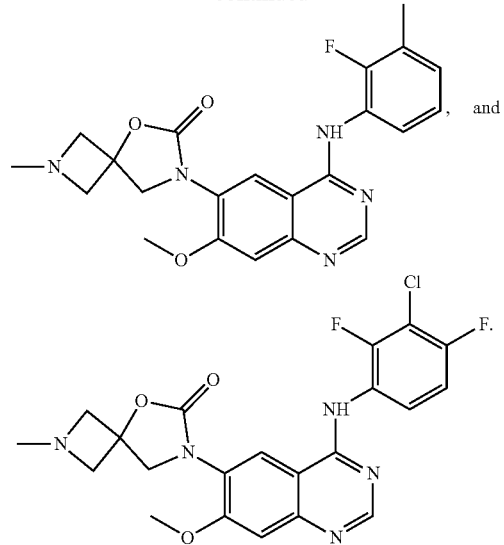

23. A pharmaceutical composition, comprising a therapeutically effective amount of the compound or pharmaceutically acceptable salt thereof or pharmaceutically acceptable carrier thereof according to claim 1.

24. A method for treating cancer, comprising administering a therapeutically effective amount of the compound and pharmaceutically acceptable salt thereof according to claim 1 to a subject in need thereof, wherein the cancer is a lung cancer or a brain metastasis.

* * * * *